United States Patent
Olea

(10) Patent No.: US 9,907,582 B1
(45) Date of Patent: Mar. 6, 2018

(54) MINIMALLY INVASIVE SPINAL FIXATION SYSTEM AND RELATED METHODS

(71) Applicant: NuVasive, Inc., San Diego, CA (US)

(72) Inventor: Fernando Olea, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/631,839

(22) Filed: Feb. 25, 2015

Related U.S. Application Data

(63) Continuation-in-part of application No. 13/456,210, filed on Apr. 25, 2012, now Pat. No. 9,198,698.

(60) Provisional application No. 61/478,658, filed on Apr. 25, 2011, provisional application No. 61/553,052, filed on Oct. 28, 2011, provisional application No. 61/944,513, filed on Feb. 25, 2014, provisional application No. 62/078,059, filed on Nov. 11, 2014.

(51) Int. Cl.
*A61B 17/70* (2006.01)
*A61B 17/66* (2006.01)
*A61B 17/60* (2006.01)

(52) U.S. Cl.
CPC .......... *A61B 17/7079* (2013.01); *A61B 17/60* (2013.01); *A61B 17/7002* (2013.01); *A61B 17/708* (2013.01); *A61B 17/7032* (2013.01); *A61B 17/7035* (2013.01); *A61B 17/7085* (2013.01)

(58) Field of Classification Search
CPC .............. A61B 17/7032; A61B 17/025; A61B 17/7077; A61B 17/7079; A61B 17/708
See application file for complete search history.

(56) References Cited

U.S. PATENT DOCUMENTS

| | | | |
|---|---|---|---|
| 1,222,478 | A | 4/1917 | Sheaff |
| 1,595,378 | A | 8/1926 | Cameron |
| 1,796,072 | A | 3/1931 | Baer |
| 2,279,068 | A | 4/1942 | Siebrandt |
| 2,301,500 | A | 11/1942 | Roger |
| 2,807,259 | A | 9/1957 | Guerriero |
| 3,547,113 | A | 12/1970 | Swanson |
| 3,977,397 | A | 8/1976 | Kalnberz |
| 4,006,740 | A | 2/1977 | Volkov |
| 4,187,841 | A | 2/1980 | Knutson |
| 4,244,360 | A | 1/1981 | Dohogne |
| 4,628,921 | A | 12/1986 | Rousso |
| 4,688,560 | A | 8/1987 | Schultz |
| 4,716,901 | A | 1/1988 | Jackson |
| 4,733,657 | A | 3/1988 | Kluger |
| 4,747,394 | A | 5/1988 | Watanabe |
| 4,829,999 | A | 5/1989 | Auth |
| 4,854,304 | A | 8/1989 | Zielke |

(Continued)

FOREIGN PATENT DOCUMENTS

| | | |
|---|---|---|
| AU | 2012200106 A1 | 2/2012 |
| BR | 6200124 U | 6/1982 |

(Continued)

*Primary Examiner* — Jacqueline Johanas
(74) *Attorney, Agent, or Firm* — Rory Schermerhorn

(57) ABSTRACT

This application describes surgical instruments and implants for building a posterior fixation construct across one or more segments of the spinal column. More specifically, the application describes instruments and methods for building a posterior fixation construct across one or more segments of the spinal column in a minimally invasive fashion.

20 Claims, 67 Drawing Sheets

(56) References Cited

U.S. PATENT DOCUMENTS

| | | |
|---|---|---|
| 4,893,618 A | 1/1990 | Herzberg |
| 4,896,661 A | 1/1990 | Bogert |
| 4,898,161 A | 2/1990 | Grundei |
| 4,929,247 A | 5/1990 | Rayhack |
| 4,936,843 A | 6/1990 | Sohngen |
| 4,957,495 A | 9/1990 | Kluger |
| 4,964,861 A | 10/1990 | Agee |
| 4,968,316 A | 11/1990 | Hergenroeder |
| 4,978,348 A | 12/1990 | Ilizarov |
| 5,000,166 A | 3/1991 | Karpf |
| 5,034,011 A | 7/1991 | Howland |
| 5,059,194 A | 10/1991 | Michelson |
| 5,108,395 A | 4/1992 | Laurain |
| 5,152,766 A | 10/1992 | Kirkley |
| 5,192,283 A | 3/1993 | Ling |
| 5,219,349 A | 6/1993 | Krag |
| 5,300,083 A | 4/1994 | Lin |
| 5,304,177 A | 4/1994 | Pennig |
| 5,391,167 A | 2/1995 | Pong |
| 5,409,488 A | 4/1995 | Ulrich |
| 5,425,732 A | 6/1995 | Ulrich |
| 5,433,720 A | 7/1995 | Faccioli |
| 5,439,465 A | 8/1995 | Tumibay |
| 5,470,336 A | 11/1995 | Ling |
| 5,478,340 A | 12/1995 | Kluger |
| 5,529,571 A | 6/1996 | Daniel |
| 5,531,751 A | 7/1996 | Schultheiss |
| D373,632 S | 9/1996 | Price |
| 5,569,253 A | 10/1996 | Farris |
| 5,591,169 A | 1/1997 | Benoist |
| D381,746 S | 7/1997 | Koros |
| 5,643,262 A | 7/1997 | Metz-Stavenhagen |
| 5,672,175 A | 9/1997 | Martin |
| 5,738,213 A | 4/1998 | Whiting |
| 5,785,648 A | 7/1998 | Min |
| 5,797,884 A | 8/1998 | Byrd |
| 5,797,910 A | 8/1998 | Martin |
| D401,335 S | 11/1998 | Koros |
| 5,868,668 A | 2/1999 | Weiss |
| 5,899,901 A | 5/1999 | Middleton |
| 5,919,192 A | 7/1999 | Shouts |
| 5,928,139 A | 7/1999 | Koros |
| 5,928,230 A | 7/1999 | Tosic |
| 5,935,151 A | 8/1999 | Broughton |
| 6,017,342 A | 1/2000 | Rinner |
| 6,090,113 A | 7/2000 | Le Couedic |
| 6,120,505 A | 9/2000 | Huebner |
| 6,126,660 A | 10/2000 | Dietz |
| 6,171,307 B1 | 1/2001 | Orlich |
| 6,235,029 B1 | 5/2001 | Faccioli |
| 6,261,296 B1 | 7/2001 | Aebi |
| 6,289,661 B1 | 9/2001 | Boland |
| 6,332,887 B1 | 12/2001 | Knox |
| 6,340,363 B1 | 1/2002 | Bolger |
| 6,364,832 B1 | 4/2002 | Propp |
| 6,371,968 B1 | 4/2002 | Kogasaka |
| 6,379,299 B1 | 4/2002 | Borodulin |
| 6,547,072 B2 | 4/2003 | Whiting |
| 6,551,316 B1 | 4/2003 | Rinner |
| 6,569,091 B2 | 5/2003 | Diokno |
| 6,569,106 B1 | 5/2003 | Ullman |
| 6,623,483 B1 | 9/2003 | Kazakov |
| 6,648,891 B2 | 11/2003 | Kim |
| D488,229 S | 4/2004 | Rinner |
| 6,716,218 B2 | 4/2004 | Holmes |
| 6,749,563 B2 | 6/2004 | Stihl |
| 6,926,718 B1 | 8/2005 | Michelson |
| 7,008,432 B2 | 3/2006 | Schläpfer |
| 7,011,658 B2 | 3/2006 | Young |
| 7,073,415 B2 | 7/2006 | Casutt |
| 7,097,647 B2 | 8/2006 | Segler |
| 7,153,281 B2 | 12/2006 | Holmes |
| 7,172,600 B2 | 2/2007 | Beger |
| 7,189,244 B2 | 3/2007 | Newton |
| 7,204,464 B2 | 4/2007 | Chandra |
| 7,229,051 B2 | 6/2007 | Mailhot |
| 7,374,534 B2 | 5/2008 | Dalton |
| 7,465,306 B2 | 12/2008 | Pond |
| 7,473,269 B1 | 1/2009 | Hynes |
| 7,494,463 B2 | 2/2009 | Nehls |
| 7,566,302 B2 | 7/2009 | Schwer |
| 7,578,822 B2 | 8/2009 | Rezach |
| 7,608,096 B2 | 10/2009 | Foley |
| 7,618,424 B2 | 11/2009 | Wilcox |
| 7,635,381 B2 | 12/2009 | Orbay |
| 7,637,863 B2 | 12/2009 | Deal |
| 7,641,659 B2 | 1/2010 | Emstad |
| 7,651,496 B2 | 1/2010 | Keegan |
| 7,699,847 B2 | 4/2010 | Sheldon |
| 7,776,051 B2 | 8/2010 | Colleran |
| 7,850,608 B2 | 12/2010 | Hamada |
| 7,875,061 B2 | 1/2011 | Bolger |
| 7,887,482 B2 | 2/2011 | Hamada |
| 7,922,710 B2 | 4/2011 | Eidenschink |
| 7,935,054 B2 | 5/2011 | Hamada |
| 7,951,152 B2 | 5/2011 | Marino |
| 7,976,463 B2 | 7/2011 | Dewey |
| 7,976,464 B2 | 7/2011 | Shluzas |
| 7,981,029 B2 | 7/2011 | Branch |
| 7,988,624 B2 | 8/2011 | Smith |
| 7,988,625 B2 | 8/2011 | Abdelgany |
| 7,988,700 B2 | 8/2011 | Shluzas |
| 7,998,144 B2 | 8/2011 | Schumacher |
| 8,002,808 B2 | 8/2011 | Morrison |
| 8,025,682 B2 | 9/2011 | Mahoney |
| 8,038,699 B2 | 10/2011 | Cohen |
| 8,038,700 B2 | 10/2011 | Colleran |
| 8,075,565 B2 | 12/2011 | Wilcox |
| 8,123,751 B2 | 2/2012 | Shluzas |
| 8,162,952 B2 | 4/2012 | Cohen |
| 8,167,911 B2 | 5/2012 | Shluzas |
| 8,192,439 B2 | 6/2012 | Songer |
| 8,197,522 B2 | 6/2012 | Park |
| 8,221,427 B2 | 7/2012 | Roh |
| 8,221,474 B2 | 7/2012 | Bridwell |
| 8,257,362 B2 | 9/2012 | Casutt |
| 8,257,407 B2 | 9/2012 | Aryan |
| 8,267,957 B1 | 9/2012 | Silver |
| 8,287,546 B2 | 10/2012 | King |
| 8,303,632 B2 | 11/2012 | Sherman |
| 8,323,292 B2 | 12/2012 | Dudasik |
| 8,366,747 B2 | 2/2013 | Shluzas |
| 8,372,081 B1 | 2/2013 | Schafer |
| 8,403,840 B2 | 3/2013 | Wagner |
| 8,403,842 B2 | 3/2013 | Sakhel |
| 8,403,940 B2 | 3/2013 | Parker |
| 8,439,193 B2 | 5/2013 | Koellhofer |
| 8,444,649 B2 * | 5/2013 | Stad ............... A61B 17/7074 606/105 |
| 8,460,310 B2 | 6/2013 | Stern |
| 8,491,582 B2 | 7/2013 | Keilen |
| 8,491,588 B2 | 7/2013 | Wall |
| 8,491,590 B2 * | 7/2013 | Stad ............... A61B 17/7077 606/86 A |
| 8,523,876 B2 | 9/2013 | Lim |
| 8,545,510 B2 | 10/2013 | Christian |
| 8,550,995 B2 | 10/2013 | Frasier |
| 8,551,141 B2 | 10/2013 | Gephart |
| 8,568,421 B2 | 10/2013 | Johnstone |
| 8,608,651 B2 | 12/2013 | Shluzas |
| 8,608,780 B2 | 12/2013 | Forton |
| 8,623,022 B2 | 1/2014 | Forton |
| 8,636,657 B2 | 1/2014 | Hamada |
| 8,641,609 B2 | 2/2014 | Hestad |
| 8,668,699 B2 | 3/2014 | Thomas |
| 8,679,129 B2 | 3/2014 | Sorrenti |
| 8,685,037 B2 | 4/2014 | Jordan |
| 8,696,558 B1 | 4/2014 | Parker |
| 8,702,601 B2 | 4/2014 | Oberlaender |
| 8,702,713 B2 | 4/2014 | Nayet |
| 8,721,688 B1 | 5/2014 | Wang |
| 8,747,409 B2 | 6/2014 | Lchelmann |
| 8,764,800 B2 | 7/2014 | Johansson |
| 8,777,954 B2 | 7/2014 | McLean |

(56) References Cited

U.S. PATENT DOCUMENTS

| | | | |
|---|---|---|---|
| 8,784,429 B2 | 7/2014 | Bryan | |
| 8,801,626 B2 | 8/2014 | Sun | |
| 8,801,757 B2 | 8/2014 | Abdou | |
| 8,834,508 B2 | 9/2014 | Chin | |
| 8,845,688 B2 | 9/2014 | Abdou | |
| 8,870,920 B2 | 10/2014 | Abdou | |
| 8,876,835 B2 | 11/2014 | Petit | |
| 8,894,573 B2 | 11/2014 | Loftus | |
| 8,894,655 B2* | 11/2014 | Fallin | A61B 17/7085 606/264 |
| 8,906,034 B2 | 12/2014 | Gleeson | |
| 8,911,441 B2 | 12/2014 | Dace | |
| 8,936,605 B2 | 1/2015 | Greenberg | |
| 8,951,257 B2 | 2/2015 | Lenke | |
| 8,951,258 B2 | 2/2015 | Peultier | |
| 8,956,362 B2 | 2/2015 | Landry | |
| 8,968,367 B2 | 3/2015 | Kretzer | |
| 8,979,749 B2 | 3/2015 | Gorek | |
| 9,011,507 B2 | 4/2015 | Schelling | |
| 9,023,051 B2 | 5/2015 | Hanson | |
| 9,060,825 B2* | 6/2015 | Hutton | A61B 17/7032 |
| 9,173,687 B2* | 11/2015 | Fowler | A61B 17/7074 |
| 2003/0149341 A1 | 8/2003 | Clifton | |
| 2004/0030336 A1 | 2/2004 | Khanna | |
| 2005/0033291 A1 | 2/2005 | Ebara | |
| 2005/0203532 A1 | 9/2005 | Ferguson | |
| 2005/0203533 A1 | 9/2005 | Ferguson | |
| 2005/0245928 A1* | 11/2005 | Colleran | A61B 17/708 606/90 |
| 2006/0052812 A1 | 3/2006 | Winer | |
| 2006/0074278 A1 | 4/2006 | Petit | |
| 2006/0195114 A1 | 8/2006 | Bertagnoli | |
| 2006/0195117 A1 | 8/2006 | Rucker | |
| 2006/0229636 A1 | 10/2006 | Woodburn | |
| 2006/0235279 A1 | 10/2006 | Hawkes | |
| 2007/0060794 A1 | 3/2007 | Efinger | |
| 2007/0173842 A1 | 7/2007 | Abdou | |
| 2007/0191856 A1 | 8/2007 | Gil | |
| 2007/0213716 A1* | 9/2007 | Lenke | A61B 17/025 606/264 |
| 2007/0225709 A1 | 9/2007 | Falahee | |
| 2007/0288026 A1* | 12/2007 | Shluzas | A61B 17/02 606/86 A |
| 2007/0299444 A1* | 12/2007 | DiPoto | A61B 17/02 606/86 A |
| 2008/0009863 A1 | 1/2008 | Bond | |
| 2008/0015582 A1* | 1/2008 | DiPoto | A61B 17/02 606/86 A |
| 2008/0033251 A1 | 2/2008 | Araghi | |
| 2008/0045973 A1 | 2/2008 | Gill | |
| 2008/0058810 A1 | 3/2008 | Abdou | |
| 2008/0077155 A1 | 3/2008 | Diederich | |
| 2008/0119862 A1 | 5/2008 | Wicker | |
| 2008/0172062 A1 | 7/2008 | Donahue | |
| 2008/0183214 A1 | 7/2008 | Copp | |
| 2008/0255567 A1 | 10/2008 | Accordino | |
| 2008/0262494 A1 | 10/2008 | Moore | |
| 2008/0300630 A1 | 12/2008 | Bonnema | |
| 2009/0018401 A1 | 1/2009 | Kim | |
| 2009/0043311 A1 | 2/2009 | Koros | |
| 2009/0062858 A1* | 3/2009 | Dziedzic | A61B 17/7089 606/278 |
| 2009/0076515 A1 | 3/2009 | Lamartina | |
| 2009/0082775 A1* | 3/2009 | Altarac | A61B 17/025 606/90 |
| 2009/0131943 A1 | 5/2009 | Fischer | |
| 2009/0149892 A1* | 6/2009 | Stad | A61B 17/7077 606/86 A |
| 2009/0171391 A1* | 7/2009 | Hutton | A61B 17/7032 606/246 |
| 2009/0177198 A1 | 7/2009 | Theodoros | |
| 2009/0187080 A1 | 7/2009 | Seex | |
| 2009/0216237 A1 | 8/2009 | Frezal | |
| 2009/0228053 A1* | 9/2009 | Kolb | A61B 17/7076 606/86 A |
| 2009/0259262 A1 | 10/2009 | Nayet | |
| 2009/0275952 A1 | 11/2009 | Lawson | |
| 2010/0004695 A1* | 1/2010 | Stad | A61B 17/7074 606/86 A |
| 2010/0024487 A1 | 2/2010 | Khoo | |
| 2010/0036443 A1* | 2/2010 | Hutton | A61B 17/7032 606/86 R |
| 2010/0042149 A1 | 2/2010 | Chao | |
| 2010/0069972 A1* | 3/2010 | Jones | A61B 17/7091 606/86 A |
| 2010/0228167 A1 | 9/2010 | Ilovich | |
| 2010/0239365 A1 | 9/2010 | Wernecke | |
| 2010/0262198 A1 | 10/2010 | Braunschweiler | |
| 2010/0268284 A1 | 10/2010 | Bankoski | |
| 2010/0274252 A1 | 10/2010 | Bottomley | |
| 2010/0274298 A1 | 10/2010 | Schiff | |
| 2010/0305407 A1 | 12/2010 | Farley | |
| 2010/0312248 A1 | 12/2010 | Karlsson | |
| 2010/0324610 A1* | 12/2010 | Bridwell | A61B 17/025 606/86 A |
| 2010/0331849 A1 | 12/2010 | Riesinger | |
| 2010/0331901 A1* | 12/2010 | Iott | A61B 17/701 606/86 A |
| 2011/0152955 A1 | 6/2011 | Keller | |
| 2011/0166610 A1 | 7/2011 | Altarac | |
| 2011/0172674 A1 | 7/2011 | Bankoski | |
| 2012/0083662 A1 | 4/2012 | Hamada | |
| 2012/0083849 A1 | 4/2012 | Neubardt | |
| 2012/0116467 A1* | 5/2012 | King | A61B 17/7037 606/86 A |
| 2012/0123476 A1 | 5/2012 | Perez-Cruet | |
| 2012/0197297 A1 | 8/2012 | Bootwala | |
| 2012/0197302 A1* | 8/2012 | Fallin | A61B 17/8863 606/279 |
| 2012/0199704 A1 | 8/2012 | Taylor | |
| 2012/0226315 A1 | 9/2012 | Altarac | |
| 2012/0253402 A1* | 10/2012 | McLean | A61B 17/7032 606/264 |
| 2012/0296171 A1 | 11/2012 | Lovell | |
| 2012/0303062 A1 | 11/2012 | Amstutz | |
| 2012/0303067 A1 | 11/2012 | Van Citters | |
| 2012/0310249 A1 | 12/2012 | Seex | |
| 2012/0316608 A1 | 12/2012 | Foley | |
| 2012/0316609 A1* | 12/2012 | Wall | A61B 17/7079 606/86 A |
| 2012/0323146 A1 | 12/2012 | Eden | |
| 2013/0072939 A1 | 3/2013 | Gauthier | |
| 2013/0090691 A1 | 4/2013 | Zhang | |
| 2013/0096624 A1* | 4/2013 | Di Lauro | A61B 17/7011 606/279 |
| 2013/0103036 A1 | 4/2013 | Mcghie | |
| 2013/0110110 A1 | 5/2013 | Waisman | |
| 2013/0184763 A1 | 7/2013 | McClintock | |
| 2013/0238037 A1 | 9/2013 | Stad | |
| 2013/0245691 A1* | 9/2013 | Hutton | A61B 17/7032 606/278 |
| 2013/0245692 A1 | 9/2013 | Hayes | |
| 2013/0274804 A1* | 10/2013 | Hutton | A61B 17/7032 606/264 |
| 2013/0331892 A1 | 12/2013 | Peterson | |
| 2014/0012269 A1 | 1/2014 | Bass | |
| 2014/0014117 A1 | 1/2014 | Weinberg | |
| 2014/0018633 A1 | 1/2014 | Woolley | |
| 2014/0031874 A1 | 1/2014 | Kucharzyk | |
| 2014/0039557 A1 | 2/2014 | Stad | |
| 2014/0039567 A1 | 2/2014 | Hoefer | |
| 2014/0058210 A1 | 2/2014 | Raymond | |
| 2014/0066718 A1 | 3/2014 | Fiechter | |
| 2014/0066940 A1 | 3/2014 | Fang | |
| 2014/0074106 A1 | 3/2014 | Shin | |
| 2014/0100613 A1 | 4/2014 | Iott | |
| 2014/0100618 A1 | 4/2014 | Kolb | |
| 2014/0100619 A1 | 4/2014 | Dipaola | |
| 2014/0107656 A1 | 4/2014 | Masson | |
| 2014/0107709 A1 | 4/2014 | Schmitz | |
| 2014/0114360 A1 | 4/2014 | Gephart | |

(56) References Cited

U.S. PATENT DOCUMENTS

| | | | |
|---|---|---|---|
| 2014/0135855 A1 | 5/2014 | Jones | |
| 2014/0188182 A1 | 7/2014 | Chao | |
| 2014/0222083 A1 | 8/2014 | Anderson | |
| 2014/0222092 A1 | 8/2014 | Anderson | |
| 2014/0243903 A1 | 8/2014 | Didomenico | |
| 2014/0277151 A1 | 9/2014 | Fowler | |
| 2014/0277167 A1* | 9/2014 | Hutton | A61B 17/7032 606/279 |
| 2014/0277168 A1 | 9/2014 | Hutton | |
| 2014/0330318 A1 | 11/2014 | Hestad | |
| 2014/0330321 A1 | 11/2014 | Castaneda | |
| 2014/0350604 A1 | 11/2014 | Hutton | |
| 2015/0005882 A1 | 1/2015 | Abdou | |
| 2015/0012049 A1 | 1/2015 | McLean | |
| 2015/0045793 A1 | 2/2015 | Ibrahim | |
| 2015/0066042 A1 | 3/2015 | Cummins | |
| 2015/0066091 A1 | 3/2015 | Wing | |
| 2015/0073428 A1 | 3/2015 | Butters | |
| 2015/0080958 A1 | 3/2015 | Kretzer | |
| 2015/0080974 A1 | 3/2015 | Jackson | |
| 2015/0088144 A1 | 3/2015 | Patel | |
| 2015/0297264 A1* | 10/2015 | King | A61B 17/7037 606/279 |
| 2015/0297277 A1* | 10/2015 | Jones | A61B 17/7091 606/90 |
| 2015/0320457 A1* | 11/2015 | DiPoto | A61B 17/02 606/279 |

FOREIGN PATENT DOCUMENTS

| | | |
|---|---|---|
| CN | 2245433 Y | 1/1997 |
| CN | 2824858 Y | 10/2006 |
| CN | 2889191 Y | 4/2007 |
| CN | 201328885 A | 10/2009 |
| CN | 102247201 A | 11/2011 |
| CN | 102319111 A | 1/2012 |
| CN | 102415912 A | 4/2012 |
| CN | 202207197 A | 5/2012 |
| CN | 102499747 A | 6/2012 |
| CN | 202263044 A | 6/2012 |
| CN | 202397574 A | 8/2012 |
| CN | 102743216 A | 10/2012 |
| CN | 202654245 U | 1/2013 |
| CN | 202801774 U | 3/2013 |
| CN | 203059931 U | 7/2013 |
| CN | 203074837 U | 7/2013 |
| CN | 203107249 U | 8/2013 |
| CN | 203315056 U | 12/2013 |
| CN | 103519874 A | 1/2014 |
| CN | 203408077 U | 1/2014 |
| CN | 203609490 U | 5/2014 |
| CN | 203609491 U | 5/2014 |
| CN | 203619645 U | 6/2015 |
| DE | 7315277 U | 8/1973 |
| DE | 8632371 U1 | 9/1987 |
| DE | 4115548 A1 | 11/1991 |
| DE | 9320834 U1 | 3/1995 |
| DE | 19828137 A1 | 1/2000 |
| DE | 19836498 A1 | 2/2000 |
| DE | 19911315 A1 | 9/2000 |
| DE | 19947587 A1 | 9/2000 |
| DE | 10028181 A1 | 12/2001 |
| DE | 10134505 A1 | 1/2003 |
| DE | 10229308 A1 | 1/2004 |
| DE | 10255553 A1 | 7/2004 |
| DE | 202004014768 U1 | 11/2004 |
| DE | 102004036377 A1 | 3/2006 |
| DE | 102006033783 A1 | 1/2008 |
| DE | 202007003452 U1 | 7/2008 |
| DE | 102009014527 A1 | 9/2010 |
| DE | 202012100745 U1 | 5/2012 |
| DE | 202011109871 U1 | 6/2012 |
| DE | 102011102109 A1 | 11/2012 |
| DE | 102011106172 A1 | 1/2013 |
| DE | 102012101780 A1 | 9/2013 |
| EP | 0027726 | 7/1984 |
| EP | 0465866 A1 | 1/1992 |
| EP | 0528177 | 9/1996 |
| EP | 2644140 A1 | 10/2013 |
| EP | 2228024 | 5/2014 |
| FR | 2656214 A1 | 6/1991 |
| FR | 2821264 A1 | 8/2002 |
| FR | 2821543 A1 | 9/2002 |
| FR | 2932375 A1 | 12/2009 |
| IT | 1239604 B | 11/1993 |
| JP | 10248855 A | 9/1998 |
| KR | 20000062352 A | 10/2000 |
| KR | 20060008598 A | 1/2006 |
| KR | 20130077045 A | 7/2013 |
| PL | 175176 B1 | 11/1998 |
| RU | 2019148 C1 | 9/1994 |
| RU | 2055537 C1 | 3/1996 |
| RU | 4904 | 9/1997 |
| RU | 2108763 C1 | 4/1998 |
| RU | 2115381 C1 | 7/1998 |
| RU | 2118133 C1 | 8/1998 |
| RU | 2140774 C1 | 11/1999 |
| RU | 2218118 C2 | 12/2003 |
| RU | 2312621 C1 | 12/2007 |
| SE | 0801246 L | 11/2009 |
| SU | 839513 A1 | 6/1981 |
| UA | 17735 U | 10/2006 |
| WO | WO-19990002527 | 3/1990 |
| WO | WO-19992005262 | 4/1992 |
| WO | WO-19940000067 | 1/1994 |
| WO | WO-19996031166 | 10/1996 |
| WO | WO-20010045576 | 6/2001 |
| WO | WO-20020094114 | 11/2002 |
| WO | WO-20050079684 | 9/2005 |
| WO | WO-20060045089 | 4/2006 |
| WO | WO-20070086876 | 8/2007 |
| WO | WO-20080116600 | 10/2008 |
| WO | WO-20080134758 | 11/2008 |
| WO | WO-20100031581 | 3/2010 |
| WO | WO-20110133160 | 10/2011 |
| WO | WO-20120177087 | 12/2012 |
| WO | WO-20130063865 | 5/2013 |

* cited by examiner

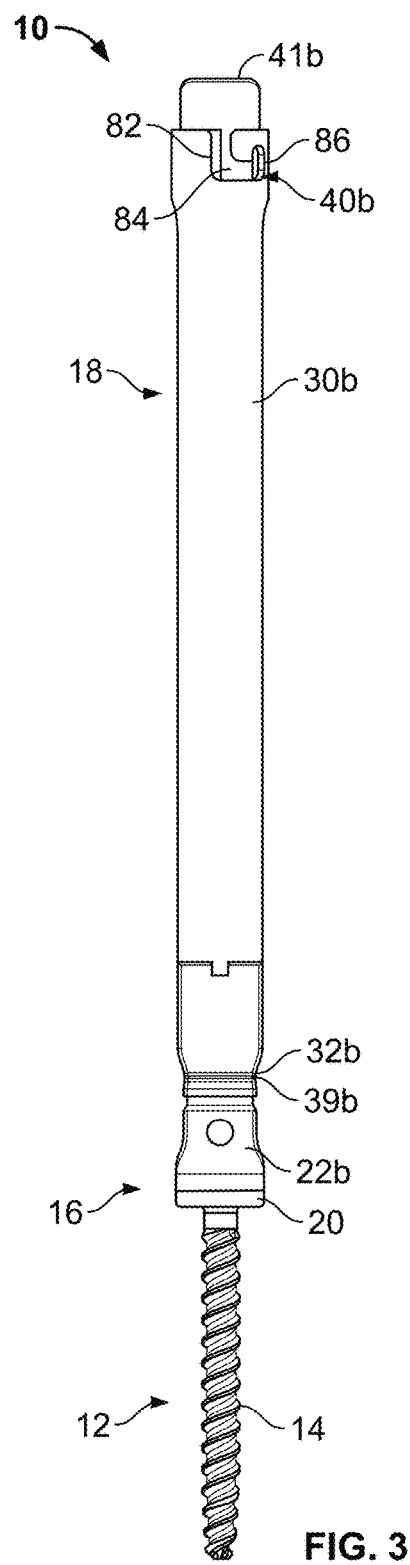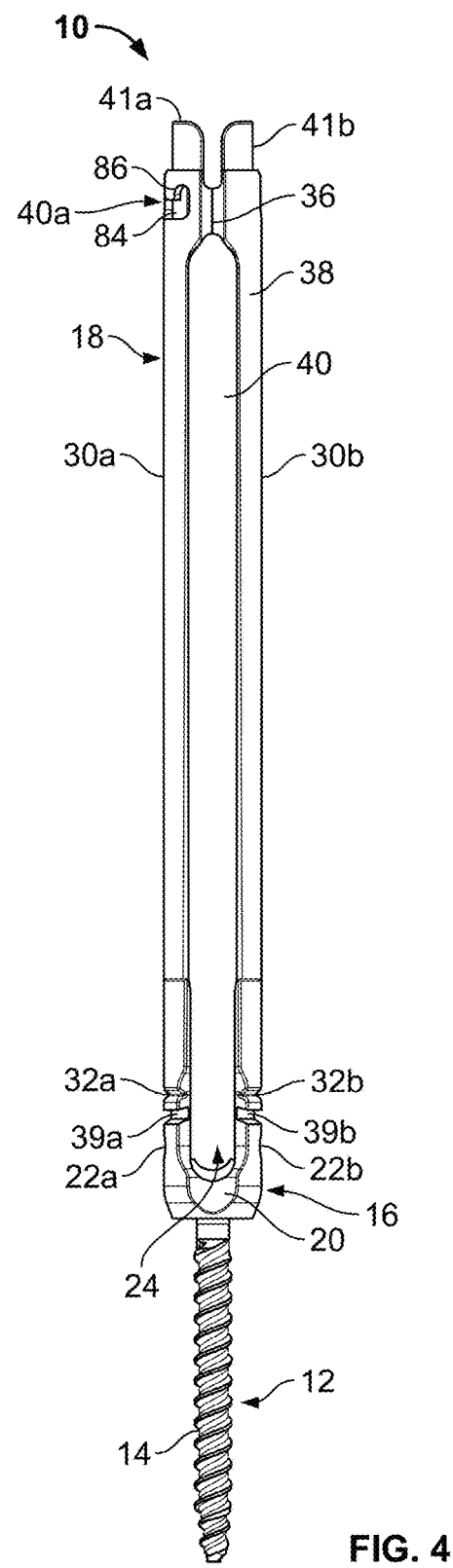
FIG. 3
FIG. 4

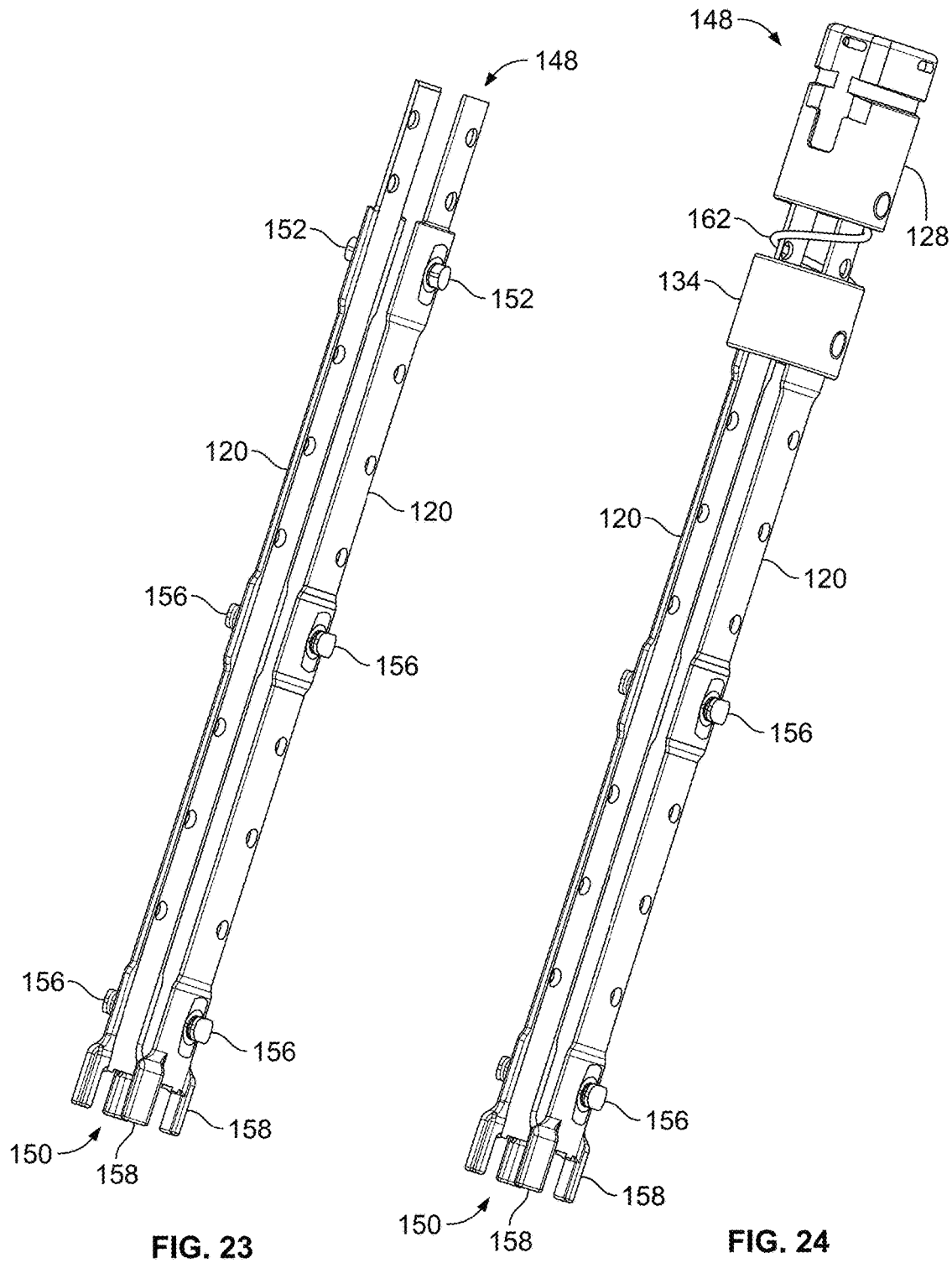

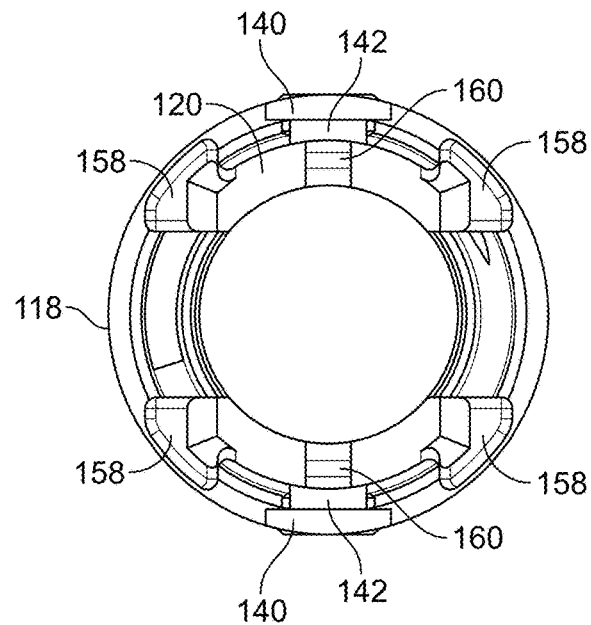
FIG. 27
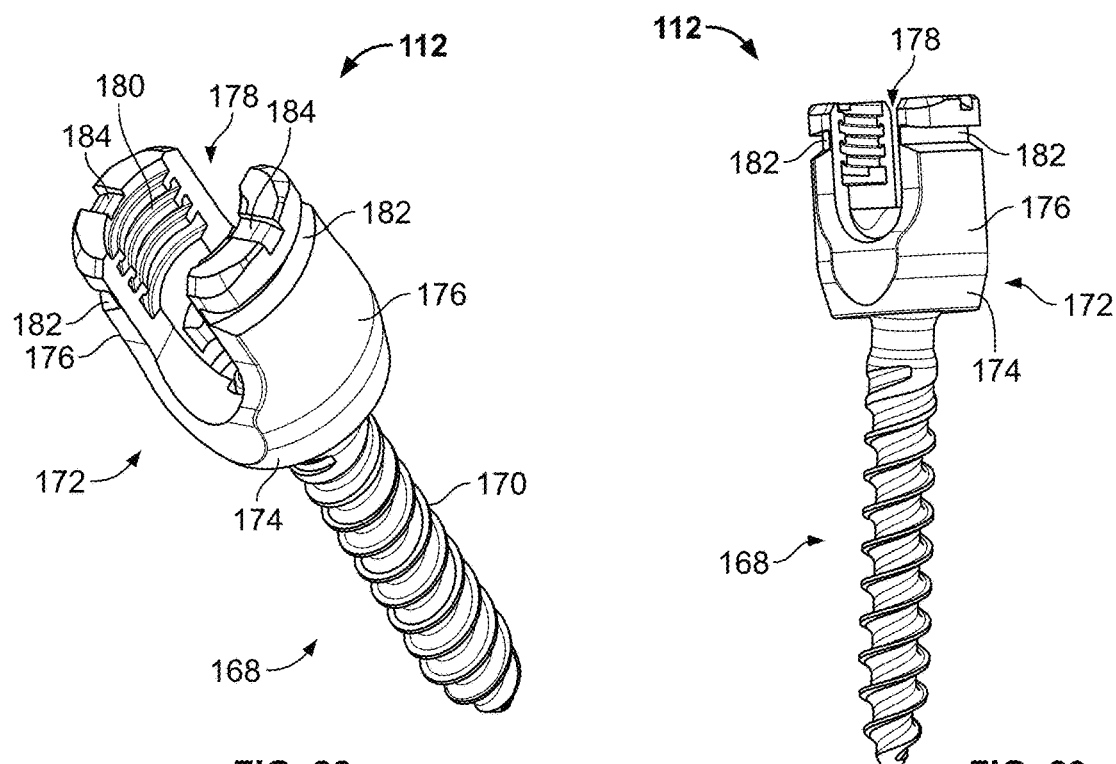
FIG. 28
FIG. 29

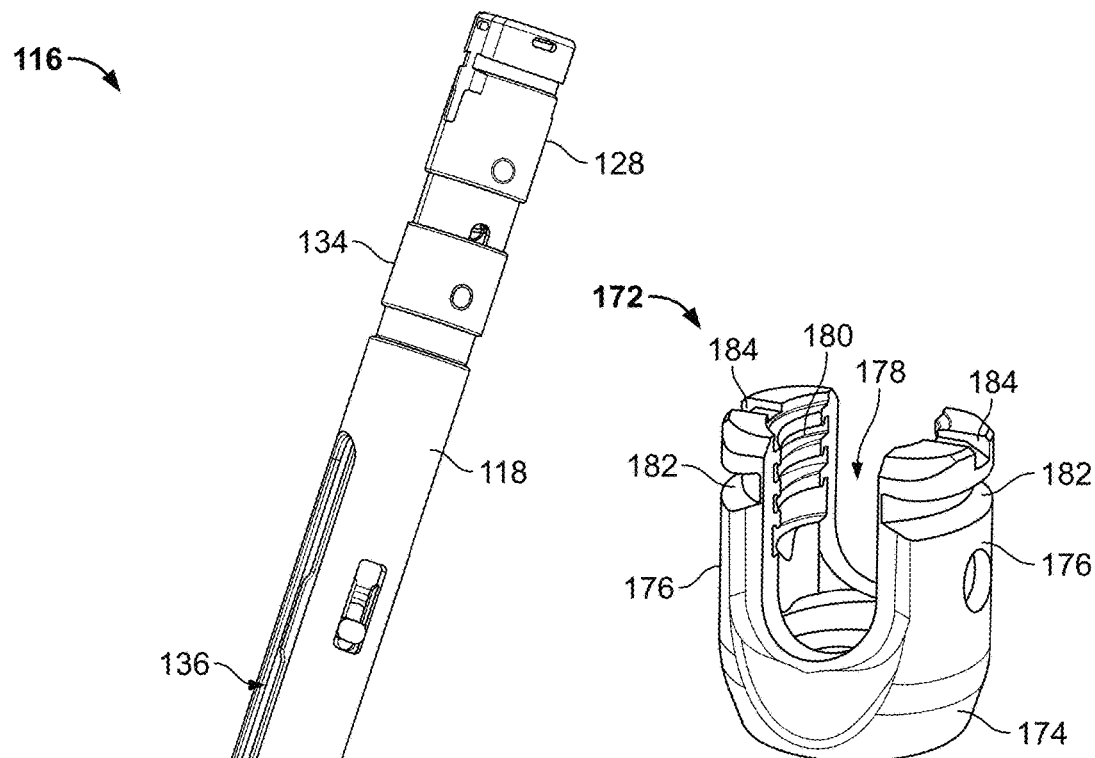
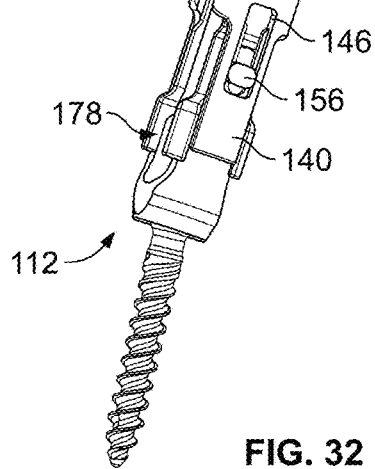
FIG. 32
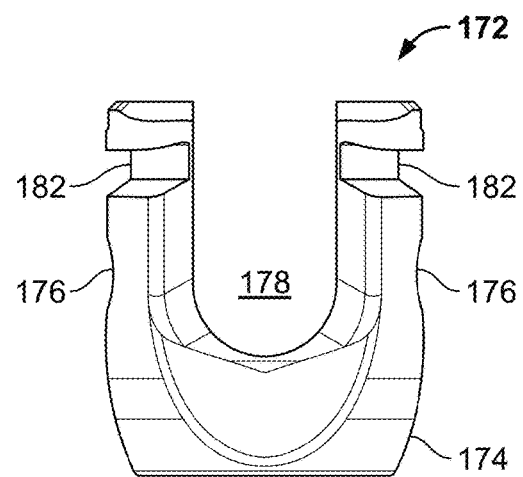

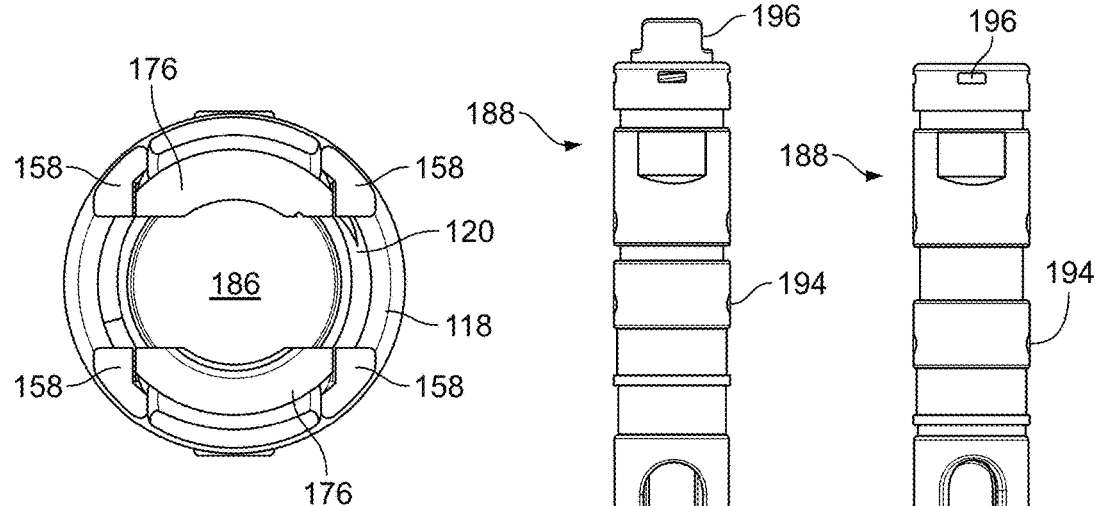
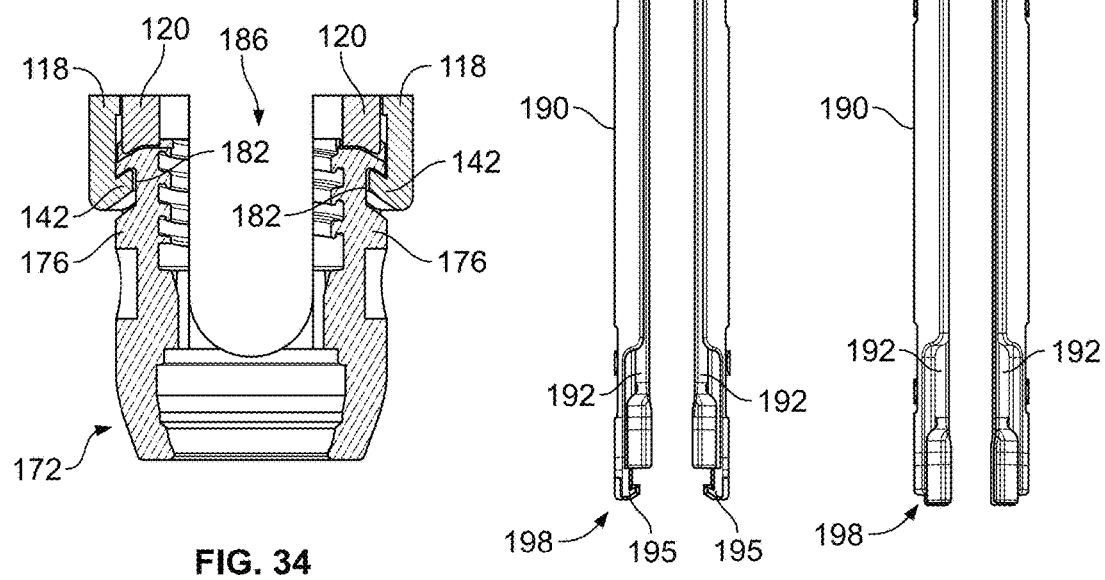
FIG. 33
FIG. 34
FIG. 35
FIG. 36

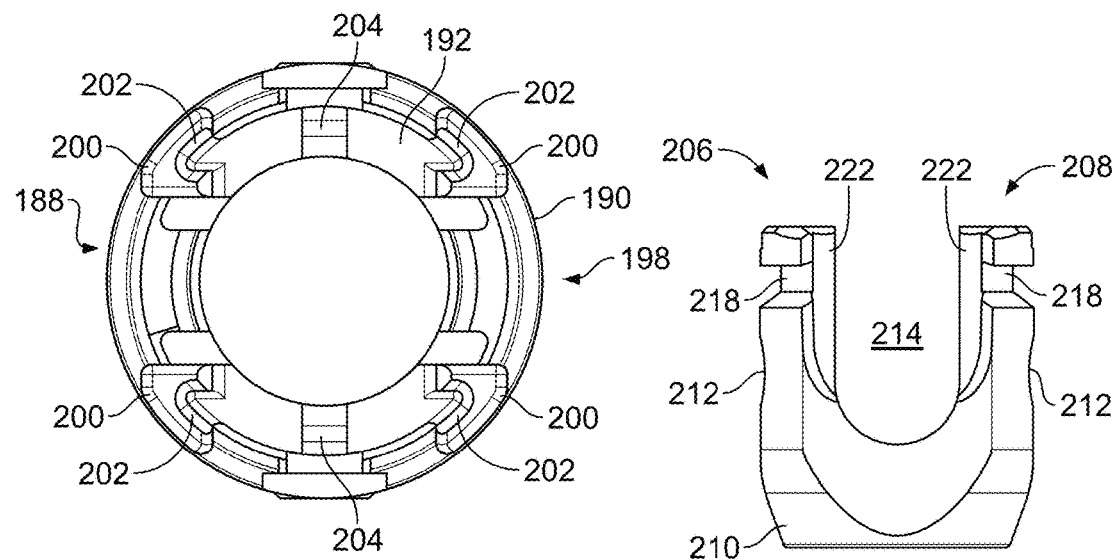
FIG. 37
FIG. 38
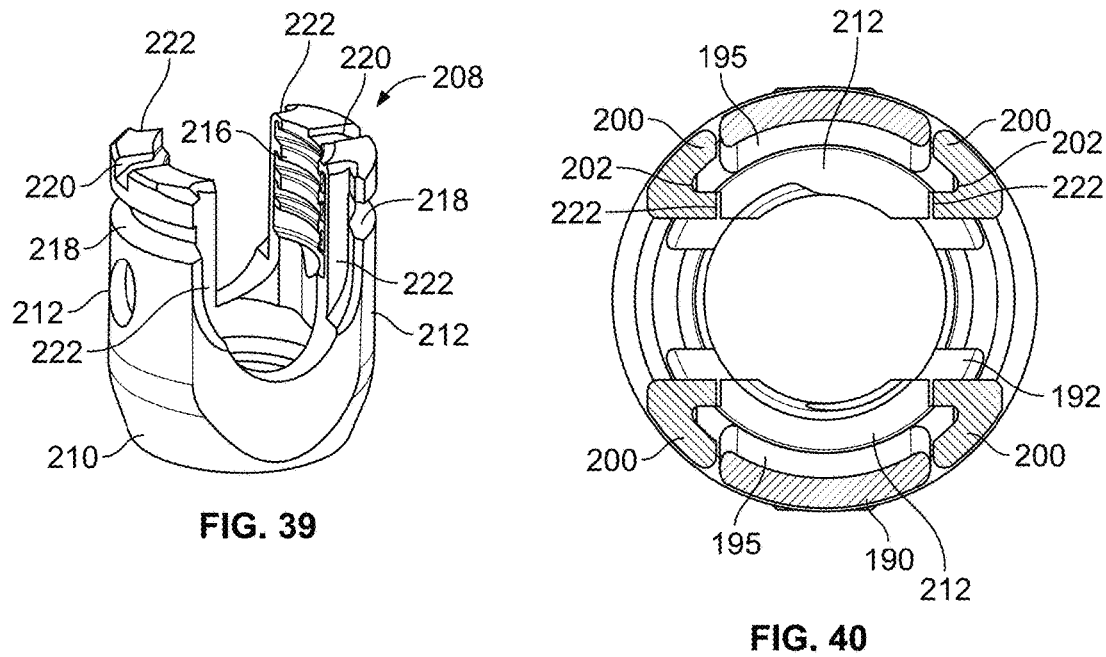
FIG. 39
FIG. 40

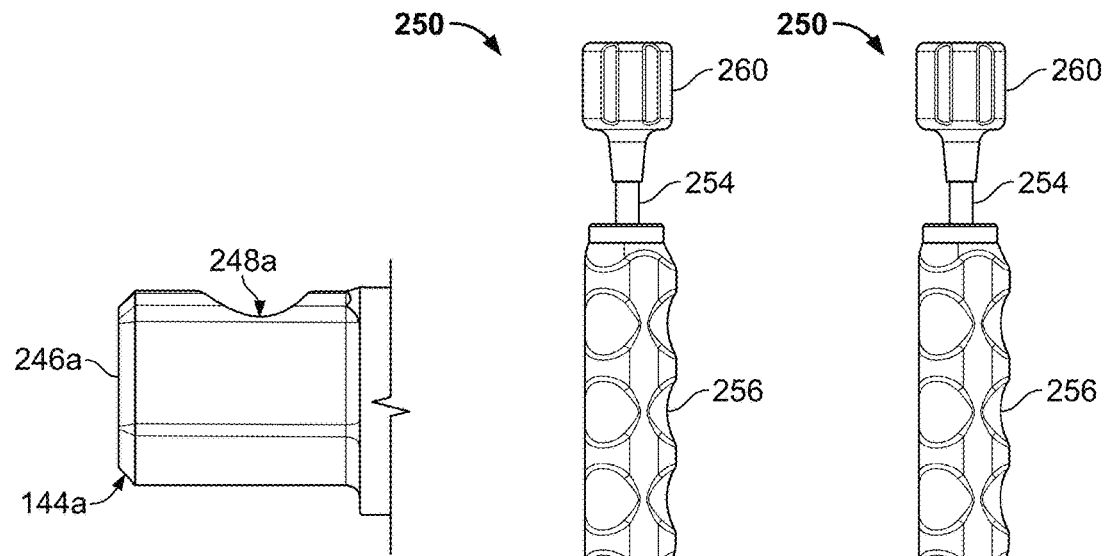
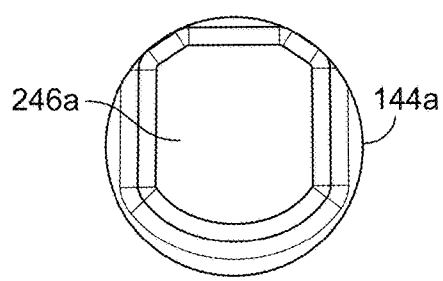
FIG. 51
FIG. 52
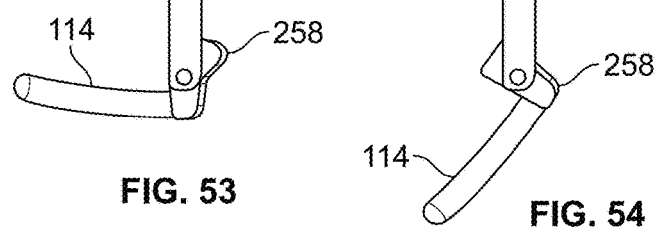
FIG. 53
FIG. 54

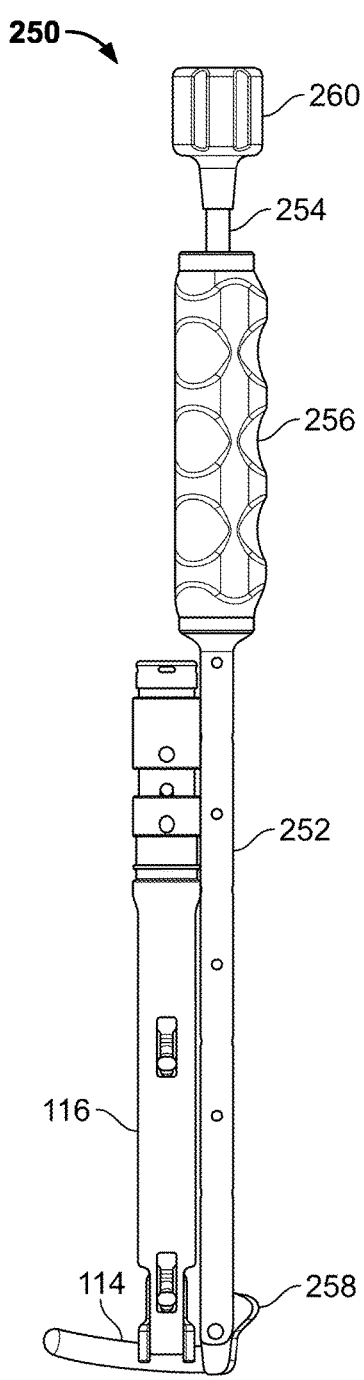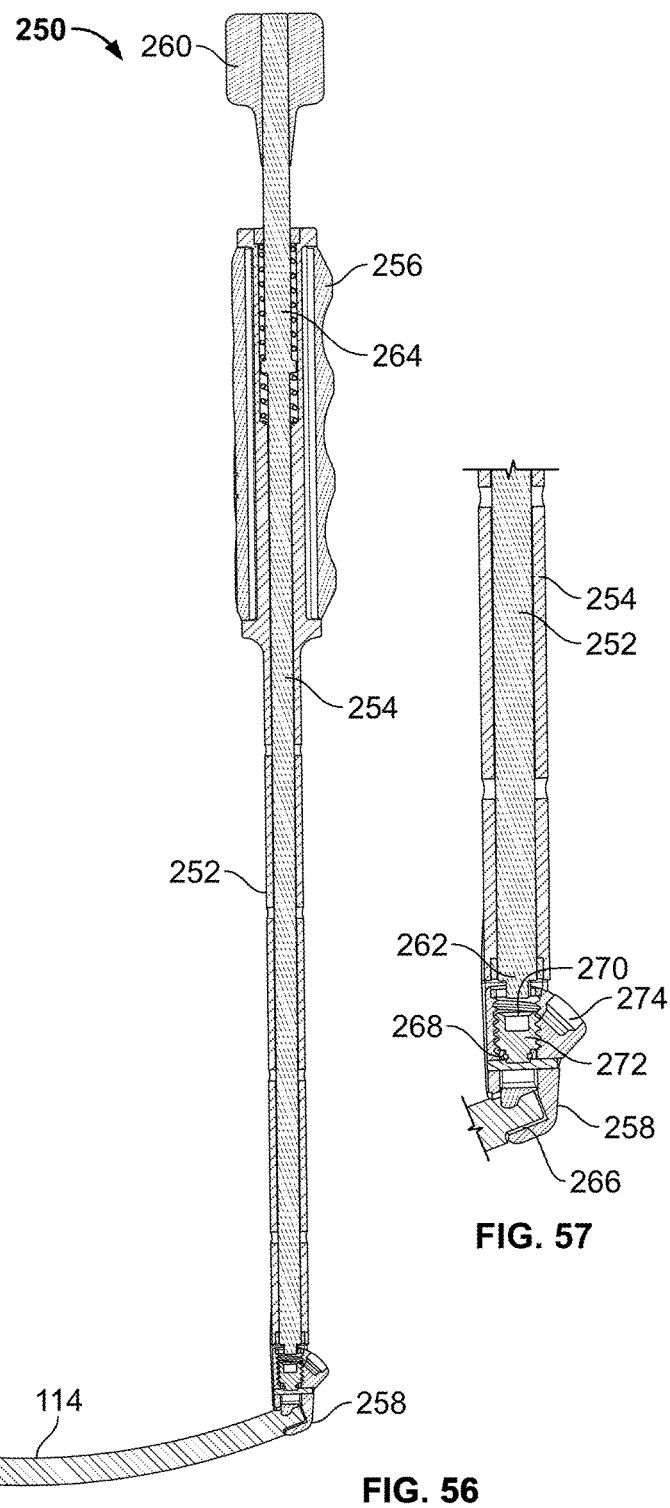
FIG. 55
FIG. 56
FIG. 57

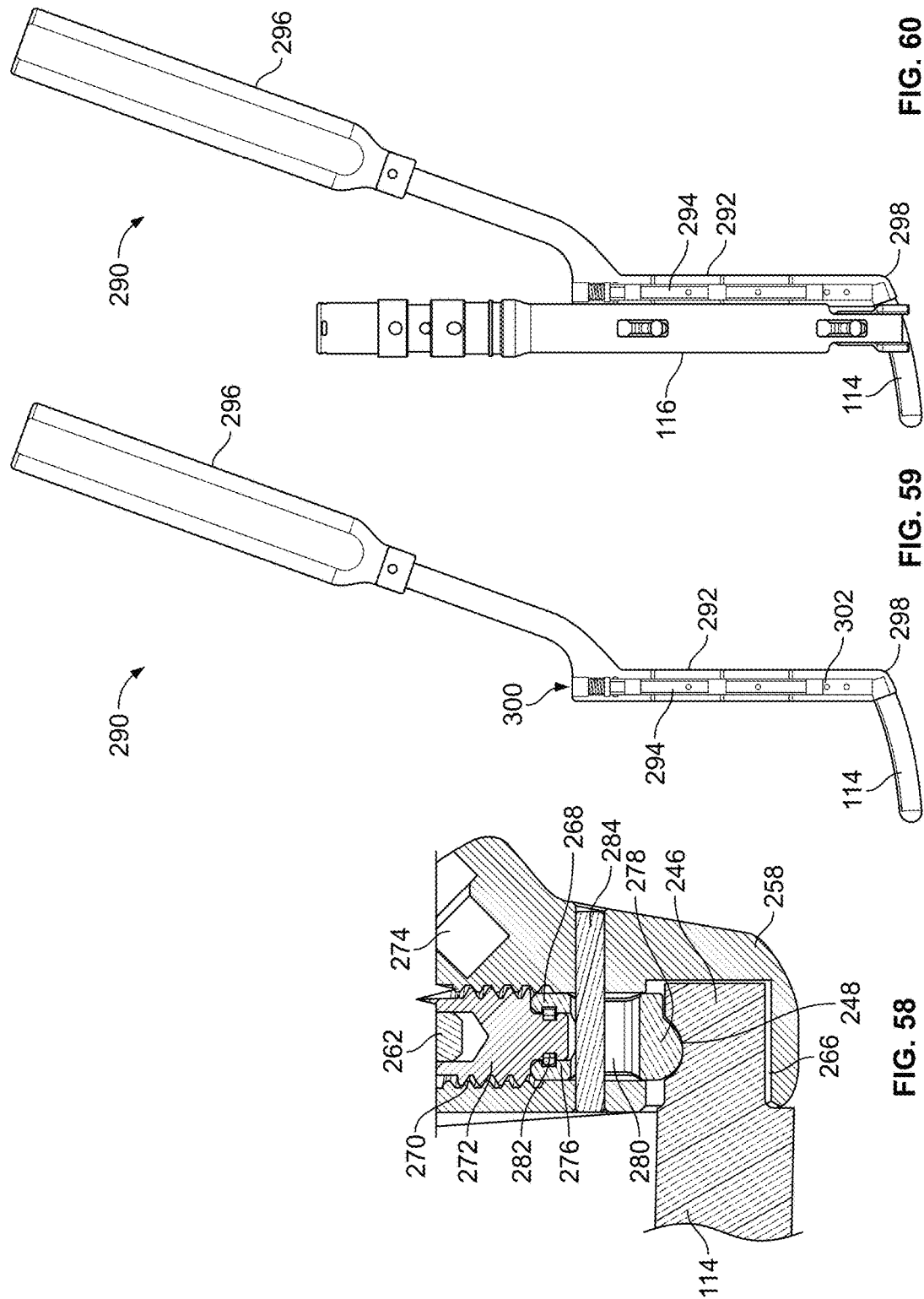

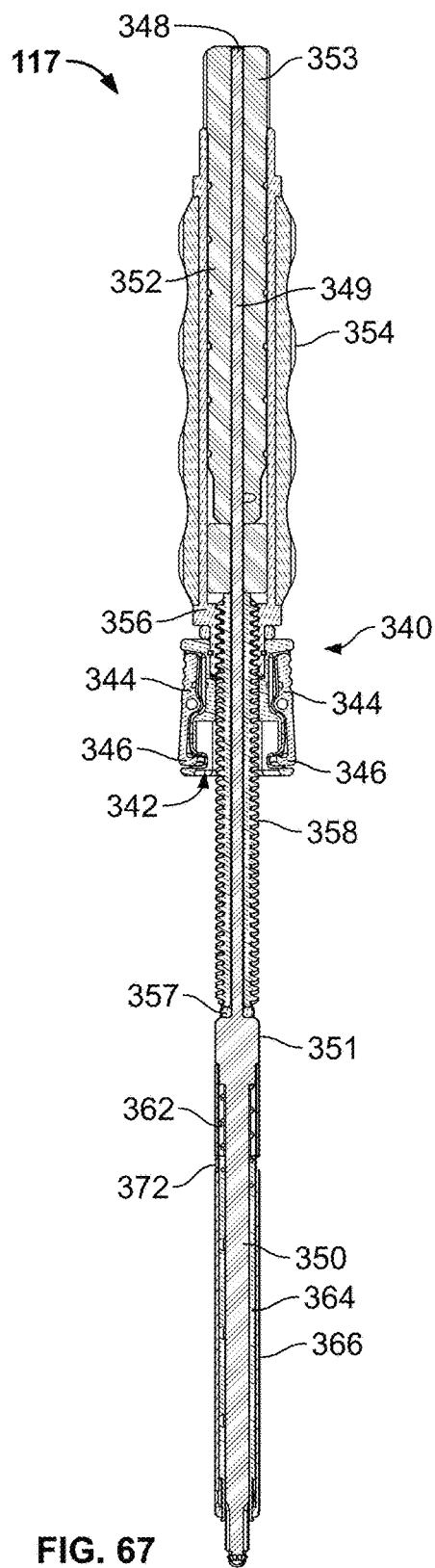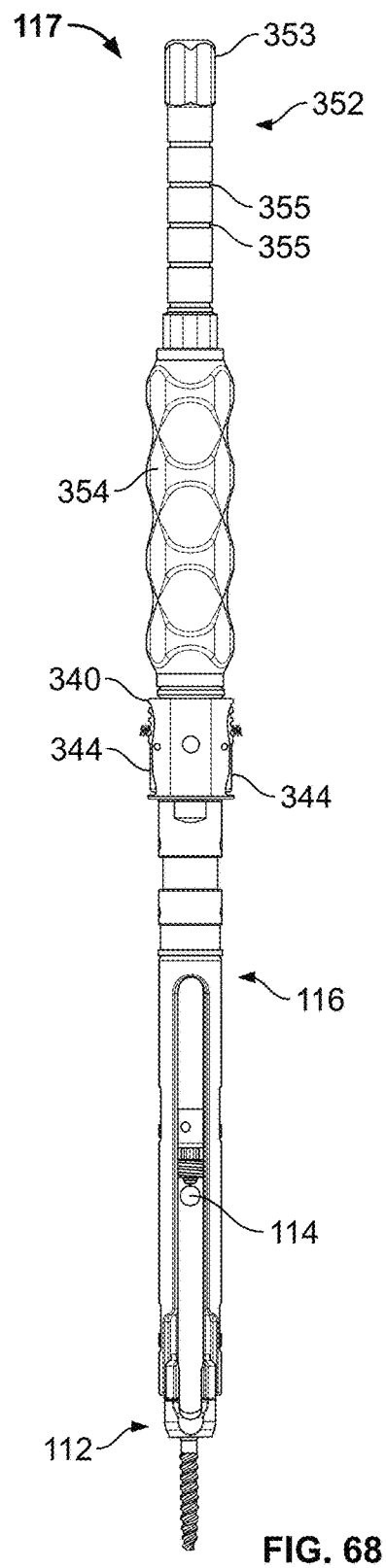
FIG. 67
FIG. 68

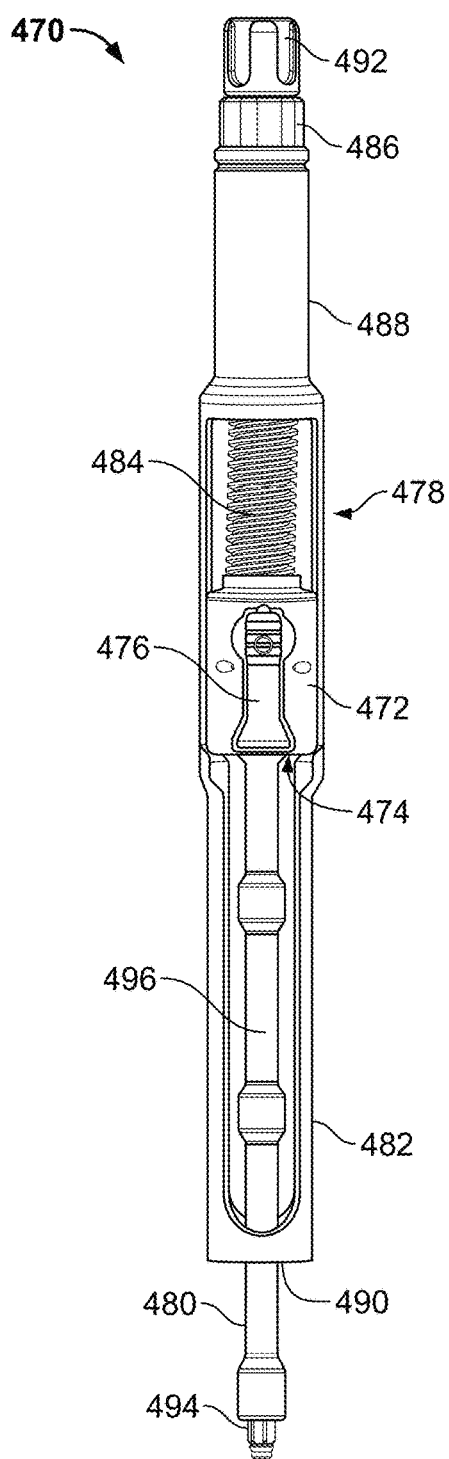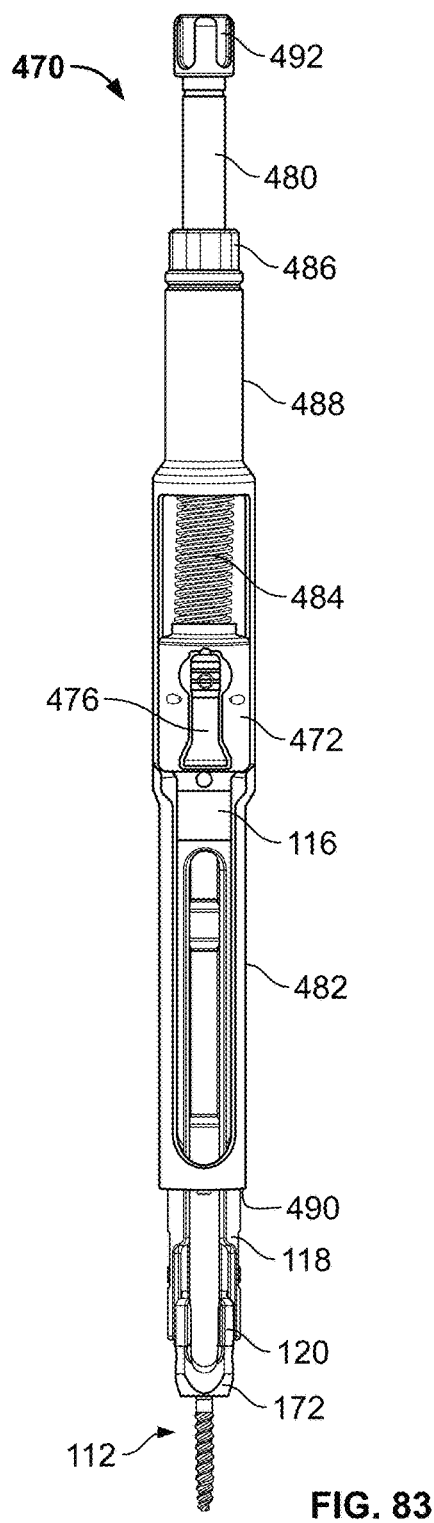
FIG. 82
FIG. 83

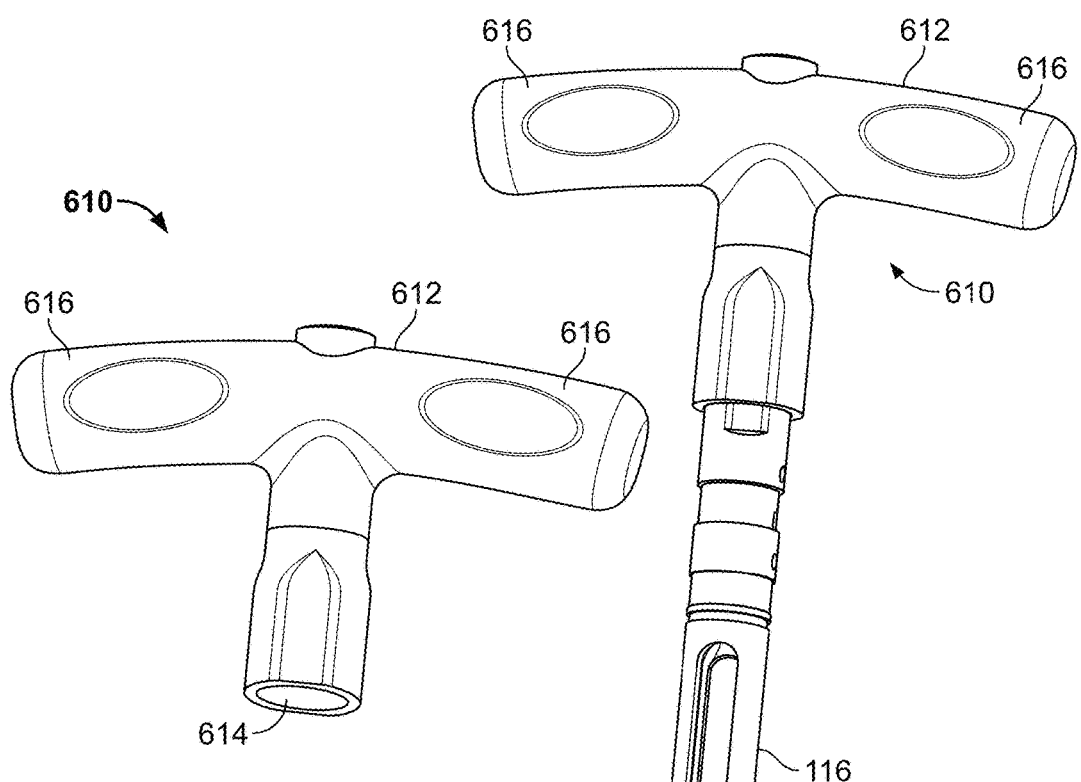
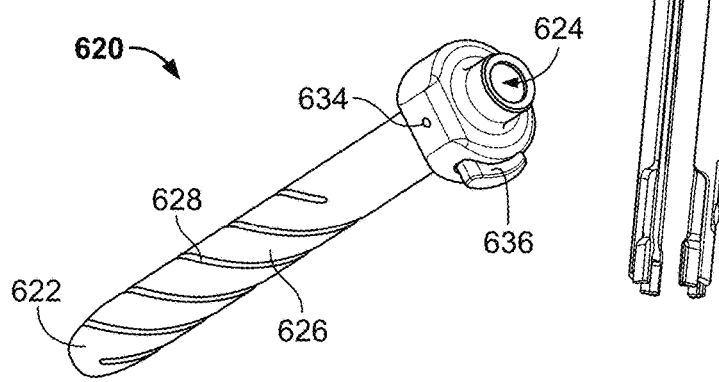
FIG. 97
FIG. 98
FIG. 99

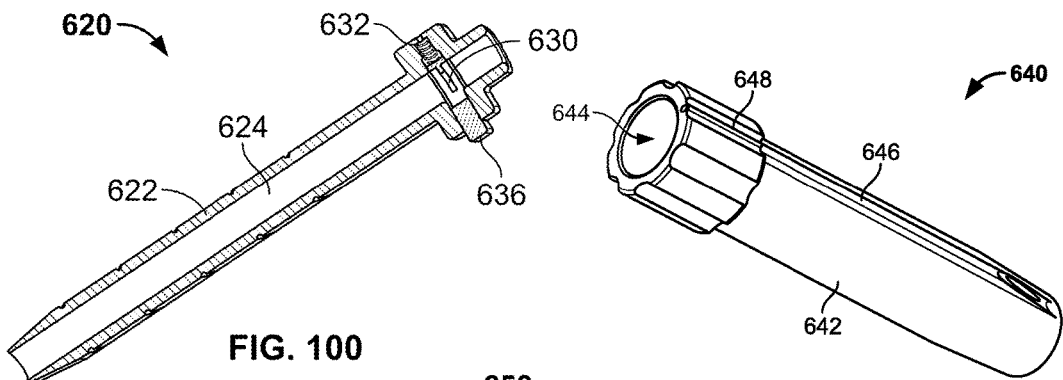
FIG. 100
FIG. 101
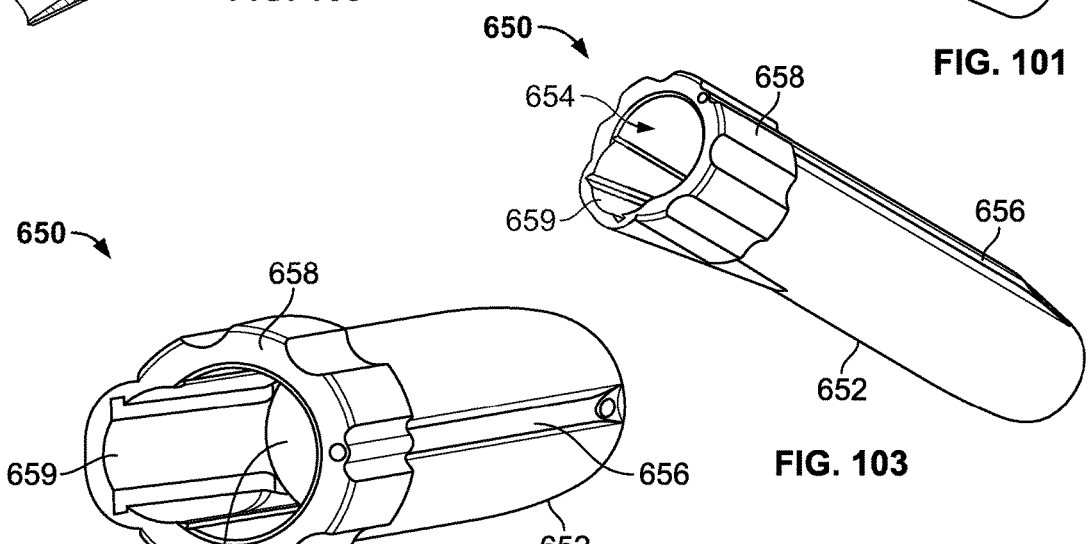
FIG. 102
FIG. 103
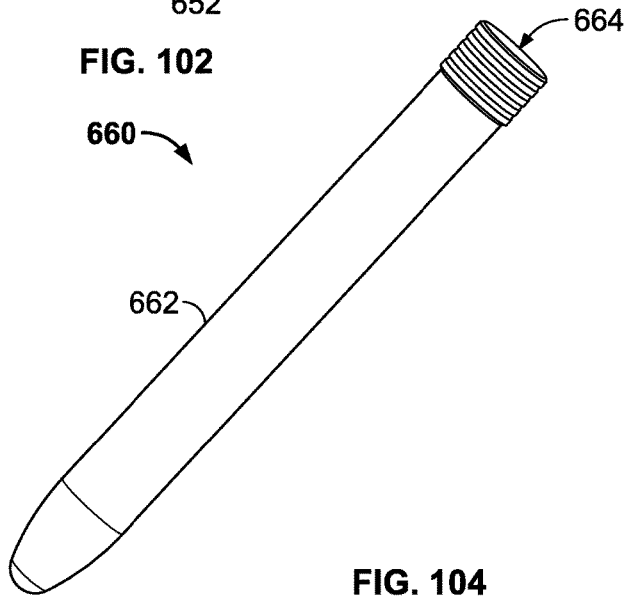
FIG. 104

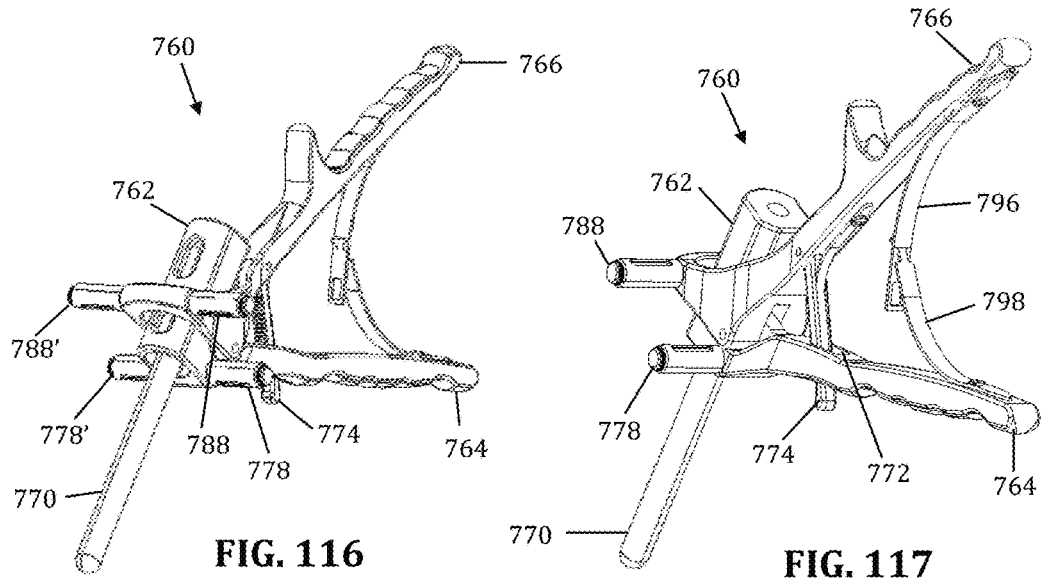
FIG. 116
FIG. 117
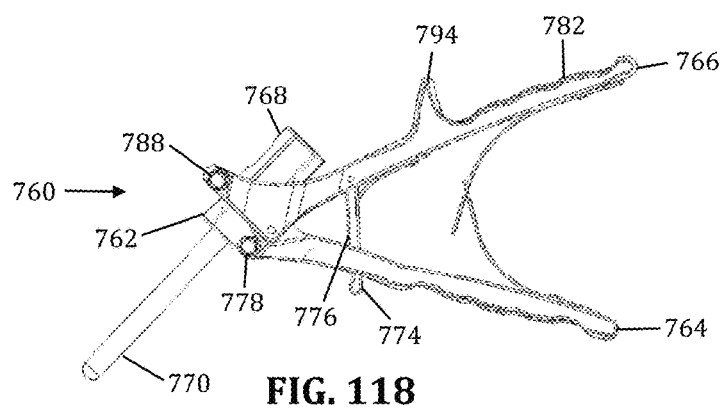
FIG. 118
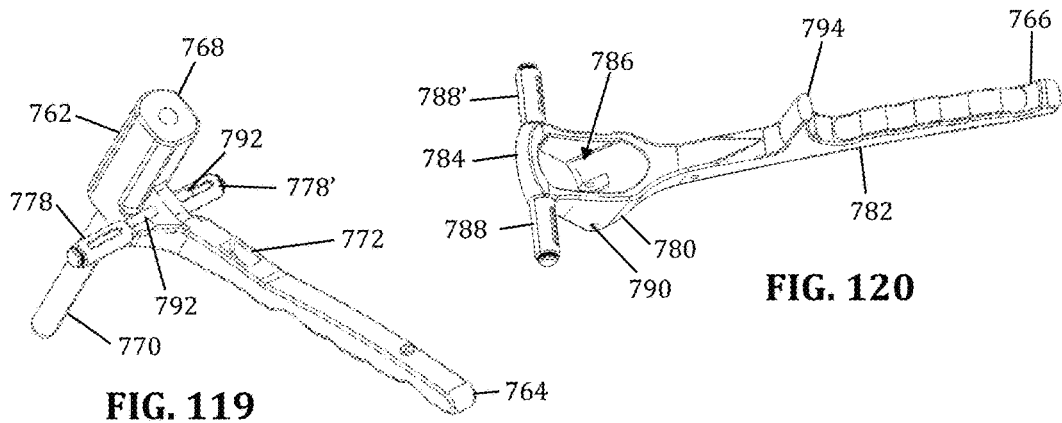
FIG. 119
FIG. 120

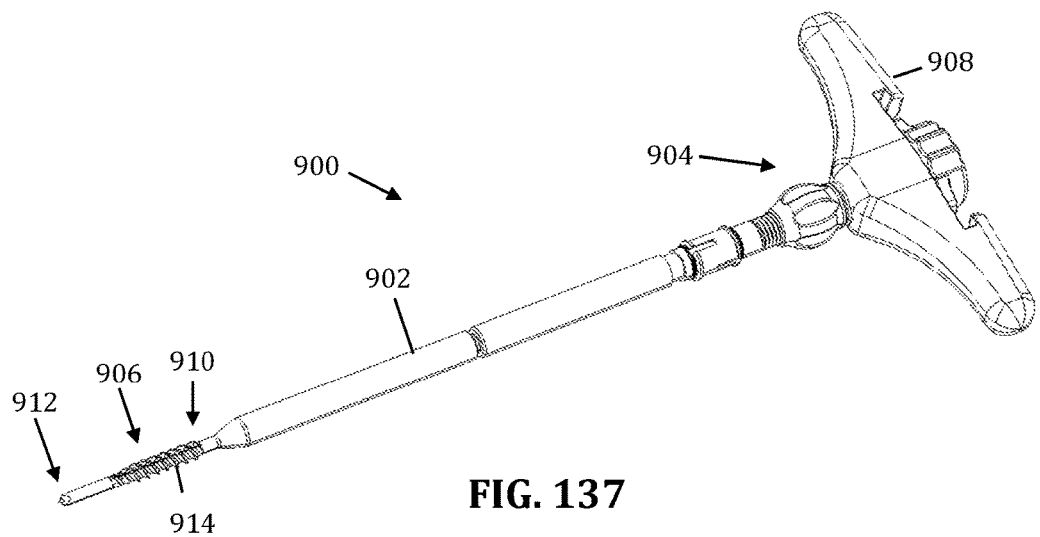
FIG. 137
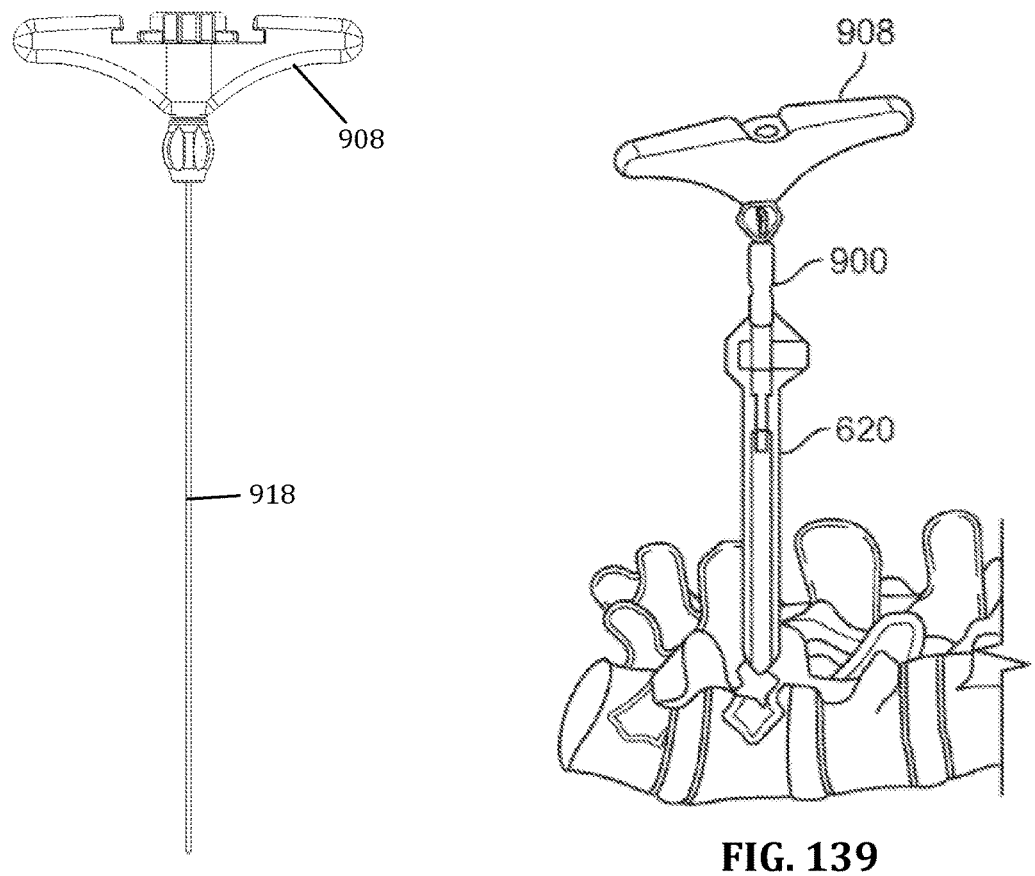
FIG. 138
FIG. 139

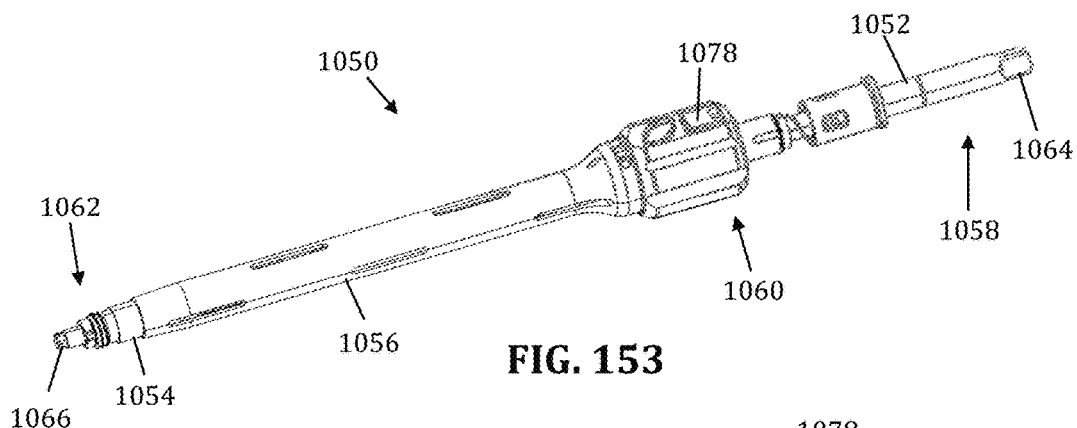
FIG. 153
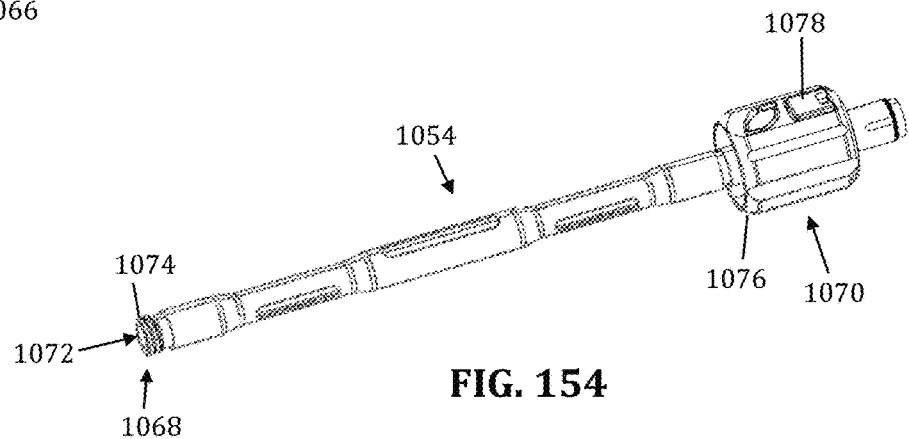
FIG. 154
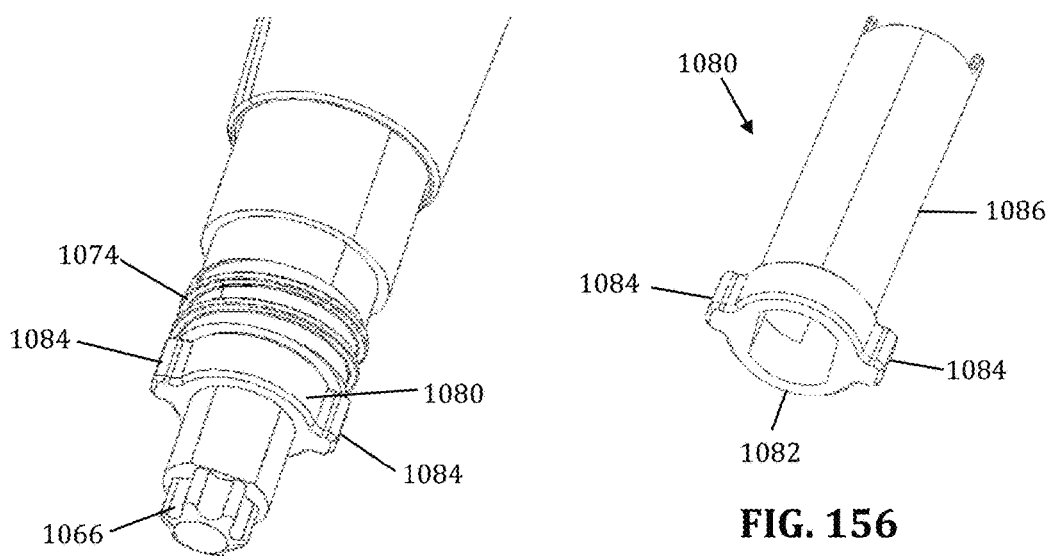
FIG. 155
FIG. 156

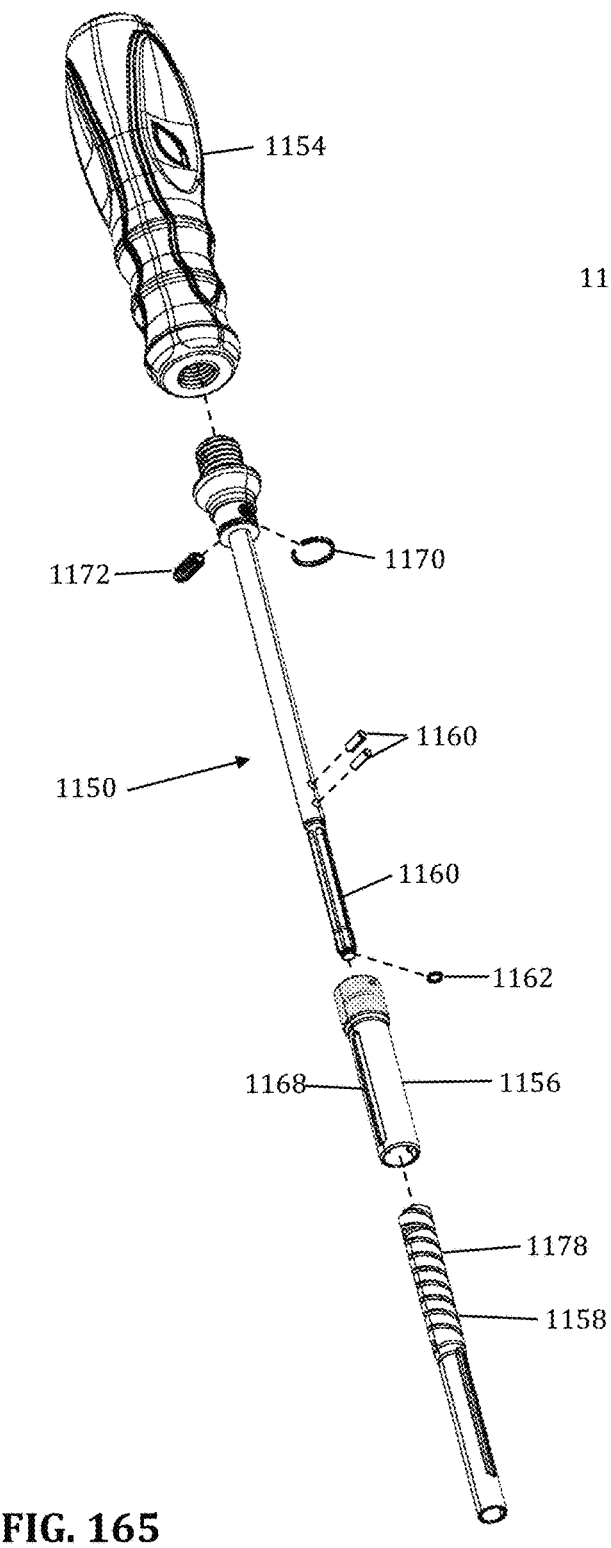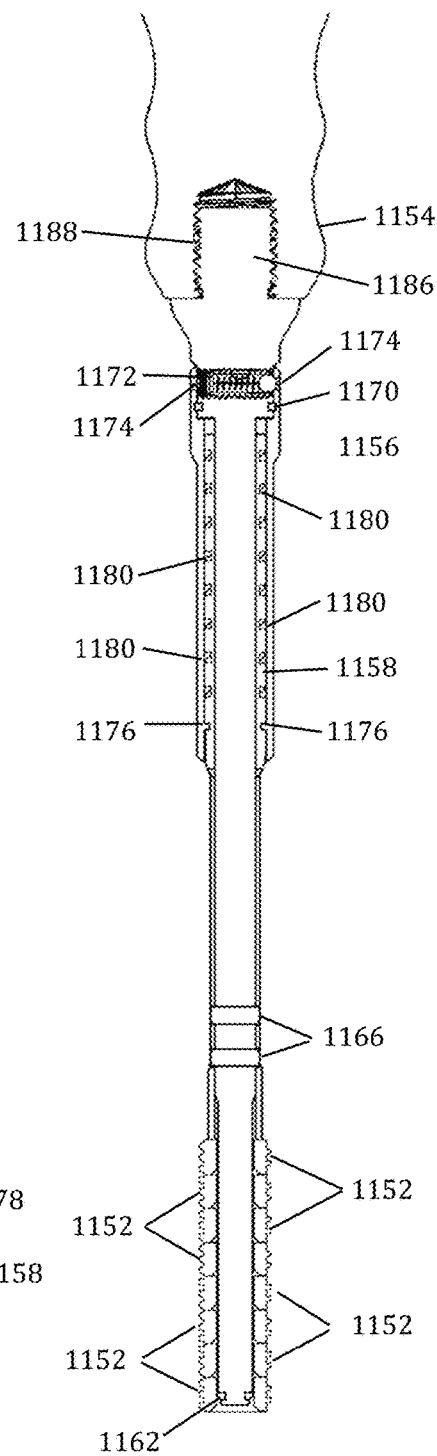
FIG. 165
FIG. 166

MINIMALLY INVASIVE SPINAL FIXATION SYSTEM AND RELATED METHODS

CROSS-REFERENCES TO RELATED APPLICATIONS

This application is a continuation-in-part of U.S. patent application Ser. No. 13/456,210, filed Apr. 25, 2012, which claims priority from U.S. Provisional Patent Application Ser. No. 61/478,658 filed on Apr. 25, 2011 and U.S. Provisional Patent Application Ser. No. 61/553,052 filed on Oct. 28, 2011. This application also claims priority to U.S. Provisional Application Ser. No. 61/944,513 filed on Feb. 25, 2014 and U.S. Provisional Patent Application Ser. No. 62/078,059 filed on Nov. 11, 2014, the entire contents of which are each hereby expressly incorporated by reference into this disclosure as if set forth in its entirety herein.

FIELD

This application describes surgical instruments and implants for building a posterior fixation construct across one or more segments of the spinal column.

BACKGROUND

Spinal fixation constructs are utilized to provide stability to the spine. Most often the fixation construct is used as an adjunct to fusion surgery during which adjacent vertebrae are prepared to facilitate bone growth between them, thereby eliminating motion between the vertebrae. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved. Fixation constructs of various forms are well known in the art. Most commonly, the fixation construct is a plate anchored to the anterior column with multiple bone anchors or a posterior fixation construct including multiple anchors and a connecting rod anchored to the posterior elements of the spine. For a posterior fixation construct the anchors (typically pedicle screws) are anchored into the pedicles of each vertebra of the target motion segment. The anchors are then connected by a fixation rod that is locked to each anchor, thus eliminating motion between the adjacent vertebrae of the motion segment. The posterior fixation construct may be applied unilaterally or bilaterally. Additionally the posterior fixation construct may be applied across multiple levels or motion segments.

The fixation anchors utilized in posterior fixation constructs generally include an anchor portion and a rod housing. The rod housing includes a pair of upstanding arms separated by a rod channel in which the fixation rod is captured and locked. When constructing the posterior fixation construct the surgeon must align and seat the rod in the rod channel. This can be a challenge, particularly when one or more of the vertebrae to be connected is out of alignment leaving the associated anchor offset vertically and/or horizontally from the remaining anchor(s) of the construct. Constructing the posterior fixation construct under minimally invasive access conditions (e.g. minimizing overall incision length and muscle stripping as compared to traditional open procedures) also increases the difficulty of aligning the rod with the rod channel of the anchor.

The instruments, tools, and techniques described herein are directed towards reducing these challenges and others associated with posterior spinal fixation.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 3-4 are side and front views, respectively, of the spinal fixation anchor of FIG. 1;

FIGS. 23-24 are perspective views of an inner member forming part of the guide assembly of FIG. 21, shown without the outer sleeve;

FIG. 27 is a plan view of the distal end of the guide assembly of FIG. 21;

FIGS. 28-29 are perspective views of an example of a pedicle screw forming part of the spinal fixation system of FIG. 19;

FIGS. 30-31 are perspective and plan views, respectively, of one example of a tulip forming part of the pedicle screw of FIG. 28;

FIG. 32 is a perspective view of the guide assembly of FIG. 21 engaged with a pedicle screw of FIG. 28;

FIG. 33 is a plan view of the distal end of the guide assembly of FIG. 21 engaged with the tulip of FIG. 30;

FIG. 34 is a sectional view of the distal end of the guide assembly of FIG. 21 engaged with the tulip of FIG. 30;

FIG. 35 is a plan view of a second example of a guide assembly forming part of the spinal fixation system of FIG. 19, shown in an unlocked configuration;

FIG. 36 is a plan view of the guide assembly of FIG. 35, shown in a locked configuration;

FIG. 37 is a plan view of the distal end of the guide assembly of FIG. 35;

FIGS. 38-39 are plan and perspective views, respectively, of a second example of a tulip forming part of the pedicle screw of FIG. 28;

FIGS. 40-41 are plan and sectional views, respectively, of the distal end of the guide assembly of FIG. 35 coupled with the tulip of FIG. 38;

FIGS. 50-52 are perspective, side plan, and end plan views of one end of the spinal rod of FIG. 49;

FIG. 53 is a plan view of an example of an adjustable angle rod inserter configured for use with the spinal fixation system of FIG. 19, shown in a first position;

FIG. 54 is a plan view of the rod inserter of FIG. 53, shown in a second position;

FIG. 55 is a plan view of the rod inserter of FIG. 53 coupled with a guide assembly of FIG. 21;

FIG. 56 is a sectional view of the rod inserter of FIG. 53;

FIGS. 57-58 are sectional views of the distal end of the rod inserter of FIG. 53;

FIG. 59 is a plan view of one example of a fixed angle rod inserter configured for use with the spinal fixation system of FIG. 19;

FIG. 60 is a plan view of the rod inserter of FIG. 59 coupled with a guide assembly of FIG. 21;

FIG. 67 is a sectional view of the reduction instrument of FIG. 64;

FIG. 68 is a plan view of the reduction instrument of FIG. 64 coupled with a guide assembly of FIG. 21, which in turn is coupled to a pedicle screw of FIG. 28;

FIG. 82 is a plan view of still another example of a reduction instrument configured for use with the spinal fixation system of FIG. 19;

FIG. 83 is a plan view of the reduction instrument of FIG. 82 coupled with a pedicle screw of FIG. 28;

FIG. 97 is a perspective view of an example of a guide adjuster configured for use with the guide assembly of FIG. 21;

FIG. 98 is a perspective view of the guide adjuster of FIG. 97 coupled with the guide assembly of FIG. 21;

FIGS. 99-100 are perspective and sectional views, respectively, of an example of a tap guide for use with the spinal fixation system of FIG. 19;

FIG. 101 is a perspective view of an example of an offset dilator configured for use with the spinal fixation system of FIG. 19;

FIGS. 102-103 are perspective views of another example of an offset dilator configured for use with the spinal fixation system of FIG. 19;

FIG. 104 is a plan view of a secondary dilator configured for use with the spinal fixation system of FIG. 19;

FIGS. 116-117 are perspective views of a compression instrument according to another embodiment FIG. 118 is a plan view of the compression system of FIG. 116;

FIG. 119 is a perspective view of a base member and first handle member forming part of the compression instrument of FIG. 116;

FIG. 120 is a perspective view of a second handle member forming part of the compression instrument of FIG. 116;

FIG. 137 is a perspective view of an awl-tap combo according to one embodiment;

FIG. 138 is a plan view of a needle and handle forming part of the awl-tap combo of FIG. 137;

FIG. 139 is a perspective view of the awl-tap combo in use;

FIG. 153 is a plan view of a screwdriver according to an example embodiment;

FIG. 154 is a perspective view of an inner sleeve forming part of the screwdriver of FIG. 153;

FIG. 155 is a perspective view of the distal tip of the screwdriver of FIG. 153;

FIG. 156 is a perspective view of one part of the screwdriver of FIG. 155;

FIG. 159 is a perspective view of a polyaxial reduction screw;

FIG. 160 is a perspective view of a K-wire holder according to an example embodiment;

FIG. 161 is an exploded plan view of the K-wore holder of FIG. 160;

FIGS. 162-163 are perspective views of a lock screw inserter according to an example embodiment;

FIG. 164 is a perspective view of the lock screw inserter of FIG. 162 with lock screws engaged;

FIG. 165 is an exploded perspective view of the lock screw inserter of FIG. 162;

FIG. 166 is a sectional view of the lock screw inserter of FIG. 162;

FIG. 167 is a perspective view of the distal region of the lock screw inserter of FIG. 162;

FIG. 168 is an enlarged perspective view of a portion of the distal region of the lock screw inserter of FIG. 162; and FIG. 169 is a plan view of a series of steps in the use of the lock screw inserter of FIG. 162.

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fixation system disclosed herein boasts a variety of inventive features and components that warrant patent protection, both individually and in combination.

The present application describes a spinal fixation system that may be utilized to form a fixation construct across one or more spinal levels of a patient. The spinal fixation system may be especially useful in forming fixation constructs across multiple spinal levels and/or spines with alignment deformities requiring correction. The spinal fixation system includes bone anchors (e.g. anchors 16, 112, 206), anchor guides (e.g. 18, 116, 188, 224), rods (50, 114), and various instruments (e.g. reduction instruments, rod inserters, compression instruments, etc. . . . ) that can be used in various combinations to form the fixation construct. The spinal fixation system may used for the installation of the fixation construct under minimally invasive conditions. That is, the overall length of skin incisions required to install the fixation construct may be minimized compared to traditionally open pedicle screw procedures. For example, the spinal fixation system includes a guide that extends distally out of the patient when the anchor is engaged to the spine. An elongated rod channel through the guide helps direct the rod into the proper position without requiring the extended incisions needed to fully expose the spinal segments to be fixated.

Figures 1, 2:
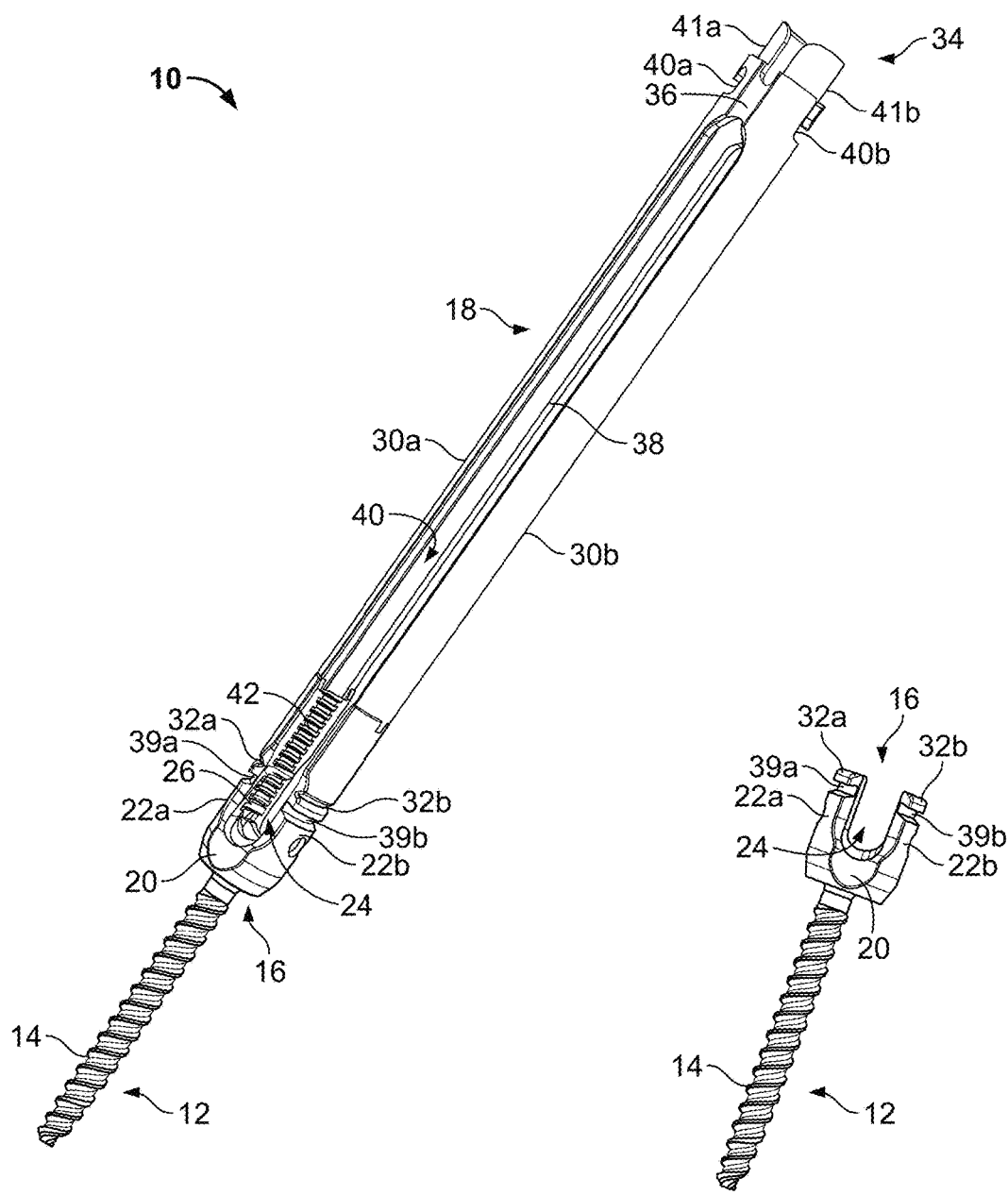
FIG. 1 is a perspective view of the spinal fixation anchor according to an example embodiment.
FIG. 2 is a perspective view of an implantable portion of the fixation anchor of FIG. 1 after removal of an extension guide.

Turning to FIGS. 1-2, there is depicted a spinal fixation anchor 10, according to an example embodiment. The spinal fixation anchor includes integral reduction features that may be utilized to seat a fixation rod in the anchor while realigning the position of the associated vertebra relative to other vertebra associated with the fixation construct. Additionally, separate reduction tools that cooperate with the spinal fixation anchor may be utilized to help seat the rod and realign the associated spinal segment. The fixation anchor 10 includes a bone anchor 12 (e.g. shank with thread feature 14) suitable for stable fixation to vertebral bone and a housing 16 for capturing and locking a fixation rod 50. Attached to the housing 16 is a break-off extension guide 18. The extension guide 18 helps align the rod 50 with the housing 16 and also helps reduce the rod into the housing when necessary. After the rod 50 is locked within housing 16 the extension guide 18 can be removed from the housing so the incision can be closed over the fixation construct (FIG. 2 depicts the fixation anchor with the extension guide 18 completely removed).

The housing 16 has a base 20 that mates with the bone anchor 12 and a pair of upstanding arms 22a and 22b separated by a rod channel 24. The arms 22a and 22b are equipped with a locking cap guide and advancement feature 26, such as by way of example, a helically wound flange feature disposed on the interior face of each arm 22a and 22b. The locking cap guide and advancement feature mates with a complementary guide and advancement feature on a locking cap 51. The locking cap 51 engages the upstanding arms via the complementary guide and advancement features to press and lock the fixation rod 50 into the housing 16.

The housing 16 and anchor 12 may be mated with a polyaxial engagement such that the housing 16 can pivot relative to the anchor 12 in any direction. The engagement may also be such that the pivoting movement may be inhibited in one or more directions. By way of example, the housing 16 and anchor 12 may be mated with a uniplanar engagement such that the housing pivots relative to the anchor 12 in a single plane. The housing 16 and anchor 12 may also be fixed such that no movement is possible between the housing 16 and anchor 12.

Break-off extension guide 18 extends from the top of housing 16 and includes a pair of extension arms 30a and 30b. Extension arm 30a attaches to housing arm 22a via an integral but breakable distal joint 32a. Extension arm 30b attaches to the housing arm 22b via an integral but breakable distal joint 32b. The breakable distal joints 32a and 32b are formed by surface grooves which reduce the material thickness along the entire junction between the extension arms 30a, 30b and housing arms 22a, 22b, respectively, such that directing an appropriate force to the extension arm will snap the associated breakable joint. The extension arms 30a and 30b are dimensioned with a length such that the extension guide 18 extends from the housing 16 to a location outside of the patient when the fixation anchor 10 is in a fully implanted position and securely anchored to the vertebra. At a proximal end 34 of the extension guide 18 the extension arms 30a and 30b come together to form a pair of integral but breakable proximal joints 36. Opposed vertical surface grooves above the guide slots 38 reduce material thickness along each junction between the extension arms 30a and 30b to form the breakable proximal joints 36.

Figure 9:
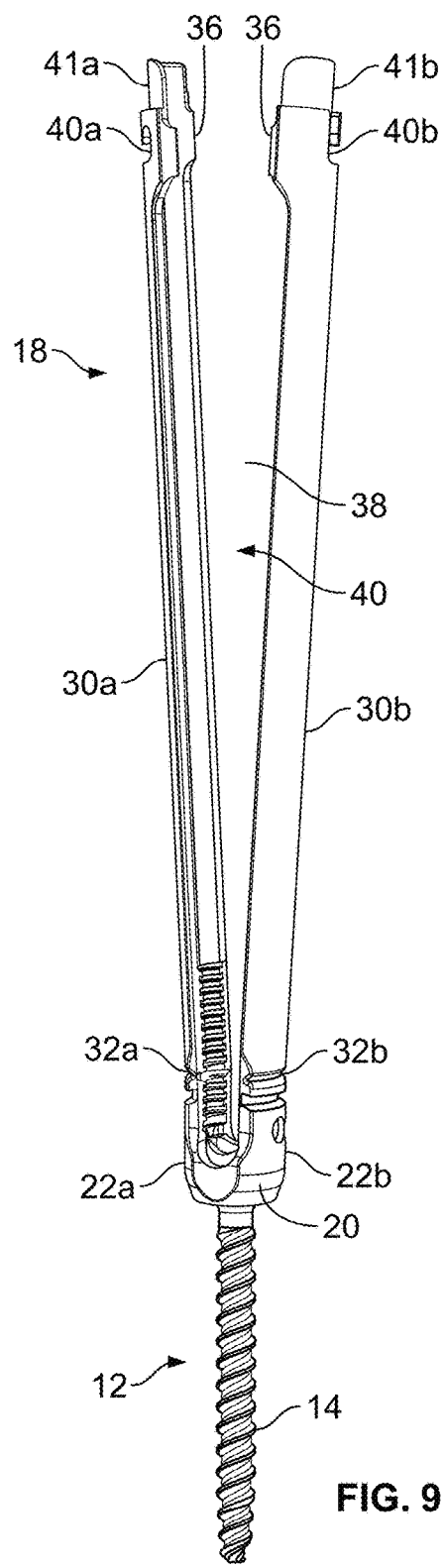
FIG. 9 is a front view of the fixation anchor of FIG. 1, after proximal joints are broken to allow the arms to separate.
Figure 10:
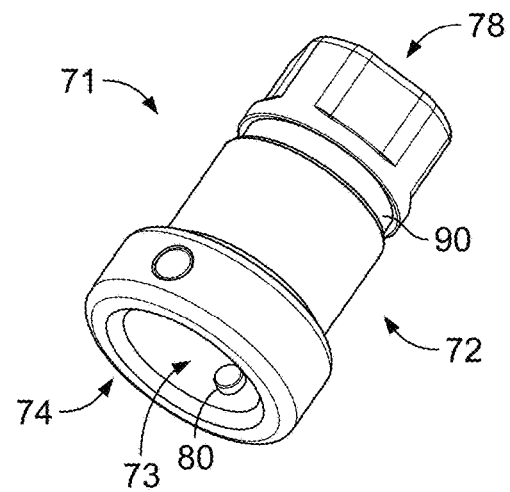
FIG. 10 is a perspective view of a guide cap for use with the fixation anchor of FIG. 1, according to one example embodiment.
Figure 11:
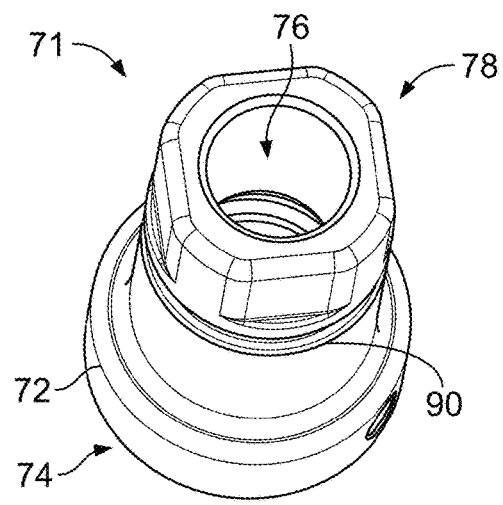
FIG. 11 is another perspective view of the guide cap of FIG. 10.
Figure 12:
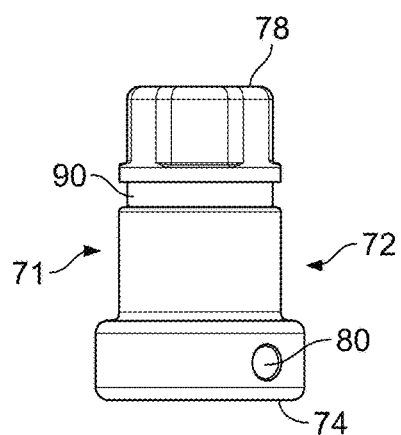
FIG. 12 is a side view of the guide cap of FIG. 10.
Figure 13:
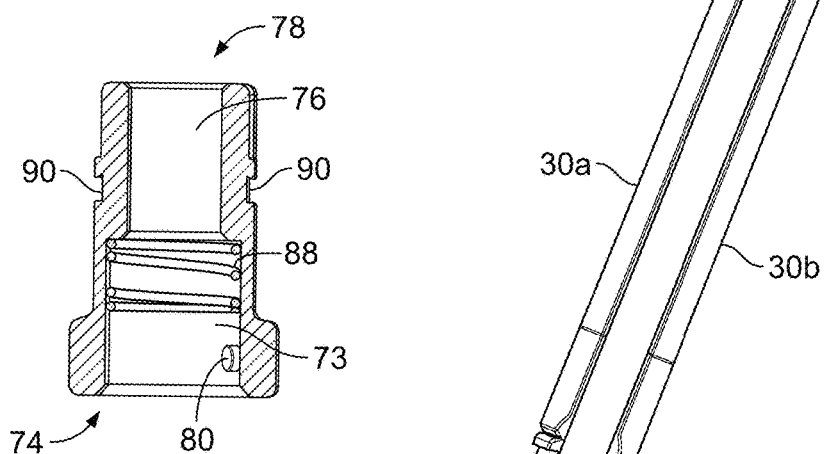
FIG. 13 is a cross section view of the guide cap as shown in FIG. 12.
Figure 14:
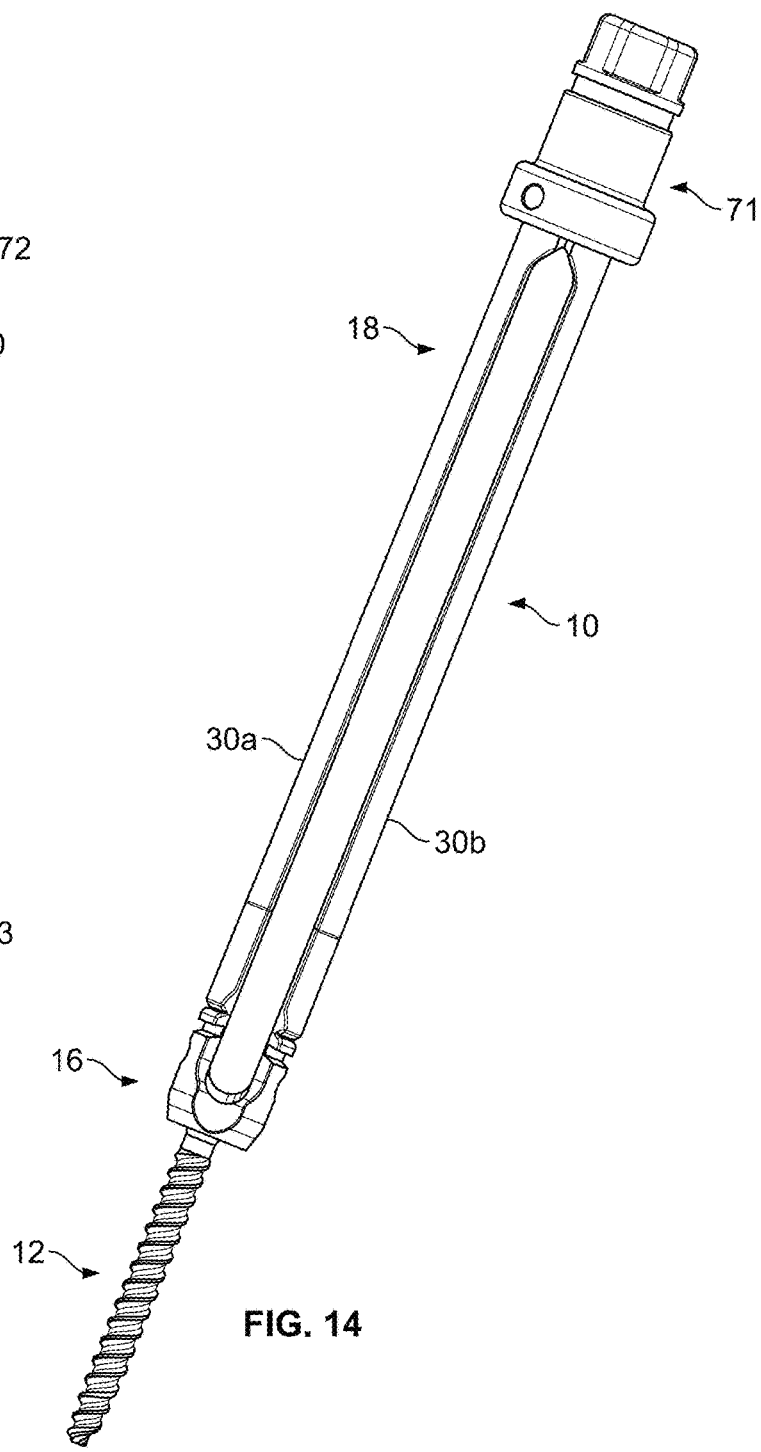
FIG. 14 is a perspective view of the guide cap of FIG. 10 coupled to the fixation anchor of FIG. 1.

Opposed guide slots 38 formed between arms 30a and 30b align with the rod channel 24 of the anchor housing 16 to define an enclosed guide channel 40 which is dimensioned to allow passage of a fixation rod 50. Utilizing the guide channel 40 to align the rod 50 with the housing rod channel 24 reduces the need for fiddlesome manipulation of the housing and/or rod down near the target site, as well as the associated need to fully visualize the housing 16 during rod insertion. Thus, the overall size of the incision required to implant a fixation construct using fixation anchors 10 is significantly reduced compared to open procedures. Though not necessary, after the anchor 10 is implanted, and to help facilitate rod insertion, the proximal joints 36 may be broken, thereby severing the proximal connection of the extension arms 30a and 30b and allowing the arms 30a and 30b to flex apart (FIG. 9). After breaking the proximal joints 36, a guide cap 71 (described below) may be used to reassociate the extension arms 30a and 30b if desired. Recess 40a on the proximal end of extension arm 30a and recess 40b on the proximal end of extension arm 30b facilitate the releasable coupling of the guide cap 71 to the proximal end 34 of the extension guide 18.

Figure 5:
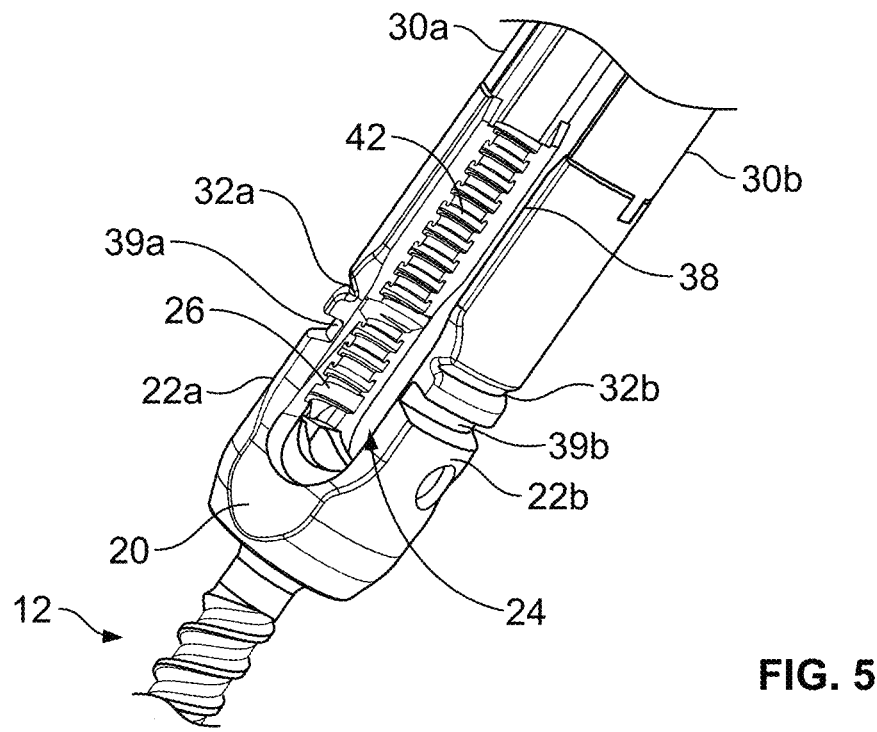
FIG. 5 is an enlarged perspective view of the junction between the implantable portion and extension guide of the fixation anchor of FIG. 1.
Figure 6:
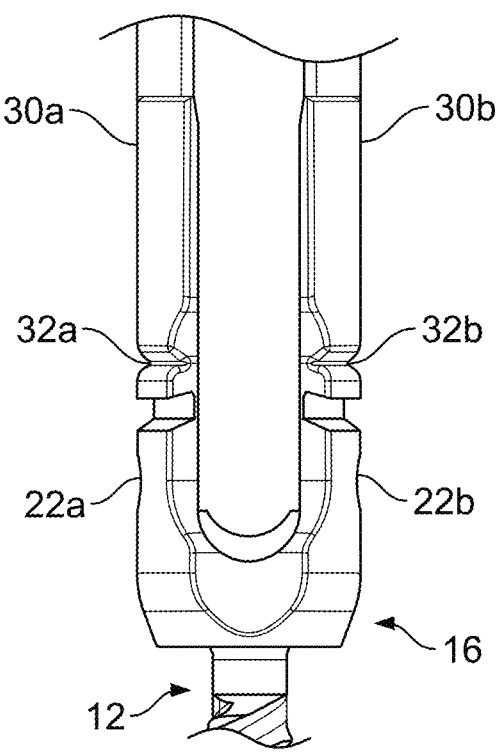
FIG. 6 is an enlarged front view of the junction region between the implantable portion and extension guide of the fixation anchor of FIG. 1.

As best pictured in FIG. 5, the fixation anchor 10 includes an integral reduction feature which provides for effective, single step reduction and locking when the spinal alignment necessitates the rod be reduced into the housing 16. The distal ends of extension arms 30a and 30b are appointed with a locking cap guide and advancement feature 42 situated adjacent to the breakable distal joints 32a and 32b. The guide and advancement feature 42 matches the guide and advancement feature 26 on the interior face of arms 22a and 22b. Further, the guide and advancement feature 42 is timed with the guide and advancement feature 26 such that the locking cap 51 advances seamlessly from the extension guide 18 to the housing 16. This configuration provides a mechanical advantage when advancing the locking cap 51 along the guide and advancement features 42 and 26, allowing the locking cap 51 to drive the rod into the housing 16 until it is fully seated and locked in position.

At some point during the surgical procedure after the fixation anchor(s) are anchored securely to their respective vertebra, the breakable distal joints 32a, 32b and the breakable proximal joints 36 must be broken in order to remove the break-off extension guide 18. The distal joints 32a and 32b are preferably broken only after the rod 50 is seated in the housing 16 and the locking cap 51 is fully engaged. In the event the extension guide 18 is removed prematurely and a guide structure is still desirable (e.g. for rod insertion, locking cap engagement, and/or reduction purposes), an attachment groove 39*a* is formed in the housing arm 22*a* and an attachment groove 39*b* is formed in housing arm 22*b*. A slip on guide structure (not shown) may be advanced and releasably coupled to the housing via the attachment grooves 39*a*, 39*b*. The proximal breaking joints 36 are preferably broken first before attempting break the distal joints 32*a*, 32*b*. This may be done just prior to breaking the distal joints to remove the extension guide after the rod 50 is seated and the locking cap 51 fully engaged in the housing 16. Alternatively, the surgeon may want to sever the connection between the extension arms 30*a*, 30*b* at an earlier point during the procedure. By way of example, the proximal joints 36 may be severed prior to rod insertion in order to facilitate easier rod insertion.

Figure 7:
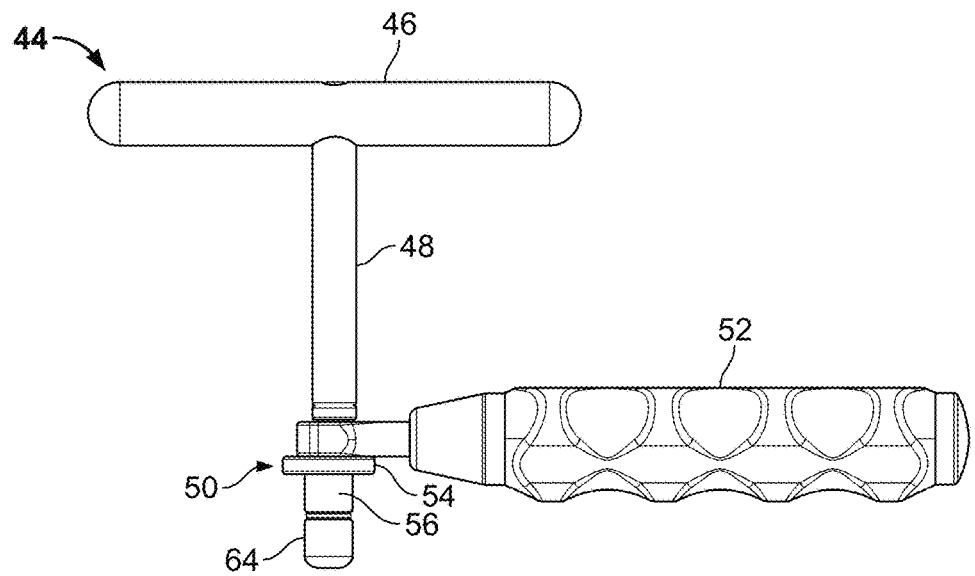
FIG. 7 is a side view of a breaking tool, according to an example embodiment.
Figure 8:
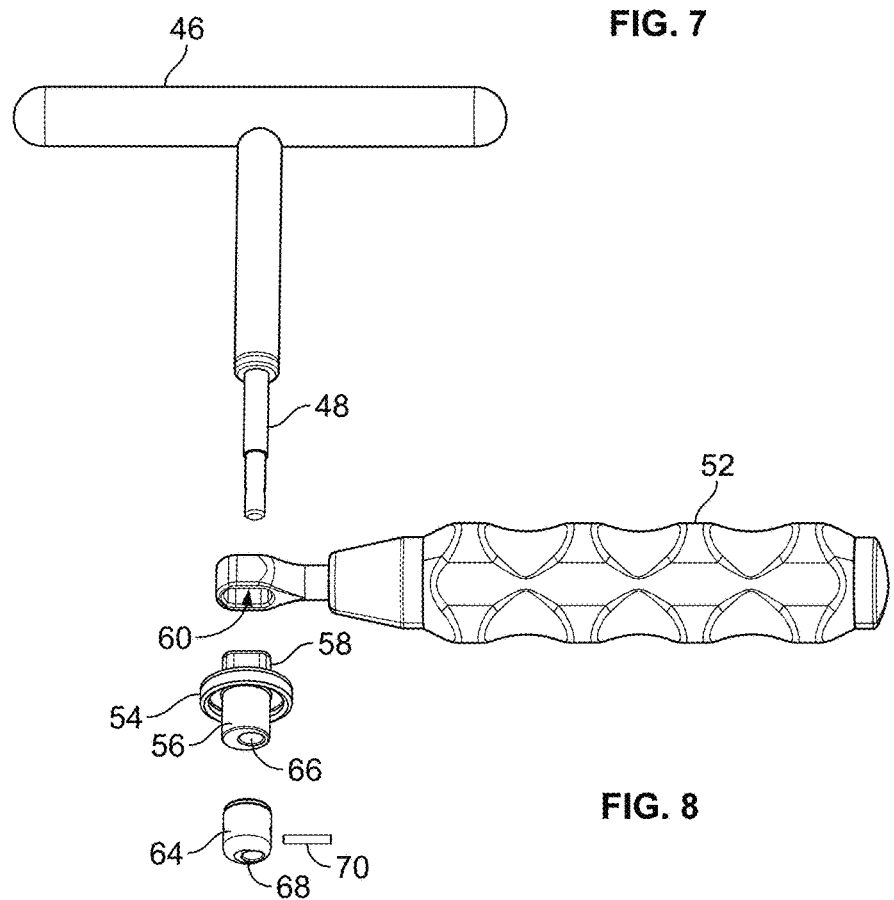
FIG. 8 is an exploded perspective view of the breaking tool of FIG. 7.

With reference to FIGS. 7-8, an example embodiment of a breaking tool 44 that may be utilized to break the proximal joints 36 is illustrated. The breaking tool 44 is designed to apply an outwardly directed force to the proximal joints 36 from inside the extension guide 18. The breaking tool 44 is a cam driver and includes a handle 46, rotating drive shaft 48, a cam 64 coupled to a distal end of the drive shaft 48, a hub 50, and a counter torque handle 52. The hub 50 has central cap 54 from which a cylinder 56 extends distally and a faceted block 58 extends proximally. The cylinder 56 has an exterior diameter that is slightly smaller than an interior diameter of the extension guide 18 such that the cylinder 56 can be passed into the extension guide 18. The central cap 54 has a diameter that is larger than the extension guide 18 such that the cap 54 controls the depth of insertion into the extension guide 18, ensuring force is applied in the right locations (i.e. on or near the proximal joints 36). The faceted block 58 mates with a complementary receptacle 60 attached to the counter torque handle 52 to prevent rotation of the hub 50 when the drive shaft 48 is operated.

A tunnel 66 dimensioned to receive a portion of the drive shaft 48 therethrough extends through the hub 50 along a line offset from a center axis of the cylinder 56. The cam 64 has a diameter that matches approximately the diameter of the cylinder 56 and a tunnel 68 for receiving the drive shaft 48 that is offset from the center axis of the cam. The cam 64 is fixed to the drive shaft 48 via pin 70 such that rotation of the drive shaft 48 causes the cam 64 to rotate relative to the cylinder 56. When the cam 64 and cylinder 56 are aligned they can slide together into the extension guide 18. As the cam 64 is rotated relative to the cylinder 56 the combined diameter of the two components expands, directing an outward force onto the extension arms 30*a*, 30*b* which causes the breakable proximal joints 36 to break, allowing the extension arms 30*a*, 30*b* to separate, as shown in FIG. 9. With the proximal joints 36 severed, the distal breakable joints 32*a* and 32*b* can be broken simply by bending the associated extension arm until the joint snaps. This can be done using a common grasping tool, such as forceps for example, or grasping the extensions arms directly with the hand.

While breaking the proximal joints 36 may have desirable consequences prior to and during rod insertion, it may also be desirable to have the rigidity associated with the unbroken guide extension 18 at later points during the surgery. To this end, a guide cap 71 is provided which may be used to hold the arm extensions 30*a* and 30*b* together and restore the rigidity of the unbroken guide extension 18. The guide cap 71 has a body 72 with a first internal cavity 73 opening out to a distal end 74 and a second internal cavity 76 opening out to a proximal end 78. The first internal cavity 73 has an internal diameter that is just larger than the external diameter of the extension guide 18 such that the proximal end of the extension guide may be received in the first internal cavity 73. The second internal cavity 76 has a diameter smaller than the first internal cavity 73, to provide a shelf for spring 88, approximating the internal diameter of the extension guide 18 and large enough to pass a locking cap 51 therethrough. A pair of opposed projections 80 extend into the first internal cavity 73 and engage with the recesses 40*a* and 40*b* on the extension arms 30*a* and 30*b* to releasably couple the guide cap 71 to the extension guide 18. The recesses 40*a* and 40*b* each include an open vertical slot 82 connected to one end of a horizontal slot 84, and a closed vertical slot 86 connected to the opposite end of the horizontal slot. To attach the guide cap 71, the projections 80 are aligned with the open vertical slots 82 and pressure is applied to the guide cap 71 such that the cap advances onto the extension guide 18. When the projections 80 reach the bottom of the open vertical slot 82 the cap is rotated until the projections 80 reach the end of the horizontal slot 84. Pressure is then released from the guide cap 71 and a spring 88 working against proximal tabs 41*a*, 41*b* of the extension arms draws the projections 80 into the closed vertical slots 86, thereby securing the guide cap 71 to the extension guide 18.

Figure 15:
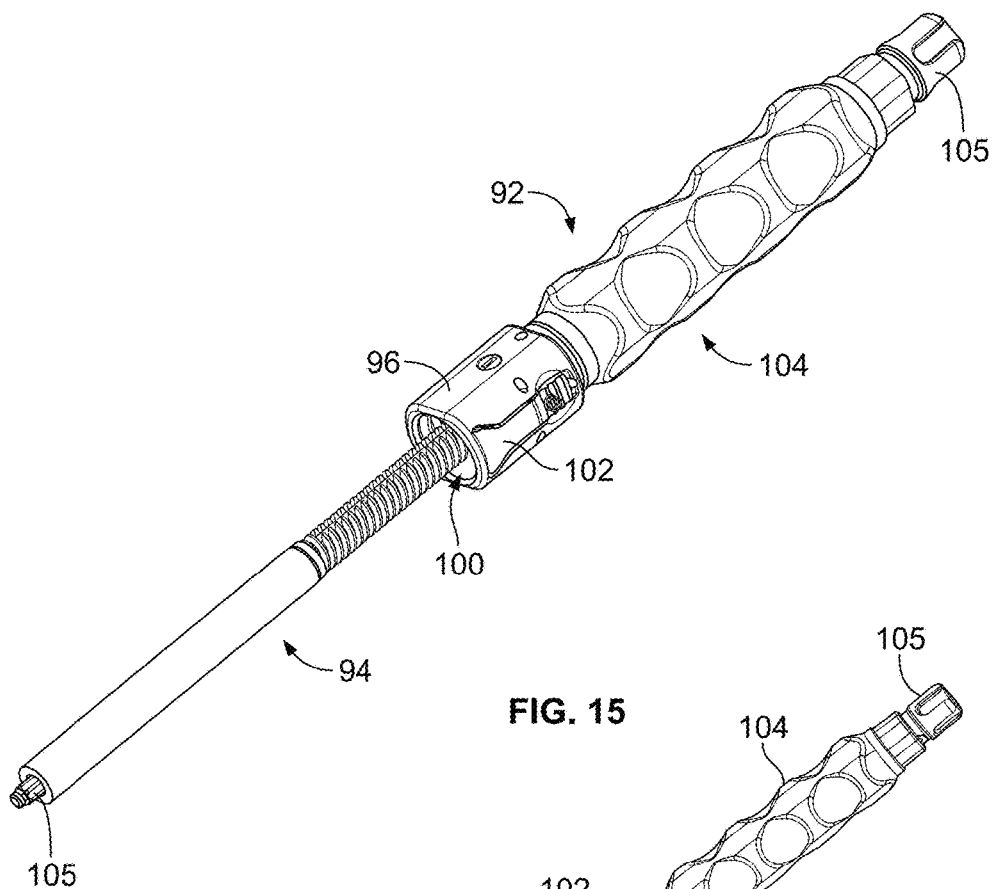
FIG. 15 is a perspective view of an independent reduction tool that may be used with the guide cap and fixation anchor of FIG. 14.

The reduction capabilities of the extension guide 18 are enhanced with the use of the guide cap 71. By way of example, the integral reduction features described above are less effective when the extension arms 40*a* and 40*b* are flexible and allowed to splay. The guide cap 71 negates this challenge such that the surgeon is not required to choose between easier rod insertion or better reduction. In addition, the body 72 of the guide cap 71 is adapted to releasably mate with independent reduction instruments should such an instrument be desired over the integral reduction features of the extension guide 18. One example of such an independent reduction instrument is depicted in FIG. 15.

Figure 16:
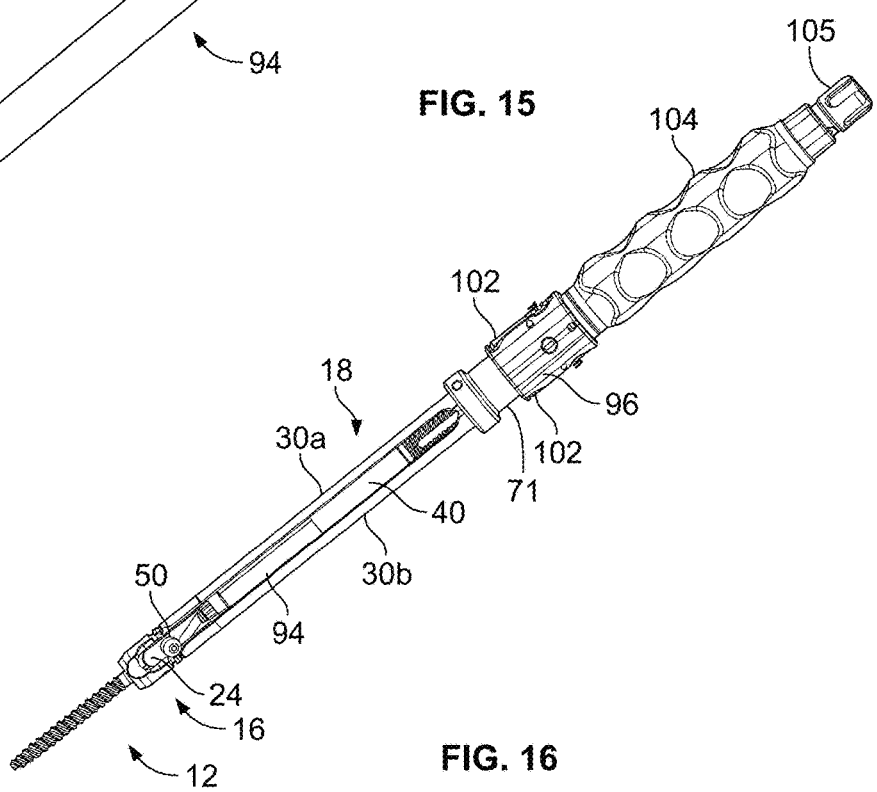
FIG. 16 is a front view of the independent reduction tool coupled to the guide cap and fixation anchor of FIG. 14.
Figure 17:
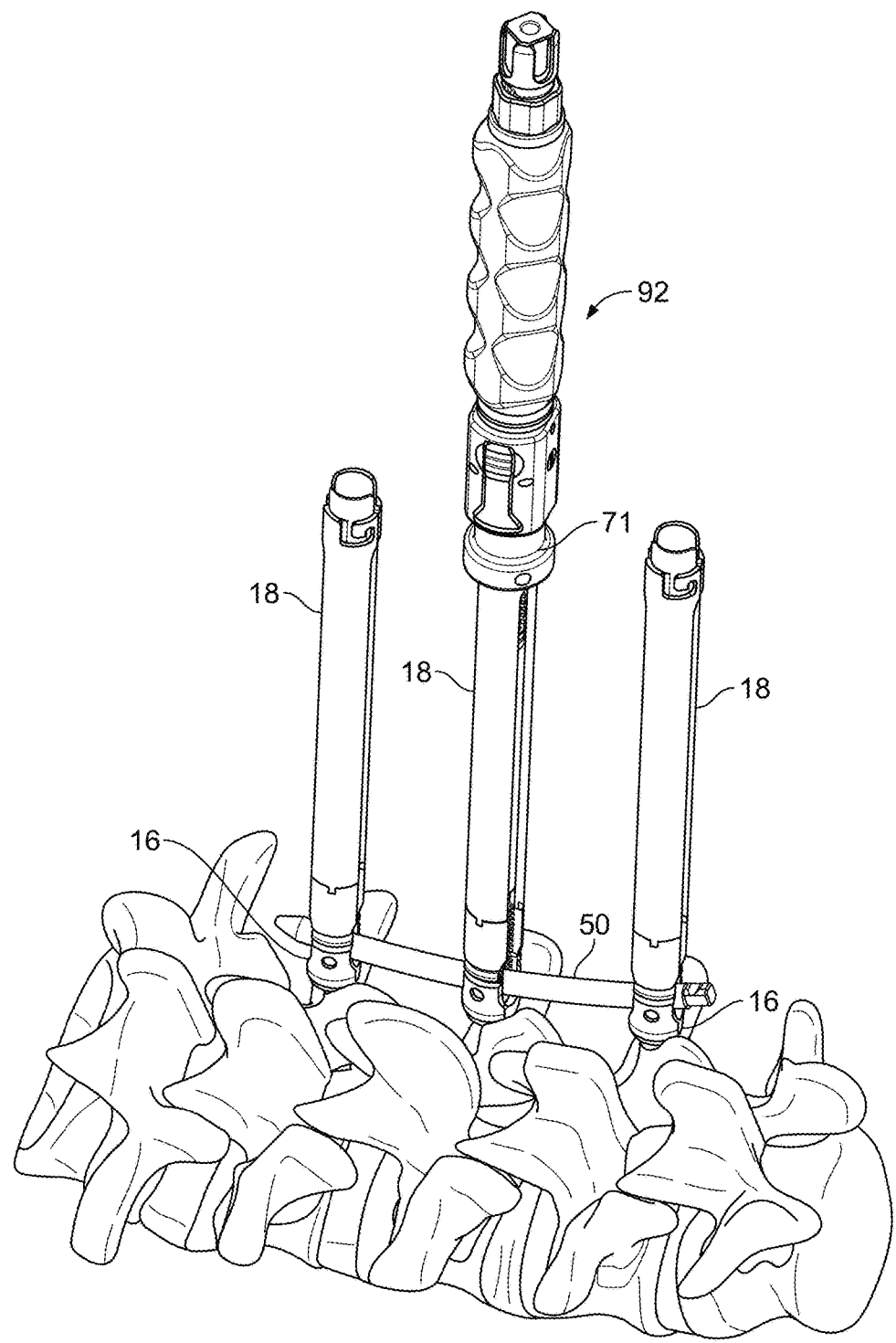
FIG. 17 is a perspective view of a lumbar spine illustrating the use of spinal fixation anchors of FIG. 1 with the guide cap of FIG. 10 and independent reduction instrument of FIG. 15 to implant a two level fixation construct, according to one example.

The reduction instrument 92 includes a connector 96 that releasably couples the reduction instrument to the extension guide (via guide cap 71). The connector 96 has a receptacle 100 into which the proximal end 78 of the guide cap 71 is received. The proximal end 78 is keyed to the receptacle 100 so as to prevent rotation of the guide cap 71 and attached extension guide 18 relative to reduction instrument 92. Spring clips 102 on the connector engage a groove 90 situated below the proximal end 78 to prevent translation of the guide cap 71 and attached extension guide 18 relative to the reduction instrument 92. The spring clips 102 have a tapered distal edge that extends into the receptacle 100. The tapered edge allows the proximal end 78 to push past the spring clips 102 until the tapered edge returns to rest in groove 90. To release the connection between the reduction instrument 92 and the guide cap 71 the proximal ends of the spring clips can be depressed and the connector 96 lifted off the proximal end 78. In use, the reduction shaft 94 is inserted through the guide cap 71 into extension guide 18 until the proximal end 78 of the guide cap 71 is locked into the receptacle 100, as illustrated in FIGS. 16-17. A reduction handle 104 may then be operated to translate the reduction shaft 94 distally relative to the extension guide 18 to drive the rod 50 through the guide channel 40 until the rod is fully seated in the housing 16. A locking cap driver 105 may then be operated to advance the locking cap 51 into the housing 16 and lock the rod 50 in place.

Having described the various features of the fixation anchor 10 and associated instruments, an example method for the minimally invasive implantation of a spinal fixation construct will now be described. First, a spinal fixation anchor is anchored through the pedicle of each vertebra to be fixated (e.g. three vertebra as shown in FIG. 17). At least one of the spinal fixation anchors is the spinal fixation anchor 10. The remaining fixation anchors may also be the fixation anchor 10 (as in FIG. 17). Alternatively, the remaining fixation anchors may be anchors adapted for use with independent guide structures that releasably couple to the anchors, as are generally known in the art.

With the fixation anchors 10 in position, a rod 50 appropriately sized to span the distance between the end anchors is selected. At this point, the proximal joints 36 on one or more of the fixation anchors 10 may be broken if the surgeon chooses to do so. By way of example, the surgeon may choose to break the proximal joints 36 of the fixation anchor 10 at the opposite end of the construct from which rod insertion will be directed. During some insertion techniques the rod is inserted into the guide channel of the first fixation anchor 10 generally parallel to the extension guide while the insertion instrument is angled back towards the remainder of the extension guides 18. As the inserter is rocked towards the insertion end, the rod advances through each guide. Severing the proximal joints 36 on the extension guide 18 at the opposite end of the construct from rod insertion allows the inserter to advance between the extension arms 30a, 30b of the end anchor (instead of having to work the inserter around the outside of the guide extension 18). This simplifies passage of the rod by facilitating proper alignment of the rod during insertion. If the surgeon chooses to break the proximal joints 36, the cam 64 and cylinder 56 of the breaking tool 44 are aligned and inserted into the extension guide 18 until the cap 54 rests on the proximal end of the extension guide 18. The cam 64 is then rotated with one hand while the counter torque handle 52 is held in the other hand until the proximal joints 36 break apart. The rod 50 is then inserted through the guide channels 40.

If necessary, (for example, if the rod 50 does not fully seat within the anchor housing 16 as would be the case if or more of the vertebrae are not vertically aligned) one or more of the reduction methods described above may be employed to reduce the rod 50. If the rod 50 is seated low enough in the guide channel 40 that the guide and advancement features 42 are accessible above the rod then reduction may be accomplished by engaging a locking cap 51 with the guide and advancement features 42 and advancing the locking cap 51 until the rod 50 and locking cap 51 are fully seated in the housing 16. If this reduction is to be carried out on a fixation anchor 10 whose proximal joints 36 had been previously broken, the guide cap 71 should preferably be coupled to the extension guide 18 prior to reduction. Alternatively, if the rod 50 sits above the guide and advancement features 42 or the surgeon simply prefers to utilize an independent reduction tool, the guide cap 71 should be attached to the appropriate fixation anchor 10 whether or not the proximal joints 36 of that anchor have been broken. The independent reduction instrument 92 is then coupled to the extension guide 18 and operated to reduce the rod 50 into the housing 16 and a locking cap 51 is engaged to lock the rod 50 in place. The surgeon may choose to utilize both the integral reduction features for reduction at one fixation anchor 10 and the independent reduction instrument for reduction at another of the fixation anchors 10. Reduction (when necessary) and locking cap engagement is completed for each spinal fixation anchor in the construct.

Figure 18:
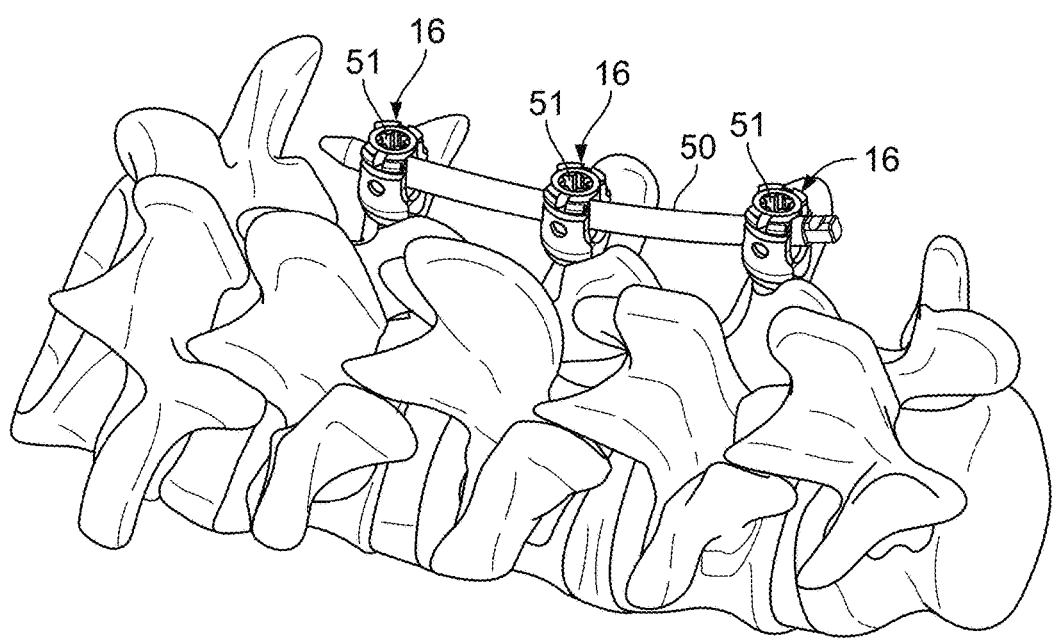
FIG. 18 is a perspective view of the lumbar spine of FIG. 17 after the locking caps have been deployed and extension guides have been removed to leave the final fixation construct.

With the rod 50 locked down along the entire construct the extension guide 18 should be removed. First, any guide caps 71 utilized during the procedure should be removed. Then the breaking tool 44 is used to break the proximal joints 36 of all extension guides 18 whose proximal joints 36 remain intact. Finally, the extension arms 30a and 30b of each spinal anchor 10 are removed by breaking the distal joints 40a and 40b, respectively. According to an alternative sequence, the extension guide 18 can be removed from each fixation anchor 10 in sequence as the rod 50 is locked to each anchor 10. Once the extension guides 18 are removed from each anchor 12, the final fixation construct is complete, as illustrated in FIG. 18, and the incision(s) can be closed.

Figure 19:
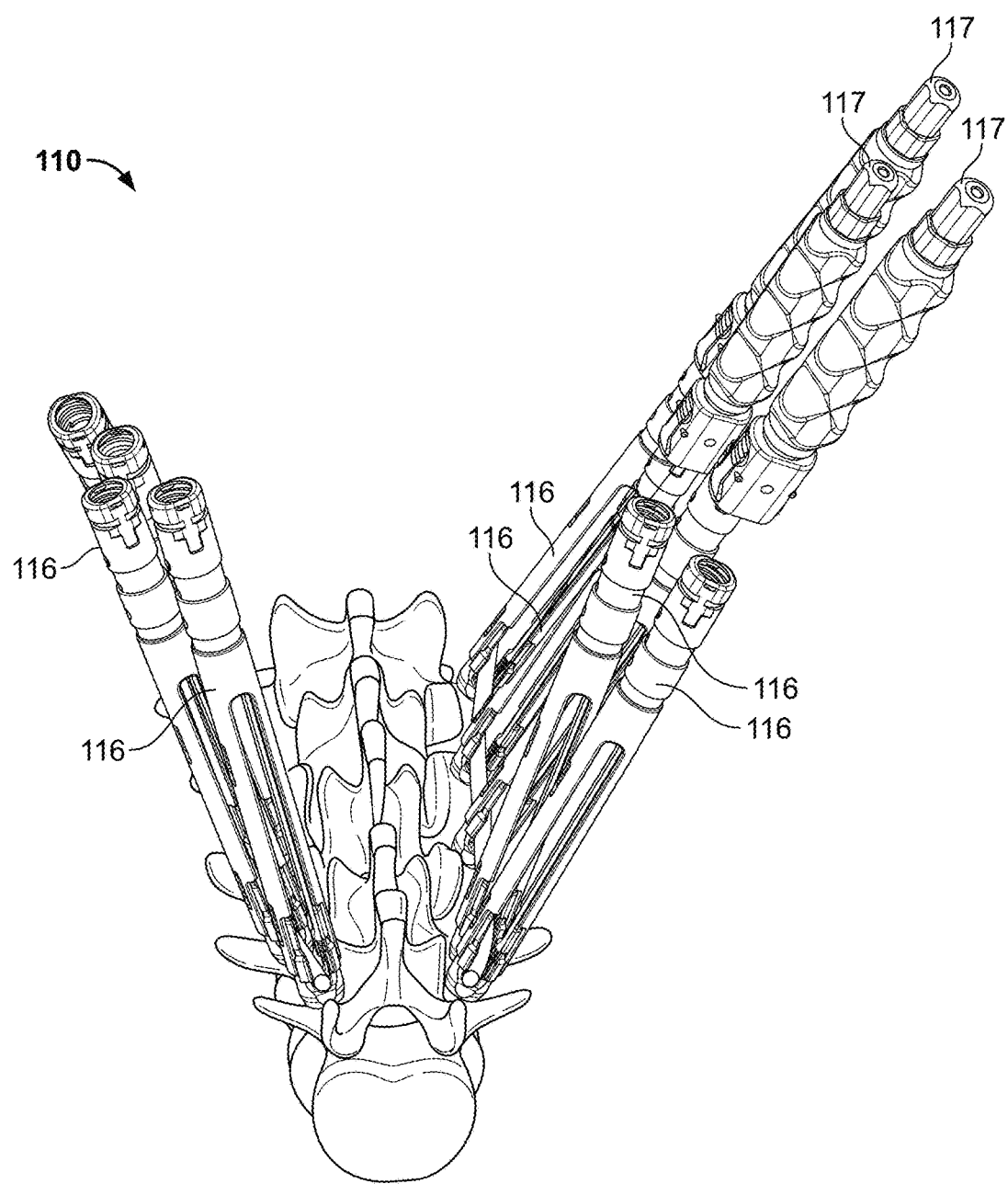
FIGS. 19-20 are perspective and side views, respectively, of a lumbar spine illustrating the use of a spinal fixation system according to one example embodiment.
Figure 20:
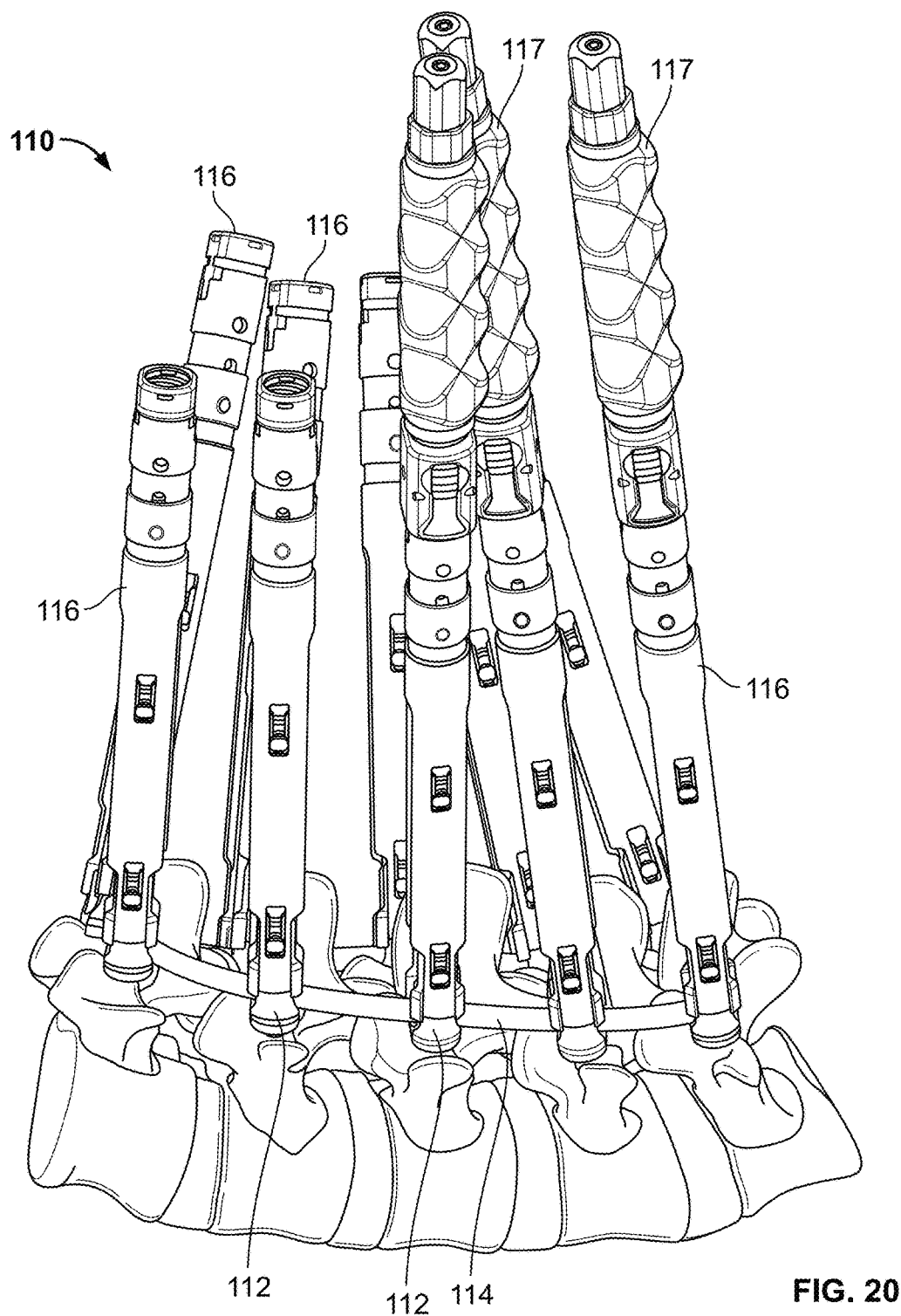
Figure 21:
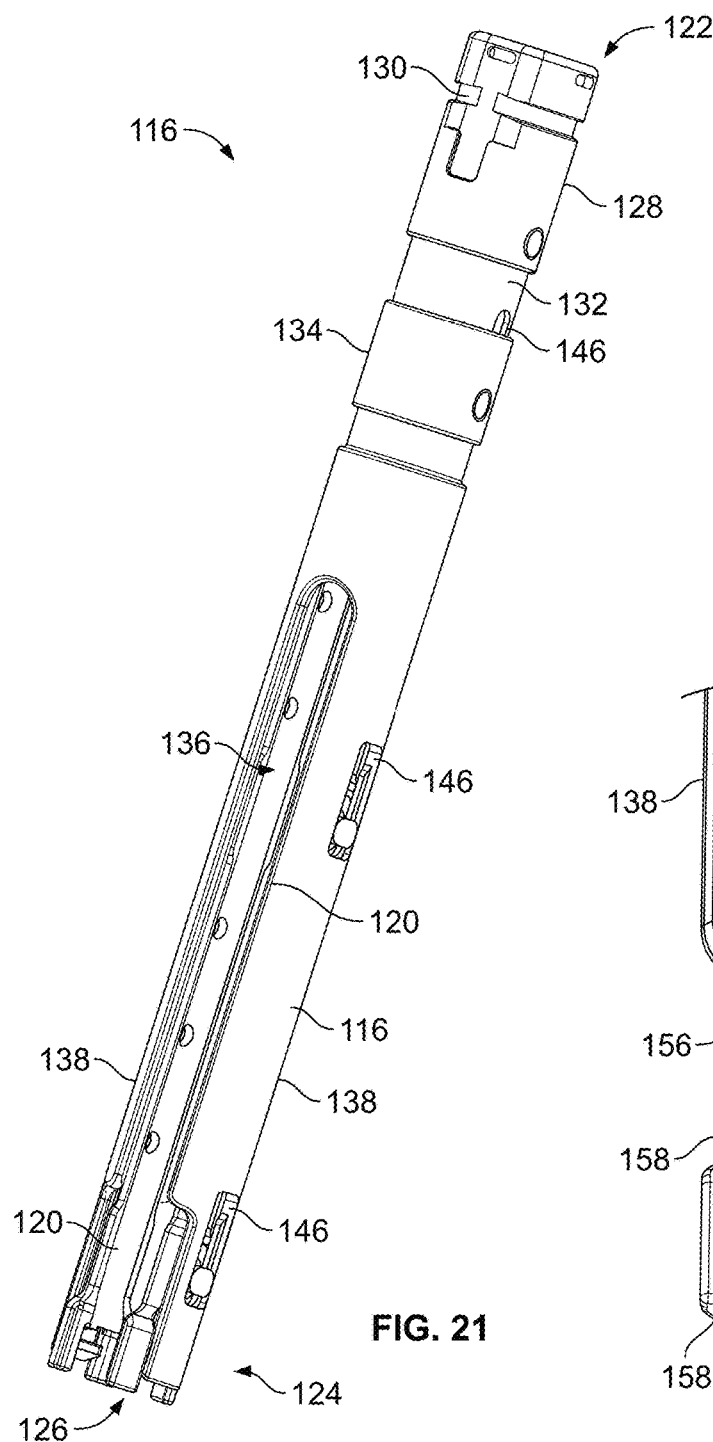
FIG. 21 is a perspective view of an example of a guide assembly forming part of the spinal fixation system of FIG. 19.
Figure 22:
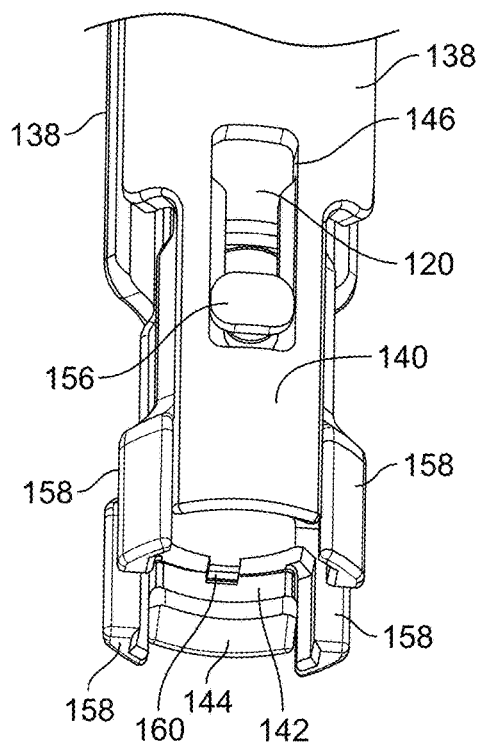
FIG. 22 is a perspective view of the distal end of the guide assembly of FIG. 21.
Figure 25:
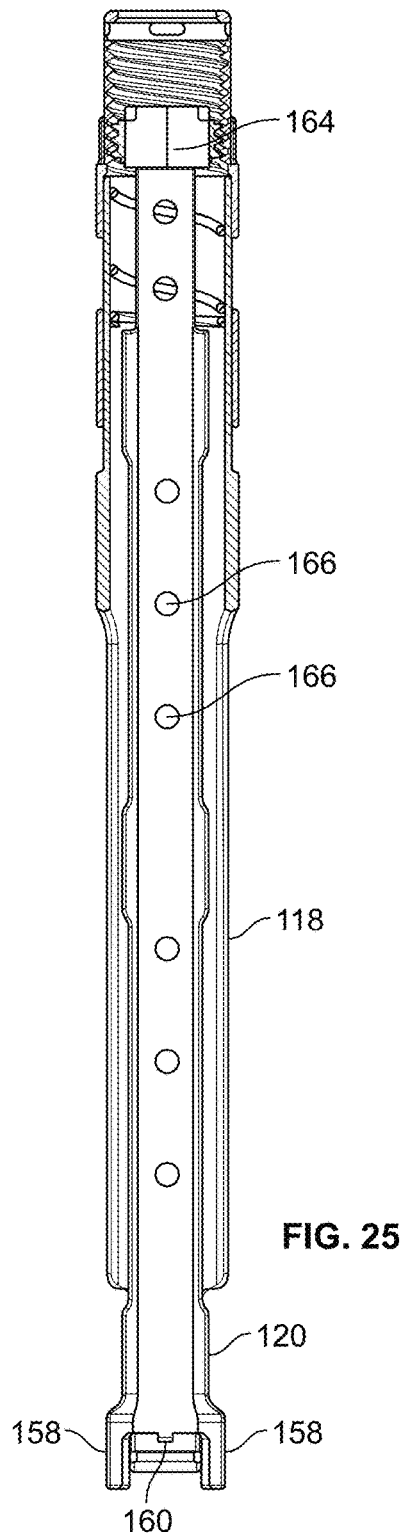
FIGS. 25-26 are sectional views of the inner member of FIG. 23.
Figure 26:
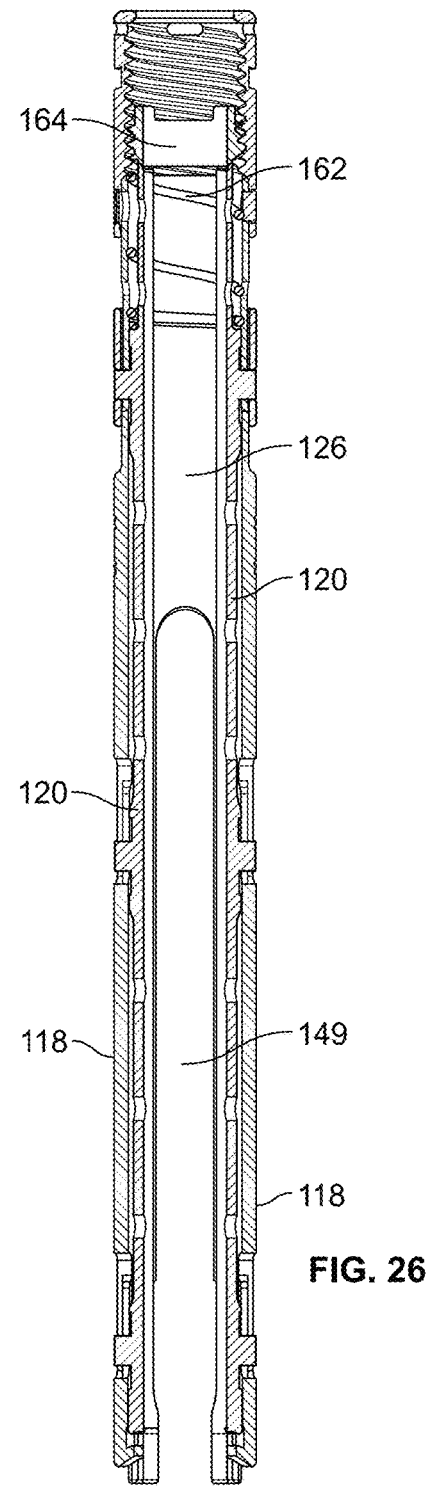

FIGS. 19 and 20 illustrate a spinal fixation system 110 configured for introducing and building a posterior spinal fixation construct such as that described above, according to one example embodiment. According to one example, the spinal fixation system 110 includes a pedicle screw 112, an elongated spinal rod 114, and a guide assembly 116. Pedicle screws 112 are inserted bilaterally or unilaterally into multiple vertebra across one or more levels. In addition, fixation anchor 10 can be utilized in place of pedicle screw 112 in one or more vertebra. The spinal fixation system 110 may further include any of a variety of instruments configured to perform the installation and assembly of the spinal fixation construct, including by way of example a reduction instrument 117 shown in FIGS. 19 and 20, as well as rod inserters, compression instruments, lock screw inserters, guide adjusters, tap guides, and dilators, of which various embodiments are described in further detail below.

FIGS. 21-27 illustrate one example of a guide assembly 116 for minimally invasive implantation of the pedicle screw 112 and for guiding the spinal rod 114 into position. By way of example only, the guide assembly 116 includes an outer sleeve 118 and a pair of inner arm members 120 positioned within the outer sleeve 118. The arm members 120 are configured to releasably engage the housing 172 of the pedicle screw 112. The arm members 120 are moveable between a first position and a second position. When in the first "unlocked" position, the arm members 120 are not engaged with in the pedicle screw 112. In the second, "locked" position, the arm members 120 are engaged with the pedicle screw 112, and the pedicle screw 112 is "locked" to the guide assembly 116.

The outer sleeve 118 is a generally tubular member having a proximal end 122, a distal end 124, and a lumen 126 extending longitudinally through the outer sleeve 118. The proximal end 124 includes a cap 128 that is configured to engage the inner arm members 120 (on the inside of the cap 128) and a reduction instrument 117 (on the outside of the cap 128). A circumferential groove 130 is positioned near the proximal end 122 and configured to receive the ridges 346 of the spring lock 344 of the reduction instrument 117. In this fashion, the guide assembly 116 may be releasably coupled to the reduction instrument 117. The outer sleeve 118 further includes a cylindrical recess 132 formed distally of the circumferential groove 130 but in the proximal half of the outer sleeve 118. The cylindrical recess 132 is configured to receive an actuator 134 and is further configured to allow translation of the actuator 134 in a proximal/distal direction within the cylindrical recess 132. The outer sleeve 118 further includes a pair of longitudinal slots 136 extending proximally from the distal end 124 of the outer sleeve 118. The longitudinal slots 136 act in concert for form a channel 149 to guide the spinal rod 114 to the surgical target site during implantation of the surgical fixation construct. By way of example only, the slots 136 extend a little over half way along the outer sleeve 118. The slots 136 effectively divide the distal portion of the outer sleeve 118 into first and second outer arms 138. The distal end of the outer arms 138 each includes a distal extension 140. The distal extension 140 is an extension of the outer sleeve 118 however it is narrower in width than the outer sleeve 118. A ridge 142 dimensioned to engage the housing 172 of the pedicle screw 112 is positioned on the interior surface of the distal extension 140. The ridge 142 is configured to engage the attachment groove 182 of the housing 172 to releasably lock the guide assembly 116 to the pedicle screw 112. The ridge 142 includes a tapered surface 144 that enables the ridge 142 to slide over the top of the housing 172 of the pedicle screw 112 during the engagement process. The outer sleeve 118 is further provided with a plurality of elongated apertures 146 positioned opposite one another on either side of the outer sleeve 118 and configured to receive protrusions 154 of the inner arm members 120 to facilitate the secure engagement of the inner arms 120 to the outer sleeve 118.

The arm members 120 are each comprised of an elongated partially-cylindrical member having a proximal end 148 and a distal end 150. The proximal ends 148 of the arm members 120 are dimensioned to be received within the cap 128 of the outer sleeve 118. The arm members 120 each include a proximal protrusion 152 extending laterally from the outer surface of the arm member 120 and dimensioned to extend through a corresponding slot 146 positioned within the cylindrical recess 132 of the outer sleeve 118 and fixedly engage the actuator 134. In this fashion, translation of the actuator 134 causes translation the first and second arm members 120. Additional protrusions 156 are positioned along the arm members 120 such that they are aligned with and received within corresponding slots 146 in the outer sleeve 118. The distal ends 150 of the members 120 are configured to securely receive the top of the housing 172 of the pedicle screw 112. To facilitate this secure engagement, the distal ends 150 of the arm members 120 include a plurality of prongs 158 configured to extend vertically along the sides of the housing 172 upon engagement, as will be explained in further detail below. Additionally, a raised protrusion 160 is provided between the prongs 158 to engage a recess 184 in the top of the pedicle screw 112. The prongs 158 and raised protrusion 160 act in concert to prevent rotation of the housing 172 of the pedicle screw 112 during implantation of the spinal fixation construct.

The actuator 134 is positioned on the outside of the outer sleeve 118 and is fixedly attached to the inner arms 120. As stated previously, translation of the actuator 134 causes translation the inner arms 120. A spring 162 is provided that exerts a force distally the actuator and the inner arms 120 in order to bias the actuator 134 and inner arms 120 in a "locked" position. A stopper 164 is provided within the cap 132 to provide a distal stop for the spring 162 and the inner arms 120. The inner arms 120 may optionally be provided with a plurality of smaller apertures 166 to aid in the sterilization process.

The pedicle screw 112 includes a bone anchor 168 (e.g. shank with thread feature 170) suitable for stable fixation to vertebral bone and a housing 172 for capturing and locking a spinal rod 114. The housing 172 has a base 174 that mates with the bone anchor 168 and a pair of upstanding arms 176 separated by a rod channel 178. The arms 176 are equipped with a locking cap guide and advancement feature 180, such as by way of example, a helically wound flange feature disposed on the interior face of each arm 176. The locking cap guide and advancement feature 180 mates with a complementary guide and advancement feature on a lock screw (not shown, but similar to the lock screw 119 shown and described in relation to FIGS. 69-74). The lock screw 119 engages the upstanding arms 176 via the complementary guide and advancement features 180, 376 to press and lock the fixation rod 114 into the housing 172.

The housing 172 and anchor 168 may be mated with a polyaxial engagement such that the housing 172 can pivot relative to the anchor 168 in any direction. The engagement may also be such that the pivoting movement may be inhibited in one or more directions. By way of example, the housing 172 and anchor 168 may be mated with a uniplanar engagement such that the housing pivots relative to the anchor 168 in a single plane. The housing 172 and anchor 168 may also be fixed such that no movement is possible between the housing 172 and anchor 168.

The housing 172 further includes a pair of attachment grooves 182, one attachment groove 182 formed in each of the upstanding arms 176. The attachment grooves are dimensioned to receive the ridges 142 on the outer sleeve 118 of the guide assembly 116 to releasably lock the guide assembly 116 to the pedicle screw 112. The top of each arm 176 further includes a recess 184 formed therein. The recesses 184 have a corresponding shape and are dimensioned to receive the raised protrusions 160 on the distal end of the inner arm members 120 of the guide assembly 116. This interaction helps to prevent rotation of the housing 172 of the pedicle screw 112 during implantation of the spinal fixation construct.

FIGS. 32-34 illustrate the guide assembly 116 engaged to a pedicle screw 112. In order to accomplish this, once the pedicle screw 112 has been seated in the appropriate position in the surgical target site, the guide assembly 116 is advanced distally along the operative corridor until the distal end of the outer sleeve 118 contacts the housing 172 of the pedicle screw 112. The guide assembly 116 is then further advanced such that the ridges 142 snap into the attachment grooves 182 on the housing 172. At this point the outer sleeve 118 is secured to the pedicle screw 112. The actuator 134 is then advanced in a distal direction, which causes the simultaneous distal advancement of the inner arms 120 of the guide assembly 116. The inner arms 120 are advanced such that and until each pair of prongs 158 are positioned on either side of the upstanding arms 176 of the housing 172 and the raised protrusions 160 are seated within recesses 184 on the housing 172. At this point the inner arms 120 are secured to the pedicle screw 112 and the housing 172 is prevented from rotation relative to the guide assembly 116. Upon coupling of the guide assembly 116 and the pedicle screw 112, the opposed guide slots 168 formed between the outer arms 138 of the outer sleeve 118 of the guide assembly 116 align with the rod channel 178 of the housing 172 to define an enclosed guide channel 186 that is dimensioned to allow passage of a fixation rod 114. Utilizing the guide channel 186 to align the rod 114 with the housing rod channel 178 reduces the need for fiddlesome manipulation of the housing 172 and/or rod 114 near the surgical target site, as well as the associated need to fully visualize the pedicle screw 112 and/or the housing 172 during rod insertion. Thus, the overall size of the incision required to implant a fixation construct using the described fixation system 110 is significantly reduced compared to open procedures. Once the rod 114 has been seated in the housing 172 and secured with a lock screw 119 (as described below), the guide assembly 116 may be removed from the operative corridor. To accomplish this, a proximal force is applied to the actuator 134, which will disengage the inner arms 120 from the housing 172. The outer sleeve 118 may be disengaged from the housing 172 by applying an appropriate amount of proximal force on the guide assembly 116. Once both the outer sleeve 118 and the inner arms 120 have been disengaged from the housing 172, the guide assembly 116 may be removed from the operative corridor.

FIGS. 35-37 illustrate an example of a guide assembly 188 according to an alternative embodiment of the present invention for use with the spinal fixation system 110 described above. The guide assembly 188 is substantially similar to the guide assembly 116 described above, such that repeat description of like parts is unnecessary. By way of example only, the guide assembly 188 includes an outer sleeve 190 and a pair of inner arm members 192 positioned within the outer sleeve 190. The arm members 192 are configured to releasably engage the housing 208 of the pedicle screw 206 (FIGS. 38-39). The arm members 192 are moveable between a first position and a second position. When in the first "unlocked" position, the arm members 192 are not engaged with in the pedicle screw 206. In the second, "locked" position, the arm members 192 are engaged with the pedicle screw 206, and the pedicle screw 206 is "locked" to the guide assembly 116. As with the guide assembly 116, the guide assembly 188 includes an actuator 194 that facilitates the movement of the arm members 192 from the first to the second position.

The guide assembly 188 is substantially identical to the guide assembly 116 with the exception of two features that will be discussed in detail below. It is to be understood that any or all of other features described in conjunction with the guide assembly 116 may be present with respect to the guide assembly 188 in both structure and function. Therefore, repeat description of common features is not necessary. In addition to many of the features described in conjunction with the guide assembly 116, the guide assembly 188 includes a castle nut 196 protruding from the top of the outer sleeve 190. The castle nut 196 interacts with the actuator 194 and serves as a visual indicator of whether the guide assembly 188 is locked to the pedicle screw 206. More specifically, when the inner arm members 192 are in the first, "unlocked" position, the castle nut 196 protrudes from the top of the outer sleeve 190 (FIG. 35). When the inner arm members 192 are in the second position, the castle nut can be advanced (blocking return of the inner arm members), making the second position the "locked" position as the guides cannot be disengaged from the pedicle screw 206. The guide is "locked" when the castle nut 196 sits flush the top of the outer sleeve 190 (FIG. 36) and thus serves as a visual indication as to whether the guide assembly 188 is locked to the pedicle screw 206.

Referring to FIG. 37, the second major difference between the guide assembly 188 and the guide assembly 116 is in the distal engagement ends 198 of the inner arm members 192. The distal ends 198 of the arm members 192 are configured to securely receive the top of the housing 208 of the pedicle screw 206. To facilitate this secure engagement, the distal ends 198 of the arm members 192 include a plurality of prongs 200 configured to extend vertically along the sides of the housing 208 upon engagement. The prongs 200 differ from the prongs 158 in that each prong 200 includes an additional cutout area 202 on a pedicle screw engagement surface that interacts with the pedicle screw 206 to provide a more secure engagement, as will be described below. As with the first example described above, a raised protrusion 204 is provided between the prongs 200 to engage a recess 220 in the top of the pedicle screw 206. The prongs 200 and raised protrusion 204 act in concert to prevent rotation of the housing 208 of the pedicle screw 206 during implantation of the spinal fixation construct.

FIGS. 38-39 illustrate a pedicle screw 206 configured for use with the guide assembly 188 according to an alternative example. The pedicle screw 206 is similar to the pedicle screw 112 described above in that it includes a bone anchor (e.g. shank with thread feature—not shown) suitable for stable fixation to vertebral bone and a housing 208 for capturing and locking a spinal rod 114. The bone anchor portion of the pedicle screw 206 is identical to the bone anchor portion of pedicle screw 112 described above. The housing 208 has a base 210 that mates with the bone anchor and a pair of upstanding arms 212 separated by a rod channel 214. The arms 212 are equipped with a locking cap guide and advancement feature 216, such as by way of example, a helically wound flange feature disposed on the interior face of each arm 212. The locking cap guide and advancement feature 216 mates with a complementary guide and advancement feature on a lock screw (not shown, but similar to the lock screw 119 shown and described in relation to FIGS. 69-74). The lock screw engages the upstanding arms 212 via the complementary guide and advancement features 216, 376 to press and lock the fixation rod 114 into the housing 208.

Figure 41:
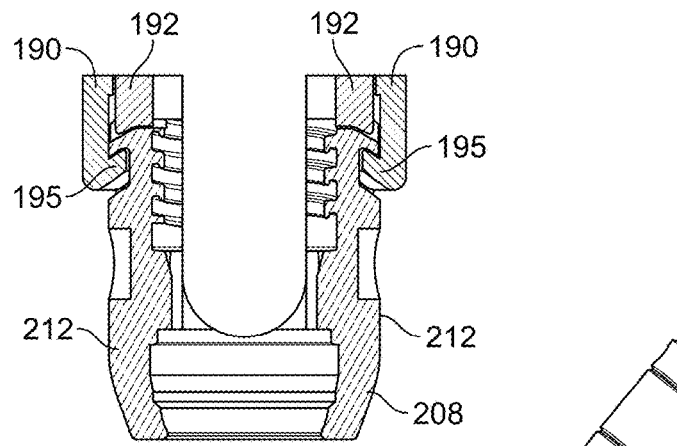

The housing 208 further includes a pair of attachment grooves 218, one attachment groove 218 formed in each of the upstanding arms 212. The attachment grooves 218 are dimensioned to receive the ridges 195 (FIG. 35) on the outer sleeve 190 of the guide assembly 188 to releasably lock the guide assembly 188 to the pedicle screw 206. The top of each arm 212 further includes a recess 220 formed therein. The recesses 220 have a corresponding shape and are dimensioned to receive the raised protrusions 204 on the distal end of the inner arm members 192 of the guide assembly 188. This interaction helps to prevent rotation of the housing 208 of the pedicle screw 206 during implantation of the spinal fixation construct. The housing 208 also includes a plurality of vertical cutouts 222 formed in each upstanding arm 212 on either side of the rod channel 214. The vertical cutouts 222 interact with the prongs 200 of the inner arm members 192 to provide a more secure engagement between the guide assembly 188 and the pedicle screw 206. More specifically, the cutout areas 202 of the prongs 200 are complimentary in shape to the vertical cutouts 222 on the arms 212 such that upon engagement, each prong 200 will contact at least three distinct surfaces of the corresponding upstanding arm 212. FIGS. 40-41 illustrate the guide assembly 188 engaged to the housing 208 of a pedicle screw 206.

Figure 42:
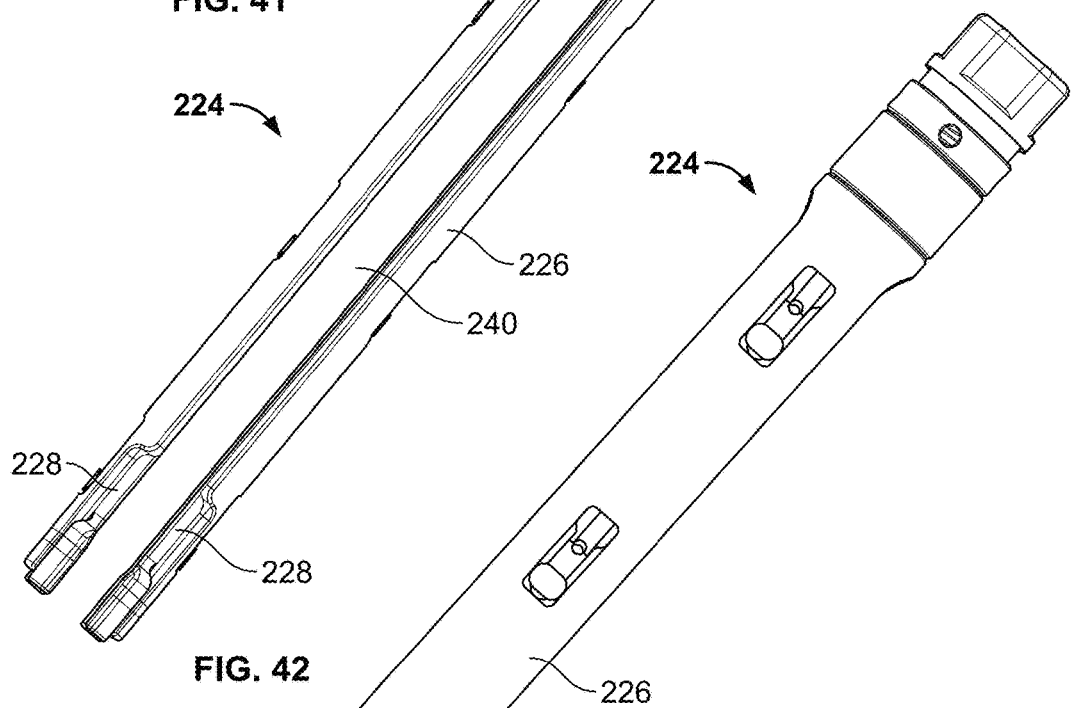
FIGS. 42-44 are plan, perspective, and exploded perspective views, respectively, of a third example of a guide assembly forming part of the spinal fixation system of FIG. 19.
Figure 43:
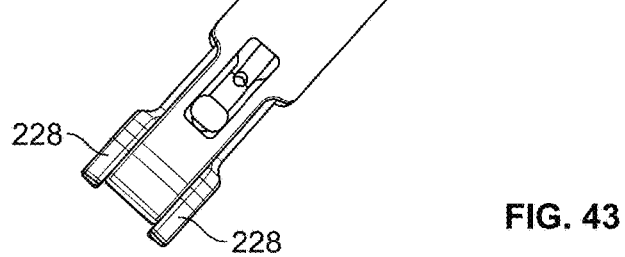
Figure 44:
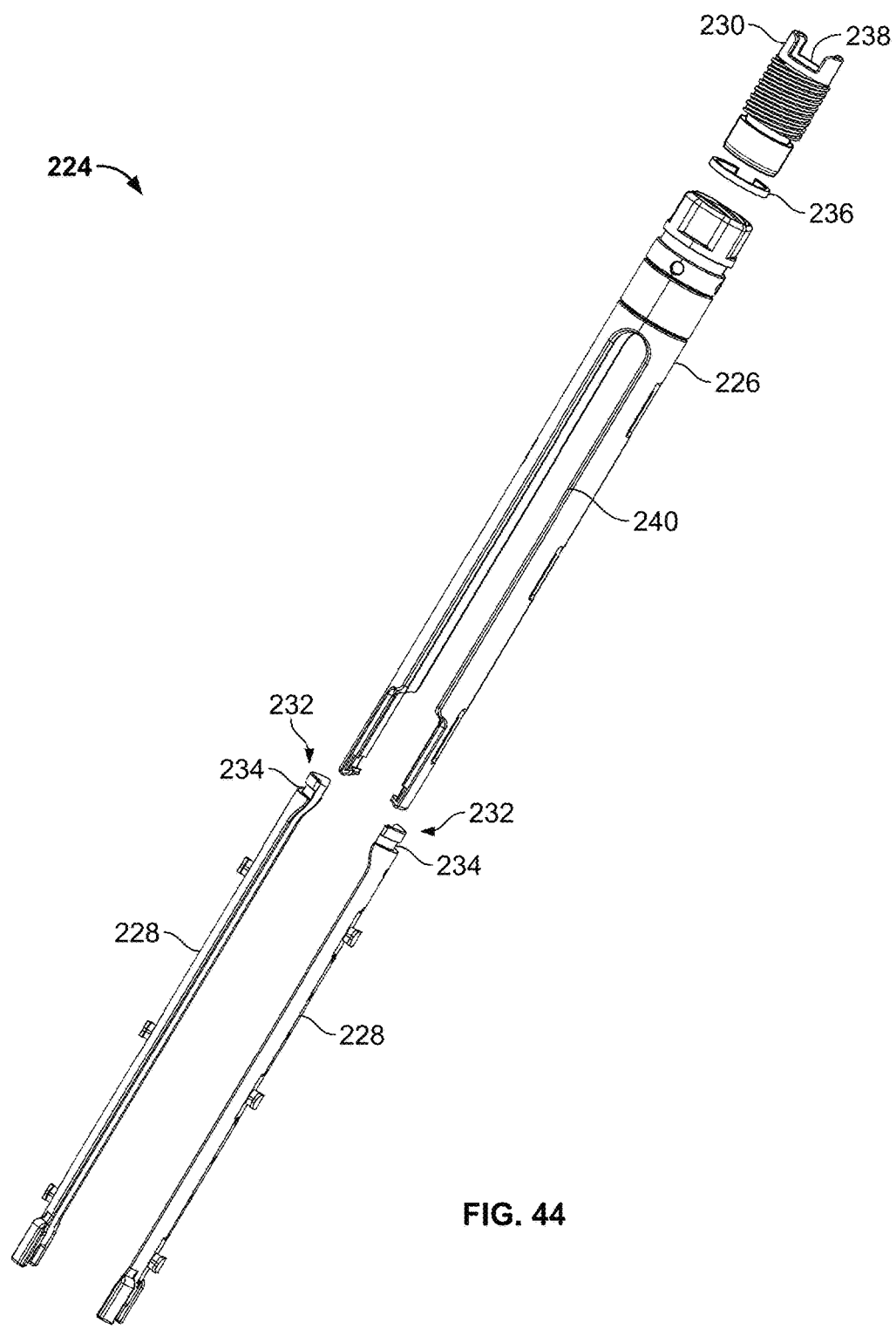
Figure 45:
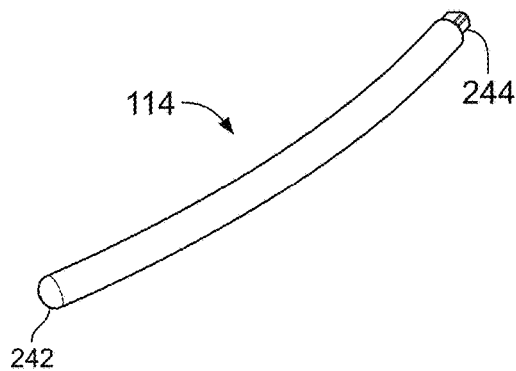
FIG. 45 is one example of a spinal rod forming part of the spinal fixation system of FIG. 19.
Figure 46:
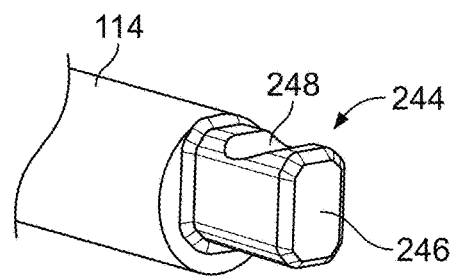
FIGS. 46-48 are perspective, side plan, and end plan views of one end of the spinal rod of FIG. 45.
Figure 47:
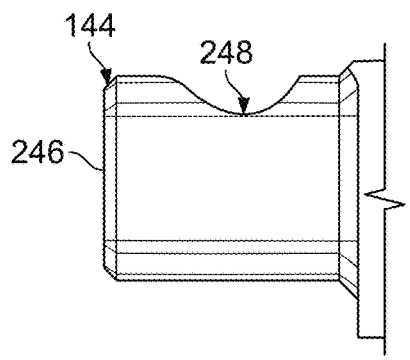
Figure 48:
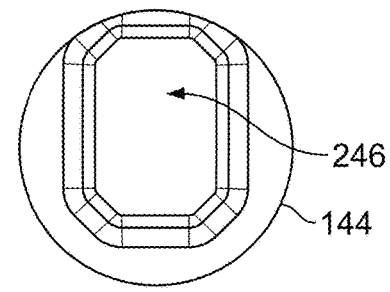
Figure 49:
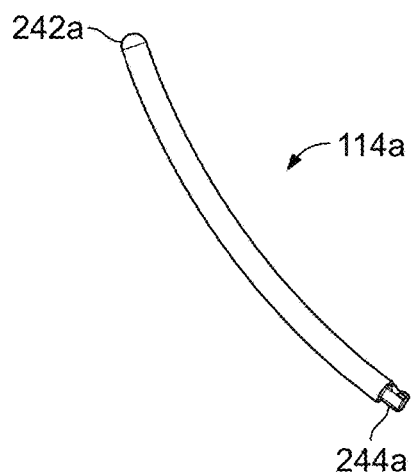
FIG. 49 is another example of a spinal rod forming part of the spinal fixation system of FIG. 19.
Figure 50:
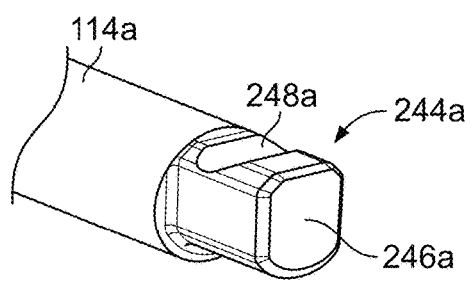

FIGS. 42-44 illustrate an example of a guide assembly 224 according to a third example embodiment of the present invention for use with the spinal fixation system 110 described above. The guide assembly 224 is substantially similar to the guide assemblies 116, 188 described above, such that repeat description of like parts is unnecessary. It is to be understood that any or all of other features described in conjunction with the guide assemblies 116, 188 may be present with respect to the guide assembly 224 in both structure and function. By way of example only, the guide assembly 224 includes an outer sleeve 226 and a pair of independent inner arm members 228 positioned within the outer sleeve 224. The arm members 228 are configured to releasably engage the housing 228 of the pedicle screw 206 (FIGS. 38-39). The distal engagement region of the arm members 228 and the interaction with the pedicle screw 206 is identical to that described in relation to the guide assembly 188. As with the previously described examples, the arm members 228 are moveable between a first position and a second position. When in the first "unlocked" position, the arm members 228 are not engaged with in the pedicle screw 206. In the second, "locked" position, the arm members 228 are engaged with the pedicle screw 206, and the pedicle screw 206 is "locked" to the guide assembly 224. Unlike the guide assemblies 116, 188, however, the guide assembly 224 does not include the same actuator to facilitate the movement of the arm members 228 from the first to the second position. As will be described below, the guide assembly 224 instead has a castle nut 230 that acts as the actuator. The castle nut 230 attaches directly to the arm members 228, and controls the advancement (and retreat) of the arms.

In addition to many of the features described in conjunction with the guide assemblies 116, 188, the guide assembly 224 includes a castle nut 230 protruding from the top of the outer sleeve 226. As with the guide assembly 188, the castle nut 230 serves as a visual indicator of whether the guide assembly 224 is locked to the pedicle screw 206. More specifically, when the inner arm members 228 are in the first, "unlocked" position, the castle nut 230 protrudes from the top of the outer sleeve 226. When the inner arm members 228 are in the second, "locked" position and engaged to a pedicle screw 206, the castle nut 230 is flush with the guide and consequently not visible above the top of the outer sleeve 226 (FIG. 42).

Unlike the guide assembly 188 described, the castle nut 230 not only locks the position of the inner arms after the arms move into position, the castle nut 230 also acts as the actuator to control the translation of the inner arms 228. To do this the inner arms 228 are attached directly to the castle nut 230. The proximal ends 232 of the inner arms 228 include a groove 234 that is dimensioned to engage a corresponding ridge 236 in the interior of the castle nut 230. Alternatively, the proximal ends 232 of the inner arms 228 may be provided with ridges that are received within corresponding grooves formed in the interior of the castle nut (not shown). Any combination of grooves and ridges may be employed to mate the inner arms 228 with the castle nut 230. In any case, by way of example only, the inner arms 228 may be mated with the castle nut 230 via a ridge/groove interaction. A tool (not shown) may be attached to the castle nut 230 (for example via slot 238) to help rotate the nut and lock or unlock the inner arms 228 and pedicle screw 206. The groove/ridge interaction between the castle nut 230 and the inner arms 228 ensure that the castle nut 230 is able to rotate freely relative to the inner arms 228 while still controlling translation. The guide assembly 224 may be provided with guide slots 240 that extend substantially the length of the outer sleeve 226. Relative to guide assemblies 116, 188, the longer guide slots 240 on the guide assembly 224 are possible due to the absence of an actuator to control translation of the inner arms 228.

FIGS. 45-52 illustrate several examples of spinal rods 114, 114a configured for use with the surgical fixation system described herein. By way of example, the spinal rod 114, 114a may be provided in any length corresponding to the number of spinal levels to be fixed. The spinal rods 114, 114a are generally cylindrical elongated rods. The spinal rods 114, 114a may be straight or curved. By way of example only, the spinal rods 114, 114a have a first end 242, 242a that is generally rounded and a second end 244, 244a that is configured to engage a rod inserter such as the rod inserter 250 shown and described below in relation to FIG. 53. The second end 244, 244a includes a post 246, 246a having a shape corresponding to the shape of the rod cavity 266 on the rod inserter 250. By way of example only, the spinal rod 114 includes a post 246 having a generally octagonal cross-sectional footprint. Post 246a is similar but is wider and has a rounded edge. The post 246, 246a also includes a recess 248, 248a formed on an upper surface of the post 246, 246a and configured to receive the distal lip 278 of the locking element 268 on the rod inserter 250. The recess 248, 248a and distal lip 278 cooperate to temporarily secure the rod 114, 114a to the rod inserter 250.

FIGS. 53-58 illustrate a first example of a rod inserter 250 configured for use with the spinal fixation system 110 according to one embodiment of the present invention. By way of example only, the rod inserter 250 is an adjustable-angle rod inserter that introduces the spinal rod 114 through the operative corridor at one angle (relative to the inserter), and then pivots the rod at the surgical target site. This enables longer spinal rods 114 to be inserted through an operative corridor, and it also allows for smaller incisions because less room is needed to insert the spinal rod.

By way of example only, the rod inserter 250 includes an outer sleeve 252, an inner shaft 254, a handle 256, and a rod holder 258. The outer sleeve 252 is an elongated cylindrical member having an inner lumen extending throughout. The inner shaft 254 is an elongated rod member having a knob 260 at the proximal end and an engagement post 262 at the distal end. The knob 260 is configured for handling by a user, and allows to user to pull up (proximally) on the knob to disengage the post 262 from the first and/or second shaft recesses 270, 274. The knob 260 can also be rotated in a clockwise or counterclockwise direction in order to lock or unlock the setscrew 272, as will be described below. The engagement post 262 is configured to engage the first and second shaft recesses 270, 274 to maintain the rod inserter 250 in either the first or second position. A spring 264 is located within the handle 256 and acts to bias the inner shaft 254 in a distal direction. This ensures that the rod inserter 250 is secured in either the first or second positions, and a positive action is required by the user to effect a change in position.

The rod holder 258 is pivotably attached to the distal end of the outer sleeve 252, and is configured to be pivoted from a first position to a second position and then back to the first position. The rod holder 258 includes a rod cavity 266, a locking element 268, first shaft recess 270, a setscrew 272, and second shaft recess 274. The rod cavity 266 is configured to receive the post 246 of the spinal rod 114. The locking element 268 is positioned within the rod holder 258 and is moveable from a first unlocked position to a second locked position. The locking element 268 includes a proximal recess 276, a distal lip 278, and a central cavity 280. The proximal recess 276 is configured to receive the setscrew 272, and is firmly attached to the setscrew via a snap ring 282. The snap ring allows the setscrew 272 to rotate within the proximal recess 276 while being advanced or retreated by the inner shaft 254, and also ensures that the locking element 268 is advanced and/or retreated along with the setscrew 272. A lockstop 284 in the form of a pin (by way of example only) extending through the cavity prevents the locking element 268 (and setscrew 272) from being retreated so much that it becomes disengaged entirely from the rod holder 258. The distal lip 278 is configured to be seated within the recess 248 of the spinal rod 114 such that when the rod inserter is in the locked position, the spinal rod 114 is secured within the rod cavity 266 and will not become dislodged therefrom. The setscrew 272 is positioned within the first shaft recess 270. The second shaft recess 274 is configured to receive engagement post 262 when the rod holder 250 is in the second position. This interaction temporarily locks the rod holder 250 in the second position.

In use, the rod inserter 250 is initially provided in a first position (FIG. 53) without the spinal rod 114 and the rod holder 258 in an unlocked position. In this first position, the first shaft recess 270 (and consequently the setscrew 272) is in alignment with the central lumen of the outer shaft 252.

The spinal rod 114 is then mated with the rod holder 258 by inserting the post 246 into the rod cavity 266 such that the recess 248 is facing the locking element 268. The knob 260 is rotated in a clockwise direction, which advances the setscrew 272 and locking element 268 in a distal direction until the distal lip 278 of the locking element 268 is seated within the recess 248. At this point the spinal rod 114 is secured to the rod inserter 250. The user then exerts a proximal force on the knob 260 causing the inner shaft 254 to move in a proximal direction and further causing the engagement post 262 to become disengaged from the first shaft recess 270. The rod holder 258 will then pivot (due to the pull of gravity on the spinal rod 114) such that the second shaft recess 274 becomes aligned with the outer shaft 252. The user may then release the knob 260, which due to the spring 264 advances the inner shaft 254 distally and causes the engagement post 262 to be received within the second shaft recess 274. The rod holder 258 is now secured in the second position (FIG. 54). In the second position, the spinal rod 114 is positioned at an obtuse angle relative to the rod inserter 250, which reduces the size of the operative corridor required to advance the rod. The rod 114 may be advanced through the operative corridor using a guide assembly such as the guide assembly 116 (or any of the other examples) described above.

As the distal tip of the rod reaches the target site it may become necessary to pivot the rod to further its advancement. This may be accomplished by once again applying a proximal force on the knob 260 to release the engagement post 262 from the second shaft recess 274. This allows the rod holder 258 to pivot toward the first position. Once the rod 114 is fully inserted, the user may release the knob 260 to reengage the engagement post 262 and the first shaft recess 270. The rod holder 258 is once again in the first position (FIG. 55). Once the rod 114 is seated within the pedicle screw 112 and secured as described above (and below), the rod 114 is ready to be detached from the rod inserter 250. To accomplish this, it is necessary to return the rod holder 258 to the first position (as just described) if it has not already been done during insertion of the rod. With the rod holder 258 in the first position, the knob 260 is turned counterclockwise to translate the setscrew 272 (and locking element 268) in a distal direction, which removes the distal lip 278 from the recess 248 and unlocks the rod 114. The rod inserter 250 may then be safely removed from the surgical target site through the operative corridor.

Figure 61:
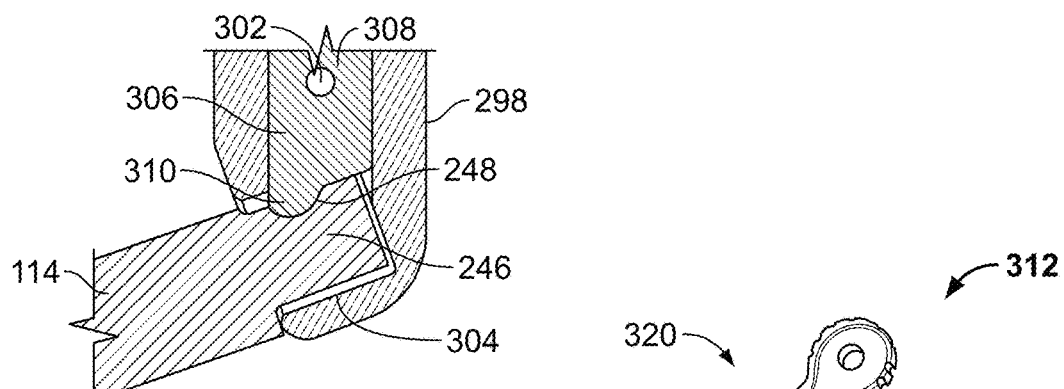
FIG. 61 is a sectional view of the distal end of the rod inserter of FIG. 59.

FIGS. 59-61 illustrate a second example of a rod inserter 290 configured for use with the spinal fixation system 110 according to another embodiment of the present invention. By way of example only, the rod inserter 290 is a fixed-angle rod inserter that introduces the spinal rod 114 through the operative corridor at one angle (relative to the inserter).

By way of example only, the rod inserter 290 includes a housing tube 292, a center screw 294, a handle 296, and a rod holder 298. The housing tube 292 is an elongated cylindrical member having an inner lumen extending throughout. The center screw 294 is an elongated rod member having a driver engagement recess 300 at the proximal end and an engagement post 302 at the distal end. The driver engagement recess 300 is configured to receive an engagement end of a suitable driver instrument (not shown). The center screw 294 can be rotated in a clockwise or counterclockwise direction in order to lock or unlock the spinal rod 114 to the rod inserter 290, as will be described below. The engagement post 302 is configured to engage the locking element 306. A spring (not shown) is located within the housing tube 292 and acts to bias the locking element 306 in an unlocked position.

The rod holder 298 is formed in the distal end of the housing tube 292. The rod holder 298 includes a rod cavity 304 and a locking element 306. The rod cavity 304 is configured to receive the post 246 of the spinal rod 114. The locking element 306 is positioned within the rod holder 298 and is moveable from a first unlocked position to a second locked position. The locking element 298 includes a proximal recess 308 and a distal lip 310. The proximal recess 308 is configured to receive the engagement post 302. The distal lip 310 is configured to be seated within the recess 248 of the spinal rod 114 such that when the rod inserter 290 is in the locked position, the spinal rod 114 is secured within the rod cavity 266 and will not become dislodged therefrom.

In use, the rod inserter 290 is initially provided without the spinal rod 114 and the rod holder 298 in an unlocked position. The spinal rod 114 is then mated with the rod holder 298 by inserting the post 246 into the rod cavity 304 such that the recess 248 is facing the locking element 306. The center screw 294 is rotated in a clockwise direction, which advances the locking element 306 in a distal direction until the distal lip 310 of the locking element 306 is seated within the recess 248. At this point the spinal rod 114 is secured to the rod inserter 290. The rod 114 may be advanced through the operative corridor using a guide assembly such as the guide assembly 116 (or any of the other examples) described above. Once the rod 114 is seated within the pedicle screw 112 and secured as described above (and below), the rod 114 is ready to be detached from the rod inserter 290. To accomplish this, the center screw 294 is turned counterclockwise to translate the locking element 306 in a distal direction, which removes the distal lip 310 from the recess 248 and unlocks the rod 114. The rod inserter 290 may then be safely removed from the surgical target site through the operative corridor.

Figure 62:
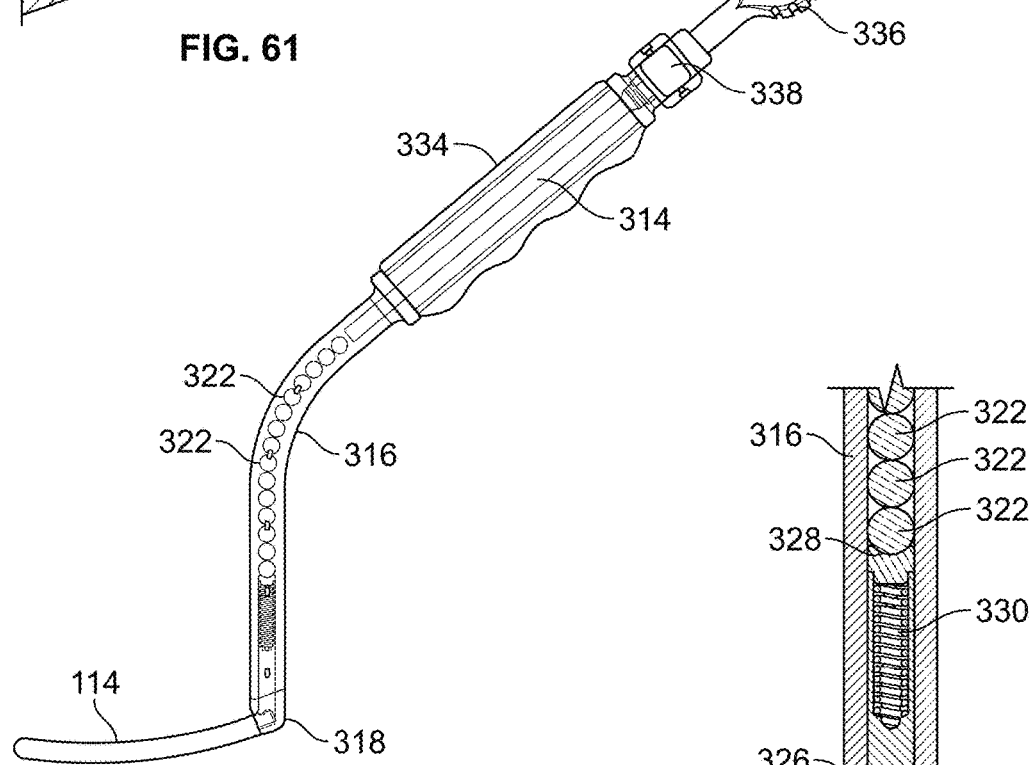
FIG. 62 is a plan view of another example of a fixed angle rod inserter configured for use with the spinal fixation system of FIG. 19.
Figure 63:
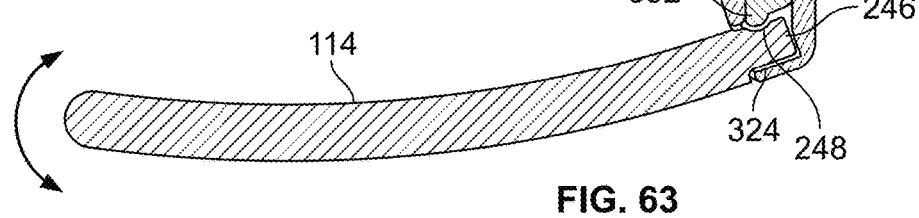
FIG. 63 is a sectional view of the distal end of the rod inserter of FIG. 62.

FIGS. 62-63 illustrate a third example of a rod inserter 312 configured for use with the spinal fixation system 110 according to another embodiment of the present invention. By way of example only, the rod inserter 312 is a mostly fixed-angle rod inserter that capable of slight variation in the introduction angle that introduces the spinal rod 114 through the operative corridor at one angle (relative to the inserter), and then allows for a slight adjustment in the angle (for example ±15°) for easier final seating of the rod 114 within the pedicle screw 112.

By way of example only, the rod inserter 312 includes a handle 314, a housing tube 316, a rod holder 318, an attached driver 320, and a ball linkage 322. The housing tube 316 is an elongated cylindrical member having an inner lumen extending throughout. The housing tube 316 may be curved so that the handle 314 is oriented at an angle (as opposed to linear) relative to the operative corridor. This allows for improved visualization of the surgical target site by the surgeon as the rod is being inserted. The rod holder 318 is formed in the distal end of the housing tube 316. The rod holder 318 includes a rod cavity 324 and a locking element 326. The rod cavity 324 is configured to receive the post 246 of the spinal rod 114. The locking element 326 is positioned partially within the rod holder 318 and partially within the inner lumen of the housing tube 316, and is moveable from a first unlocked position to a second locked position. The locking element 326 includes a proximal recess 328, a spring element 330, and a distal lip 332. The proximal recess 328 is configured to receive the distal end of the ball linkage 322. The spring element 330 helps to bias the locking element 326 in a distal direction. The distal lip 332 is configured to be seated within the recess 248 of the spinal rod 114 such that when the rod inserter 312 is in the locked position, the spinal rod 114 is secured within the rod cavity 324 and will not become dislodged therefrom.

The rod inserter 312 includes an attached driver 320 at the proximal end of the handle 314. The driver 320 includes a drive shaft 334, a driver handle 336, and a push button 338. The drive shaft 334 is partially threaded (and interacts with a partially threaded lumen inside the handle 314) such that rotating the driver handle 336 in a clockwise direction advances the drive shaft 334 in a distal direction, and rotating the driver handle 336 in a counterclockwise direction retreats the drive shaft 334 in a proximal direction. The distal end of the drive shaft 334 abuts with the ball linkage 322, and thus distal advancement of the drive shaft 334 causes distal advancement of the ball linkage 322. The ball linkage is a series of spheres abutting one another that extend between the distal end of the drive shaft 334 and the proximal recess 328 of the locking element 326. Further advancement of the drive shaft 334 will then cause the locking element 326 to engage the spinal rod 112 and lock it within the rod holder 318. Thus, the ball linkage 322 enables direct control of the locking element 326 even though the housing tube 316 is curved. The push button 338 provides an internal stop which allows the user to loosen the rod slightly (while still retaining the rod) which allows for a slight adjustment in the angle (for example ±15°) for easier final seating of the rod 114 within the pedicle screw 112.

In use, the rod inserter 312 is initially provided without the spinal rod 114 and the rod holder 318 in an unlocked position. The spinal rod 114 is then mated with the rod holder 318 by inserting the post 246 into the rod cavity 324 such that the recess 248 is facing the locking element 326. The driver handle 336 is rotated in a clockwise direction, which as described above advances the locking element 326 in a distal direction until the distal lip 332 of the locking element 326 is seated within the recess 248. At this point the spinal rod 114 is secured to the rod inserter 312. The rod 114 may be advanced through the operative corridor using a guide assembly such as the guide assembly 116 (or any of the other examples) described above. During final seating of the rod 114 within the pedicle screw 112, it may become desirable to have a slight variation of the angle of insertion. This may be accomplished by pressing the push button 338, which loosens the rod 114 slightly (while still retaining the rod) which allows for a slight adjustment in the angle (for example ±15°). Once the rod 114 is seated within the pedicle screw 112 and secured as described above (and below), the rod 114 is ready to be detached from the rod inserter 312. To accomplish this, the driver handle 336 is turned counterclockwise to translate the locking element 326 in a distal direction, which removes the distal lip 332 from the recess 248 and unlocks the rod 114. The rod inserter 312 may then be safely removed from the surgical target site through the operative corridor.

FIGS. 64-70 illustrate a reduction instrument 117 according to one example embodiment of the spinal fixation system 110. Generally, the reduction instrument 117 is used to fully seat ("reduce") the spinal rod 114 into the pedicle screw 112 and thereafter insert a lock screw 119 to secure the rod 114 to the screw 112. The reduction instrument 117 is configured for use with any of the guide assemblies described above (e.g. 18, 116, 188, 224), however for the purpose of illustration the reduction instrument 117 will be described in use with the guide assembly 116 shown and described in relation to FIG. 21 et seq. The reduction instrument 117 includes a connector 340 that releasably couples the reduction instrument 117 to the guide assembly 116 (via the cap 128). The connector 340 has a guide cavity 342 into which the proximal end 122 of the outer sleeve 118 (featuring the cap 128) is received. The proximal end 122 is keyed to the guide cavity 342 so as to prevent rotation of the guide assembly 116 relative to the reduction instrument 117. Spring locks 344 on the connector 340 are provided to prevent translation of the guide cap 128 and attached guide assembly 116 relative to the reduction instrument 117. Specifically, the spring locks 344 include ridges 346 that extend through the connector 340 into the guide cavity 342 and engage the circumferential groove 130 situated below the proximal end 122 when the guide assembly 116 is mated with the reduction tool 117. The ridges 346 allow the proximal end 122 of the guide assembly 116 to push past the spring locks 344 until the ridges 346 snap into place within the circumferential groove 130. To release the connection between the reduction instrument 117 and the guide assembly 116, the proximal ends of the spring locks 344 can be depressed causing the ridges 346 to lift out of the circumferential groove 130, thus allowing the removal of the connector 128 from the guide cavity 342.

The reduction instrument 117 has an elongated central shaft 348 extending longitudinally through the entire length of reduction instrument 117. The reduction instrument 117 further includes a rotation handle 352, a translation handle 354, a threaded shaft 358, a spring 362, an inner sleeve 364, and an outer sleeve 366. The central shaft 348 has a proximal portion 349, a distal portion 350, and a block portion 351 that is situated between the proximal portion 349 and the distal portion 350. The proximal portion 349 is generally cylindrical and extends proximally from the block portion 351 through the threaded shaft 358, translation handle 354, and rotation handle 352. The distal portion 350 is generally cylindrical (with a greater diameter than the proximal portion 349) and extends distally from the block portion 351. The rotation handle 352 extends through the translation handle 354 and has a proximal knob 353 configured for manipulation by a user. The rotation handle is fixedly attached to the central shaft 348, and thus rotation of the rotation handle causes rotation of the central shaft 348. The rotation handle 352 may be provided with band markers 355 spaced apart at a specific distance (e.g. 10 mm) to indicate the amount of reduction. The translation handle 354 has a threaded aperture 356 that is dimensioned to receive the proximal end of the threaded shaft 358. The translation handle 354 is rotatable in both clockwise and counterclockwise directions. As will be explained, turning the translation handle 354 in a clockwise direction ultimately advances the central shaft 348 and reduces the spinal rod 114 into the pedicle screw 112. As will be explained, the rotation handle 352 rotates independently of the translation handle 354 in both a clockwise and counterclockwise direction, and turning the rotation handle 352 in a clockwise direction advances the lock screw 119 into the housing 172 of the pedicle screw 112.

Figure 64:
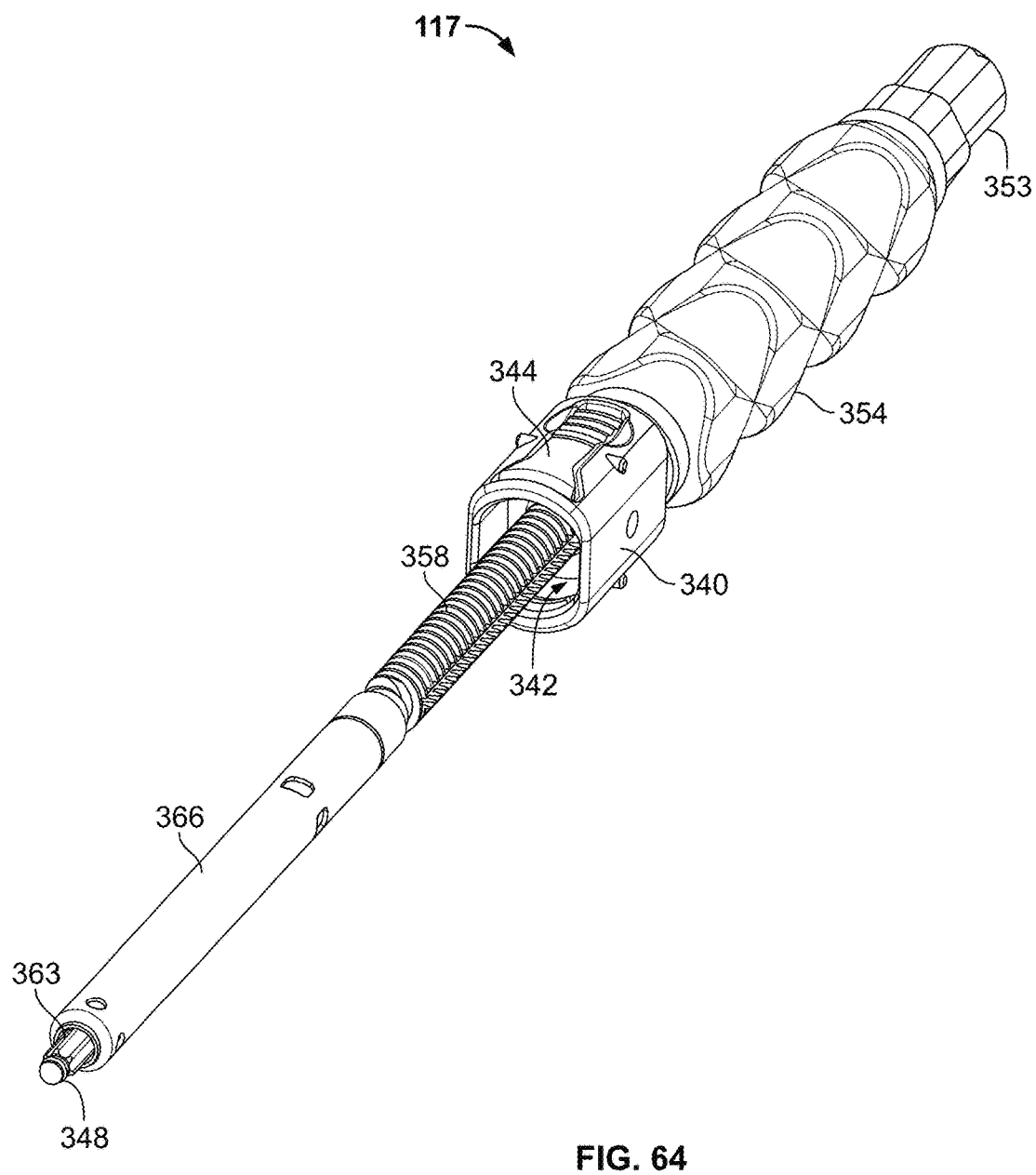
FIGS. 64-65 are perspective views of one example of a reduction instrument configured for use with the spinal fixation system of FIG. 19.
Figure 65:
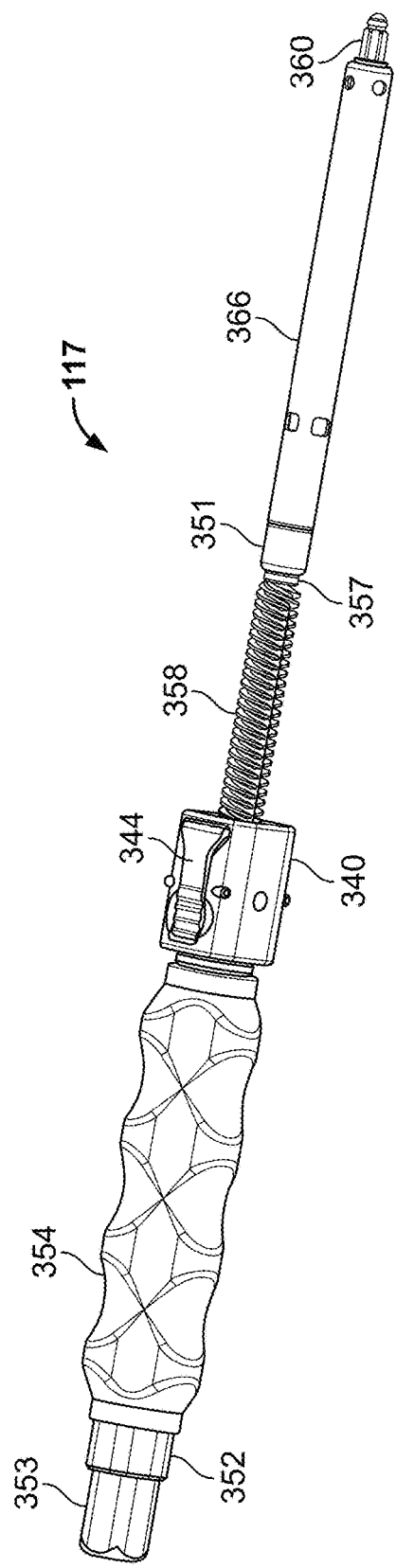
Figure 74:
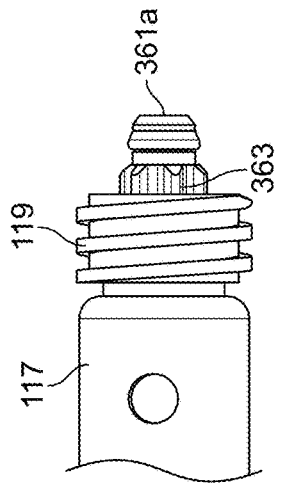
FIGS. 73-74 are perspective and plan views, respectively, of the reduction instrument of FIG. 71 coupled with a lock screw of FIG. 66.
Figure 73:
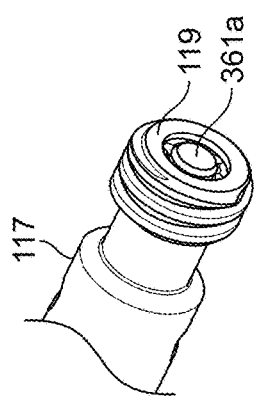

The threaded shaft 358 is mated at its proximal end with the threaded aperture 356 of the translation handle 354 and engages with the central shaft 348 at the proximal side of the block portion 351. An abutment insert 357 is positioned proximally of the block portion 351 and provides an abutment surface for the threaded shaft 358. Rotation of the translation handle 354 causes the threaded shaft 358 to translate up or down through the threaded aperture 356, translating the central shaft 348 and rotation handle 352 up or down with it. The distal portion 350 of the central shaft 348 extends distally from the block portion 351. The distal portion 350 extends through a spring 362 and an inner sleeve 364. The spring 362 is positioned just distally of the block portion 351, between the block portion 351 and the inner sleeve 364. The spring 362 and inner sleeve 364 are contained within an outer sleeve 366. The distal portion 350 of the central shaft 348 has a distal rounded reduction end 361 that is configured to engage the spinal rod 114 and reduce it into the housing 172. Alternatively, the distal reduction end 361 may be a generally planar rather than rounded (for example, FIGS. 71-74 illustrate a reduction instrument 117 with a generally planar reduction end 361a). A snap ring 368 is positioned within a recess 370 formed just proximally of the distal rounded reduction end 361. The snap ring 368 is sized and configured to prohibit passage of the lock screw 119 until the spinal rod 114 is fully reduced into the housing 172 and an appropriate distal force is applied to the lock screw 119 by the inner shaft (as will be explained below). A lock screw engagement feature 363 is provided on the distal portion 350 just proximally of the recess 370. The lock screw engagement feature 363 is configured to temporarily hold a lock screw 119 while preventing rotation of the lock screw 119 relative to the central shaft 348. By way of example only, the lock screw engagement feature 363 may have a hexalobe shape as shown in FIGS. 64 and 74, however other shapes that prevent rotation of the lock screw 119 relative to the central shaft 348 are possible. One or more windows 372 may be formed in the outer sleeve 366 near the top of the inner sleeve 364. The windows 372 may provide a visual indication (for example, a color coded indication) of when the rod 114 is fully reduced and the lock screw 119 is in position at the top of the housing 172 awaiting engagement.

The lock screw 119 has a central aperture 374 configured to allow passage of the distal portion 350 of the central shaft 348 therethrough. The central aperture 374 has a shape complimentary to the lock screw engagement feature 363 of the central shaft 348. By way of example only, that shape is hexalobe, however other shapes are possible. The lock screw 119 also has a guide and advancement feature 376 such as by way of example, a helically wound flange feature disposed on the outer circumference of the lock screw 119. The guide and advancement feature 376 mates with a complementary locking cap guide and advancement feature 180 on the housing 172. The lock screw 119 engages the housing 172 via the complementary guide and advancement features 180, 376 to press and lock the fixation rod 114 into the housing 172.

In use, once the pedicle screws 112 have been properly seated and a rod 114 introduced, the reduction instrument 117 is engaged to a guide assembly 116 as previously described. At least one lock screw 119 is attached to the lock screw engagement feature 363 of the central shaft 348. The translation handle 354 is operated in a clockwise direction to advance the central shaft 348 in a distal direction such that the distal engagement end 361 contacts the spinal rod 114. At some point during this advancement, the lock screw 119 will come into contact with the top of the housing 172. However, because the central shaft 348 (and thus the set screw) is not rotating at this point, the set screw does not engage the guide and advancement feature and advance into housing 172. However, the block portion 351 of the central shaft 348 continues to translate distally, advancing the engagement end 361 through the central aperture 374 of the lock screw 119 while the lock screw 119 remains stationary atop the housing 172. The inner sleeve 364, which abuts the lock screw 119 and extends proximally therefrom also remains stationary during this time. Spring 362 allows this movement the of the engagement end 351 relative to the lock screw 119. The spring 362, which is positioned between the block portion 351 and the inner sleeve 364, compresses due to the transfer of translational energy from the block portion 351 to the spring 362. This continues until the spinal rod 114 is fully reduced within the housing 172 of the pedicle screw 114, which may be indicated with a marker on the rotation handle (e.g. a green band near the top of the rotation handle that becomes hidden within the translation handle when the rod is fully reduced—not shown). For example, the rod 114 may be fully reduced just before the rod bottoms out in the housing 172. This prevents excessive loads on the reducer from over reduction. Though not shown, a stop may be provided to ensure reduction stops just prior to bottoming out. By way of example, the proximal end of the threaded shaft 358 may have a larger diameter than the threaded aperture 356 such that the proximal end can't pass out of the translation handle, thereby stopping translation of the threaded shaft. At this point the lock screw 119 is in position at top of the housing 172 of the pedicle screw 112, but the complementary guide and advancement features 180, 376 are not yet engaged. To do so, the rotation handle 352 may be briefly rotated in a clockwise or counterclockwise direction to align the guide and advancement features on the lock screw 119 and housing 172. Though not necessarily, an audible "click" may be heard, indicating that the guide and advancement features 180, 376 have initially mated and are ready for full installation. The rotation handle 352 is then rotated in a clockwise direction. The engagement of the guide and advancement features 180, 376 combined with the release of the energy contained in the compressed spring push the lock screw 119 down the central shaft 348 and into the housing 172. When the lock screw 119 is fully seated, the rotation handle 354 will cease to rotate. To effect removal of the reduction instrument 117, the translation handle 354 is briefly turned counterclockwise (e.g. 10 mm) to back off reduction. The spring locks 344 are disengaged as described above and the reduction instrument 117 may be removed from the operative corridor.

Figure 75:
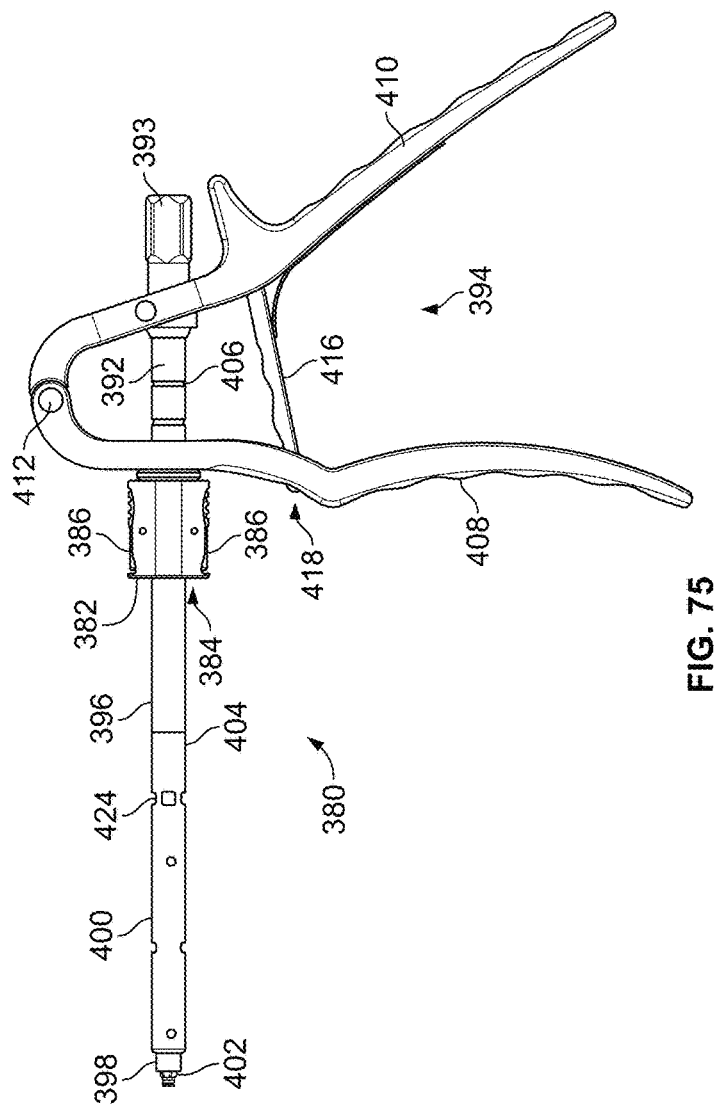
FIGS. 75-77 are plan views of another example of a reduction instrument configured for use with the spinal fixation system of FIG. 19.
Figure 76:
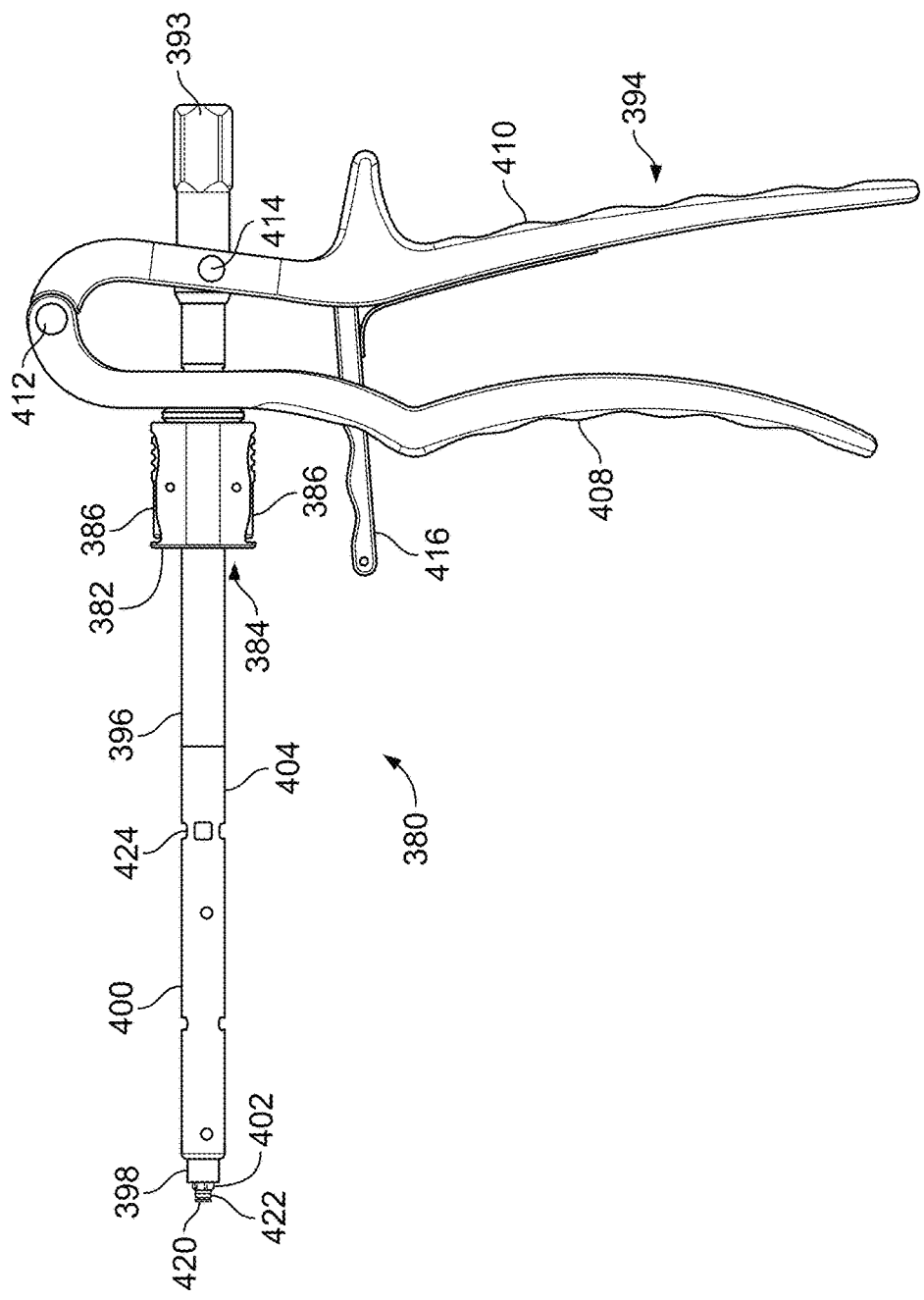
Figure 77:
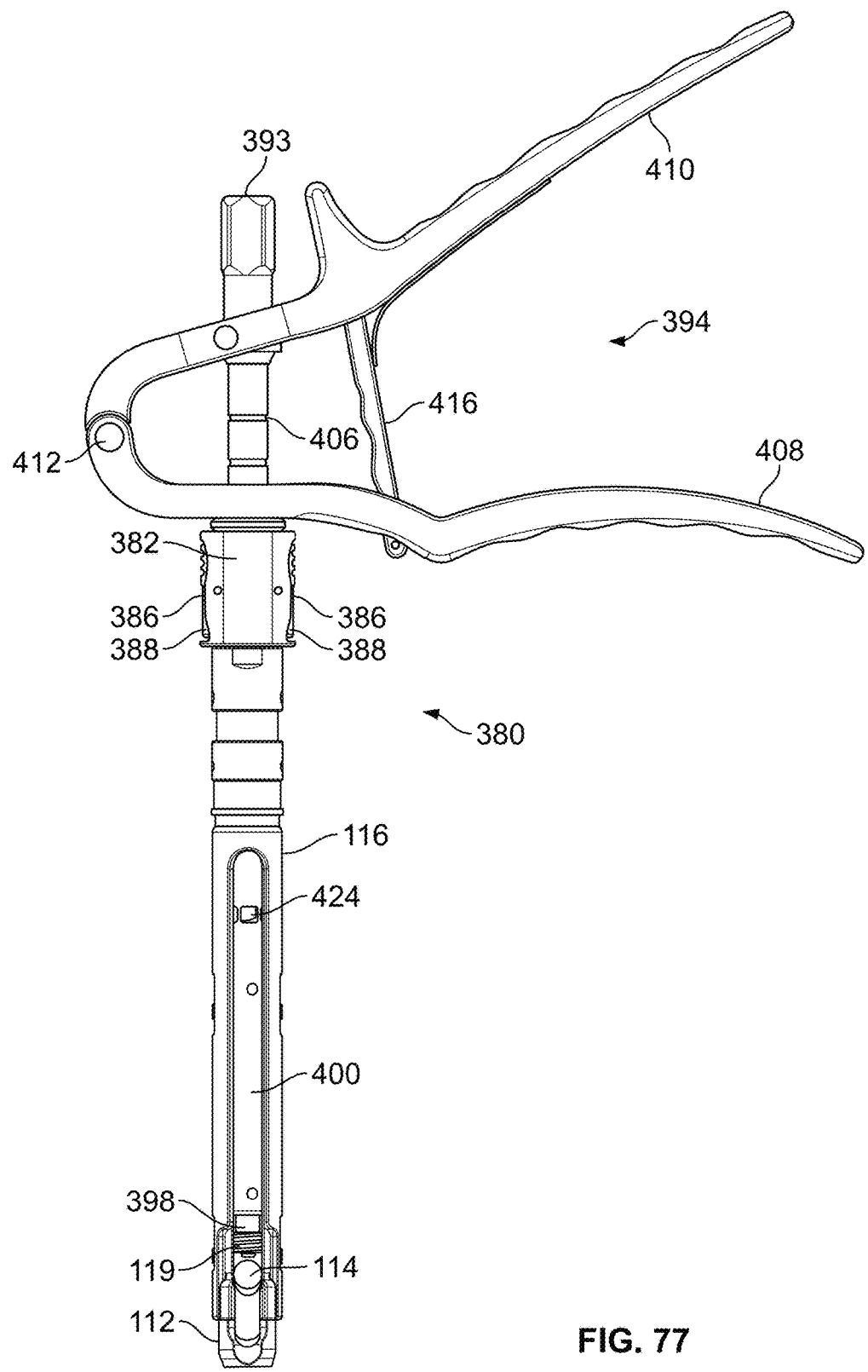
Figure 78:
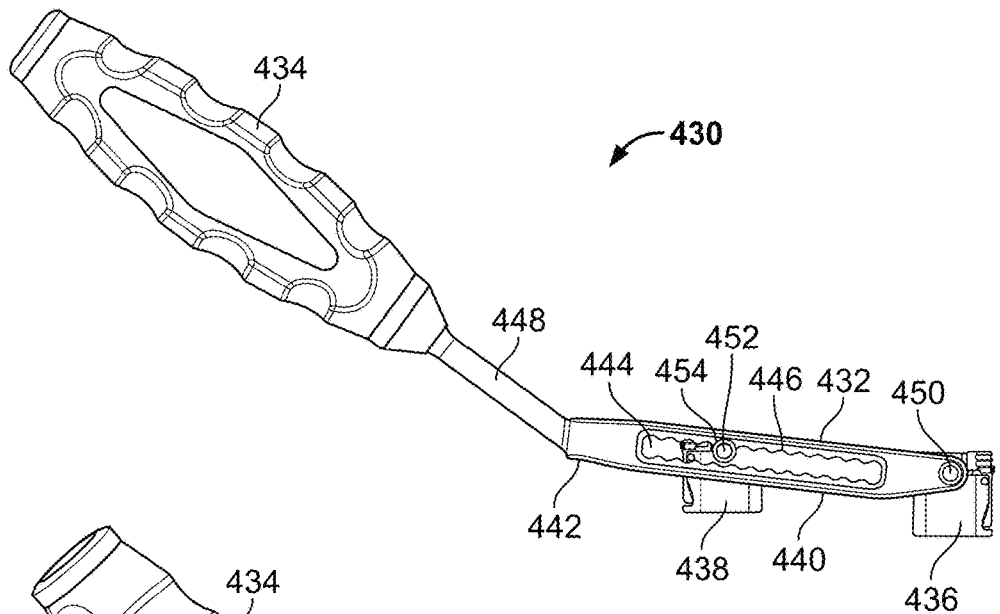
FIGS. 78-79 are plan and perspective views, respectively, of yet another example of a reduction instrument configured for use with the spinal fixation system of FIG. 19.
Figure 79:
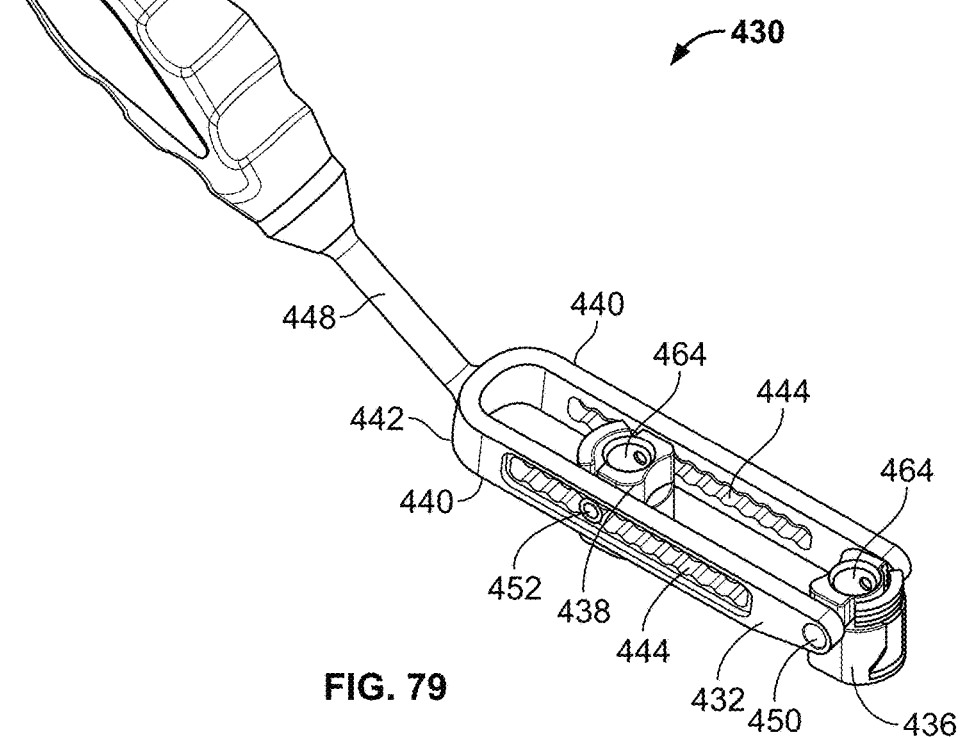
Figure 80:
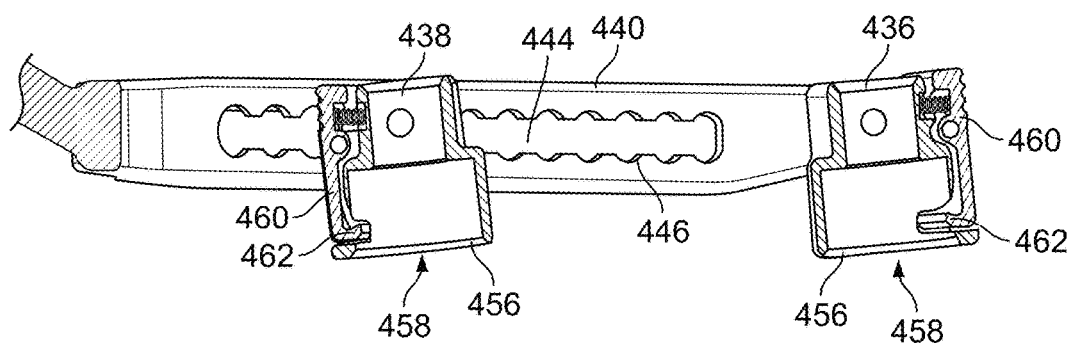
FIG. 80 is a plan view of the distal end of the reduction instrument of FIG. 78.
Figure 81:
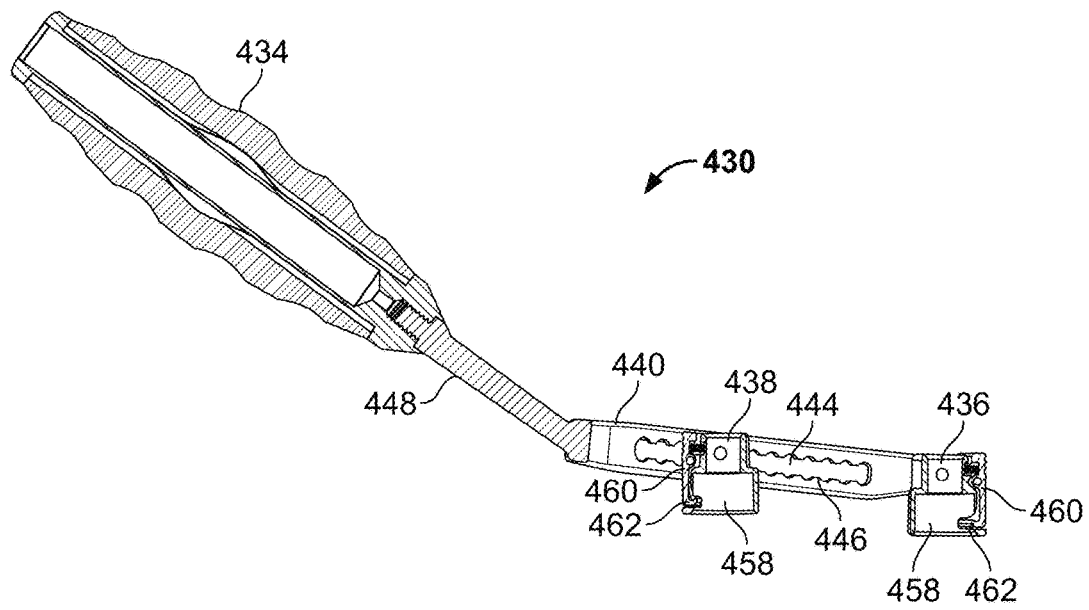
FIG. 81 is a sectional view of the reduction instrument of FIG. 78.
Figure 84:
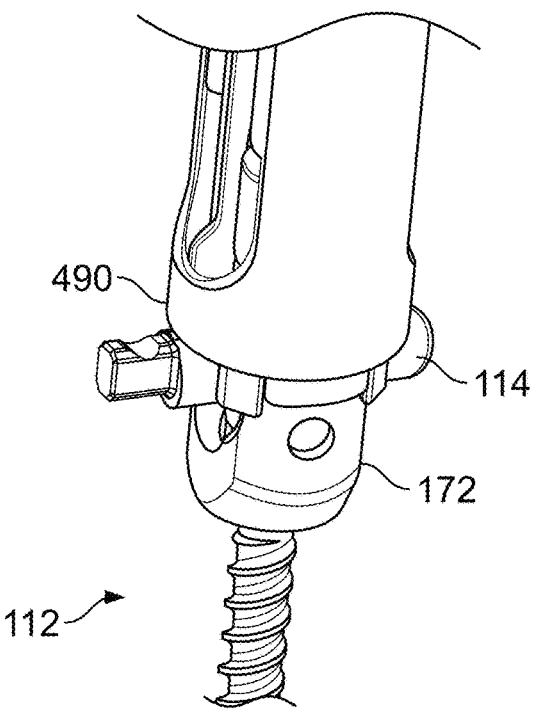
FIGS. 84-85 are perspective and sectional views, respectively, of the distal end of the reduction instrument and pedicle screw combination of FIG. 83 shown during reduction of a spinal rod.
Figure 85:
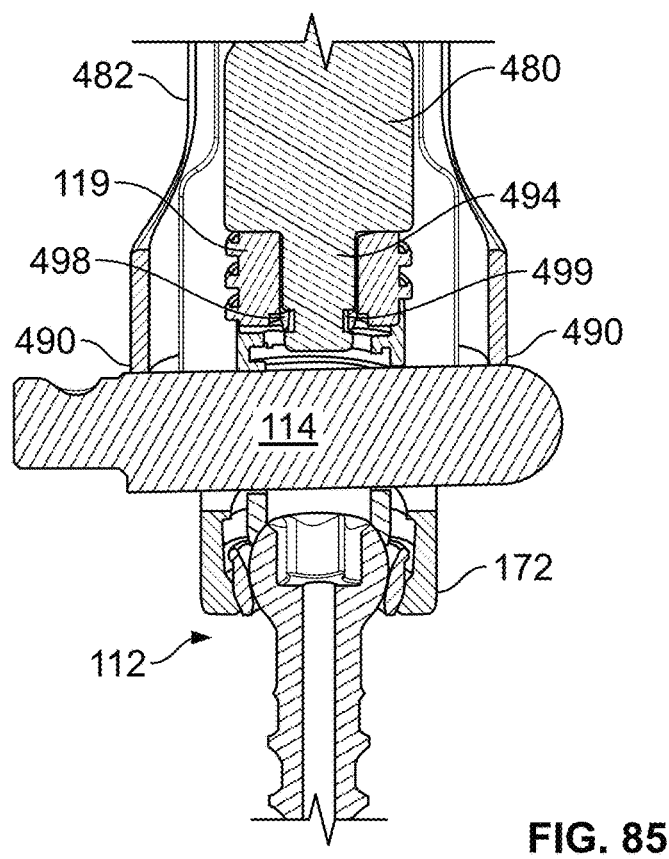

FIGS. 75-77 illustrate a reduction instrument 380 according to another example embodiment of the spinal fixation system 110. Generally, the reduction instrument 380 is used to fully seat ("reduce") the spinal rod 114 into the pedicle screw 112 and thereafter insert a lock screw 119 to secure the rod 114 to the screw 112. The reduction instrument 380 is configured for use with any of the guide assemblies described above (e.g. 18, 116, 188, 224), however for the purpose of illustration the reduction instrument 380 will be described in use with the guide assembly 116 shown and described in relation to FIG. 21 et seq. The reduction instrument 380 differs from the reduction instrument 117 previously described in that the reduction instrument 380 uses a "pistol grip" mechanism to cause translation of the central shaft 390 to reduce the rod 114. All other features are identical and it is to be understood that any feature previously described with respect to the reduction instrument 117 may be provided on the reduction instrument 380 without departing from the scope of the present invention. The reduction instrument 380 includes a connector 382 that releasably couples the reduction instrument 380 to the guide assembly 116 (via the cap 128). The connector 382 has a guide cavity 384 into which the proximal end 122 of the outer sleeve 118 (featuring the cap 128) is received. The proximal end 122 is keyed to the guide cavity 384 so as to prevent rotation of the guide assembly 116 relative to the reduction instrument 380. Spring locks 386 on the connector 382 are provided to prevent translation of the guide cap 128 and attached guide assembly 116 relative to the reduction instrument 380. Specifically, the spring locks 386 include ridges 388 that extend through the connector 382 into the guide cavity 384 and engage the circumferential groove 130 situated below the proximal end 122 when the guide assembly 116 is mated with the reduction tool 380. The ridges 388 allow the proximal end 122 of the guide assembly 116 to push past the spring locks 386 until the ridges 388 snap into place within the circumferential groove 130. To release the connection between the reduction instrument 380 and the guide assembly 116, the proximal ends of the spring locks 386 can be depressed causing the ridges 388 to lift out of the circumferential groove 130, thus allowing the removal of the connector 128 from the guide cavity 384.

The reduction instrument 380 has an elongated central shaft 390 extending longitudinally through the entire length of reduction instrument 380. The reduction instrument 380 further includes a rotation handle 392, a translation handle 394, a translation shaft 396, a spring (not pictured), an inner sleeve 398, and an outer sleeve 400. The central shaft 390 has a proximal portion (not shown), a distal portion 402, and a block portion 404 that is situated between the proximal portion and the distal portion 402. The proximal portion is generally cylindrical and extends proximally from the block portion 404 through the translation shaft 396 and rotation handle 392. The distal portion 402 is generally cylindrical (with a greater diameter than the proximal portion) and extends distally from the block portion 404. The rotation handle 392 extends through the translation handle 394 and has a proximal knob 393 configured for manipulation by a user. The rotation handle is fixedly attached to the central shaft 390, and thus rotation of the rotation handle causes rotation of the central shaft 390. The rotation handle 392 rotates independently of the translation handle 394 in both a clockwise and counterclockwise direction, and turning the rotation handle 392 in a clockwise direction advances the lock screw 119 into the housing 172 of the pedicle screw 112. The rotation handle 392 may be provided with band markers 406 spaced apart at a specific distance (e.g. 10 mm) to indicate the amount of reduction. The translation handle 394 is provided in the form of a "pistol grip" handle, and includes a stationary arm 408 joined with a pivot arm 410 at a first pivot point 412. The stationary arm 408 is fixedly connected to the top of the connector 382. The pivot arm 410 is connected to the stationary arm 408 at a first pivot point 412, which comprises the distal ends of both the stationary arm 408 and the pivot arm 410. The pivot arm 410 is also connected to the rotation handle 392 at a second pivot point 414, which causes advancement of the central shaft 390 when the pivot arm 410 is moved. A lock bar 416 is pivotably attached to the pivot arm 410 and is provided to maintain the translation handle 394 in a locked position when the rod is fully reduced. The lock bar 416 extends through an aperture 418 formed in the stationary handle 408. By way of example only, the lock par 416 may have a ratchet-type engagement with the aperture 418. Other locking engagements are possible.

The translation shaft 396 is mated at its proximal end with the rotation handle 392 and engages with the central shaft 390 at the proximal side of the block portion 404. The distal portion 402 of the central shaft 390 extends distally from the block portion 404. The distal portion 402 extends through a spring (not shown) and an inner sleeve 398. The spring is positioned just distally of the block portion 404, between the block portion 404 and the inner sleeve 398. The spring and inner sleeve 398 are contained within an outer sleeve 400.

The distal portion 402 of the central shaft 390 has a distal rounded reduction end 420 that is configured to engage the spinal rod 114 and reduce it into the housing 172. Alternatively, the distal reduction end 420 may be a generally planar rather than rounded (for example, FIGS. 71-74 illustrate a generally planar reduction end 361a). A snap ring 422 is positioned within a recess formed just proximally of the distal rounded reduction end 420. The snap ring 422 is sized and configured to prohibit passage of the lock screw 119 until the spinal rod 114 is fully seated in the housing 172 and an appropriate distal force is applied to the lock screw 119 by the inner shaft (as will be explained below). The distal portion 420 has a lock screw engagement feature as described above. One or more windows 424 may be formed in the outer sleeve 400 near the top of the inner sleeve 398. The windows 424 may provide a visual indication (for example, a color coded indication) of when the rod 114 is fully reduced and the lock screw 119 is in position at the top of the housing 172 awaiting engagement. Alternatively, the final band marker 406 may be positioned to disappear below the stationary handle 408 when the rod is fully reduced. The final band marker 406 may be colored (e.g. green) to aid visualization.

In use, once the pedicle screws 112 have been properly seated and a rod 114 introduced, the reduction instrument 380 is engaged to a guide assembly 116 as previously described. At least one lock screw 119 is attached to the lock screw engagement feature of the central shaft 390. The translation handle 394 is operated by squeezing the pivot arm 410, which advances the central shaft 390 in a distal direction such that the distal engagement end 420 contacts the spinal rod 114. At some point during this advancement, the lock screw 119 will come into contact with the top of the housing 172. However, because the central shaft 390 is not rotating at this point, the distal engagement end 420 continues to advance through the central aperture 374 of the lock screw 119 while the lock screw 119 remains stationary atop the housing 172. The inner sleeve 398, which abuts the lock screw 119 and extends proximally therefrom, consequently also remains stationary during this time as well. However, during this additional advancement (after the lock screw 119 has come into contact with the housing 172) the block portion 404 of the central shaft 390 continues to advance distally. The spring, which is positioned between the block portion 404 and the inner shaft 398, compresses due to the transfer of translational energy from the block portion 404 to the spring. This continues until the spinal rod 114 is fully reduced within the housing 172 of the pedicle screw 114. At this point the lock screw 119 is in position at top of the housing 172 of the pedicle screw 112, but the complementary guide and advancement features are not yet engaged. To do so, the rotation handle 352 may be briefly rotated in a clockwise or counterclockwise direction to align the guide and advancement features on the lock screw 119 and housing 172. Though not necessarily, an audible "click" may be heard, indicating that the guide and advancement features 180, 376 have initially mated and are ready for full installation. The rotation handle 352 is then rotated in a clockwise direction. The engagement of the guide and advancement features combined with the release of the energy contained in the compressed spring push the lock screw 119 down the central shaft 390 and into the housing 172. When the lock screw 119 is fully seated, the rotation handle 392 will cease to rotate. To effect removal of the reduction instrument 380, the translation handle 394 is briefly turned counterclockwise (e.g. 10 mm) to back off reduction. The spring locks 344 are disengaged as described above and the reduction instrument 380 may be removed from the operative corridor.

FIGS. 78-81 illustrate an example of an alternative reduction instrument 430 according to another embodiment of the spinal fixation 110. The reduction instrument 430 may preferably be used for reduction in a single-level construct. The reduction instrument 430 is configured for use with any of the guide assemblies described above (e.g. 18, 116, 188, 224), however for the purpose of illustration the reduction instrument 430 will be described in use with the guide assembly 116 shown and described in relation to FIG. 21 et seq. By way of example only, the reduction instrument 430 includes a body 432, a handle 434, a fixed attachment assembly 436, and a translating attachment assembly 438. The body 432 includes a pair of elongated racks 440 arranged parallel to one another and joined at a proximal end by a generally curved connector 442. The racks 440 each include a translation slot 444 configured to allow the translating attachment assembly 438 to translate freely in both the proximal and distal directions. Each translation slot 444 includes a plurality of rounded openings 446 configured to allow the translating attachment assembly 438 to rest easily in a single selected position without inhibiting the overall ability to translate. The handle 434 is connected to the curved connector 442 via a shaft 448.

The fixed attachment assembly 436 is positioned between the distal ends of each of the racks 440 and is pivotably attached to each rack 440 via a swivel pin 450. The translating attachment assembly 438 is positioned between the racks 440 and is capable of freely translating therealong. The translating attachment assembly 438 includes a swivel pin 452 extending therethrough and having circular ends 454 that engage the translation slots 444 and rest in the rounded openings 446. The fixed attachment assembly 436 and translating attachment assembly 438 each comprise a connector 456 that attaches to the guide assembly 116 (via the cap 128). The connector 456 has a guide cavity 458 into which the proximal end 122 of the outer sleeve 118 (featuring the cap 128) is received. The proximal end 122 is keyed to the guide cavity 458 so as to prevent rotation of the guide assembly 116 relative to the reduction instrument 430. Spring locks 460 on the connector 456 are provided to prevent translation of the guide cap 128 and attached guide assembly 116 relative to the reduction instrument 430. Specifically, the spring locks 460 include ridges 462 that extend through the connector 456 into the guide cavity 458 and engage the circumferential groove 130 situated below the proximal end 122 when the guide assembly 116 is mated with the reduction tool 430. The ridges 462 allow the proximal end 122 of the guide assembly 116 to push past the spring locks 460 until the ridges 462 snap into place within the circumferential groove 130. The connector 456 has a central aperture 464 formed there to allow passage of a lock screw driver (not shown). To release the connection between the reduction instrument 430 and the guide assembly 116, the proximal ends of the spring locks 460 can be depressed causing the ridges 462 to lift out of the circumferential groove 130, thus allowing the removal of the connector 128 from the guide cavity 458.

In use, once the pedicle screws 112 have been properly seated and a rod 114 introduced, the reduction instrument 430 is employed by attaching the fixed attachment assembly 436 to a first guide assembly 116 at a first vertebral level and attaching the translating attachment assembly 438 to a second guide assembly 116 on a adjacent vertebral level. The attachment assemblies are attached to the guide assemblies in the manner described above. The handle 434 is then pushed downward (e.g. toward the spine), causing the body 432 to pivot around the translating attachment assembly 438, thus lifting the fixed translation assembly 436. Thus the screw 112, guide 116, and ultimately vertebra are lifted upward (i.e. reduced) to the desired position. A lock screw 119 is introduced via a lock screw inserter (not shown) and attached to the housing 172 of the pedicle screw 112. The reduction instrument 430 can then be removed and the lock screw 119 tightened via a final tightening device (not shown).

FIGS. 82-85 illustrate another alternative reduction instrument 470 according to still another example embodiment of the spinal fixation system 110. Generally, the reduction instrument 470 is used to fully seat ("reduce") the spinal rod 114 into the pedicle screw 112 and thereafter insert a lock screw 119 to secure the rod 114 to the screw 112. The reduction instrument 470 is configured for use with any of the guide assemblies described above (e.g. 18, 116, 188, 224), however for the purpose of illustration the reduction instrument 470 will be described in use with the guide assembly 116 shown and described in relation to FIG. 21 et seq. The reduction instrument 470 includes a connector 472 that releasably couples the reduction instrument 470 to the guide assembly 116 (via the cap 128). The connector 472 has a guide cavity 474 into which the proximal end 122 of the outer sleeve 118 (featuring the cap 128) is received. The proximal end 122 is keyed to the guide cavity 474 so as to prevent rotation of the guide assembly 116 relative to the reduction instrument 470. Spring locks 476 on the connector 472 are provided to prevent translation of the guide cap 128 and attached guide assembly 116 relative to the reduction instrument 470. Specifically, the spring locks 476 include ridges (not shown, but identical to those described above) that extend through the connector 472 into the guide cavity 474 and engage the circumferential groove 130 situated below the proximal end 122 when the guide assembly 116 is mated with the reduction tool 470. The ridges allow the proximal end 122 of the guide assembly 116 to push past the spring locks 476 until the ridges snap into place within the circumferential groove 130. To release the connection between the reduction instrument 470 and the guide assembly 116, the proximal ends of the spring locks 476 can be depressed causing the ridges to lift out of the circumferential groove 130, thus allowing the removal of the connector 128 from the guide cavity 474.

The reduction instrument 470 includes a reduction assembly 478 and a lock screw inserter 480. The reduction assembly includes a reduction tube 482, a threaded shaft 484, and a reduction knob 486. The reduction tube 482 has a proximal end 488, a distal end 490, and a lumen extending through the reduction tube 482 from the proximal end 488 to the distal end 490. The lumen at proximal end 488 is threaded to threadedly engage the threaded shaft 484. The distal end 490 is configured to engage the spinal rod 114 in two points. The threaded shaft 484 is connected to the reduction knob 486 at its proximal end and the connector 472 at its distal end. The connection with the reduction knob 486 is fixed such that the rotation of the reduction knob 486 causes the threaded shaft 484 to rotate. The connection with the connector 472 is fixed axially but not fixed rotationally, such that the threaded shaft 484 freely rotates against the connector 472 without causing any rotation of the connector 472. The result of this interaction is that upon rotation of the reduction knob 486 (and threaded shaft 484), the reduction tube 482 translates in a distal direction relative to the connector 472 (and attached guide assembly 116). The distal end 490 will engage a spinal rod 114 placed within the guide assembly 116 (as described above) and reduce the spinal rod 114 into the pedicle screw 112.

Figure 66:
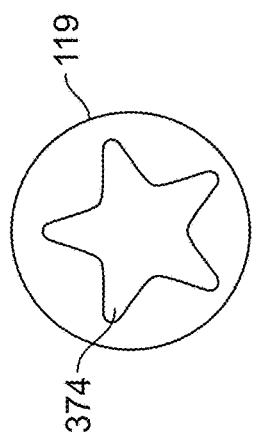
FIG. 66 is a top plan view of an example of a lock screw forming part of the spinal fixation system of FIG. 19.
Figure 69:
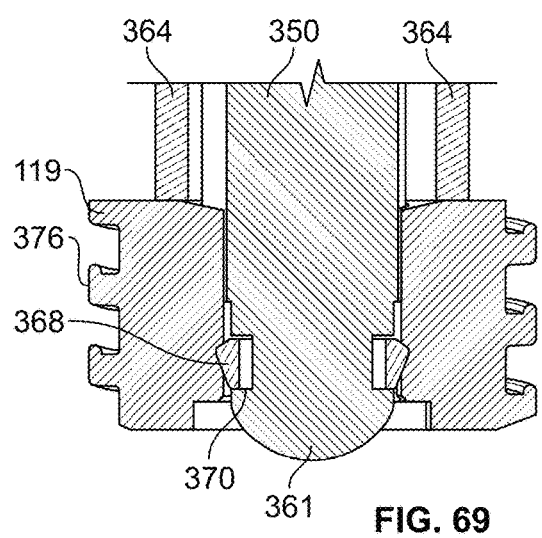
FIG. 69 is a sectional view of the distal end of the reduction instrument of FIG. 64 coupled with the lock screw of FIG. 66.
Figure 70:
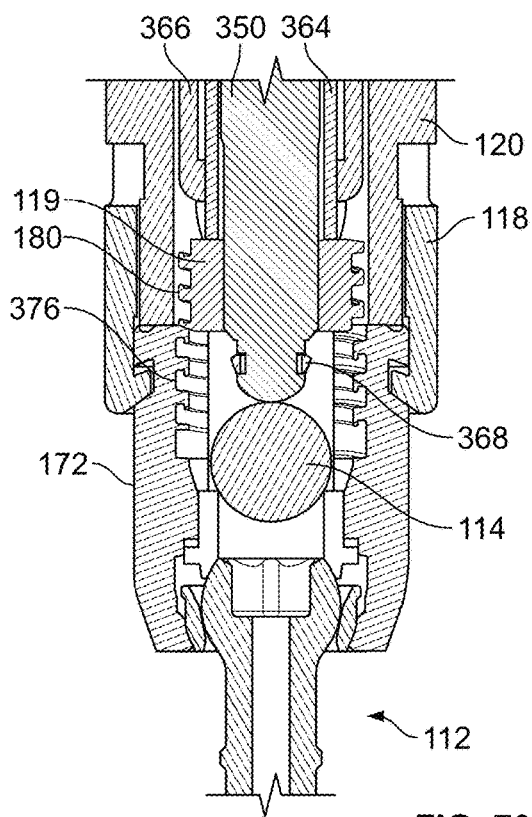
FIG. 70 is a sectional view of the reduction instrument and lock screw of FIG. 69 in combination with the guide assembly and pedicle screw of FIG. 68 upon reduction of the spinal rod and before engagement of the lock screw to the tulip.
Figure 71:
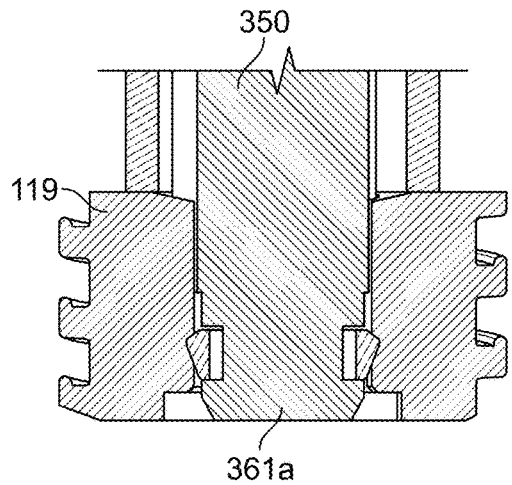
FIGS. 71-72 are sectional views of the distal end of another example of a reduction instrument configured for use with the spinal fixation system of FIG. 19, shown coupled with a lock screw of FIG. 66.
Figure 72:
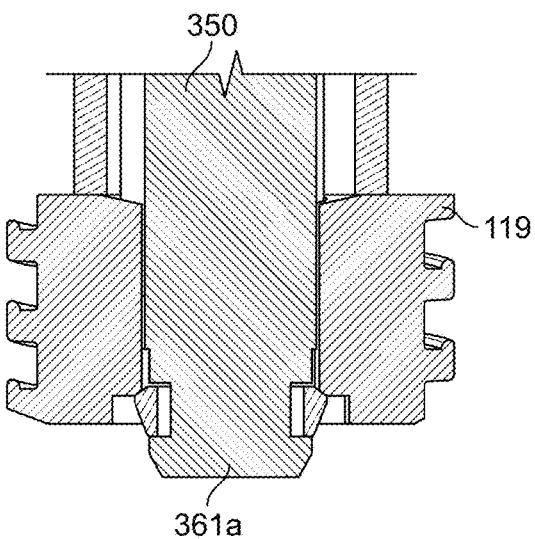

The lock screw inserter 480 extends through the reduction assembly 478 lock screw knob 492, a distal engagement post 494, and an elongated shaft 496 extending between the lock screw knob 492 and distal engagement post 494. The distal engagement post 494 is configured to receive a lock screw 119. By way of example only, the distal engagement post 494 has a hexalobe configuration that is complementary to the aperture 374 of the lock screw 119 (FIG. 66). The distal engagement post 494 further includes a snap ring 498 positioned within a recess 499. The snap ring 498 prevents premature ejection of the lock screw 119 during the implantation process.

In use, once the pedicle screws 112 have been properly seated and a rod 114 introduced, the reduction instrument 470 is engaged to a guide assembly 116 as previously described. At least one lock screw 119 is attached to the distal engagement post 494 of the lock screw inserter 480. The reduction knob 486 is operated in a clockwise direction (using an appropriate attachment device) to advance the reduction tube 482 in a distal direction such that the distal engagement end 490 contacts the spinal rod 114. Operation of the reduction knob 486 is continued until the rod is fully reduced and seated within the housing 172 of the pedicle screw 112. At this point the lock screw 119 is in position at top of the housing 172 of the pedicle screw 112, but the complementary guide and advancement features are not yet engaged. To do so, the lock screw knob 492 may be briefly rotated in a clockwise or counterclockwise direction until an audible "click" is heard, indicating that the guide and advancement features have initially mated and are ready for full installation. The lock screw knob 492 is then rotated in a clockwise direction and the lock screw 119 is introduced into the housing 172. When the lock screw 119 is fully seated, the lock screw knob 492 will cease to rotate. To effect removal of the reduction instrument 470, the reduction knob 486 is briefly turned counterclockwise (e.g. 10 mm) to back off reduction. The spring locks 476 are disengaged as described above and the reduction instrument 470 may be removed from the operative corridor.

Figure 86:
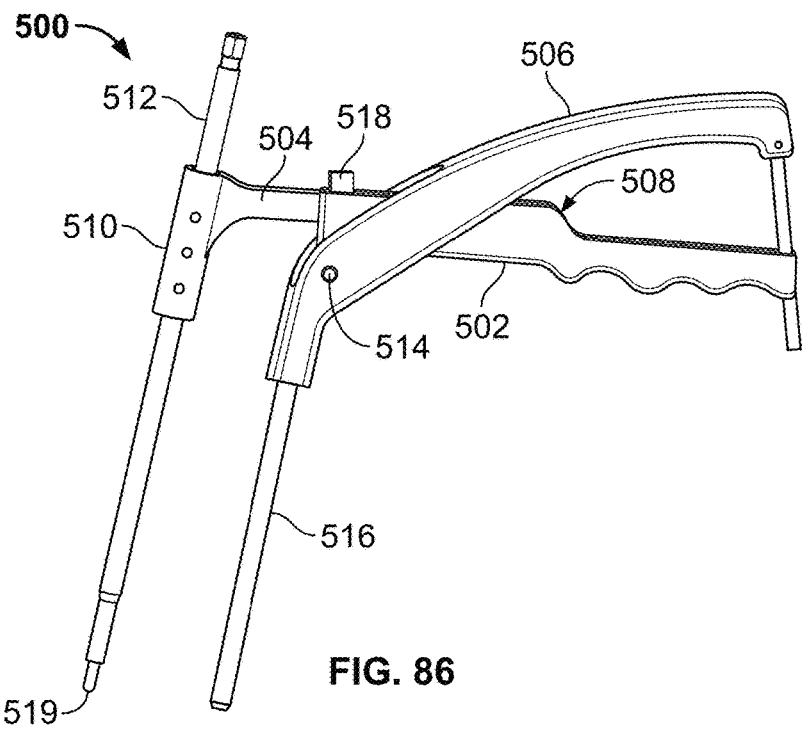
FIG. 86 is an example of a compression instrument configured for use with the spinal fixation system of FIG. 19.

FIG. 86 illustrates an example of a compression instrument 500 configured for use with the spinal fixation system 110 according to one embodiment of the present invention. By way of example only, the compression instrument 500 is a fulcrum pistol grip compressor with a main body 502, a rack 504, and a handle 506. The main body 502 includes a track 508 configured to receive the rack 504 and allow translation therein. The rack 504 is an elongated body configured to be received within the track 508. The distal end of the rack 504 includes a tubular shaft 510 oriented generally orthogonally relative to the rack 504. A lock screw driver 512 extends through the tubular shaft 510 and is configured to be mated with a lock screw 119. The handle 506 is pivotably attached to the main body 502 via a pivot 514. A handle shaft 516 extends from the distal end of the handle 506 and is configured to be received within a guide assembly 116. The lock screw driver 512 and handle shaft 516 are oriented in a generally parallel manner relative to one another. A push button 518 is provided on the distal end of the main body 502 and is configured to release the rack 504 when activated.

The compression instrument 500 may be used when at least one vertebral level to be fixed is in need of compression. Prior to using the compression instrument 500, the pedicle screws 112 are put in place and a spinal rod 114 is seated therein. At one vertebral level, the spinal rod 114 is fully reduced and the lock screw 119 is secured to the pedicle screw. A first guide assembly 116 is attached to the pedicle screw at this first level. At the adjacent level to be compressed, the spinal rod 114 is fully reduced and the lock screw 119 is applied to the pedicle screw but not finally tightened. A second guide assembly 116 is attached to the pedicle screw 112 at this second level. To use the compression instrument 500, the handle shaft 516 is inserted into the first guide assembly 116 and the lock screw driver 512 is inserted into the second guide assembly 116 such that the distal end 519 of the lock screw driver 512 engages the lock screw 119. During this insertion, the push button 518 is depressed so that the rack 504 can move freely within the main body 502. This ensures proper alignment of the lock screw driver 512 and the guide assembly 116, and engagement with the lock screw 119. When proper alignment is achieved the push button 518 is released. The user then squeezes the handle 506, which compresses the vertebra by driving the first and second guide assemblies 116 (and attached screws and vertebrae) toward one another. Once the desired compression is achieved, the second lock screw 119 is tightened using the lock screw driver 512.

Figure 87:
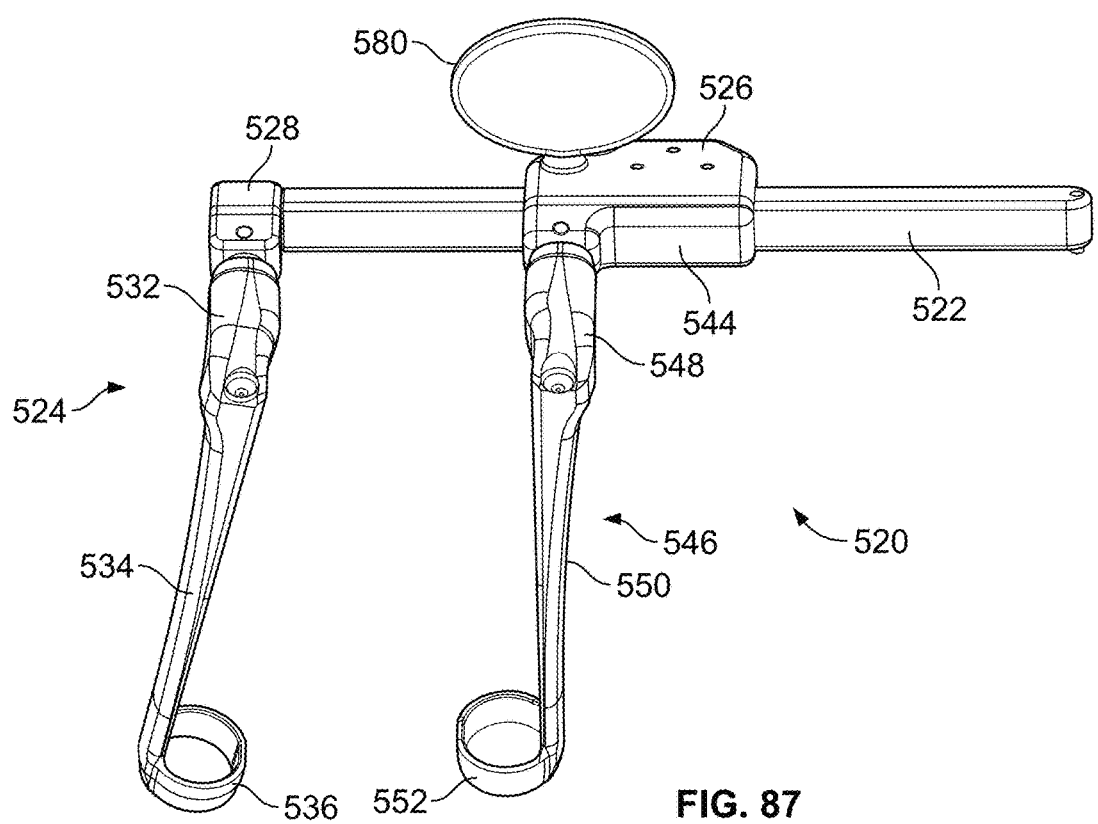
FIGS. 87-88 are perspective views of another example of a compression instrument configured for use with the spinal fixation system of FIG. 19.
Figure 88:
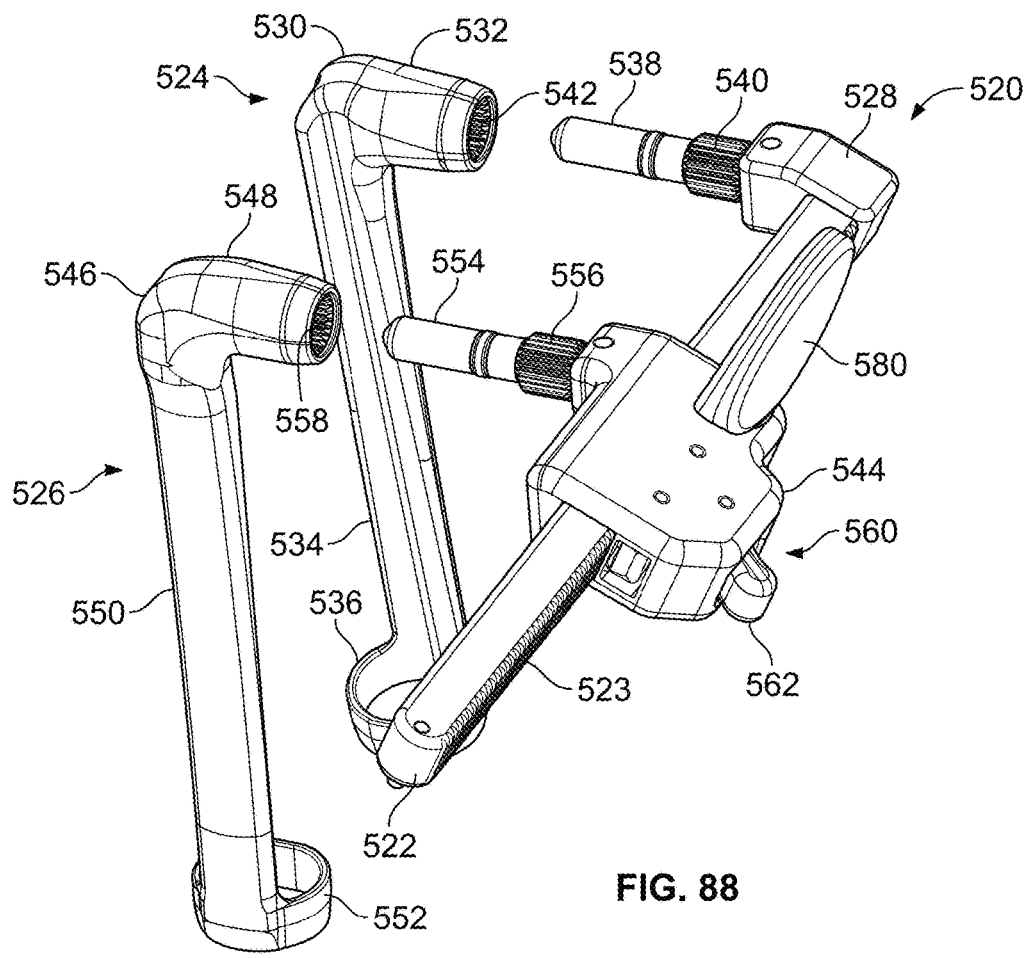
Figure 89:
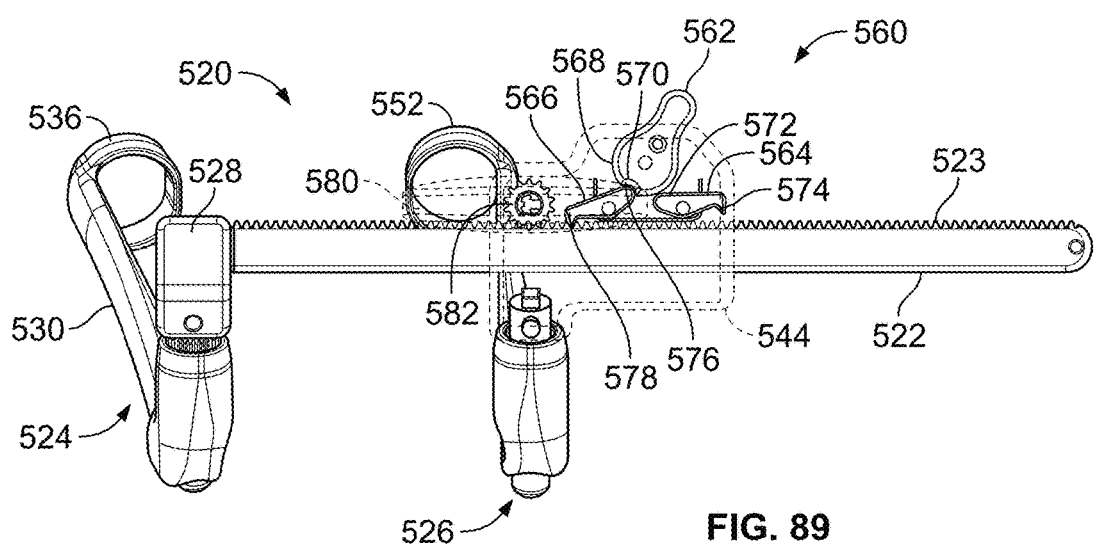
FIG. 89 is a top view of the compression instrument of FIG. 87.
Figure 90:
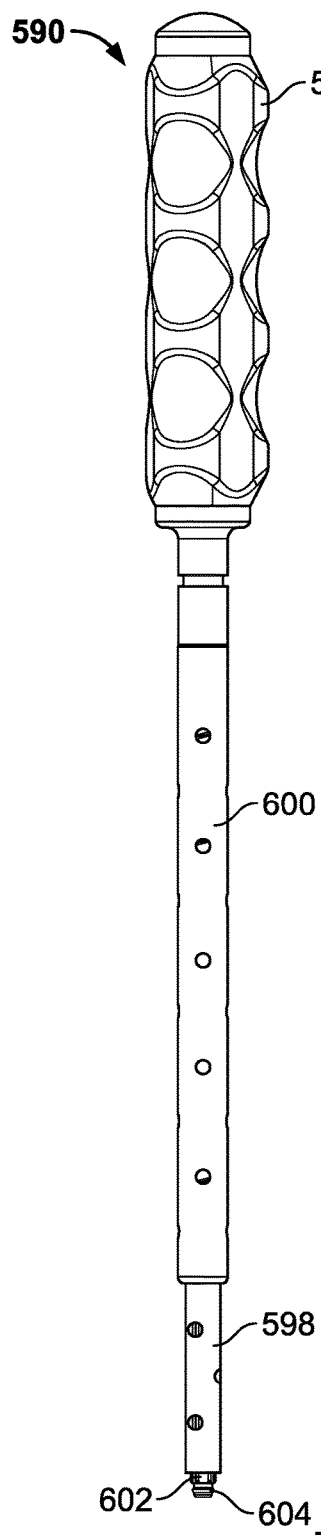
FIG. 90 is a plan view of an example of a multi-load lock screw inserter configured for use with the spinal fixation system of FIG. 19.
Figure 91:
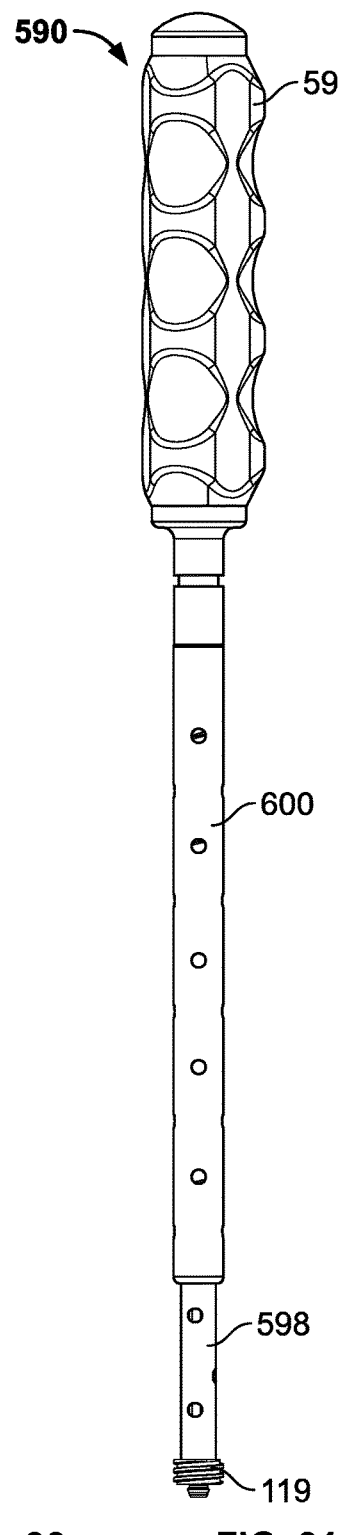
FIGS. 91-93 are plan views of the lock screw inserter of FIG. 90 coupled to various numbers of lock screws.
Figure 92:
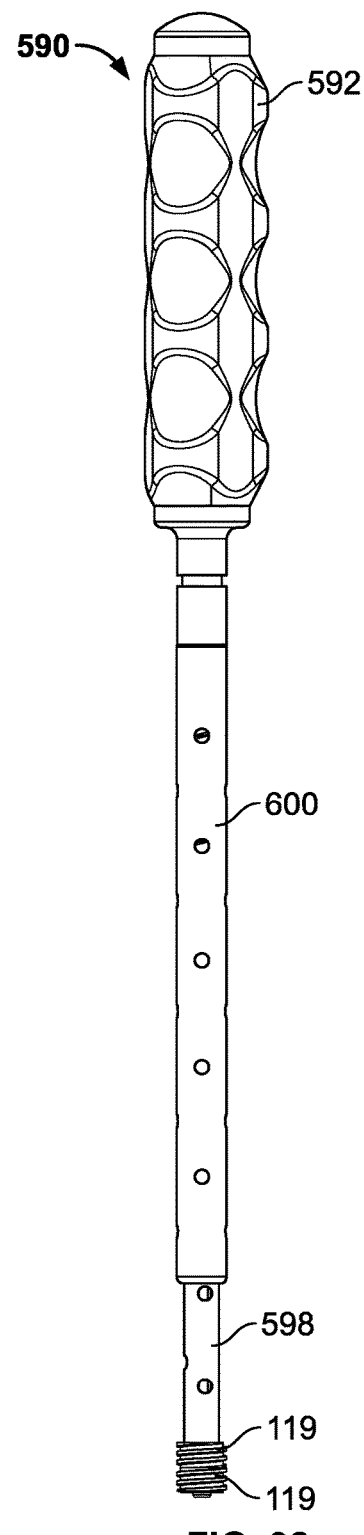
Figure 93:
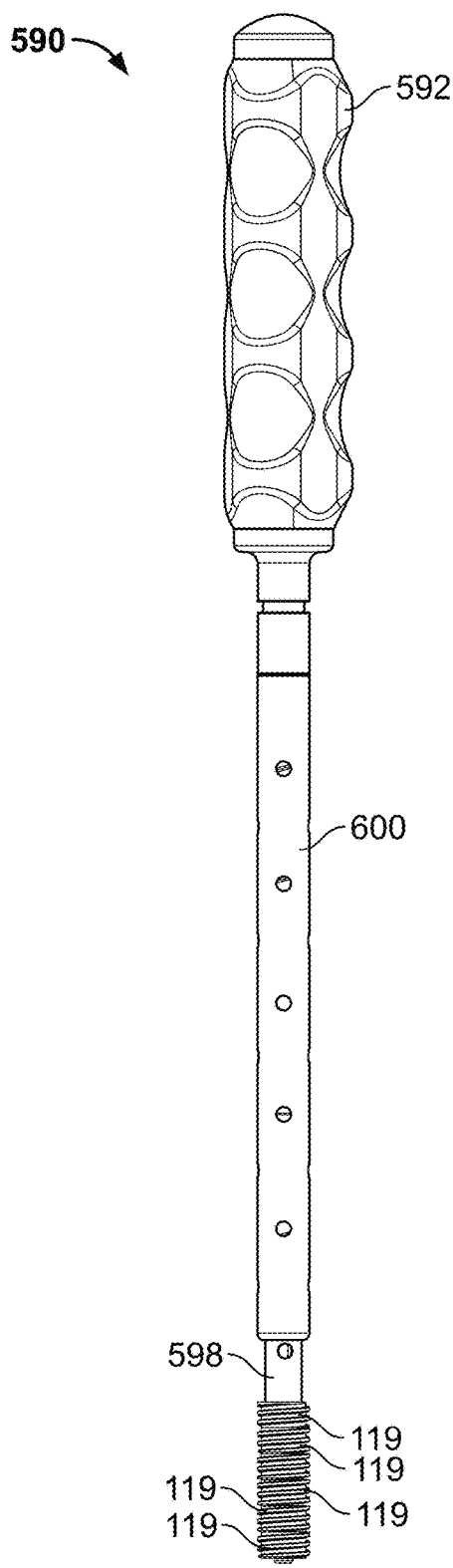
Figure 94:
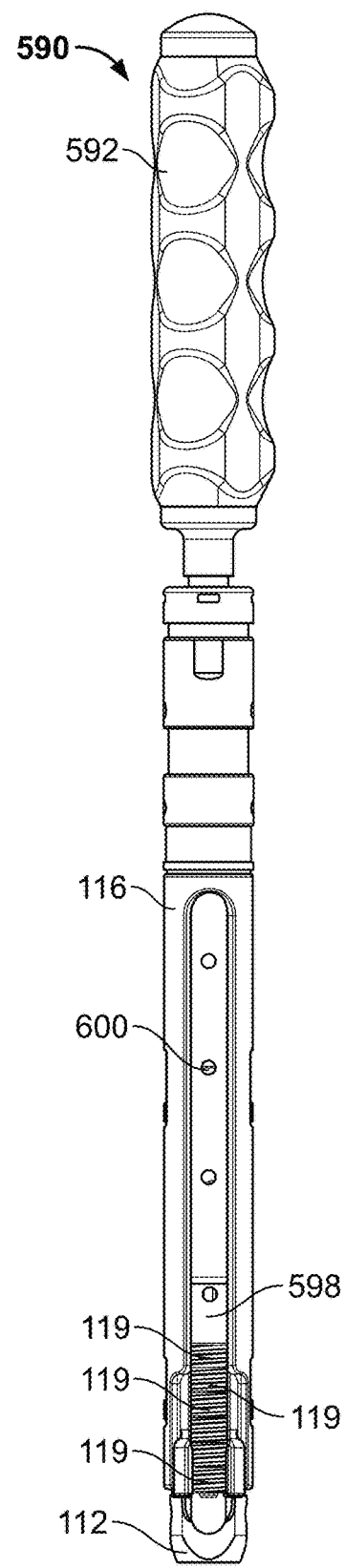
FIG. 94 is plan view of the lock screw inserter of FIG. 90 in use with the guide assembly of FIG. 21.
Figures 95, 96:
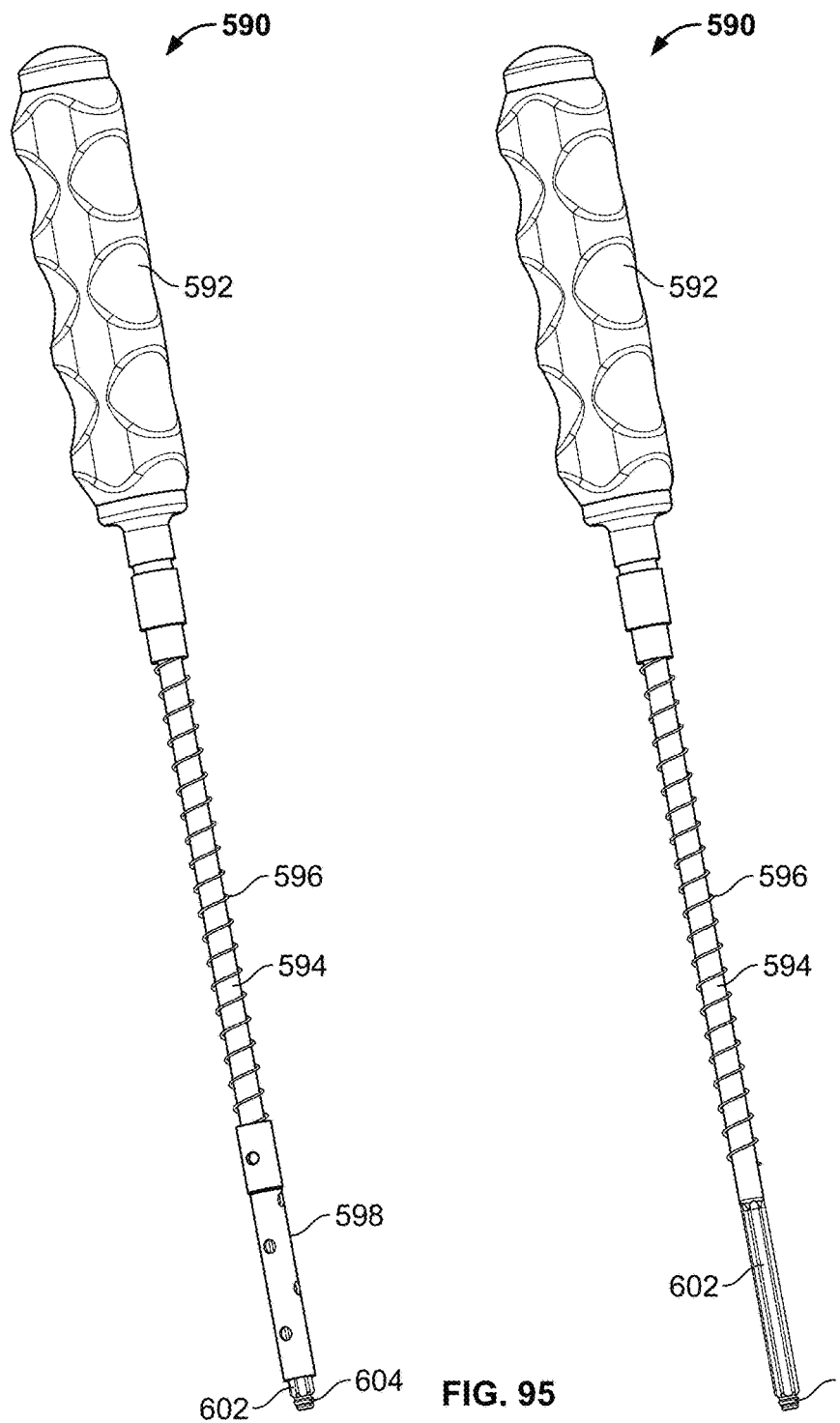
FIG. 95 is a perspective view of the lock screw inserter of FIG. 90 with the outer shaft removed for illustration.
FIG. 96 is a perspective view of the lock screw inserter of FIG. 90 with the outer shaft and the spring shaft removed for illustration.
Figure 105:
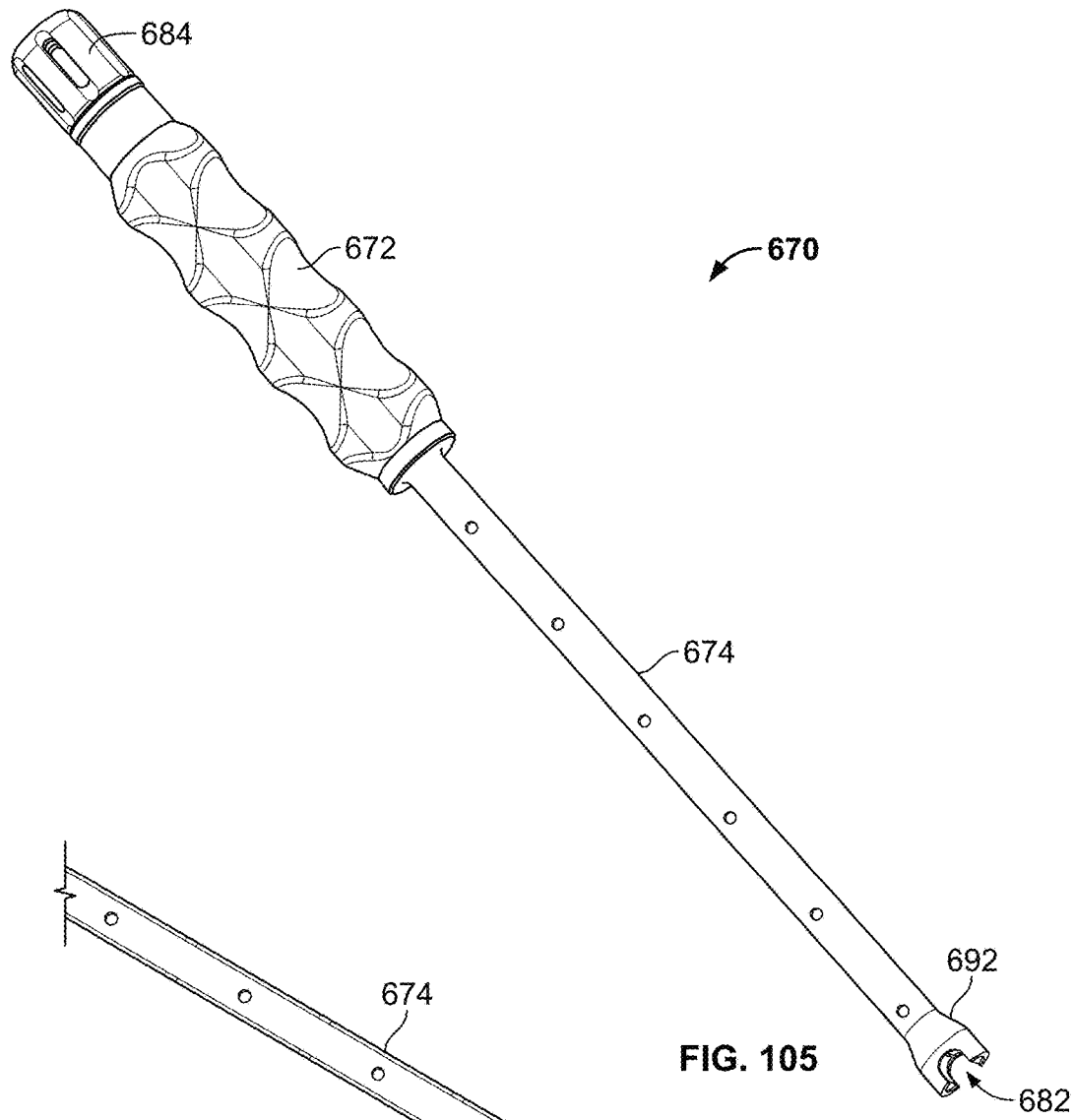
FIGS. 105-106 are perspective views of an example of a rod inserter configured for use with the spinal fixation system of FIG. 19.
Figure 106:
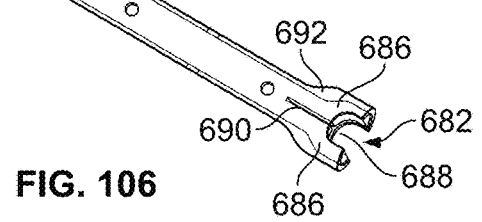
Figure 107:
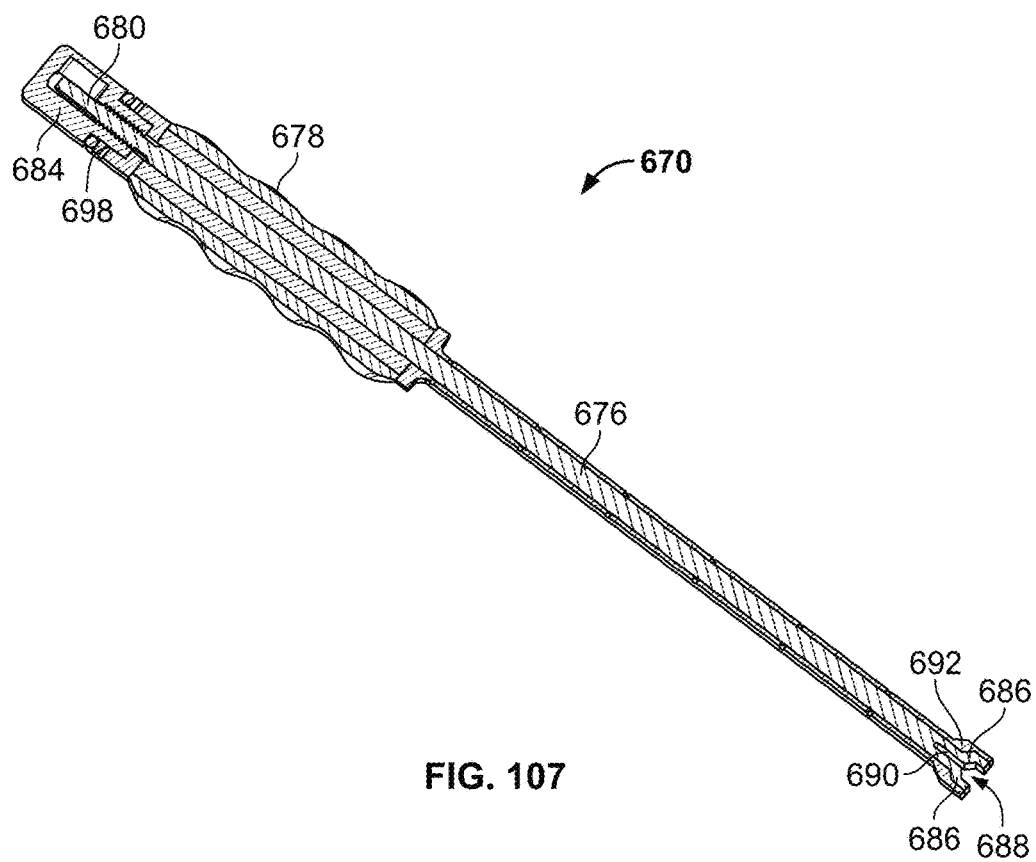
FIG. 107-108 are sectional views of the rod inserter of FIG. 105.
Figure 108:
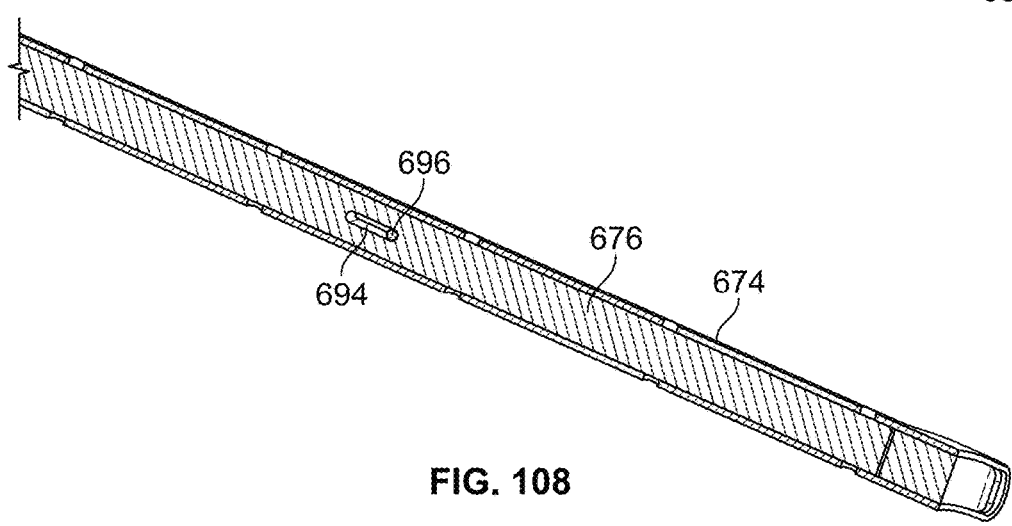

FIGS. 87-89 illustrate an alternative example of a compression instrument 520 according to another embodiment of the spinal fixation system 110. By way of example only, the compression instrument 520 is a rack compressor for compressing the distance between adjacent vertebra prior to locking the spinal rod 114 in both pedicle screws 112. The compression instrument 520 includes a rack 522 with a fixed arm 524 and a moveable arm 526. The rack 522 includes a plurality of teeth 523 provided along one side of the rack 522 and extending substantially the length of the rack 522. The fixed arm 524 is positioned at a first end of the rack 522 and includes a fixed base 528 that is attached to the rack 522 and a removable arm member 530 that includes an attachment elbow 532, an elongated arm 534, and a hoop 536. The fixed base 528 includes a cylindrical post 538 extending laterally from the fixed base 528 and a fixed gear wheel 540 at the base of the post 538 and adjacent the fixed base 528. The attachment elbow 532 extends laterally from the proximal end of the elongated arm 534 and has an aperture 542 and associated lumen for receiving the post 538. The aperture 542 contains gear slots that mate with the gear wheel 540. The hoop 536 is positioned at the distal end of the elongated arm 534 and is configured for advancement over a guide assembly 116. The moveable arm 526 includes a translating base 544 that is capable of translating along the rack 522 and a removable arm member 546 that includes an attachment elbow 548, an elongated arm 550, and a hoop 552. The translating base 544 includes a cylindrical post 554 extending laterally from the translating base 544 and a fixed gear wheel 556 at the base of the post 554 and adjacent the base 544. The attachment elbow 548 extends laterally from the proximal end of the elongated arm 550 and has an aperture 558 and associated lumen for receiving the post 554. The aperture 558 contains gear slots that mate with the gear wheel 556. The hoop 552 is positioned at the distal end of the elongated arm 550 and is configured for advancement over a guide assembly 116. This configuration allows the compressor arms to be attached to the rack assembly at a variety of angles.

The translating base 544 includes a user selectable lock 560 that prevents translation in an undesired direction (e.g. moving arms away from each other when compression is desired and moving arms toward each other when distraction is desired). The lock 560 includes a selector switch 562, a first pawl 564, a second pawl 566. The selector switch 562 is pivotably attached to the translating base 544 and includes generally smooth rounded pawl interface 568 and a recess 570 formed therein. The first pawl 564 is pivotably connected to the translating base 544 and includes a first end 572 and a second end 574. The first end 572 is generally rounded and dimensioned to be received within the recess 570 on the selector switch 562. The second end 574 includes a ratchet and is configured to engage the ridges 523 of the rack 522 to prevent movement of the translating arm 526 away from the fixed arm 524. The second pawl 566 is pivotably connected to the translating base 544 and includes a first end 576 and a second end 578. The first end 576 is generally rounded and dimensioned to be received within the recess 570 on the selector switch 562. The second end 578 includes a ratchet and is configured to engage the ridges 523 of the rack 522 to prevent movement of the moveable arm 526 toward the fixed arm 524. The translating base 544 further includes a turnkey 580 that a user may manipulate to cause the translating arm 526 to translate along the rack 522. The turnkey 580 is attached to the translating base 544 and interacts with the teeth 523 of the rack 522 via a rotating gear 582.

In use, when the turnkey 580 is operated to move the movable arm 526 towards the fixed arm 524 the guide assembly 116 (and thus pedicle screw 112 and attached vertebra) that the moveable arm 526 is attached to moves towards the other one, compressing the distance between the adjacent vertebrae. The principle also works in reverse to distract the vertebrae. The selector switch 562 is configured to adjust the lock 560 between a compression position (which allows compression and prevents distraction), a distraction position (which allows distraction and prevents compression), and an open position (which allows the moveable arm 526 to move in either direction along the rack 522). The selector switch 562 is configured to point in the general direction of the desired movement. When the lock 560 is in the compression position, the recess 570 is engaged with the first end 572 of the first pawl 564. This will force the second end 574 to engage the teeth 523 of the rack 522 and prevent movement of the moveable arm 526 away from the fixed arm 524. Simultaneously, the rounded surface 568 of the selector switch 562 forces the first end 576 end of the second pawl 566 (relatively) down, such that the second end 578 is unable to engage the teeth 523 of the rack 522. This allows for translation of the moveable arm 526 in the compression direction while preventing such movement in the distraction direction. Likewise, when the lock 560 is in the distraction position, the recess 570 is engaged with the first end 576 of the second pawl 566. This will force the second end 578 to engage the teeth 523 of the rack 522 and prevent movement of the moveable arm 526 toward the fixed arm 524. Simultaneously, the rounded surface 568 of the selector switch 562 forces the first end 572 end of the first pawl 564 (relatively) down, such that the second end 574 is unable to engage the teeth 523 of the rack 522. This allows for translation of the moveable arm 526 in the distraction direction while preventing such movement in the compression direction. When the selector switch 562 is in the open position, the recess 570 does not engage either of the first and second pawls 564, 566. The rounded surface 568 engages the first end 572 of the first pawl 564 and also the first end 576 of the second pawl 566, forcing them both (relatively) down. The result is that neither pawl 564, 566 is engaged with the teeth 523 of the rack 522, and the moveable arm 526 is able to translate in either direction and effect both distraction and compression.

FIGS. 90-96 illustrate an example of a multi-load lock screw inserter 590 configured for use with the spinal fixation system 110 according to one embodiment of the present invention. The multi-load lock screw inserter 590 is useful in that multiple lock screws 119 may be loaded on to the driver 590 such that a user may quickly move among multiple guide assemblies 116 and anchors 112 without having to load a new lock screw 119 each time. By way of example only, the multi-load lock screw inserter 590 includes a handle 592 and a central shaft 594 extending distally from the handle 592. The multi-load lock screw inserter 590 further includes a spring 596, an inner sleeve 598, and an outer sleeve 600. The spring 596 is positioned between the handle 592 and the inner sleeve 598. The spring is contained within the outer sleeve 600. The central shaft 594 extends through the spring 596, inner sleeve 598, and outer sleeve 600. The proximal end of the inner sleeve 598 abuts the distal end of the spring 596. The distal end of the inner sleeve 598 is always in contact with the proximal-most lock screw 119.

The distal portion of the central shaft 594 includes a drive feature 602 that is configured to retain and control the rotation of the attached lock screws 119. By way of example only, the drive feature 602 may have a hexalobe shape, however other shapes that prevent rotation of the lock screw 119 relative to the central shaft 594 are possible. A snap ring 604 is positioned within a recess formed just proximally of the distal end of the central shaft 594. The snap ring 604 is sized and configured to prohibit passage of the lock screw(s) 119 until an appropriate distal force is applied to the lock screw 119 by the inner sleeve 598 and/or a rotational engagement with a pedicle screw.

In use, as multiple lock screws 119 are loaded onto the multi-load lock screw inserter 590, the proximal-most lock screw 119 forces the inner sleeve 598 in proximal direction, which causes the spring 596 to compress. As lock screws 119 are engaged to pedicle screws (and removed from the multi-load lock screw inserter 590), the spring 596 exerts a distal force on the inner sleeve 598, which in turn pushes the next lock screw 119 into position. In this fashion, a user may quickly move among multiple guide assemblies 116 and anchors 112 without having to load a new lock screw 119 each time.

FIGS. 97-98 illustrate an example of a guide adjuster 610 for use with the spinal fixation system 110 of the present invention. The guide adjuster 610 is configured for use with any of the guide assemblies described above, however for the purpose of illustration the guide adjuster 610 will be described in use with the guide assembly 116 shown and described in relation to FIG. 21 et seq. The guide adjuster 610 is useful when the guide assemblies 116 are in need of twisting in order to align the guide channels. By way of example only, the guide adjuster 610 includes a handle 612 and a guide cavity 614. The handle 612 includes a pair of arms 616 enabling a user to manipulate the guide adjuster 610. The guide cavity 614 is configured to receive the proximal end 122 of the outer sleeve 118 (featuring the cap 128). The proximal end 122 is keyed to the guide cavity 614 so as to prevent rotation of the guide assembly 116 relative to the guide adjuster 610.

FIGS. 99-100 illustrate an example of a tap guide 620 including a catch mechanism for use with the spinal fixation system of the present invention. Generally, the catch mechanism is spring loaded to catch the tap in a contained position (distal end contained within dilator). Pressing the catch release allows the tap to be advanced past the distal end of the dilator. Once the hole is tapped, the tap can be pulled back and again locked in the contained position for removal. By way of example only, the tap guide 620 is a generally tubular elongated member having a shaft 622 with a lumen 624 extending therethrough. The outer surface 626 of the shaft 622 includes rifling 628, which facilitates insertion into the operative corridor. The proximal end of the shaft 622 is equipped with a catch mechanism which includes a retention tab 630, a spring 632, a retaining pin 634, and a catch release button 636. The retention tab 630 retains the tap (not shown) in the tap guide 620 during insertion into and removal from the surgical target site. This retention is facilitated by the spring 632. Once docked on the pedicle, the catch release button 636 may be pressed, allowing the tap to pass such that the distal end of the tap can extend past the end of the tap guide 620 for tapping of the pedicle. The distal end 638 of the shaft 622 includes a choke feature which facilitates the alignment of the tool.

FIG. 101 illustrates an example of an offset dilator 640 configured for use with the spinal fixation system 110 according to one embodiment of the present invention. By way of example only, the offset dilator 640 includes a tubular shaft 642 having a lumen 644 extending therethrough. A longitudinal groove 646 is formed along the outer surface of the offset dilator 640 and is configured to receive a K-wire (not shown). The offset dilator 640 may have a shaped proximal end 648 for ease of manipulation. The offset dilator 640 may be used to expose the facet for decortications and fusion. The offset dilator 640 is advanced over the K-wire via the longitudinal groove 646. The offset dilator 640 can then be rotated around the K-wire until the lumen 644 is centered over the facet.

FIGS. 102-103 illustrate an alternative example of an offset dilator 650 configured for use with the spinal fixation system 110 according to another embodiment of the present invention. By way of example only, the offset dilator 650 includes a tubular shaft 652 having a lumen 654 extending therethrough. A longitudinal groove 656 is formed along the outer surface of the offset dilator 650 and is configured to receive a K-wire (not shown). The offset dilator 650 may have a shaped proximal end 658 for ease of manipulation. The offset dilator 650 further includes a lateral slot 659 that is dimensioned to receive a light cable (not shown). The offset dilator 650 may be used to expose the facet for decortications and fusion. The offset dilator 650 is advanced over the K-wire via the longitudinal groove 656. The offset dilator 650 can then be rotated around the K-wire until the lumen 654 is centered over the facet. Once the offset dilator 650 is in position, a light cable may be employed in the lateral slot 659 to introduce light to the surgical target site.

FIG. 104 is an example of a secondary dilator 660 positioned within the offset dilators 640, 650 to facilitate advancement to the surgical target site. The secondary dilator 660 has an elongated tubular shaft 662 and a lumen 664 extending therethrough.

FIGS. 105-108 illustrate an example of an alternative rod inserter 670 for use with the spinal fixation system 110 according to another embodiment of the present invention. The rod inserter 670 is capable of lockingly engaging the cylindrical body portion of a spinal rod (as opposed to one of the ends). By way of example only, the rod inserter 670 includes a handle 672, a shaft sleeve 674, and a shaft 676. The handle 672 has an interior lumen 678. The shaft 676 is an elongated cylindrical member having a proximal threaded region 680 and a distal rod retaining head 682. The proximal threaded region 680 is threadedly received within a rotating knob 684 positioned on the proximal end of the handle 672. The distal rod retaining head 682 is formed from a pair of prongs 686 that cooperate to form a semi-cylindrical recess 688 that is configured to receive a spinal rod (not shown). A small slot 690 is formed in the shaft 676 at the distal end to allow for expansion and/or contraction of the rod retaining head 682 during rod engagement. The outer sleeve 674 includes a distal cavity 692 for receiving the rod retaining head 682 when a spinal rod is engaged and the rod inserter 670 is in a locked position. The shaft 694 includes a translation slot 694 configured to receive a translation pin 696 that is secured to the outer sleeve 674. The translation slot 694 and pin 696 combination serve to control and limit the amount of translation the shaft 676 is capable of. By way of example only, the slot 694 allows for approximately 5 mm of translation. The rotating knob 684 is secured to the handle 672 by way of an internal ring 698.

In use, a spinal rod is placed into the recess 688 at the distal end of the shaft 676. The rotating knob 684 is turned clockwise, which causes the shaft 676 to translate in a proximal direction. The distal rod retaining head 682 is then drawn into the distal cavity 692 of the outer sleeve 674. This effectively locks the spinal rod to the rod holder 670 as the prongs 686 are squeezed together by the distal cavity 692.

Figure 114:
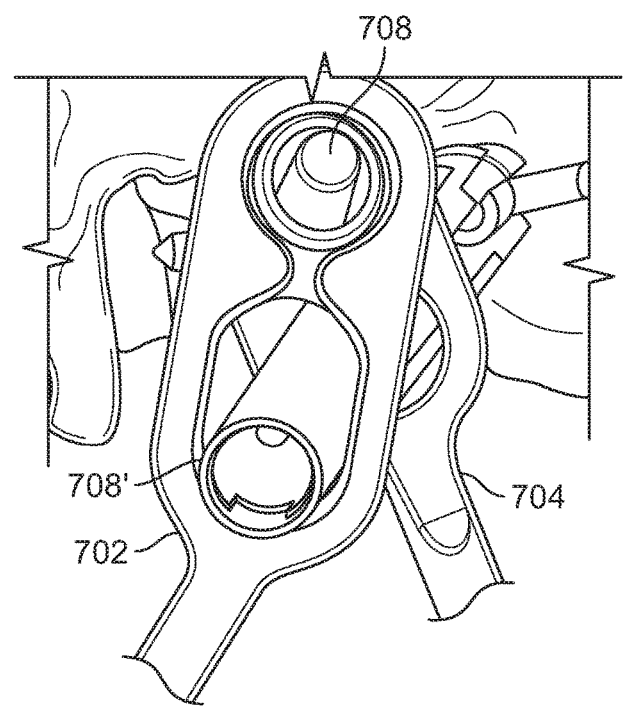
FIGS. 113-115 are perspective views of the compression system of FIG. 109 in use.
Figure 113:
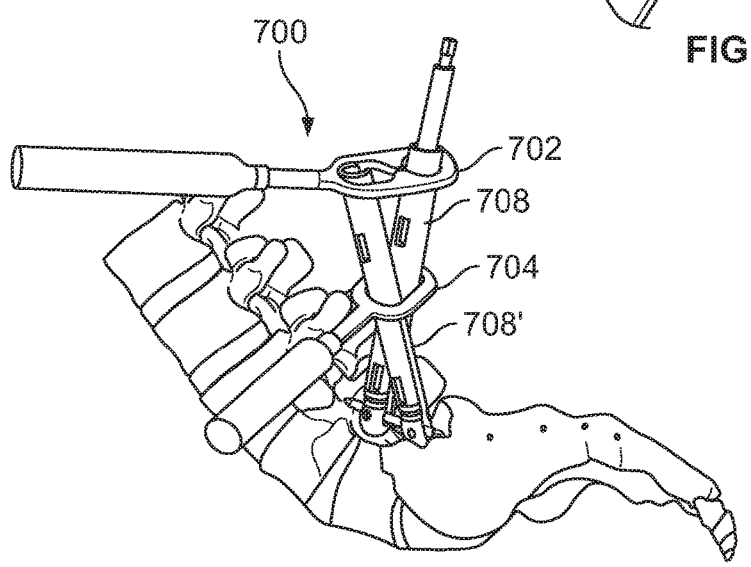
Figure 115:
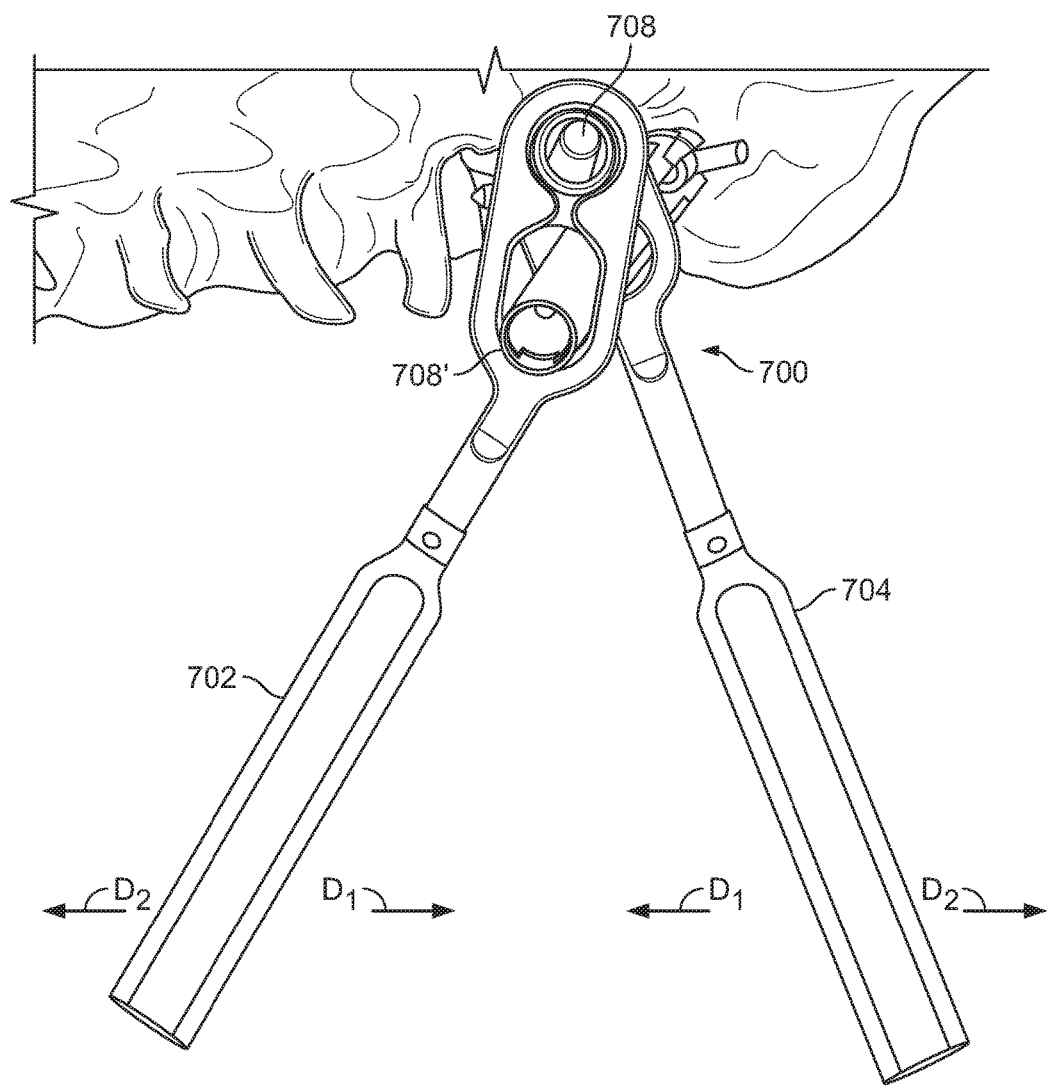

FIGS. 109-115 illustrate a compression system 700 configured for use with the spinal fixation system 110 according to an example embodiment. Compression system 700 is advantageous when guide towers are crossed or are otherwise not in line, which makes the use of a rack based or pivoting compression instrument challenging or impossible. By way of example, the compression system 700 includes a rotational tool 702, a pivot tool 704, and a hinged tool 706 (FIG. 114). The hinged tool 706 is optional and may be used in lieu of the pivot tool 704 when positioning of the guides makes inserting the pivot tool over the guides challenging.

Figure 109:
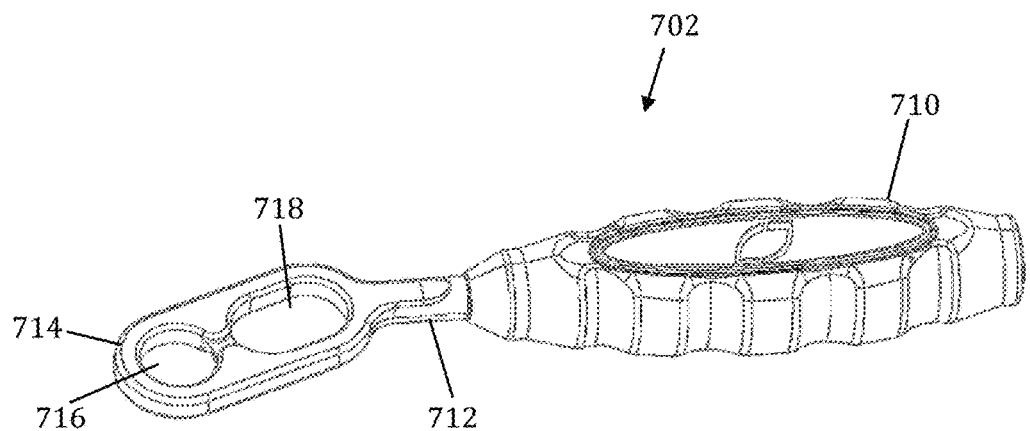
FIG. 109 is a perspective view of a compression tool forming part of a compression system according to one embodiment.

Referring to FIG. 109, the rotational tool 702 includes a handle member 710, a stem 712 extending distally from the handle member 710, and a distal paddle 714 extending distally from the stem 712. The handle 710 includes a contoured gripping surface for handling by a user. The stem 712 extends linearly from the handle 710 and has a longitudinal axis that is coaxial with the longitudinal axis of the handle 710. The distal paddle 714 has a generally elliptical perimeter and a longitudinal axis that is angularly offset from the longitudinal axis of the stem 712. The distal paddle 714 includes a first opening 716 and a second opening 718 positioned proximally of the first opening 716. The first opening 716 is generally circular in shape and is sized to snugly receive a first guide tower 708 therein. The second opening 718 is generally elliptical in shape and is dimensioned to receive a second guide tower 708 therein. The elliptical shape of the second opening 716 allows the second guide tower to move within the opening 716 in response to force applied to the rotational tool 702 by a user.

Figure 110:
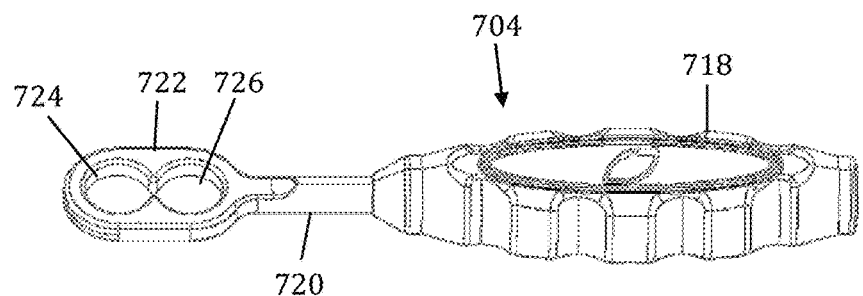
FIG. 110 is a perspective view of another compression tool forming part of the compression system of FIG. 109.
Figure 111:
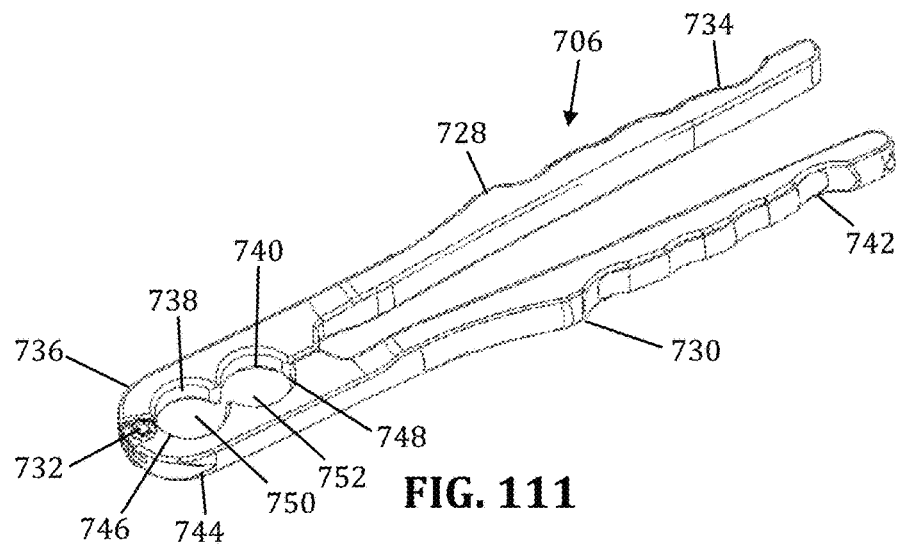
FIG. 111 is a perspective view of anther compression tool forming part of the compression system of FIG. 109.
Figure 112:
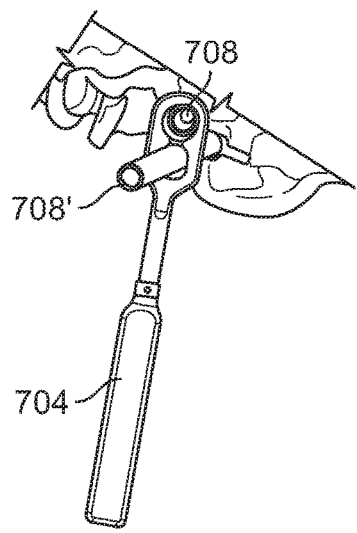
FIG. 112 is a perspective view of the compression tool of FIG. 110 in use.

Referring to FIG. 110, the pivot tool 704 includes a handle member 718, a stem 720 extending distally from the handle member 718, and a distal paddle 720 extending distally from the stem 720. The handle 718 includes a contoured gripping surface for handling by a user. The stem 720 extends linearly from the handle 718 and has a longitudinal axis that is coaxial with the longitudinal axis of the handle 718. The distal paddle 720 has a generally elliptical perimeter and a longitudinal axis that is coaxial with the longitudinal axis of the stem 720. The distal paddle 722 includes a first opening 724 and a second opening 726 positioned proximally of the first opening 724. The first and second openings 724, 726 are each generally circular in shape and sized to snugly receive a first and second guide towers 708 therein. The circular shape and snug engagement of the of the first and second openings 724, 726 prevents both guide towers 708 from moving relative to the pivot tool 704 when force applied by a user.

The paddle 714 of the rotational tool 702 and the paddle 722 of the pivot tool 704 each have unbroken enclosed perimeters. Thus, the only way to position a guide tower in either the first or second openings is the slide the tool over the top of the towers. In some circumstances it may be advantageous to be able to attach the pivot tool to the towers without having to slide them over the top of the towers. In such a circumstance (or otherwise if the user so desires) a hinged tool 706 may be used in place of the pivot tool 704. The hinged tool 706 comprises a first arm member 728 and a second arm member 730 hingedly coupled together by a distal hinge 732. The first arm member 728 has a proximal portion 734 including a contoured surface for manipulation by a user. The first arm member 728 further includes a distal portion 736 including an inner facing surface having a first concave portion 738 and a second concave portion 740. The second arm member 730 has a proximal portion 742 including a contoured surface for manipulation by a user. The second arm member 730 further includes a distal portion 744 including an inner facing surface having a first concave portion 746 and a second concave portion 748. When the hinged tool 706 is in the closed position, the first concave portion 738 of the first arm member 728 and the first concave portion 746 of the second arm member 730 act in concert to form a generally circular opening 750. Likewise, the second concave portion 740 of the first arm member 728 and the second concave portion 748 of the second arm member 730 act in concert to form a generally circular opening 752. Openings 750, 752 are dimensioned to snugly receive guide towers 708 therein.

In use, the compression system 700 is useful for enacting compression at vertebral levels that might otherwise be inaccessible for compression because the guides are converging or crossed altogether, for example at the L5-S1 level of the spine. Once the guide towers 708 are attached to the bone screws and the surgeon has a need to compress or distract the vertebrae, the first step is to engage the pivot tool 704 (or hinged tool 706) with the guide towers 708, 708'. When performing compression or distraction using the compression system 700, one of the guide towers 708 remains stationary while the other guide tower (denoted 708' in FIGS. 112-115) moves in response to the force applied by the user. The pivot tool 708 is positioned such that the guide tower 708 that is to remain stationary is placed within the first opening 724, which is the distal-most opening. The guide tower that is allowed to move is placed within the second opening 726 (the proximal-most opening). The pivot tool 704 is advanced distally along the guide towers 708, 708' until it is placed in the desired pivot point. Most often, this pivot point will be immediately adjacent the patient's skin, as a lower pivot point will allow more torque to be applied to the guide tower 708'. The rotational tool 702 is then engaged with the guide towers 708, 708' at the most proximal location possible (to ensure that the user has the maximum torque available). Since guide tower 708 in the present example is to remain stationary, it is placed within first opening 716 (the distal-most, circular opening). Accordingly, guide tower 708' is positioned within the second opening 718 (the proximal-most, elliptical opening). Compression or distraction is then achieved by maneuvering the handles 710, 718 either toward or away from each other. If compression is desired, then the user rotates the handles 710, 718 toward one another (direction $D_1$ in FIG. 115). If distraction is desired, then the user rotates the handles 710, 718 away from one another (direction $D_2$ in FIG. 115). Once the desired compression (or distraction) is achieved, the user then holds compression (and distraction) while provisionally tightening the set screw in the housing of the bone anchor. The compression system 700 is then completely removed and the sets crew may be final-tightened using an appropriate instrument.

FIGS. 116-122 illustrate a compression instrument 760 configured for use with the spinal fixation system 110 according to another example embodiment. As with compression system 700, compression instrument 760 is advantageous when guide towers 761, 761' are crossed or are otherwise not in line, which makes the use of a rack based or pivoting compression instrument challenging or impossible. By way of example, the compression instrument 760 includes a compressor body 762, a first handle member 764 integrally formed and extending away from the compressor body 762, and a second handle member 766 hingedly attached to the compressor body 762.

Figure 121:
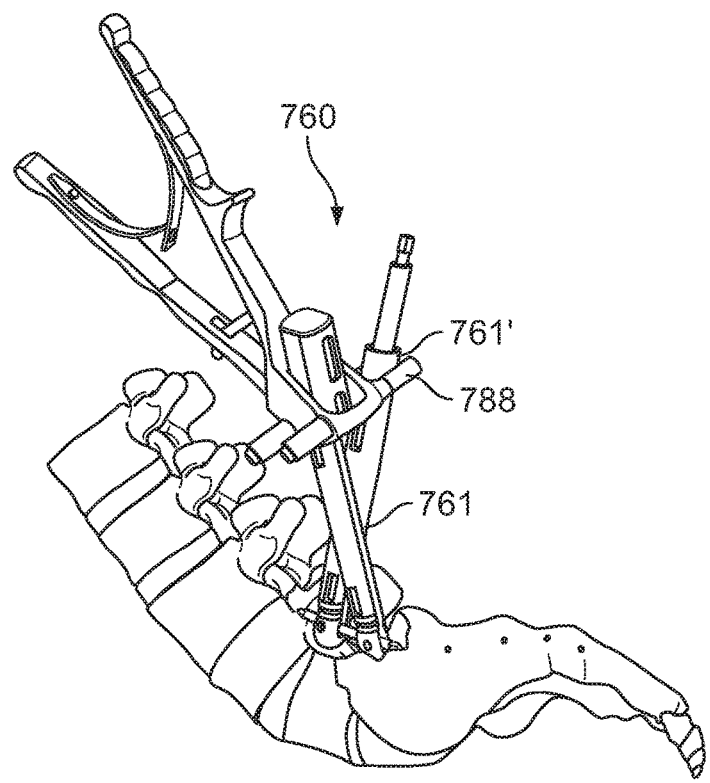
FIGS. 121-122 are perspective views of the compression instrument of FIG. 116 in use.

The compressor body 762 includes a base 768 and an elongated post 770 extending distally from the bottom portion of the base 768. The elongated post 770 is generally cylindrical in shape and is configured for insertion into the lumen of a stationary guide tower 761 (FIG. 121). The first handle member 764 is an elongated member extending laterally away from the base 768, preferably at an upward angle relative to the elongated post 770. That is, the angle that is formed between the first handle member 764 and the elongated post 770 is preferably obtuse. A generally rectangular aperture 772 is formed in the first handle member 764 as a vertically-oriented through-hole. The aperture 772 is dimensioned to receive a ratchet bar 774 extending from the second handle member 766. The aperture 772 further includes a ridged or angled surface (not shown) adapted to engage ratchet teeth 776 on the ratchet bar 774 to enable the compression instrument 760 to hold compression if desired by the user. To release compression, the ratchet bar 774 is simply manually disengaged from the ridged or angled surface within the aperture 772. A pair of lateral posts 778, 778' are positioned at the intersection of the base 762 and the first handle member 764. The lateral posts 778, 778' are positioned on opposite sides of the first handle member 764 and extend generally perpendicularly away from the handle member 764.

The second handle member 766 has a base 780 and a handle arm 782 extending away from the base 780. The base 780 includes a distal end 784 and a large central aperture 786 sized and configured to receive the base 768 of the compressor body 762. A pair of lateral posts 788, 788' are positioned on either side of the base 780 and extend generally perpendicularly away from the base 780. A pair of hinge apertures 790 are located on the proximal end of the base 780 and are configured to receive a hinge pin 792, which hingedly connects the second handle member 766 to the compressor body 762. A grip stop 794 projects upward from the top surface of the handle arm 782 and is configured to provide a bumper for a user's hand to help ensure the user's grip does not slip during use. A resistance member 796 is attached to the bottom surface of the handle arm 782 and mates with a resistance member 798 that is attached to the upper surface of the first handle member 764. The mated resistance members 796, 798 bias the first and second handle members 764, 766 apart with a force that is relatively easily overcome by a user's hand.

Figure 122:
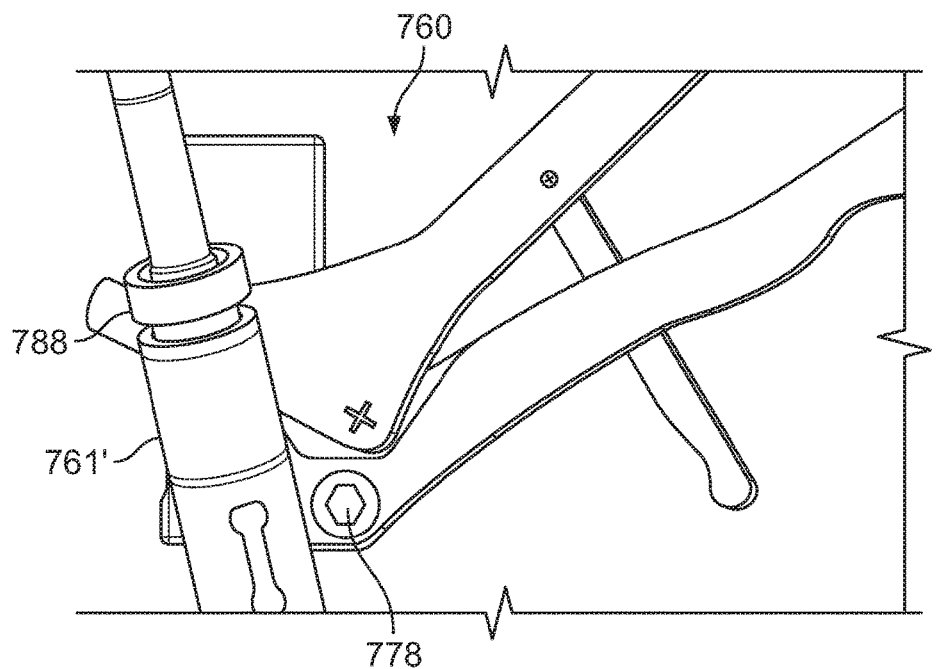
Figure 123:
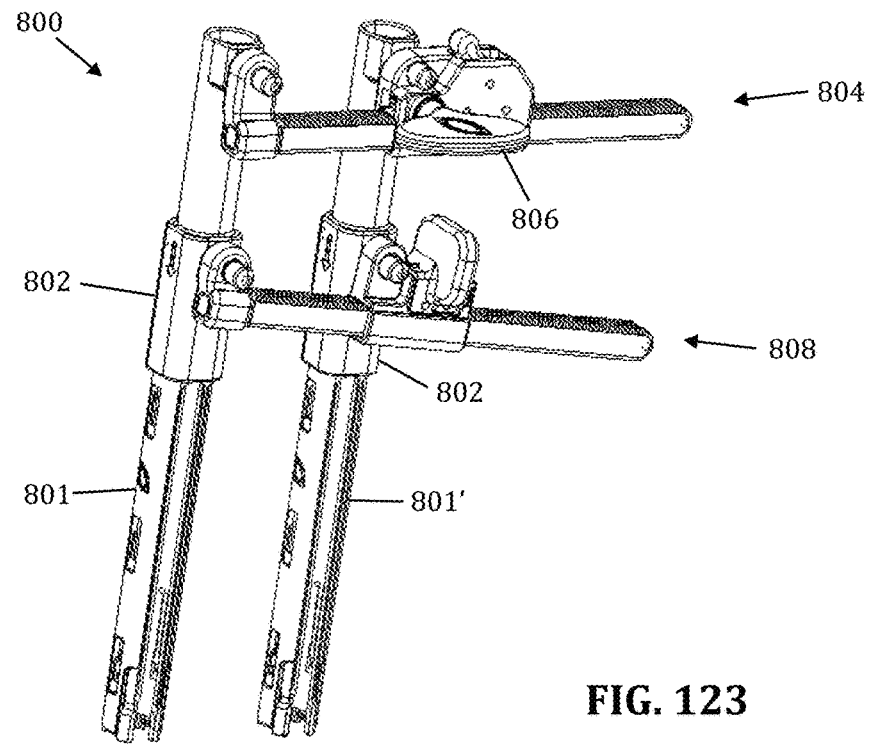
FIG. 123 is a perspective view of another compression system according to another example embodiment.
Figure 124:
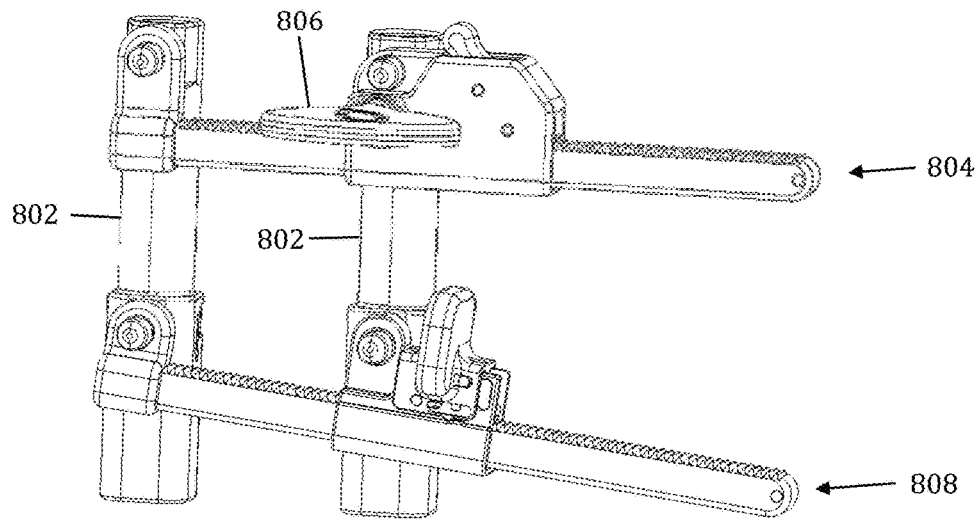
FIG. 124 is a perspective view of the compression system of FIG. 123.

FIGS. 121 and 122 illustrate the compression instrument 760 being employed during an example surgical procedure. Before the compression instrument 760 is used, however, the user must first final tighten the set screw in guide tower 761 (i.e. the stationary guide). A set screw may be engaged (loosely) to the anchor that guide tower 761' is attached to (i.e. the guide spanning the level(s) to be compressed). The compression instrument 760 is then employed by inserting the elongated post 770 into the guide tower 761. Guide tower 761' is then positioned adjacent the compression instrument 760, between one set of lateral posts (i.e. lateral posts 778, 788 OR lateral posts 778', 788'). The compressor body 762 may be equipped with laser markings or other visual indicia to aid the user in choosing a correct orientation for guide 761'. The user then compresses as needed by squeezing the first and second handle members 764, 766 together. This causes the second handle member 766 to hingedly rotate, which in turn causes the lateral posts 788', 788' to be pulled into the guide tower 761'. Since the other lateral posts 778, 778' are stationary, they act as a fulcrum to the guide tower's lever, causing the distal end of the guide tower, and consequently the bone anchor and the vertebral body it is implanted in to be compressed. Compression is held while a setscrew is provisionally tightened in the compressed bone anchor. The compression instrument 760 is removed before the setscrew is final tightened using an appropriate instrument.

FIGS. 123-136 illustrate a compression instrument 800 according to another example embodiment. By way of example only, the compression instrument 800 is a rack compressor for compressing the distance between adjacent vertebra. Compression is performed after locking the spinal rod 114 in one pedicle screw 112 but prior to locking the spinal rod 114 in the pedicle screws 112 spanning the vertebral bodies to be compressed. The compression instrument 800 includes a pair of tower extensions 802, a ratcheting rack assembly 804, a thumb key driver 806, and a locking rack assembly 808.

Figure 125:
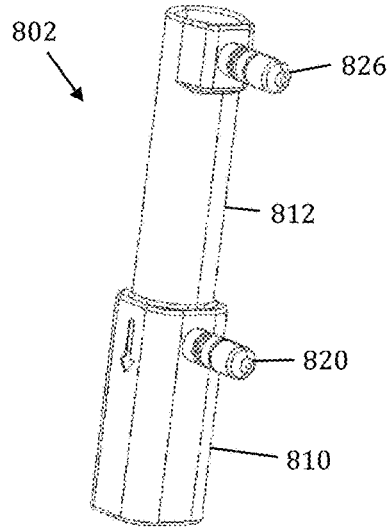
FIGS. 125-126 are perspective views of an extension tower forming part of the compression system of FIG. 123.
Figure 126:
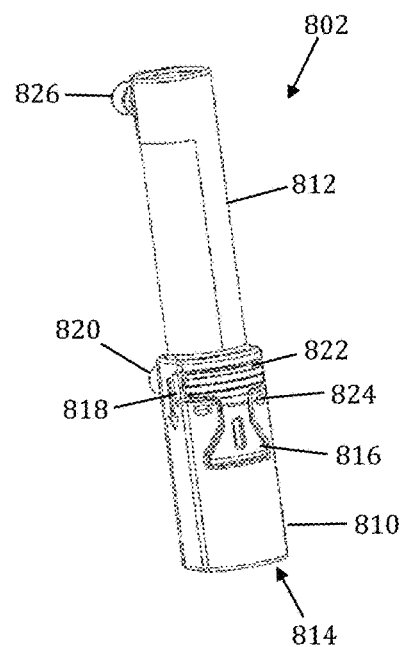
Figure 127:
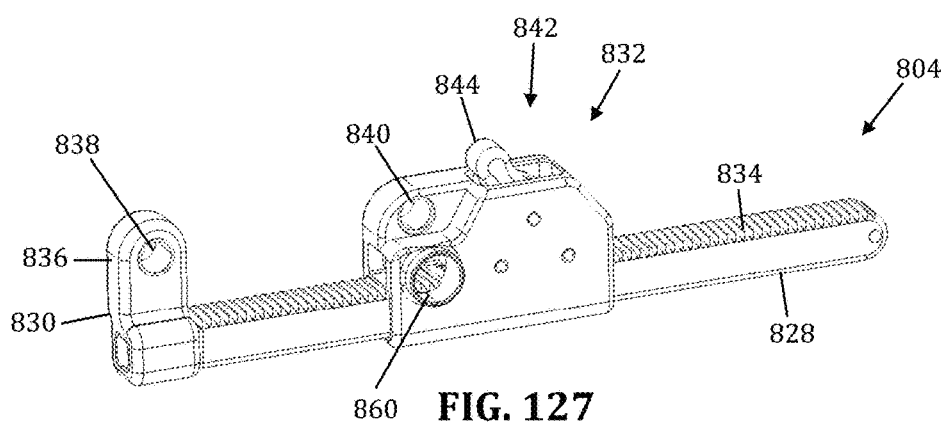
FIG. 127 is a perspective view of a translating rack forming part of the compression system of FIG. 123.

With reference to FIGS. 125-126, the tower extension 802 will be described in further detail. Tower extension 802 has a base portion 810 and an extension portion 812 extending proximally away from the base portion 810. The base portion 810 is configured to attach to the proximal end of a guide tower 801, 801' that is already coupled to a spinal anchor implanted in a vertebral body. The base portion 810 is a generally tubular member having a interior lumen 814 dimensioned to fit over the top of a guide tower 801. The exterior of the base portion 810 further includes a locking clip 816 positioned in a recess 818 and a first post 820 mounted opposite the locking clip 816 and extending perpendicularly away from the tower extension 802. The outer surface of the locking clip 816 includes a set of ridges 822 or other surface roughening to provide a user some frictional purchase to enable use. The inner surface of the locking clip 816 opposite the ridges 822 includes a generally circular recess for receiving a portion of a bias spring (not shown) therein. The locking clip 816 is pivotally connected to the base 810 via pivot pin 824.

The inner surface of the lower portion of the locking clip 816 includes an attachment feature (not shown) that extends generally perpendicularly from the inner surface and is configured to engage an attachment feature on the guide tower 801, for example a circumferential recess positioned near the proximal end of the guide tower 801. To enable this engagement, the recess 818 includes an aperture formed therein and extending between the outer surface of the base portion 810 and the lumen 814. The attachment feature may include a distal-facing tapered surface that is inwardly tapered so as to automatically deflect the attachment feature outward as the top of the guide tower 801 (for example) is advanced into the lumen 814, permitting the attachment feature to pass the top of the tower 801 until it engages a suitable attachment area thereon. As deflection occurs (by the attachment feature being physically pushed aside by the top of the guide tower 801), the locking clip 816 pivots about the pivot pin 824, causing the upper portion of the locking clip 816 to be received further in the recess 818. Once the top of the tower advances past the attachment feature, the attachment feature encounters the circumferential recess (for example). The spring acts on the upper portion of the locking clip 816 causing the locking clip 816 to pivot about the pivot pin 824 in the opposite direction, urging the attachment feature into the recess, which secures the tower extension 802 to the guide tower 801. This way, the tower extension 802 can be positioned over the guide tower 801 and quickly snapped onto and secured to the tower with the simple application of downward pressure. To later disengage the tower extension 802 from the guide tower, the user simply needs to apply a compressive force (e.g. using a thumb and forefinger) on the ridged portion 822 of the locking clip 816. This will cause the lower portion of the locking clip 816 to pivot outward and disengage the attachment feature from the circumferential recess. The tower extension 816 may then be removed from the area.

The proximal end of the extension portion 812 includes a second post 826 mounted directly above the first post 820. As will be explained, the first post 820 is configured to mate with the locking rack assembly 808 and the second post 826 is configured to mate with the ratcheting rack assembly 804 such that the locking rack assembly 808 and ratcheting rack assembly are locked to the extensions but are permitted to rotate or pivot relative to them.

The ratcheting rack assembly 804 includes a rack 828, fixed attachment tab 830, and a translating base 832. The rack 828 includes a plurality of teeth 834 provided along one side of the rack 828 and extending substantially the length of the rack 828. The fixed attachment tab 830 is positioned at one end of the rack 828 and includes a flange 836 extending vertically away from the rack 828. The flange 836 includes an attachment aperture 838 configured to receive the second post 826 of the tower extension 802 positioned on the fixed guide 801.

Figure 128:
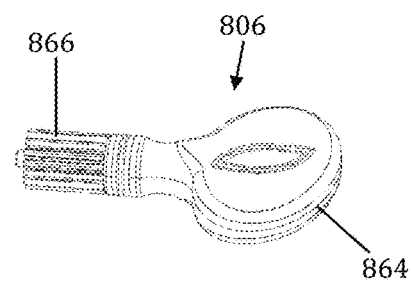
FIG. 128 is a perspective view of a thumb key driver forming part of the translating rack of FIG. 127.
Figure 129:
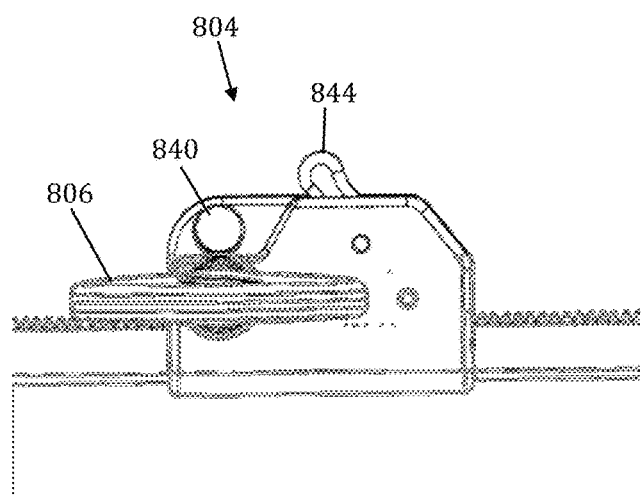
FIG. 129 is a plan view of the translating rack of FIG. 127.
Figure 130:
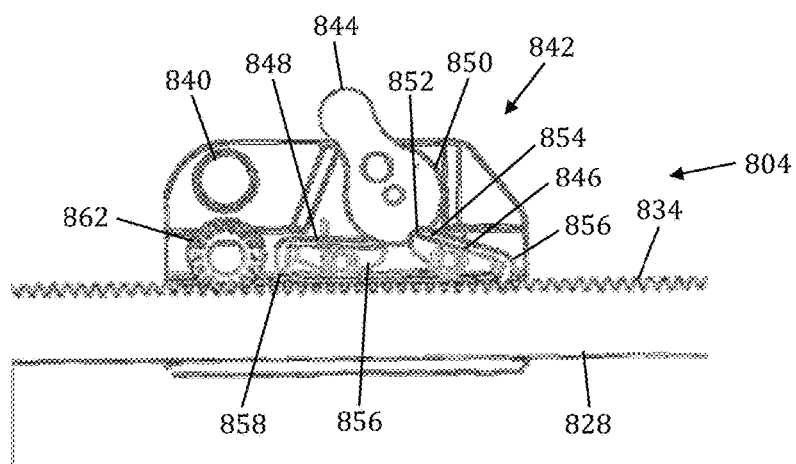
FIG. 130 is a sectional plan view of the translating rack of FIG. 127.
Figure 131:
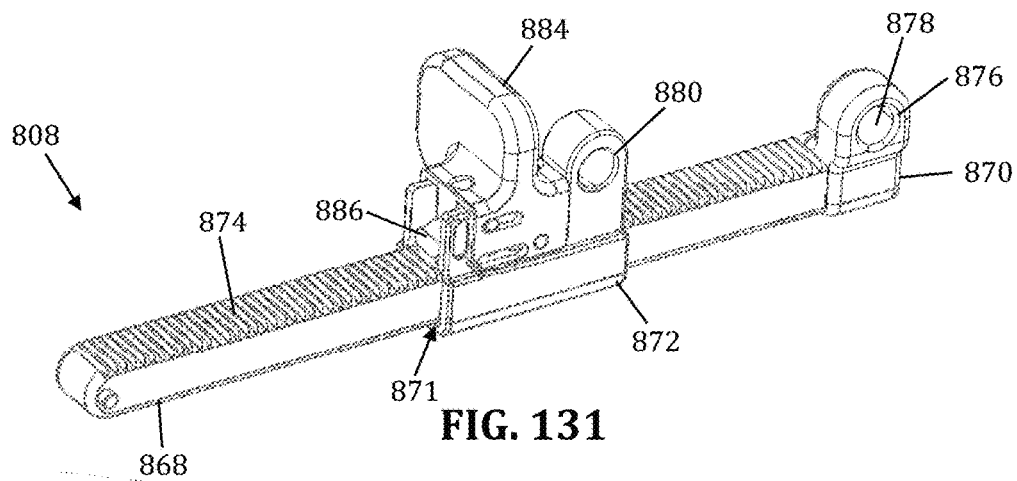
FIG. 131 is a perspective view of a locking rack forming part of the compression system of FIG. 23.
Figure 132:
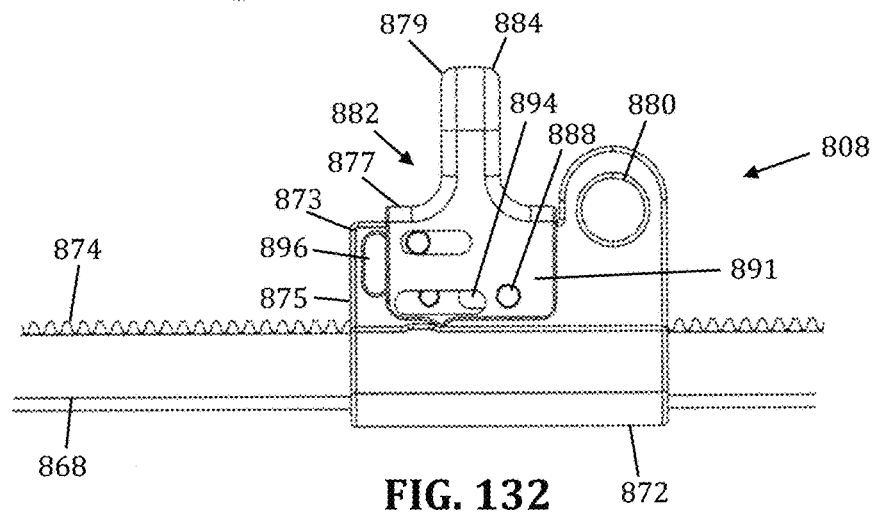
FIG. 132 is a plan view of the locking rack of FIG. 131
Figure 133:
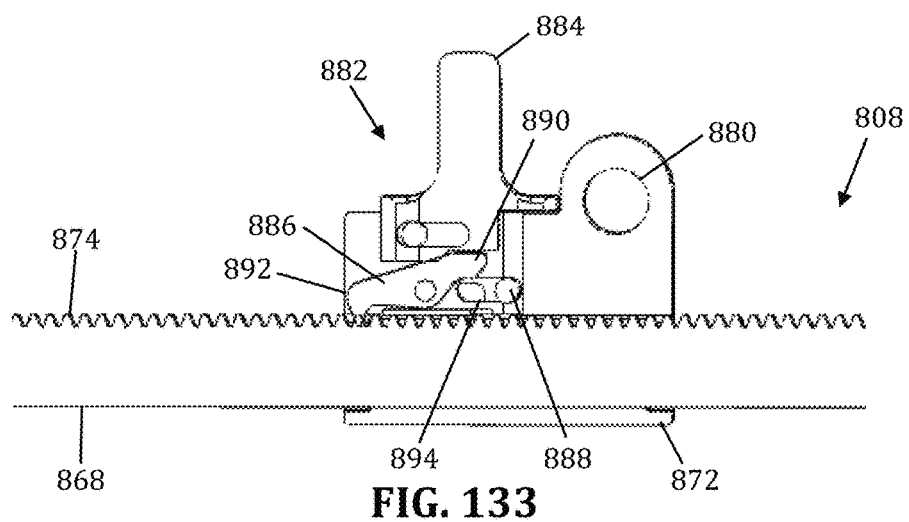
FIG. 133 is a sectional plan view of the locking rack of FIG. 131.

The translating base 832 includes an attachment aperture 840 configured to receive the second post 826 of the tower extension 802 positioned on the guide 801' spanning the level to be compressed. The translating base 832 further includes a user selectable lock 842 that prevents translation in an undesired direction (e.g. toward the fixed end when compression is desired and away from the fixed end when distraction is desired). The lock 842 includes a selector switch 844, a first pawl 846, and a second pawl 848. The selector switch 844 is pivotably attached to the translating base 832 and includes generally smooth rounded pawl interface 850 and a recess 852 formed therein. The first pawl 846 is pivotably connected to the translating base 832 and includes a first end 854 and a second end 856. The first end 854 is generally rounded and dimensioned to be received within the recess 852 on the selector switch 844. The second end 856 includes a ratchet and is configured to engage the ridges 834 of the rack 828 to prevent movement of the translating base 832 away from the fixed end. The second pawl 848 is pivotably connected to the translating base 832 and includes a first end 856 and a second end 858. The first end 856 is generally rounded and dimensioned to be received within the recess 852 on the selector switch 844. The second end 858 includes a ratchet and is configured to engage the ridges 834 of the rack 828 to prevent movement of the translating base 832 toward the fixed end. The translating base 832 further includes a turn key aperture 860 configured to receive a turn key driver 806 therein that a user may manipulate to cause the translating base 832 to translate along the rack 834. The turn key driver 806 removeably engages the translating base 832 and interacts with the teeth 834 of the rack 828 via a rotating gear 862. As shown in FIG. 128, the turn key driver 806 proximal handle 864 and a distal gear shaft 866 that engages the rotating gear 862.

The locking rack assembly 808 includes rack 868, a fixed attachment tab 870, and a locking base 872. The rack 868 includes a plurality of teeth 874 provided along one side of the rack 868 and extending substantially the length of the rack 868. The fixed attachment tab 870 is positioned at one end of the rack 868 and includes a flange 876 extending vertically away from the rack 868. The flange 876 includes an attachment aperture 878 configured to receive the first post 820 of the tower extension 802 positioned on the fixed guide 801.

The locking base 872 includes an attachment aperture 880 configured to receive the first post 820 of the tower extension 802 positioned on the guide 801' spanning the level to be compressed. The locking base 872 further includes a lower channel 871 that houses the rack, a user selectable lock 882 that prevents translation in either direction when the lock is engaged, and an upper housing 873 including sidewalls 875 to contain the various components of the lock 882. The lock 882 includes a selector switch 884, pawl 886, and a locking pin 888. The selector switch 884 is slidably attached to the translating base 872 and is moveable from a first position in which the locking base 872 is unlocked to a second position in which the locking base 872 is locked. The selector switch includes base surface 877, a superior flange 879, and a pair of inferior flanges 891 positioned on opposing sides of the base surface 877 and extending inferiorly so as to extend along the exterior of the sidewalls 875. The pawl 886 is pivotably connected to the locking base 872 via a pivot pin 887 extending between the sidewalls 875 and includes a first end 890 and a second end 892. The first end 890 has an inferior notch so as to form a ledge dimensioned engage the locking pin 888 when the selector switch 884 is in the locked position. The second end 892 includes a ratchet and is configured to engage the ridges 874 of the rack 868 to prevent movement of the locking base 872 in any direction when the selector switch 888 is in the locked position. The locking pin 888 is attached to and spans between the inferior flanges 891 of the selector switch 884 and extends through a horizontal slot 894 formed in each of the sidewalls 875. The horizontal slot 894 is oriented so that one end of the slot 894 is underneath the first end 890 of the pawl. When the selector switch 884 is moved from an unlocked position to a locked position, the locking pin 888 moves with it along the horizontal slot 894 until it rests at the end of the slot 894 underneath the first end 890 of the pawl 886, preventing the pawl 886 from pivoting. In this position, the second end 892 is unable to disengage from the ratchet teeth 874 and thus the locking base 872 is unable to move in any direction.

The outside surface of the sidewalls 875 may include one or more visual indicators 896 that help alert the user as to which position the locking base 872 is in (i.e. locked or unlocked). By way of example, the visual indicators 896 may include color-coded indicia. By further example the color-coded indicia may include green and red panels, where the red panel located in an area that is covered by the inferior flanges 891 when the locking base 872 is unlocked while simultaneously the green panel is located in an area that is not covered by the inferior flanges 891, thereby giving the user visual indication that the locking base 872 is unlocked. Sliding the selector switch 884 into the locked position causes the inferior flanges 891 to cover the green panel and expose the red panel, indicating that the locking base 872 is now locked.

Figure 134:
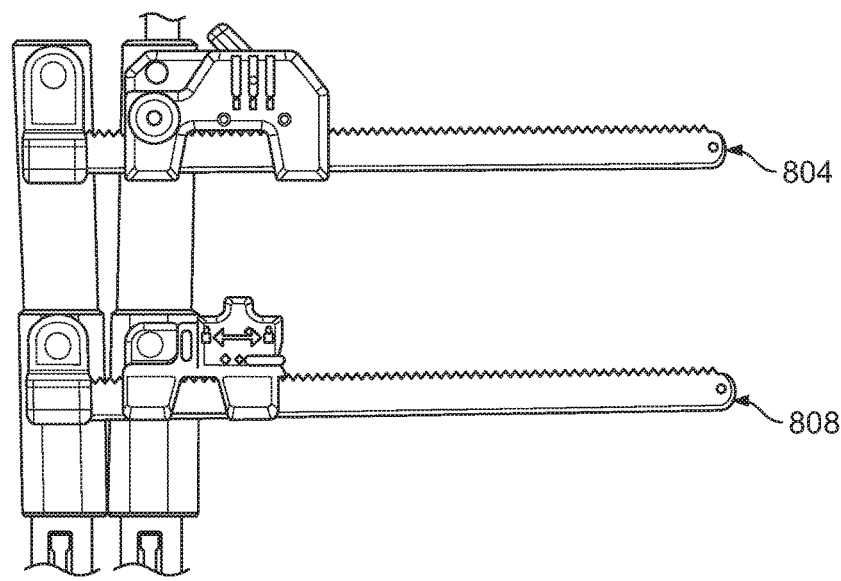
FIG. 134-136 are perspective views of the compression system of FIG. 23 in use.

In use, the user must first determine whether compression or distraction is needed. If compression is needed, then the user should preferably begin with the guide towers slightly toed in at the top of the rack. The locking rack is locked to create a pivot point by sliding the selector switch to the locked position as described above. The selector switch on the ratcheting rack is then set to in the direction that will allow compression by increasing the distance between the top of the guides and causing the distal end of the guide to pivot towards each other. The turn key driver is then rotated clockwise causing the ratcheting rack to separate which pivots the distal end of the guides towards until the desired compression is received. For distraction, the user begins with the towers slightly toed out at the top of the rack (FIG. 134). The locking rack is locked in position to establish the pivot point, and the selector switch on the ratcheting rack is put in the position that allows for distraction by drawing the top of the guides closer together which causes the distal end of the guides to pivot away from each other. The turnkey driver may then be turned counterclockwise to effect distraction.

Figures 135, 136:
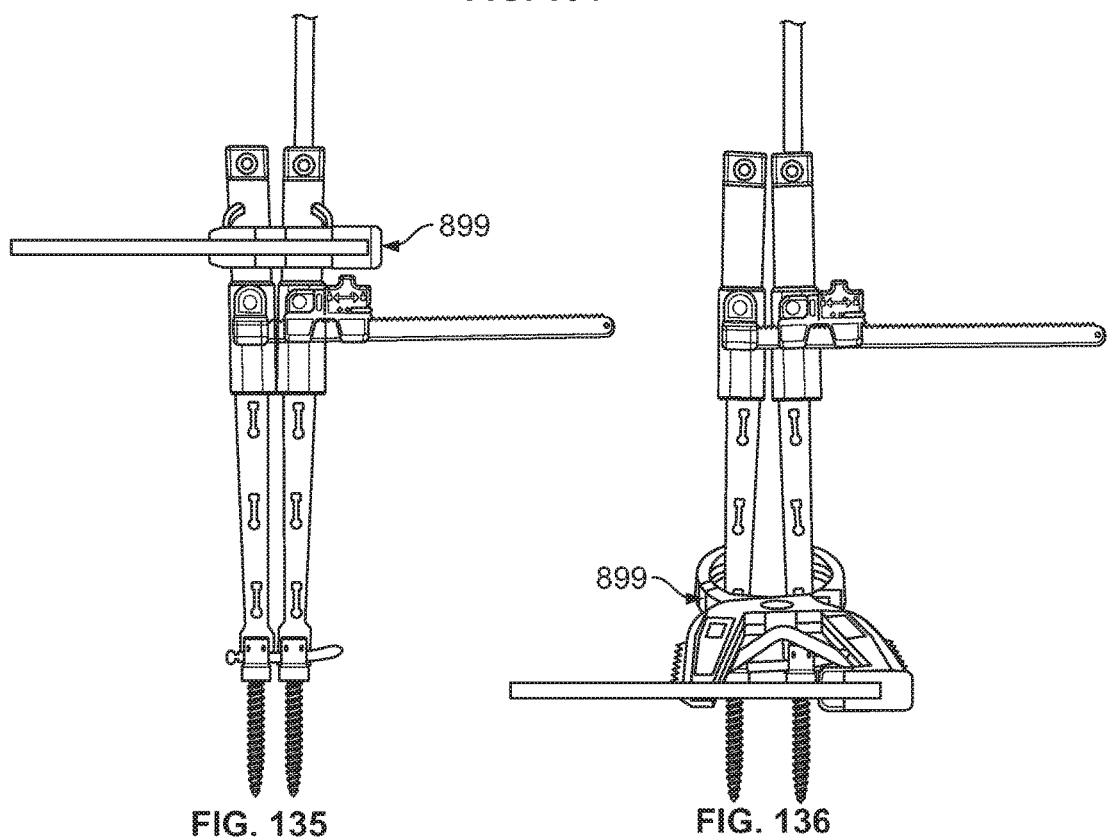
Figure 140:
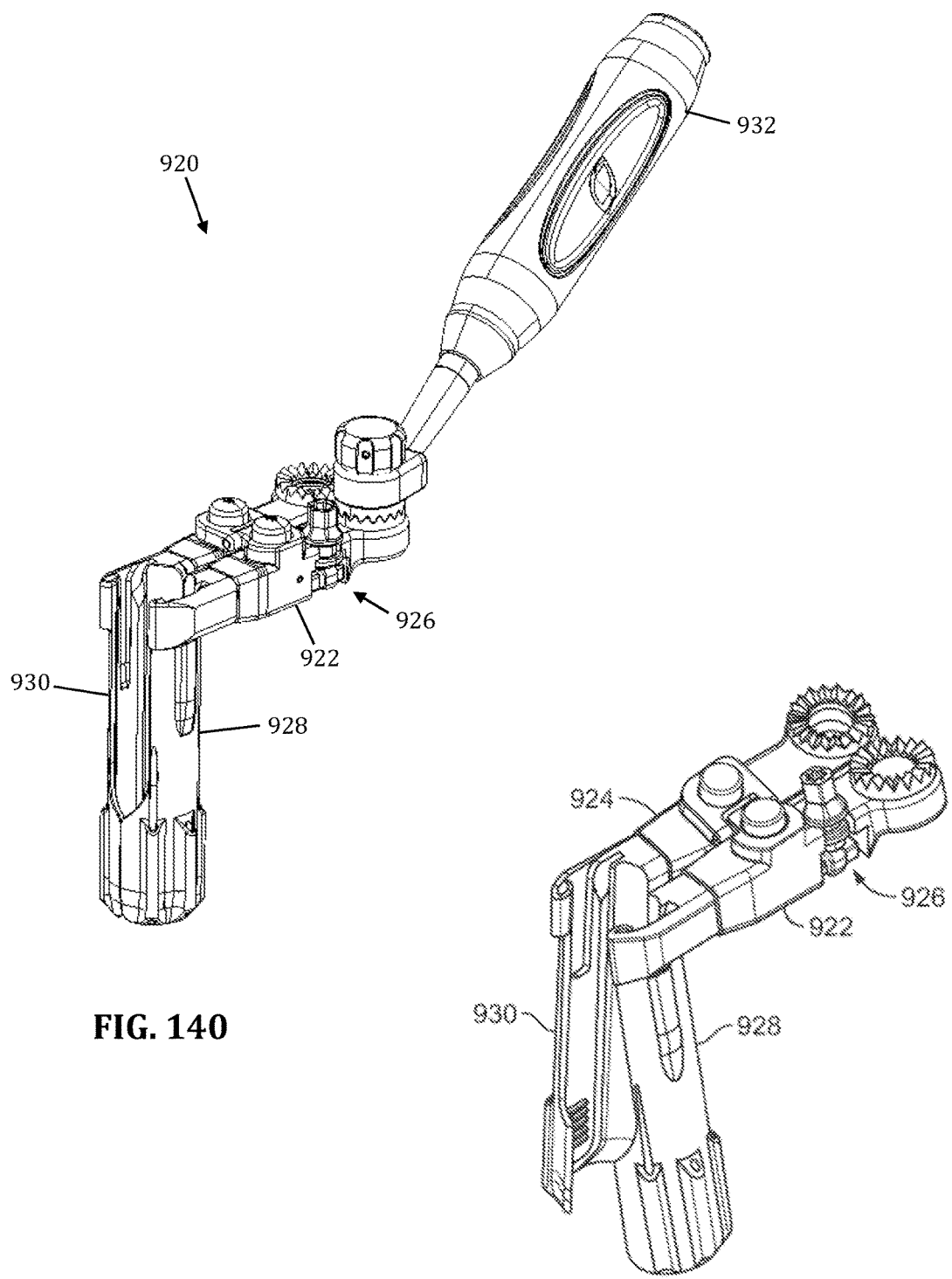
FIG. 140-141 are perspective views of a surgical retractor according to an example embodiment.
Figure 141:
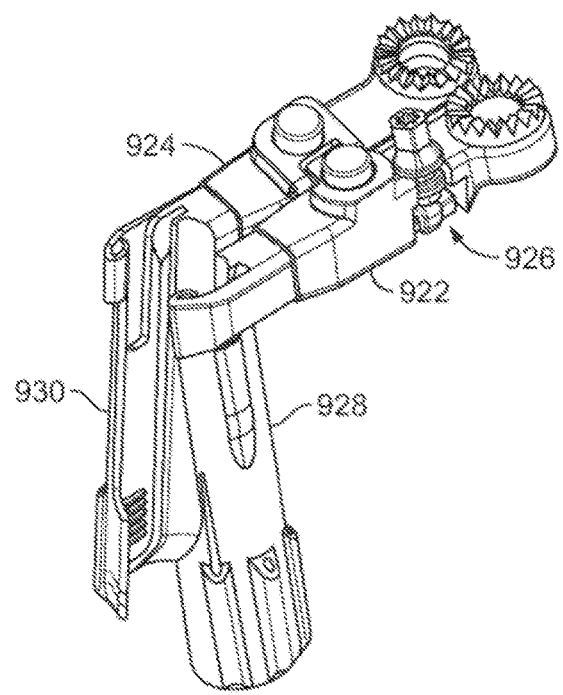
Figure 142:
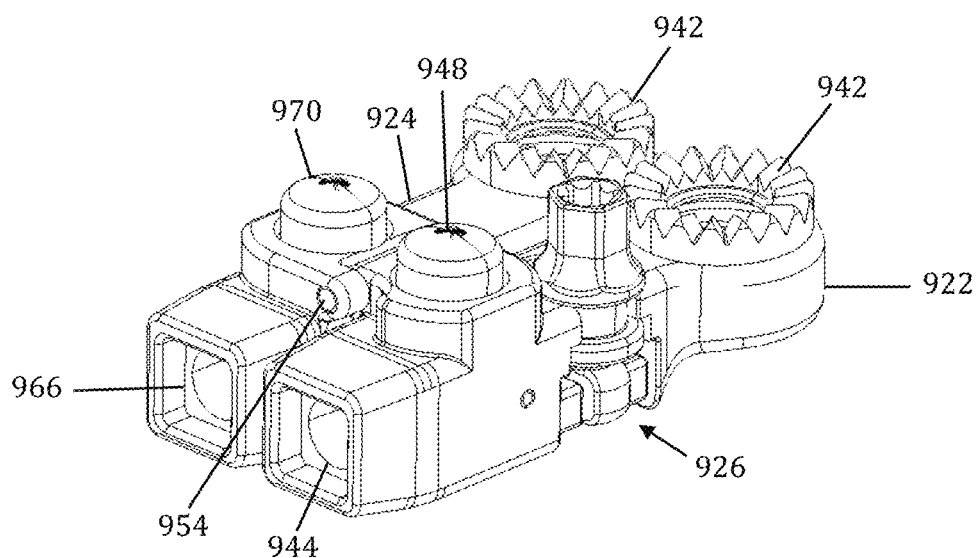
FIG. 142 is a perspective view of a retractor arm assembly forming part of the surgical retractor of FIG. 140.
Figure 143:
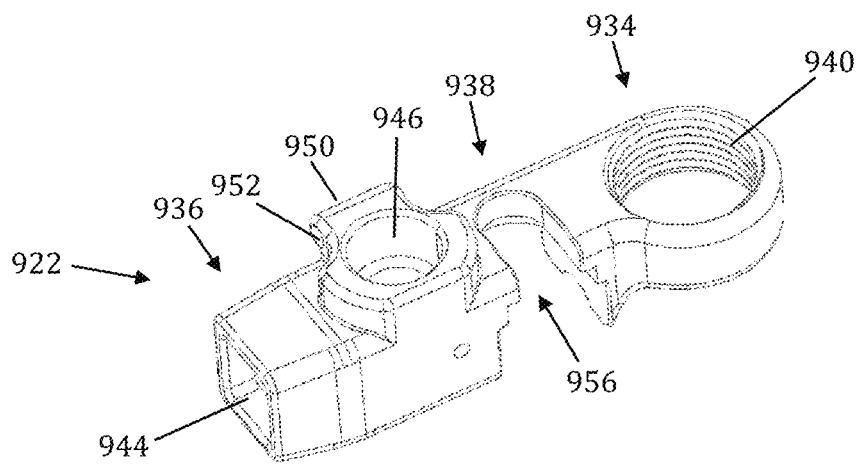
FIG. 143 is a perspective view of a first retractor arm forming part of the surgical retractor of FIG. 140.
Figure 144:
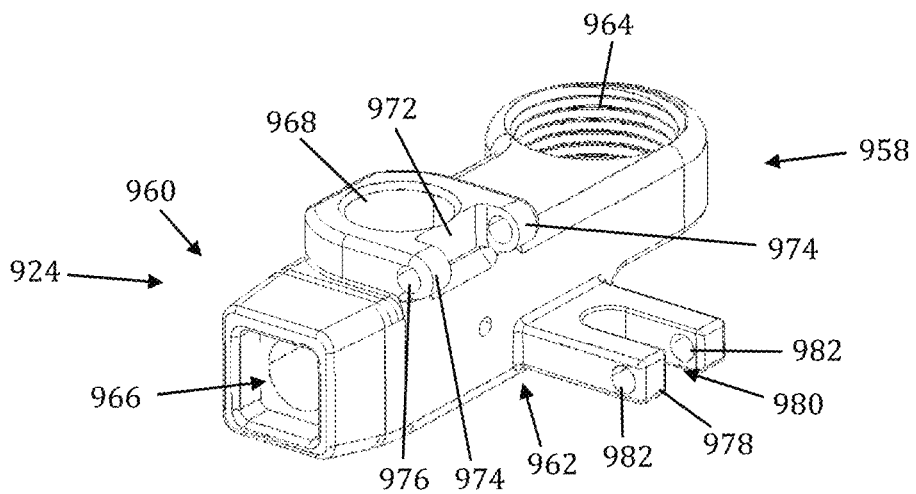
FIG. 144 is a perspective view of a second retractor arm forming part of the surgical retractor of FIG. 140.
Figure 145:
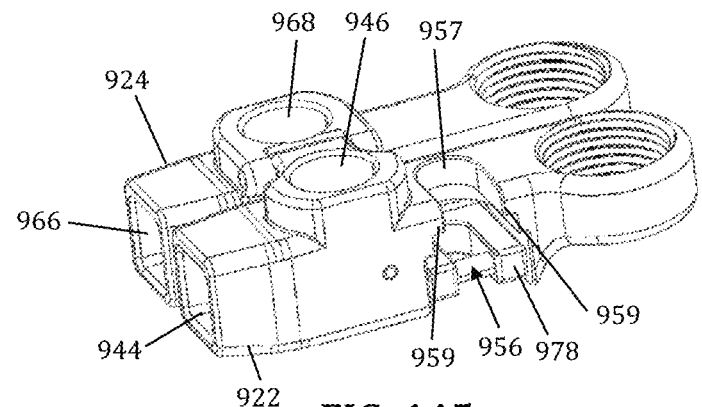
FIG. 145-146 are perspective views of the retractor arm assembly of FIG. 142.
Figure 146:
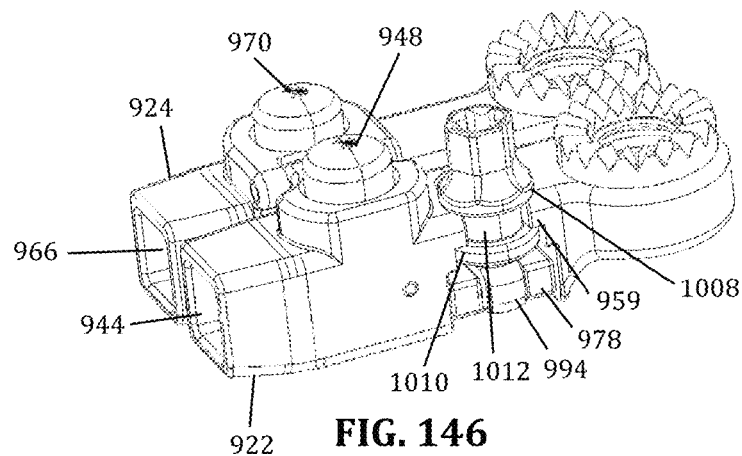

With reference to FIGS. 135 and 136, it is also possible to use the locking rack assembly 808 to achieve compression or distraction without the ratcheting rack assembly 804. Instead, the locking rack may be used as previously described to establish a pivot point between the guides, and a simple hinged compressor 899 can be used to apply force to the guides. For example, as shown in FIG. 135 to distract the locking rack assembly 808 is locked with the guides slightly toed out above the rack. The hinged compressor 899 is positioned above the locking rack and compresses the guides together to cause the distal ends of the guides to pivot away from each other. Conversely, as depicted in FIG. 136, to compress the locking rack assembly is locked with the guides slightly toed in above the rack. The hinged compressor 899 is positioned below the locking rack and compresses the guides together causing the distal ends of the guides to pivot towards each other.

FIG. 137 illustrates a combination awl-tap 900 according to an example embodiment. The combination awl-tap 900 of the instant example eliminates the need for a K-wire prior to tapping a screw hole. By way of example only, the combination awl-tap 900 includes an elongated shaft 902 having a proximal end 904 and a distal end 906. The proximal end 902 includes engagement structure for engaging a handle 908. The distal end 906 comprises a shank a proximal portion 910 and a distal portion 912. The proximal portion 910 of the shank includes a threaded region 914 configured to tap a thread into the screw hole. This constitutes the tap portion of the awl-tap combo. The distal portion 916 of the shank comprises a nonthreaded portion having a sharp tip. This constitutes the awl portion of the combination. In addition to the shaft 902 and handle 908, the combination awl-tap 900 may include a center needle 918 attached to the handle 908 and extending through the interior of the shaft 902.

By way of example, the combination awl-tap 900 may be used by first inserting the combination awl-tap 900 through a tap guide 620 as shown in FIG. 139 and described above in relation to FIGS. 99-100. The combination awl-tap 900 and tap dilator 620 is advanced to a target pedicle. The user pushes the catch release button 636 to release the awl-tap combo and enable it to access the pedicle. Using a mallet (or other suitable instrument), the user urges the awl portion of the combination awl-tap 900 into the pedicle. Approximately 15 mm into the pedicle, the threads of the tap portion 914 will engage the bone. The user can then rotate the handle 908 to thread the tap portion 914 into the bone. Once the tap portion 914 has reached the desired depth, the user may remove the center needle 918 and insert a K-wire. The tap portion 914 is then unthreaded and the combination awl-tap 900 is removed from the surgical site.

FIGS. 140-152 illustrate a split-tube retractor 920 according to an example embodiment. The split-tube retractor 920 of the instant embodiment includes a first retractor arm 922, second retractor arm 924, actuator assembly 926, first retractor blade 928, second retractor blade 930, and a handle 932. The first retractor arm 922 has a proximal end 934, distal end 936, and a central portion 938 between the proximal and distal ends. The proximal end 934 includes a threaded aperture 940 dimensioned to receive an attachment ring 942 therein. By way of example only, the attachment ring 942 may be used to attach any suitable equipment, such as for example an articulating arm (not shown). The distal end 936 includes a blade aperture 944 for attaching a retractor blade (e.g. first retractor blade 928) and a button aperture 946 for housing a blade release button 948 therein. A lateral flange 950 is positioned adjacent the button aperture 946 and extends laterally toward the second retractor arm 924. The lateral flange 950 includes a hinge aperture 952 configured to receive a pivot pin 954 therein. The central portion 938 includes a recess 956 formed in the underside of the first retractor arm 924 that is sized and configured to house the actuator assembly 926 therein. The central portion 938 further includes an aperture 957 formed in the top surface and extend through to the recess 956. The edge of the plate that forms the lip of the aperture constitutes an overhang 959, which interacts with the circumferential recess 1012 of the actuator nut 1002 to secure the actuator nut 1002 to the first retractor arm 922.

The second retractor arm 924 has a proximal end 958, distal end 960, and a central portion 962 between the proximal and distal ends. The proximal end 958 includes a threaded aperture 964 dimensioned to receive an attachment ring 942 therein. The distal end 960 includes a blade aperture 966 for attaching a retractor blade (e.g. second retractor blade 930) and a button aperture 968 for housing a blade release button 970 therein. A lateral recess 972 is positioned adjacent the button aperture 968 and is configured to receive the lateral flange 950 of the first retractor arm 922. Flanking the lateral recess 972 is a pair of flanges 974 having hinge apertures 976 formed therein and configured to receive the pivot pin 954 therein. Thus, the interaction between the lateral flange 950 of the first retractor arm 922, lateral recess 972 of the second retractor arm 924, and the pivot pin 954 result in a hinged coupling of the first and second retractor arms 922, 924. The central portion 938 includes a protrusion 978 extending laterally toward the first retractor arm 922. The protrusion 978 includes a slot 980 formed therein for receiving the inferior aspect of the I-bolt 994. A connector pin (not shown) extends through the base of the I-bolt 994 and into pin apertures 982 positioned on either side of slot 980 to secure the I-bolt 994 to the second retraction arm 924 (by way of protrusion 978).

Figure 147:
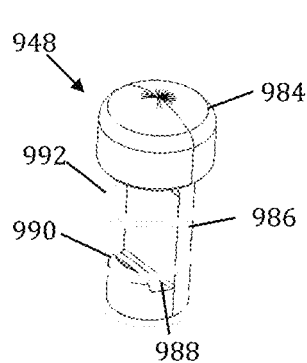
FIG. 147 is a perspective view of a blade release button forming part of the surgical retractor of FIG. 140.

FIG. 147 illustrates the release button 948/970 in greater detail. Release button 948 is identical to release button 970 so the various features will be described in relation to release button 948 but apply equally to release button 970. Release button 948 has a button head 984 and a post 986 extending distally below the button head 984. The distal end of the post 986 has a recess 988 and upper-facing ridge forming a catch 990 that interacts with a similarly formed and complementary catch on the retractor blade. A spring 992 coils around the post 986, and functions to bias the release button 970 so that the catch 990 remains engaged with the catch 1022 of the retractor blade until the release button 948 is depressed. When that happens, the catches are released, and the blades can be removed from the blade apertures 944, 966.

Figure 148:
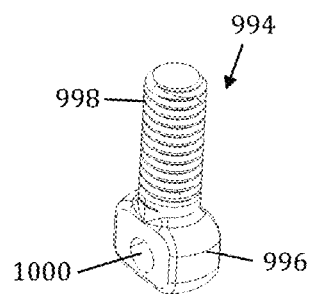
FIG. 148 is a perspective view of an I-bolt forming part of the surgical retractor of FIG. 140.
Figure 149:
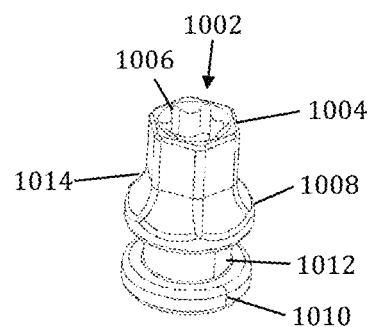
FIG. 149 is a perspective view of a actuator nut forming part of the surgical retractor of FIG. 140.

FIG. 148 illustrates the I-bolt 994 that forms part of the actuator assembly 926. The I-bolt 994 includes a head 996 and a threaded shank 998 extending proximally from the head 996. The head further includes a lateral through-hole 1000 configured to receive a connector pin to connect the I-bolt 994 to the second retractor arm 924. FIG. 149 illustrates the actuator nut 1002 that forms part of the actuator assembly in greater detail. The actuator nut 1002 includes a head 1004, a driver recess 1006, an upper lip 1008, a lower lip 1010, and a circumferential recess 1012. The head 1004 is sized and dimensioned to be mated with a drive tool, whether using the driver recess 1006 formed in the top of the head 1004 or the contoured side surface 1014 to grip with an instrument (or the user's hand). The actuator nut 1002 is placed with the aperture 957 of the first retractor arm 922 such that upper lip 1008 extends beyond the aperture lip 959 to contact the upper surface of the retractor arm 922. Simultaneously, the lower lip 1010 extends beyond the aperture lip 959 to contact the underside of the overhang. The circumferential recess 1012 is then fully contained within the aperture 957. As a result, the actuator nut 1002 is securely mated with the aperture 957 but is free to rotate. The I-bolt 994 cannot rotate due to the connector pin securing it to the second retractor arm 924. However, as the actuator nut 1002 rotates, the threaded engagement with the I-bolt 994 causes the I-bolt 994 to translate along the threaded portion. Because the second retractor arm 924 is connected to the I-bolt 994, the second retractor arm 924 will move in response to the I-bolt 924 movement. And further, since the first retractor arm 922 is hingedly coupled to the second retractor arm 924, the first retractor arm 922 will also move in response to the I-bolt 924 movement. Thus, when the actuator assembly 926 is operated by engaging a driver (not shown) with the driver recess 1006 and rotating counterclockwise, the I-bolt 994 translates outward, pushing on the lateral protrusion 978 of the second retractor blade 924. This causes the second retractor blade 924 to splay outward, which in turn causes the first retractor blade 924 to splay outward. Conversely, clockwise rotation of the actuator nut 1002 causes the blades to come together. If one of the retractor blades is attached to an articulating arm, then that blade will remain still and only the other blade will move.

Figure 150:
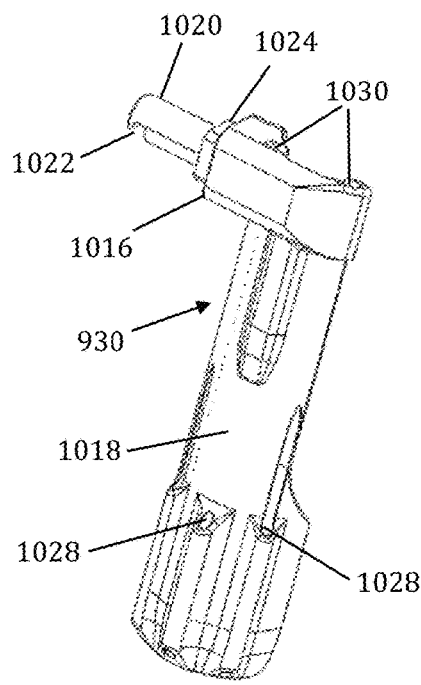
FIGS. 150-151 are perspective views of a retractor blade forming part of the surgical retractor of FIG. 140.
Figure 151:
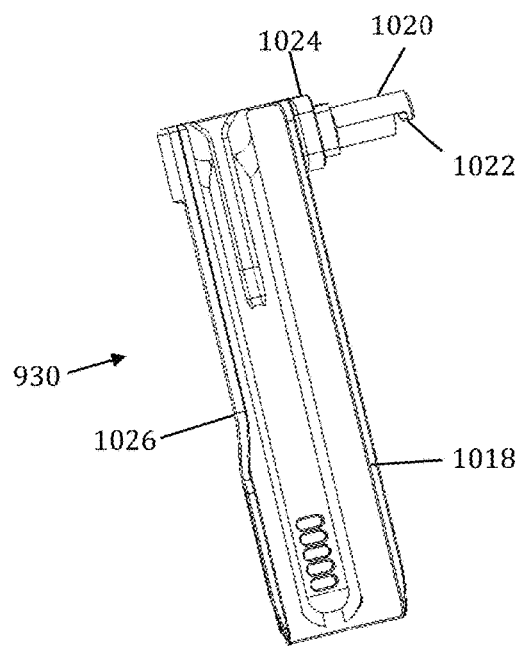
Figure 152:
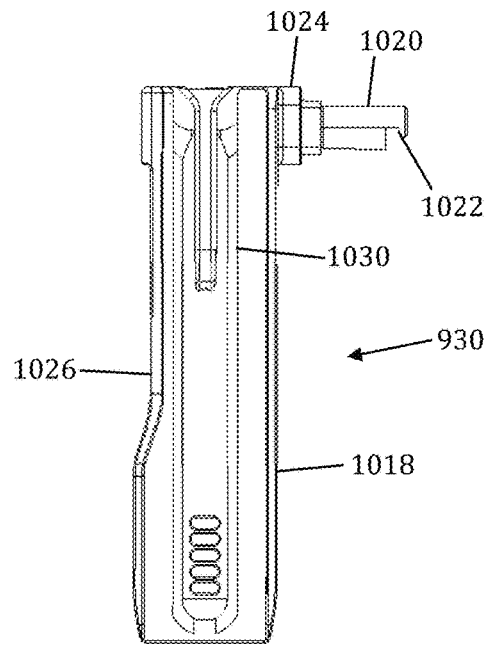
FIG. 152 is a plan view of the retractor blade of FIG. 150.

FIGS. 150-152 illustrate a retractor blade 930 in greater detail. First and second retractor blades 928, 930 are virtually identical save for being mirror images of one another, so any feature described with respect to one of the retractor blades applies to each retractor blade. Retractor blade 930 includes an arm member 1016 and a blade member 1018 extending distally from the arm member 1016. The arm member 1016 further includes an attachment post 1020 extending away from the arm member 1016. The attachment post 1020 includes a recess and a lip that form a catch 1022 that is configured to mate with the catch 990 of the release button 970 as described above. The attachment post 1020 further includes a generally square-shaped base portion 1024, which interacts with the generally square-shaped opening of the blade aperture 966 to help ensure the retractor blade 930 doesn't rotate independently of the retractor arm 924. The blade member 1018 has a cutaway portion 1026 on one side for increased visualization by allowing the user to angle instruments out from between the blades. The blade member 1018 also includes a plurality of channels 1028 on the external surface of the blade that are configured to receive a K-wire therethrough. A track 1030 extends along the inside surface of the blade and is configured to attach accessories such as a light cable or shim.

By way of example, the split-tube retractor may be especially well suited facet preparation in conjunction with the application of a minimally invasive fixation construct. To utilize the split-tube retractor over a K-wire, the pedicle caudal to the facet is targeted with a K-wire and dilators are advanced over the K-wire. According to one example, the dilators may be only half circles such that dilation extends in only a single direction, towards the facet. The split blade retractor may then be advanced with the K-wire passing through one of the blade cannulations. With the retractor oriented such that the non-articulating blade (i.e. the blade attached to retractor arm 924 without the articulating assembly) is on the K-wire, the articulating blade will open over the target facet joint. Once docked split tube retractor that is advanced over the K-wire may be coupled to the table mount and the blades articulated open. A light source may be advanced down the blade. The Facet may then be decorticated and graft material placed.

Figure 158:
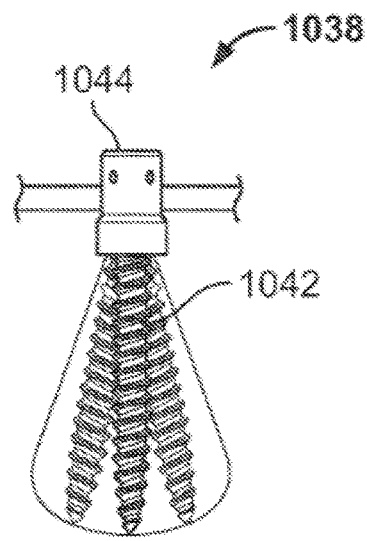
FIG. 158 is a perspective view of a polyaxial pedicle screw.
Figure 159:
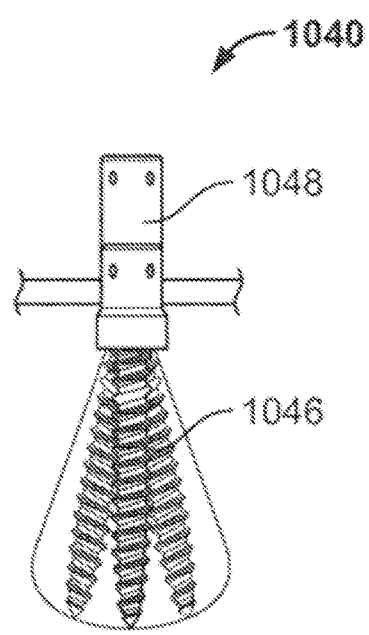

When performing spinal fixation techniques like some of those described herein, one problem that arises is that often times different types of screws require the use of several different drivers during one procedure. Referring first to FIGS. 158 and 159, a polyaxial pedicle screw 1038 (FIG. 158) and a polyaxial reduction screw 1040 (FIG. 159) are shown by way of example for the purposes of illustration. The pedicle screw 1038 has a threaded shank 1042 and a rod housing 1044. The threaded shank has a head portion (not shown) that is nesting in the base of the rod housing. The head has a hexalobe shaped (for example) drive recess configured to mate with a distal tip of a screwdriver. The upper arms of the rod housing 1044 have an interior threaded region that is primarily intended to receive a lock screw therein, however the threaded region can serve another purpose such as providing a secondary engagement for the screw driver. The screwdriver may have an additional engagement feature in the form of a distal insert having wings that engage the rod channel. The result is a screwdriver that can stabilize the rod housing 1044 while simultaneously driving the shank 1042. The polyaxial reduction screw 1040 also has a threaded shank 1046 and a rod housing 1048. As with the pedicle screw 1038, the reduction screw 1040 has threads at the top of the rod housing 1048 and a drive recess in the head of the shank 1046. However a problem arises in that the distance between the drive recess at the top of the shank and the threaded region at the top of the tulip is much greater than with the pedicle screw. As a result, often times the surgeon is forced to change screwdrivers to accommodate one of them. This can be time consuming if the particular technique calls for a lot of these different types of screws.

Figure 160:
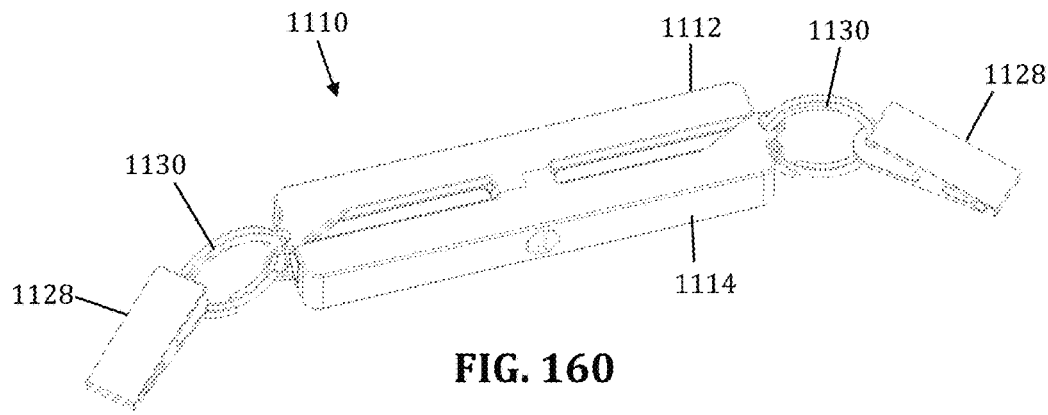

FIGS. 153-159 illustrate a screwdriver 1050 according to one example embodiment that is capable of driving multiple types of screws with the same driver, and in particular is capable of having a 3-way engagement with both pedicle screws and reduction screws. The screwdriver 1050 includes an inner shaft 1052, inner sleeve 1054, and outer sleeve 1056. The inner shaft 1050 has a proximal end 1058, middle portion 1060, and distal end 1062. The proximal end 1058 includes a shaped end 1064 configured for attachment to a suitable instrument or other attachment. The distal end includes a shaped driver 1066, for example a hexalobe driver that is configured to interact with the driver recess of the shank 1042 of a polyaxial pedicle screw 1038 (FIG. 158) and the driver recess of the shank 1046 of the polyaxial reduction screw 1040 (FIG. 160).

The inner sleeve 1054 has a distal end 1068, a proximal end 1070, and a central lumen 1072 extending through the instrument. The distal end 1068 has a threaded region 1074 that is configured to mate with the threads on the inside top of the rod housing 1044 of polyaxial pedicle screw 1038 (FIG. 158) and the threads on the inside top of the rod housing 1048 of the polyaxial reduction screw 1040 (FIG. 160). The proximal end 1070 includes a housing unit 1076 and a spring-biased release button 1078, which will be discussed in greater detail below.

FIG. 155 is a close up view of the distal tip of the assembled screwdriver 1050. Nestled in between the inner shaft 1052 and the inner sleeve 1054 is a rod channel engagement piece 1080. The rod channel engagement piece 1080 (shown in isolation in FIG. 156) includes an outer ring 1082 having a pair of opposing flanges 1084 and a tubular shaft 1086 extending proximally of the outer ring 1082. The outer ring 1082 is sized and configured to snugly fit within the rod housings 1044, 1048 without engaging the threads. The flanges 1084 are sized and configured to extend into the lower portion of the rod channel at the base of the housings 1044, 1048. The rod channel engagement piece 1080 prevents the rod housing from rotating when driving the screw. The tubular shaft 1086 is configured to extend the rod channel engagement piece 1080 so that the outer ring 1082 can still rest at the base of the rod channel in the rod housing 1048 of the reduction screw 1040.

Figure 157:
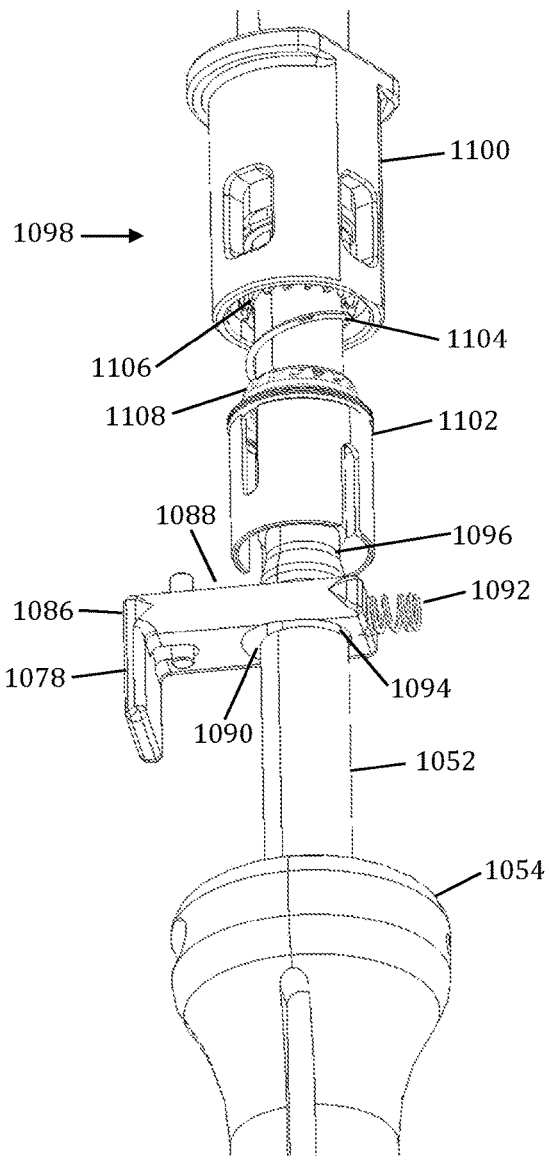
FIG. 157 is a perspective view of a central portion of the screwdriver with a portion removed.

FIG. 157 is a close up view of the middle part 1060 of the inner shaft in conjunction with the proximal end 1070 of the inner sleeve 1054 with the housing unit 1076 removed for clarity. The release button 1078 has a front-facing user interface 1086 and a block 1088 extending laterally behind the user interface 1086. The block 1088 has an aperture 1090 through which the inner shaft 1052 extends. A spring 1092 positioned behind the block 1088 biases the block 1088 outward in a locked position. The block 1088 as shown in FIG. 157 is received with a recess 1094 formed in the inner shaft 1052. A second recess 1096 is positioned proximally of the first recess 1094 at a distance that corresponds to the difference in size between the rod housing 1044 of the pedicle screw 1038 and the rod housing 1048 of the reduction screw 1040. As such, a user may adjust the arrangement of the distal portions of the inner shaft 1052 and inner sleeve 1054 by pressing the release button 1078. This compresses the spring 1092 and dislodges the aperture 1090 from the recess 1094. The user then urges the inner shaft 1052 forward until the block 1088 snaps into the second recess 1096. At this point the distal tip of the inner shaft 1052 (with the hexalobe driver) and the rod channel engagement piece 1080 will be extending a greater distance away from the distal end of the inner sleeve 1054 (with the threaded surface), which will correspond to the difference in size between the rod housing 1044 the pedicle screw and the rod housing 1048 of the reduction screw 1040.

Optionally, a locking apparatus may be employed to cause the inner shaft 1052 to automatically stop turning in the even that the screw is advanced too far. With continued reference to FIG. 157, a locking feature 1098 is provided proximally of the release button 1078. The locking feature 1098 includes a superior locking unit 1100 and an inferior locking unit 1102. The superior locking unit has a toothed ring 1106 that is configured to engage toothed ring 1108 of the inferior locking unit 1102. A spring 1104 acts to draw the superior and inferior locking units 1100, 1102 together as the inner shaft 1052 rotates (as the screw is being driven by the screwdriver 1050). When the toothed rings 1106, 1108 engage one another the inner shaft 1052 will no longer be able to rotate and advancement of the screw ceases.

Figure 161:
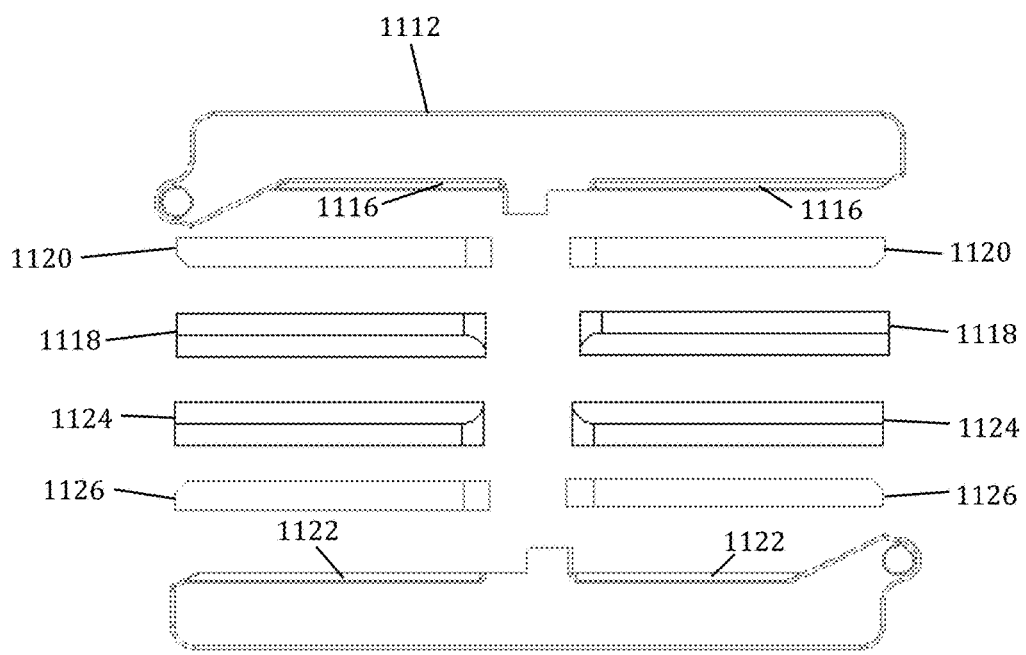
Figure 162:
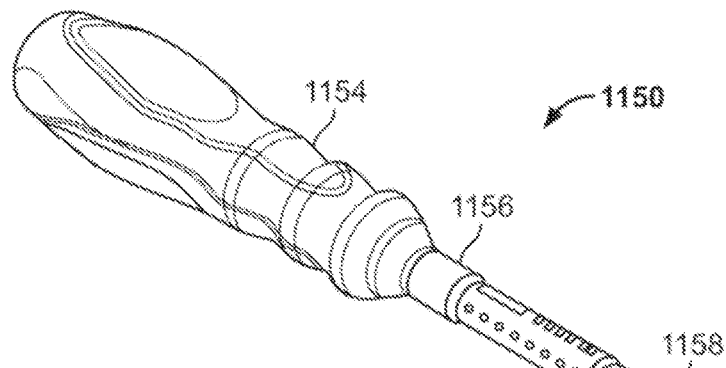
Figure 163:
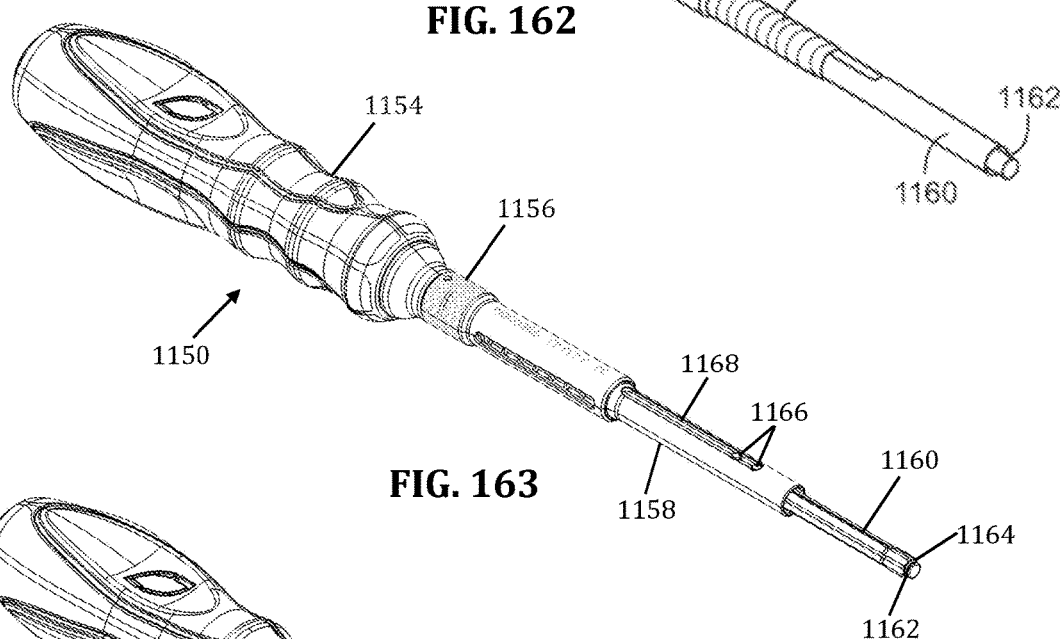
Figure 164:
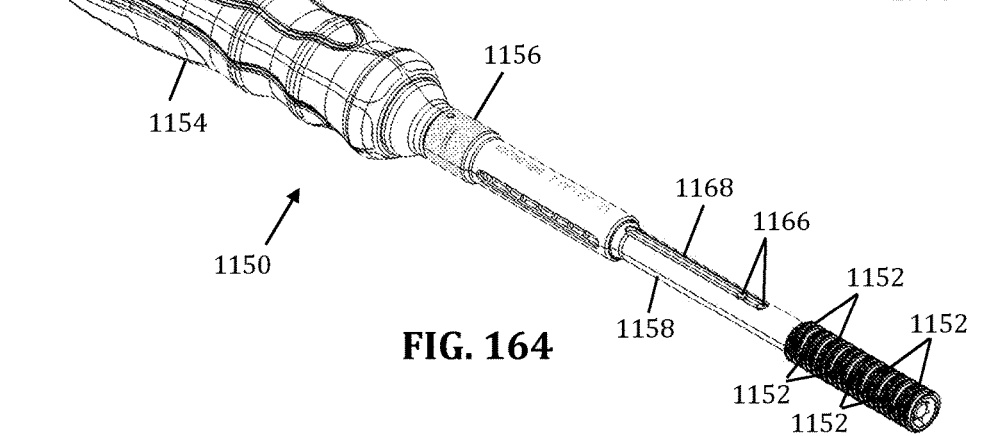

FIGS. 160-161 illustrate a K-wire holder 1110 according to an example embodiment for use with the various fixation systems disclosed herein. When performing a multi-level spine surgery with a plurality of screws, often there are a lot of K-wires in use, and they can be a nuisance and in the way as the surgical personnel work around them. The K-wire holder 1110 offers an effective way to keep the K-wires under control without disrupting the surgery every time a K-wire needs to be added or removed from the holder 1110.

By way of example only, the K-wire holder includes a superior clamp body 1112 and an inferior clamp body 1114. The superior clamp body 1112 has a pair of recesses 1116 configured to hold a pair of silicone inserts 1118. By way of example only, the silicone inserts 1118 may have metal (or plastic or other suitable material) bases 1120. Similarly, the inferior clamp body 1114 has a pair of recesses 1122 configured to hold a pair of silicone inserts 1124. By way of example only, the silicone inserts 1124 may have metal (or plastic or other suitable material) bases 1126. When assembled, the opposing silicone inserts 1118, 1124 flushly contact one another to form a retention slit that is configured to hold a plurality of K-wires therein. The K-wires can be inserted and removed by hand. The pliable silicone material allows individual K-wires to be inserted or removed without disturbing the others in the same slit. The K-wire holder 1110 further includes at least one attachment feature 1128 to attach the holder 1110 to a drape or other secure point on the surgical table. By way of example, the attachment feature 1128 is a clip or clamp, however other attachment features are possible. The attachment features 1128 are attached to the K-wire holder by way of a coiled ring 1030.

The techniques discussed herein present several challenges. One such challenge is being able to efficiently and effectively deliver a plurality of lock screws to successive bone anchors 12 while performing multi-level fixation surgery. The multi-load lock screw inserter described by way of example herein addresses this need by holding a plurality of lock screws simultaneously and providing for controlled sequential delivery of each lock screw to the target tulips before having to reload the inserter with more lock screws. Instead of a spring, the multi-load lock screw inserter described herein utilizes a threaded mechanism to advance each successive lock screw into position for insertion. By using a threaded mechanism in lieu of a spring, the constant distal force enacted by the spring is virtually removed and consequently the force required to retain the lock screws on the inserter is much smaller. With a smaller retention force to overcome, intentional lock screw separation is much easier than with spring mechanisms. As a result, the multi-load lock screw inserter described herein will make lock screw delivery a faster process, saving the surgeon valuable operating room time, thereby reducing the patient's risk for infection.

FIGS. 162-169 illustrate an example of a multi-load lock screw inserter 1150 configured to hold a plurality of lock screws 1152 simultaneously and thereafter facilitate controlled sequential delivery of each lock screw to the target tulips 20 before having to reload the inserter with more lock screws. By way of example the multi-load lock screw inserter 1150 includes a handle 1154, rotating sleeve 1156, a threaded tube 1158, an inner shaft 1160, and a retention clip 1162.

The inner shaft 1160 has a distal tip geometry that mates with the lock screws 1152. The inner shaft 1160 holds the lock screws 1152 and allows the user to deliver the lock screws 1152 to the bone anchors 12. A retention clip 1162 is positioned near the distal tip 1164 of the inner shaft 1160 and holds the lock screws 1152 onto the device. The retention clip 1162 applies a frictional force on the inner diameter of the lock screws 1152, which prevents the lock screws 1152 from accidentally separating from the device. The handle 1154 is attached to the inner shaft 1160 to provide a means of applying torque. The threaded tube 1158 is cannulated and receives the inner shaft 1160 therethrough. The threaded tube 1158 translates the lock screws 1152 distally and primes the next lock screw for delivery. Limiter pins 1166 extend transversely through the inner shaft 1160 and engage the threaded tube 1158. More specifically, the limiter pins 1166 fit within an elongate channel 1168 on the threaded tube 1158 and prevent rotation of the threaded tube 1158 during translation. The rotating sleeve 1156 is coupled to the threaded tube 1158 and controls translation of the threaded tube 1158. For example, clockwise rotation of the rotating sleeve 1156 causes the threaded tube 1158 to translate distally, and vice versa. The rotating sleeve 1156 is held in place during rotation with a C-clip 1170. A threaded spring ball detent 1172 gives the user tactile and audible feedback when the lock screw 1152 is in the proper position. The threads on the threaded tube 1158 are timed such that the lock screws 1152 translate the distance of one lock screw for each 180° turn. Two holes 1174 positioned opposite one another on the rotating sleeve 1156 allow space for the threaded spring ball detent 1172 to engage; thus, giving the user a tactile feel and an audible click to ensure the proper amount of rotation was achieved.

The rotating sleeve 1156 is cannulated and has an interior diameter large enough to receive the threaded tube 1158 therein. Two mating pins 1176 are positioned opposite one another within the interior lumen of the rotating sleeve 1156 near the distal end. The mating pins 1176 are configured to engage the threaded portion 1178 of the threaded tube 1158. Specifically, the mating pins 1176 fit within the thread channel 1180 and translate along the thread channel 1180 when the rotating sleeve 1156 is rotated. This translation of the mating pins 1176 along the thread channel 1180 in turn causes the threaded tube 1158 (which does not rotate due to the limiter pins 1166) to then translate distally (in response to a clockwise rotation of the rotating sleeve 1156) or proximally (in response to a counterclockwise rotation of the rotating sleeve 1156).

Figure 167:
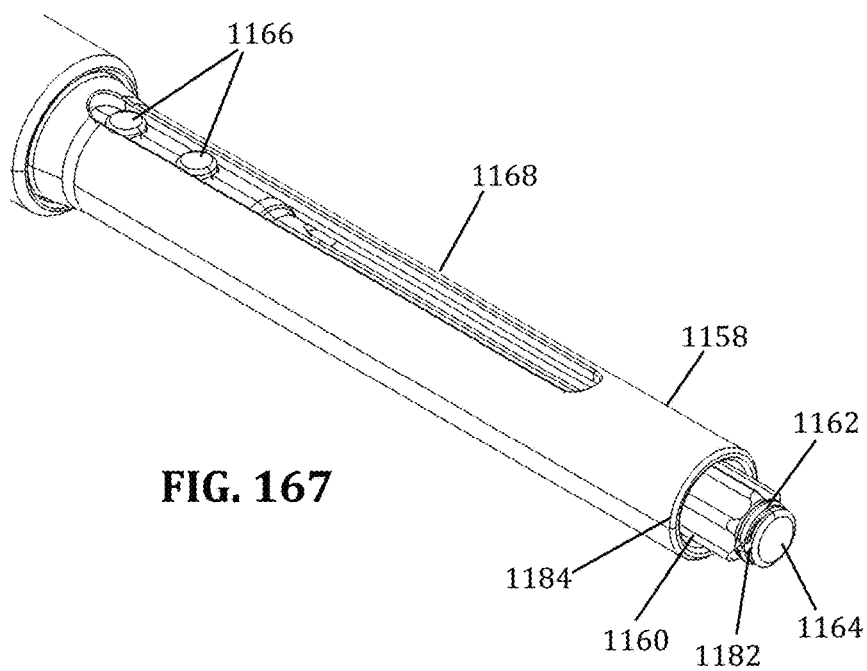

FIG. 167 illustrates the distal tip region of the multi-load lock screw inserter 1150 in greater detail, showing the distal tip region with no lock screws engaged. The inner shaft 1160 has a distal region geometry that mates with the lock screws 1152. By way of example, the distal region geometry is a hexalobe shape, however any geometry that complements the geometry of the inserter lumen of the lock screw 1152 may be used. The distal tip region further includes a retention clip 1162 positioned within a clip recess 1182 formed circumferentially about the inner shaft 1160 at the distal tip 1164. The retention clip 1162 provides a physical barrier to prevent the lock screws 1152 from accidentally separating from the inserter, but allows passage of the lock screws if sufficient force is applied. The retention clip 1162 may be composed of any material suitable to prevent unwanted release of the lock screws 1152. By way of example, the retention clip 1162 is made of cobalt chrome. The threaded tube 1158 has an inner diameter large enough to allow passage of the inner shaft 1160 therethrough but not the lock screws 1152. As a result, the distal end 1184 of the threaded tube 1158 engages with the lock screws 1152 and pushes them distally along the inner shaft 1160.

Figure 168:
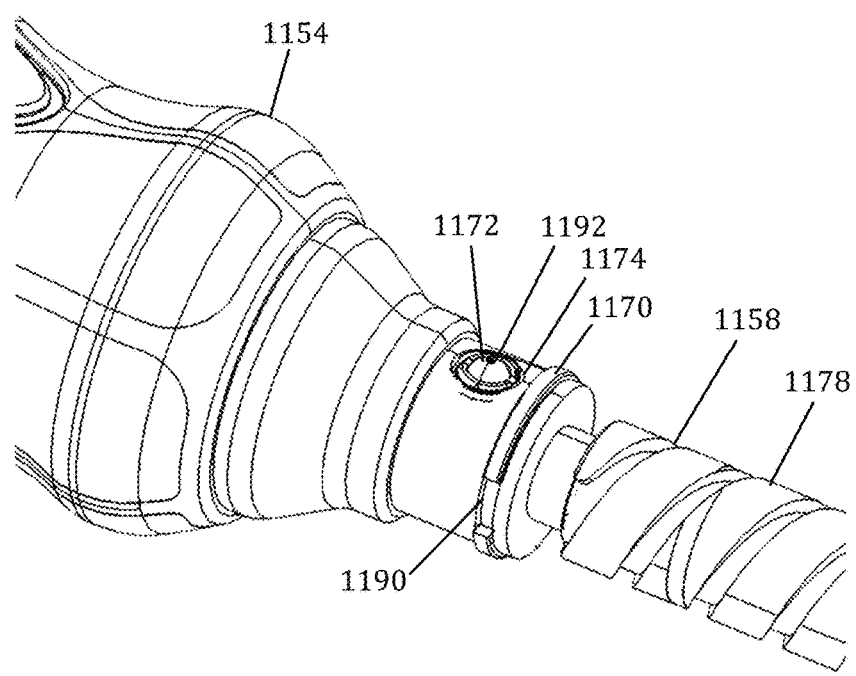

FIG. 168 is a close up view of the mating region of the rotating sleeve 1156, inner shaft 1160, and silicone handle 1154, with the rotating sleeve 1156 removed for clarity. The silicone handle 1154 is attached to the proximal end of the inner shaft 1160 by any suitable attachment mechanism. By way of example only, the proximal end of the inner shaft is provided with a threaded post 1186 that is threadedly received within a threaded aperture 1188 formed in the distal end of the silicone handle 1154 (FIG. 166). When the silicone handle 1154 is rotated, the entire instrument is in turn rotated and the lock screws 1152 may be advanced into and secured within the screw tulip 20. The proximal portion of the inner shaft 1160 further includes a circumferential recess 1190 configured to hold a C-clip 1170. The C-clip 1170 is positioned such that a portion of the C-clip resides within the circumferential recess 1190 on the inner shaft 1160 and a second portion of the C-clip 1170 resides in a corresponding circumferential recess on the inside lumen of the rotating sleeve 1156, thus securing the rotating sleeve 1156 to the inner shaft 1160 in such a way that the rotating sleeve 1156 is allowed to freely rotate about the axis defined by the inner shaft 1160, but is prevented from translating in any direction along that axis. The threaded spring ball detent 1172 is positioned at the proximal end of the inner shaft 1160 to give the user tactile and audible feedback when the lock screw 1152 is in the proper position at the distal end of the inner shaft 1160. The threaded spring ball detent 1172 comprises a ball 1192 that is biased against the interior surface of the rotating sleeve by a spring (not shown). A pair of feedback apertures 1174 is positioned opposite one another on the proximal end of the rotating sleeve 1156 and further positioned such that rotation of the rotating sleeve 1156 eventually brings the feedback aperture 1174 and threaded spring ball detent 1172 into alignment. When that happens, the ball 1192 is able to partially move into the feedback aperture 1174, giving the user tactile and audible feedback. The threads 1178 on the threaded tube 1158 are timed such that the lock screws 1152 translate the distance of one lock screw for each 180° turn of the rotating sleeve 1156. Thus, the tactile and audible feedback created by the interaction between the threaded spring ball detent 1172 and the feedback aperture 1174 is an indication to the user that the lock screw 1154 has been fully advanced and is ready to be engaged with the bone anchor 12.

Figure 169:
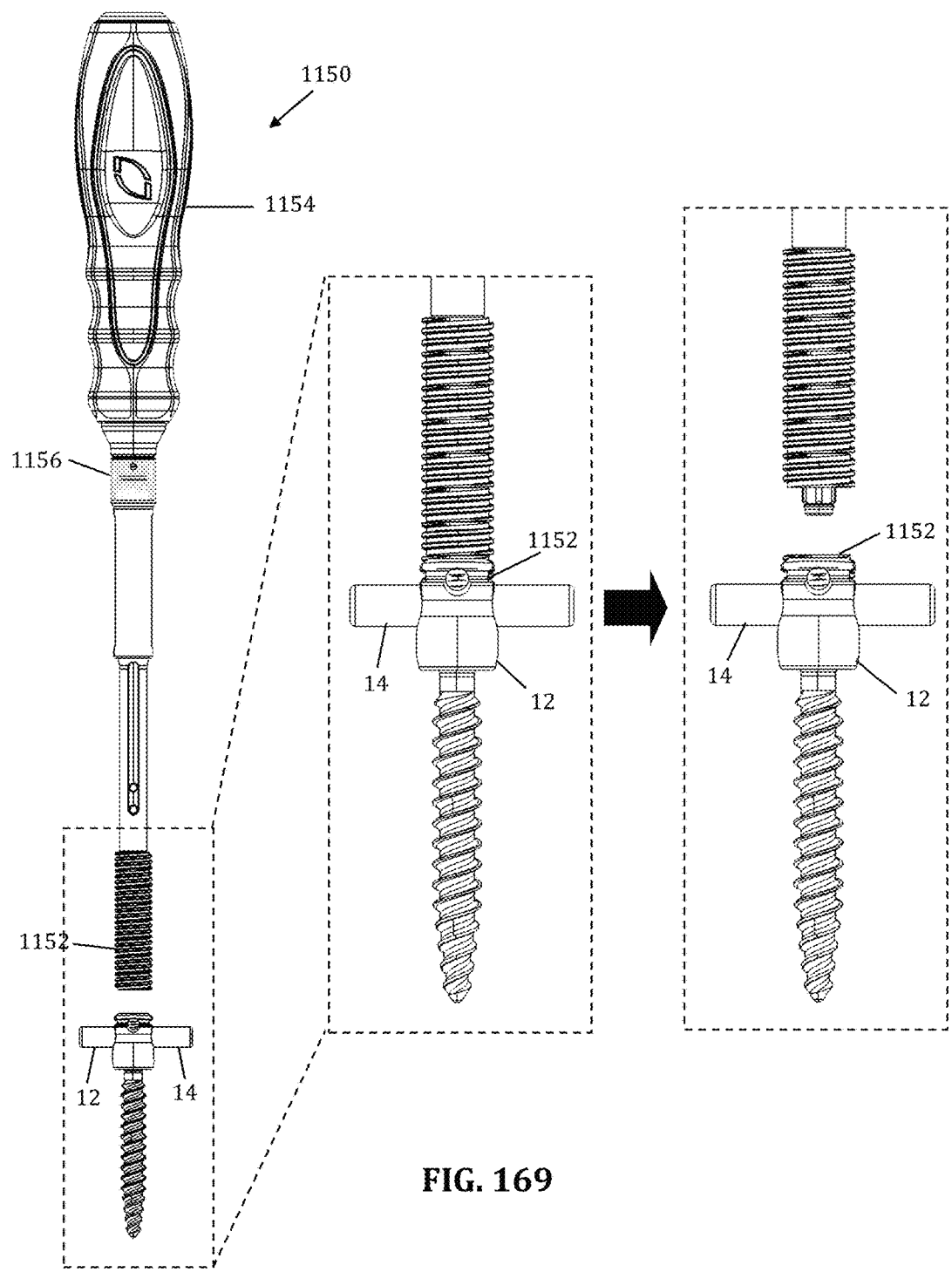

FIG. 169 illustrates a sequential view of lock screw delivery into a bone anchor. To use the multi-load lock screw inserter 1150 described herein, the user would first load a plurality of lock screws 1152 (for example up to 8 lock screws) onto the inner shaft 1160. To accomplish this, the first step is to rotate the rotating sleeve 1156 counterclockwise until the exposed inner shaft 1160 is the correct length to accommodate the desired number of lock screws 1152. The second step is to insert the inner shaft 1160 through the desired number of lock screws 1152, making sure the last lock screw to be loaded is advanced beyond the retention clip 1162 at the distal end 1164 of the inner shaft 1160. Next, as shown in FIG. 169, the user can thread the most distal lock screw 1152 into a bone anchor 12 by rotating the entire device using the silicone handle 1154. When the lock screw 1152 and rod 14 fully bottom out within the bone anchor 12, the multi-load lock screw inserter 1150 can be separated from the lock screw 1152 by pulling the inserter axially away from the bone anchor 12. Next, the user rotates the rotating sleeve 1156 180° clockwise to advance the next lock screw 1152 into position. The proper position of the lock screw will be indicated by the tactile and audible feedback from the ball detent. The process above is repeated until all lock screws have been delivered to bone anchors.

While the inventive features described herein have been described in terms of a preferred embodiment for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation, for example, the fixation of long bones.

What is claimed is:

1. A spinal fixation system for fixing a spinal segment that includes two adjacent vertebral structures and an intervertebral space between them, comprising:
   a pair of anchor assemblies, each anchor assembly having a housing member, a threaded shaft, and a locking cap, the housing member having a rod channel between a pair of upstanding arms, the upstanding arms each having a slot formed in an outside surface thereof;
   an elongated spinal rod dimensioned to connect the pair of anchor assemblies when one anchor assembly from the pair is implanted in each of the adjacent vertebral structures;
   a pair of guide assemblies, each guide assembly coupleable to one of the anchor assembly housing members, the guide assembly extending proximally from the housing member;
   a compression system configured to manipulate the guide assemblies to impart compression or distraction to the spinal segment, said compression system comprising:
      a pivot tool having a pivot handle and a pivot paddle situated distally to the pivot handle, the pivot paddle having an enclosed perimeter and first and second openings defined within the enclosed perimeter, each of the first opening and the second opening dimensioned to receive and constrain one of the guide assemblies; and
      a rotation tool having a rotation handle and a rotation paddle situated distally to the rotation handle, the rotation paddle having an enclosed perimeter and third and fourth openings defined within the enclosed perimeter, the third opening dimensioned to receive and constrain one of the guide assemblies, and the fourth opening dimensioned to receive the other of the guide assemblies while permitting movement of the guide assembly within the fourth opening.

2. The spinal fixation system of claim 1, wherein the first, second, and third openings are circular openings and the fourth opening is an elliptical opening.

3. The spinal fixation system of claim 1, wherein the pivot tool includes a pivot stem situated between and connecting the pivot handle and the pivot paddle.

4. The spinal fixation system of claim 3, wherein the pivot handle includes a contoured gripping surface for handling by a user.

5. The spinal fixation system of claim 1, wherein the pivot handle has a first longitudinal axis, the pivot paddle has a second longitudinal axis, the rotation handle has a third longitudinal axis, and the rotation paddle has a fourth longitudinal axis.

6. The spinal fixation system of claim 5, wherein the first longitudinal axis is coaxial with the second longitudinal axis.

7. The spinal fixation system of claim 5, wherein the third longitudinal axis is transverse to the fourth longitudinal axis.

8. The spinal fixation system of claim 5, wherein the first longitudinal axis is coaxial with the second longitudinal axis and the third longitudinal axis is transverse to the fourth longitudinal axis.

9. The spinal fixation system of claim 5, wherein the first opening and the second opening are aligned along the second longitudinal axis with the first opening situated distally to the second opening.

10. The spinal fixation system of claim 5, wherein the third opening and the fourth opening are aligned along the fourth longitudinal axis with the third opening situated distally to the fourth opening.

11. The spinal fixation system of claim 5, wherein the first opening and the second opening are aligned along the second longitudinal axis with the first opening situated distally to the second opening, and the third opening and the fourth opening are aligned along the fourth longitudinal axis with the third opening situated distally to the fourth opening.

12. The spinal fixation system of claim 1, wherein the pivot paddle enclosed perimeter is elliptical in shape.

13. The spinal fixation system of claim 1, wherein the rotation paddle enclosed perimeter is elliptical in shape.

14. The spinal fixation system of claim 1, wherein each of the pivot paddle and rotation handle enclosed perimeters are elliptical in shape.

15. The spinal fixation system of claim 1, wherein the enclosed perimeter of the pivot paddle is configured to open to facilitate receipt of the guide assemblies therein.

16. The spinal fixation system of claim 15, wherein the pivot paddle includes a first arm and a second arm coupled together about a hinge.

17. The spinal fixation system of claim 16, wherein the hinge is situated distally to the first and second openings.

18. The spinal system of claim 17, wherein the pivot handle includes extensions of the first and second arms.

19. The spinal fixation system of claim 1, wherein the rotation tool defines a rotation axis that extends through the third opening and perpendicular to the third longitudinal axis and wherein rotation of the rotation tool rotates the fourth opening about the rotation axis.

20. The spinal fixation system of claim 19, wherein the rotation axis extends through the first opening and is coaxial with a longitudinal axis of one from the pair of guide assemblies that is received in each of the first and third openings.

* * * * *